United States Patent
Lotz et al.

(10) Patent No.: US 11,564,619 B2
(45) Date of Patent: Jan. 31, 2023

(54) MAGNETIC RESONANCE SPECTROSCOPY SYSTEM AND METHOD FOR DIAGNOSING PAIN OR INFECTION ASSOCIATED WITH PROPIONIC ACID

(71) Applicants: ACLARION, INC., San Mateo, CA (US); THE REGENTS OF THE UNIVERSITY OF CALIFORNIA, Oakland, CA (US)

(72) Inventors: Jeffrey C. Lotz, Oakland, CA (US); James Clayton Peacock, III, Redwood City, CA (US); David S. Bradford, Sausalito, CA (US); Stefan Dudli, Bern (CH); Sergey G. Magnitsky, Oakland, CA (US)

(73) Assignees: ACLARION, INC., San Mateo, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 862 days.

(21) Appl. No.: 16/224,590

(22) Filed: Dec. 18, 2018

(65) Prior Publication Data

US 2019/0307393 A1 Oct. 10, 2019

Related U.S. Application Data

(63) Continuation of application No. PCT/US2017/038034, filed on Jun. 16, 2017.
(Continued)

(51) Int. Cl.
*A61B 5/00* (2006.01)
*G01R 33/465* (2006.01)
(Continued)

(52) U.S. Cl.
CPC ............ *A61B 5/4514* (2013.01); *A61B 5/055* (2013.01); *A61B 5/412* (2013.01); *A61B 5/4566* (2013.01);
(Continued)

(58) Field of Classification Search
CPC .... A61B 5/055; A61B 5/412; G01R 33/4828; G01R 33/483; G01R 33/485; G01R 33/46; G01R 33/5608
See application file for complete search history.

(56) References Cited

U.S. PATENT DOCUMENTS

| 4,983,920 A | 1/1991 | Lampman et al. |
| 5,068,098 A | 11/1991 | Schweighardt et al. |

(Continued)

FOREIGN PATENT DOCUMENTS

| JP | S63-204143 | 8/1988 |
| JP | H05-509162 | 12/1993 |

(Continued)

OTHER PUBLICATIONS

Chen, Z., Zheng, Y., Yuan, Y., Jiao, Y., Xiao, J., Zhou, Z., & Cao, P. (2016). Modic changes and disc degeneration caused by inoculation of Propionibacterium acnes inside intervertebral discs of rabbits: a pilot study. BioMed Research International, 2016. (Year: 2016).*

(Continued)

*Primary Examiner* — Carolyn A Pehlke
*Assistant Examiner* — Johnathan Maynard
(74) *Attorney, Agent, or Firm* — Knobbe, Martens, Olson & Bear, LLP

(57) ABSTRACT

An MR Spectroscopy (MRS) system and approach is provided for measuring spectral information corresponding with propionic acid (PA), either alone or in combination with other measurements corresponding with other chemicals, to
(Continued)

diagnose and/or monitor at least one of bacterial infection, such as associated with *P. acnes*, or conditions related thereto such as nociceptive pain associated with tissue acidity. An interfacing DDD-MRS signal processor receives output signals to produce a post-processed spectrum, with spectral regions corresponding with certain chemicals, including PA, then measured as biomarkers. A diagnostic processor derives a diagnostic value for each disc, and performs certain normalizations, based upon ratios of the spectral regions related to chemicals implicated in degenerative painful tissue pathology, such as PA and hypoxia markers of lactic acid (LA) and alanine (AL), and structural chemicals of proteoglycan (PG) and collagen or carbohydrate (CA).

25 Claims, 81 Drawing Sheets

Related U.S. Application Data

(60) Provisional application No. 62/351,963, filed on Jun. 19, 2016.

(51) Int. Cl.
```
G01R 33/48    (2006.01)
G01R 33/46    (2006.01)
G01R 33/485   (2006.01)
A61B 5/055    (2006.01)
G01R 33/56    (2006.01)
G01R 33/483   (2006.01)
```

(52) U.S. Cl.
CPC .......... *G01R 33/46* (2013.01); *G01R 33/465* (2013.01); *G01R 33/483* (2013.01); *G01R 33/485* (2013.01); *G01R 33/4828* (2013.01); *G01R 33/5608* (2013.01)

(56) References Cited

U.S. PATENT DOCUMENTS

| | | | |
|---|---|---|---|
| 5,190,039 | A | 3/1993 | Takeuchi |
| 5,201,311 | A | 4/1993 | Bottomley et al. |
| 5,207,715 | A | 5/1993 | Fossel |
| 5,270,651 | A | 12/1993 | Wehrli |
| 5,617,861 | A | 4/1997 | Ross et al. |
| 5,844,097 | A | 12/1998 | Cameron, Sr. et al. |
| 5,903,149 | A | 5/1999 | Gonen et al. |
| 6,018,675 | A | 1/2000 | Apkarian et al. |
| 6,069,478 | A | 5/2000 | Hurd |
| 6,278,891 | B1 | 8/2001 | Reiderman et al. |
| 6,418,335 | B2 | 7/2002 | Avrin |
| 6,472,871 | B1 | 10/2002 | Ryner |
| 6,552,541 | B2 | 4/2003 | Nauerth |
| 6,617,169 | B2 | 9/2003 | Ke et al. |
| 6,639,405 | B2 | 10/2003 | Liu et al. |
| 6,674,282 | B2 | 1/2004 | Pines et al. |
| 6,683,455 | B2 | 1/2004 | Ebbels et al. |
| 6,686,348 | B2 | 2/2004 | De Nanteuil et al. |
| 6,795,567 | B1 | 9/2004 | Cham et al. |
| 6,835,572 | B1 | 12/2004 | Mountford et al. |
| 6,836,114 | B2 | 12/2004 | Reddy et al. |
| 6,943,033 | B2 | 9/2005 | Van Zijl et al. |
| 6,987,997 | B1 | 1/2006 | Hurd et al. |
| 7,027,054 | B1 | 4/2006 | Cheiky et al. |
| 7,042,214 | B2 | 5/2006 | Cunningham et al. |
| 7,050,618 | B2 | 5/2006 | Belykh et al. |
| 7,116,104 | B2 | 10/2006 | Reddy et al. |
| 7,123,009 | B1 | 10/2006 | Scott |
| 7,181,348 | B2 | 2/2007 | Wishart et al. |
| 7,184,813 | B1 | 2/2007 | Hurd et al. |
| 7,288,521 | B2 | 10/2007 | Franco |
| 7,319,784 | B2 | 1/2008 | Ryner et al. |
| 7,323,871 | B2 | 1/2008 | Foo |
| 7,352,474 | B2 | 4/2008 | Bachim et al. |
| 7,411,396 | B1 | 8/2008 | Schirmer et al. |
| 7,499,745 | B2 | 3/2009 | Littrup |
| 7,514,074 | B2 | 4/2009 | Pittenger et al. |
| 7,676,254 | B2 | 3/2010 | Siddall et al. |
| 7,705,596 | B2 | 4/2010 | Witschey et al. |
| 7,741,844 | B2 | 6/2010 | Hancu et al. |
| 7,749,275 | B2 | 7/2010 | Lambrecht et al. |
| 7,916,909 | B2 | 3/2011 | Khazen et al. |
| 7,940,264 | B2 | 5/2011 | Jojic et al. |
| 8,018,570 | B2 | 9/2011 | Kameyama |
| 8,076,936 | B2 | 12/2011 | Borthakur et al. |
| 8,208,709 | B2 | 6/2012 | Ding et al. |
| 8,263,043 | B2 | 9/2012 | Ahrens et al. |
| 8,344,728 | B2 | 1/2013 | Majumdar et al. |
| 8,405,836 | B2 | 3/2013 | Yablon |
| 8,478,380 | B2 | 7/2013 | Soher |
| 8,553,037 | B2 | 10/2013 | Smith et al. |
| 8,569,482 | B2 | 10/2013 | Yamakawa et al. |
| 8,569,485 | B2 | 10/2013 | Kuppusamy et al. |
| 8,609,334 | B2 | 12/2013 | Buser et al. |
| 8,615,285 | B2 | 12/2013 | Ehman |
| 8,668,647 | B2 | 3/2014 | Eskandari |
| 8,690,057 | B2 | 4/2014 | Schoening et al. |
| 8,761,860 | B2 | 6/2014 | Peacock, III et al. |
| 8,798,351 | B2 | 8/2014 | Ding et al. |
| 8,825,131 | B2 | 9/2014 | Peacock, III et al. |
| 8,838,201 | B2 | 9/2014 | Mori et al. |
| 8,965,094 | B2 | 2/2015 | Peacock, III et al. |
| 9,161,735 | B2 | 10/2015 | Bradford et al. |
| 9,280,718 | B2 | 3/2016 | Claude et al. |
| 9,345,421 | B2 | 5/2016 | Peacock, III et al. |
| 9,392,959 | B2 | 7/2016 | Peacock, III et al. |
| 9,724,013 | B2 | 8/2017 | Peacock, III et al. |
| 9,808,177 | B2 | 11/2017 | Claude et al. |
| 9,901,285 | B2 | 2/2018 | Majumdar et al. |
| 10,045,711 | B2 | 8/2018 | Peacock, III et al. |
| 10,123,759 | B2 | 11/2018 | Bradford et al. |
| 10,251,578 | B2 | 4/2019 | Peacock, III et al. |
| 10,285,622 | B2 | 5/2019 | Peacock, III et al. |
| 2001/0003423 | A1 | 6/2001 | Wald |
| 2002/0037251 | A1 | 3/2002 | Driehuys |
| 2004/0006376 | A1 | 1/2004 | Falci |
| 2004/0214348 | A1 | 10/2004 | Nicholson et al. |
| 2005/0024051 | A1 | 3/2005 | Doddrell et al. |
| 2005/0054910 | A1 | 3/2005 | Tremblay et al. |
| 2005/0240104 | A1 | 10/2005 | Shim et al. |
| 2005/0251025 | A1 | 11/2005 | Hancu et al. |
| 2007/0167729 | A1 | 7/2007 | Mistretta et al. |
| 2007/0249928 | A1 | 10/2007 | Blezek et al. |
| 2007/0253910 | A1 | 11/2007 | Ahrens et al. |
| 2008/0039710 | A1* | 2/2008 | Majumdar ............. G01R 33/54 600/410 |
| 2008/0220530 | A1 | 9/2008 | Bahn et al. |
| 2008/0226148 | A1 | 9/2008 | Gu et al. |
| 2009/0076481 | A1 | 3/2009 | Stegmann et al. |
| 2009/0134869 | A1 | 5/2009 | Lee |
| 2009/0191131 | A1 | 7/2009 | Fossheim et al. |
| 2009/0232378 | A1 | 9/2009 | Nakamura |
| 2009/0261823 | A1 | 10/2009 | Yu et al. |
| 2010/0086185 | A1 | 4/2010 | Weiss |
| 2010/0121210 | A1 | 5/2010 | Lindner |
| 2010/0136588 | A1 | 6/2010 | Colgin |
| 2010/0166278 | A1 | 7/2010 | Witschey |
| 2010/0244834 | A1 | 9/2010 | Mori et al. |
| 2010/0264920 | A1 | 10/2010 | Witschey et al. |
| 2010/0268225 | A1 | 10/2010 | Coe et al. |
| 2011/0230755 | A1 | 9/2011 | MacFarlane et al. |
| 2011/0286630 | A1 | 11/2011 | Harder |
| 2012/0155731 | A1 | 6/2012 | Weersink et al. |
| 2013/0053658 | A1* | 2/2013 | Peacock ............... A61B 5/4566 600/309 |
| 2013/0144155 | A1* | 6/2013 | Majumdar ............. G01R 33/44 600/410 |
| 2014/0119631 | A1 | 5/2014 | Mostafavi |
| 2014/0194364 | A1 | 7/2014 | Buser et al. |
| 2015/0119688 | A1 | 4/2015 | Peacock, III et al. |

(56) References Cited

U.S. PATENT DOCUMENTS

| | | |
|---|---|---|
| 2017/0035844 A1 | 2/2017 | Buser et al. |
| 2017/0105650 A1 | 4/2017 | Peacock, III et al. |
| 2018/0192910 A1 | 7/2018 | Claude et al. |
| 2018/0317802 A1 | 11/2018 | Majumdar et al. |
| 2019/0175051 A1 | 6/2019 | Peacock, III et al. |
| 2019/0216418 A1 | 7/2019 | Bradford et al. |
| 2020/0100698 A1 | 4/2020 | Peacock, III et al. |

FOREIGN PATENT DOCUMENTS

| | | |
|---|---|---|
| JP | H06-503418 | 4/1994 |
| JP | 2003524490 | 8/2003 |
| JP | 2004526130 | 8/2004 |
| JP | 2004528559 | 9/2004 |
| KR | 10-2011-0100046 | 9/2011 |
| WO | WO 2006-081471 | 8/2006 |
| WO | WO 2007-035906 | 3/2007 |
| WO | WO 2009-058915 | 5/2009 |
| WO | WO 2009-148550 | 12/2009 |
| WO | WO 2010/052629 | 5/2010 |
| WO | WO 2011-047197 | 4/2011 |
| WO | WO 2011-060237 | 5/2011 |
| WO | WO 2011-146798 | 11/2011 |
| WO | WO 2012-071566 | 5/2012 |

OTHER PUBLICATIONS

Munshi, S. U., Rewari, B. B., Bhavesh, N. S., & Jameel, S. (2013). Nuclear magnetic resonance based profiling of biofluids reveals metabolic dysregulation in HIV-infected persons and those on anti-retroviral therapy. PLoS One, 8(5), e64298. (Year: 2013).*
Keshari, K. R., Lotz, J. C., Link, T. M., Hu, S., Majumdar, S., & Kurhanewicz, J. (2008). Lactic acid and proteoglycans as metabolic markers for discogenic back pain. Spine, 33(3), 312-317. (Year: 2008).*
Keshari, K. R., Zektzer, A. S., Swanson, M. G., Majumdar, S., Lotz, J. C., & Kurhanewicz, J. (2005). Characterization of intervertebral disc degeneration by high-resolution magic angle spinning (HR-MAS) spectroscopy. Magnetic Resonance in Medicine. (Year: 2005).*
Keshari, K. R., Lotz, J. C., Kurhanewicz, J., & Majumdar, S. (2005). Correlation of HR-MAS spectroscopy derived metabolite concentrations with collagen and proteoglycan levels and Thompson grade in the degenerative disc. Spine, 30(23), 2683-2688. (Year: 2005).*
Dudli, S., Liebenberg, E., Magnitsky, S., Miller, S., Demir-Deviren, S., & Lotz, J. C. (2016). Propionibacterium acnes infected intervertebral discs cause vertebral bone marrow lesions consistent with Modic changes. Journal of orthopaedic research, 34(8), 1447-1455. (Year: 2016).*
Rollason, J., McDowell, A., Albert, H. B., Barnard, E., Worthington, T., Hilton, A. C., . . . & Lambert, P. (2013). Genotypic and antimicrobial characterisation of Propionibacterium acnes isolates from surgically excised lumbar disc herniations. BioMed Research International, 2013. (Year: 2013).*
Dudli, S., Fields, A. J., Samartzis, D., Karppinen, J., & Lotz, J. C. (2016). Pathobiology of Modic changes. European Spine Journal, 25(11), 3723-3734. (Year: 2016).*
U.S. Appl. No. 16/869,182 Including its prosecution history, filed Jul. 5, 2020, Peacock III et al.
U.S. Appl. No. 16/729,222 Including its prosecution history, filed Dec. 27, 2019, Claude et al.
U.S. Appl. No. 16/840,136 Including its prosecution history, filed Mar. 4, 2020, Bradford, et al.
Blumenkrantz et al., "A feasibility study of in vivo T1rho imaging of the intervertebral disc," Magnetic Resonance Imaging (24)8, 1001-1007, Oct. 2006.
U.S. Appl. No. 16/376,879 Including its prosecutionhistory, filed May 4, 2019, Peacock III et al.
U.S. Appl. No. 16/408,188 Including its prosecution history, filed May 9, 2019, Peacock III et al.

Bartels, E.M., J.C. Fairbank, et al. (1998) "Oxygen and lactate concentrations measured in vivo in the intervertebral discs of patients with scoliosis and back pain." Spine 23 (1): 1-7; discussion 8.
Bottomley PA. "Spatial localization in NMR spectroscopy in vivo." Ann N Y Acad Sci 1987; 508:333-348.
Brown TR, Kincaid BM, Ugurbil K. "NMR chemical shift imaging in three dimensions." Proc. Natl. Acad. Sci. USA 1982; 79:3523-3526.
Brown, M.F., M.V. Hukkanen, et al. (1997). "Sensory and sympathetic innervation of the vertebral endplate in patients with degenerative disc disease." J Bone Joint Surg Br 79(1):147-53.
Buenaventura, R.M., R.V. Shah, et al. (2007). "Systematic review of discography as a diagnostic test for spinal pain: an update." Pain Physician 10(1): 147-64.
Carragee et al., "2009 ISSLS Prize Winner: Does Discography Cause Accelerated Progression of Degeneration Changes in the Lumbar Disc," SPINE vol. 34, No. 21, pp. 2338-2345, 2009.
Carragee, E. J., T. Lincoln, et al. (2006). "A gold standard evaluation of the "discogenic pain" diagnosis and determined by provocative discography." Spine 31(18): 2115-23.
Carragee, E.J. and T.F. Alamin (2001). "Discography, a review." Spine J 1(5): 364-72.
Carragee, E.J., T.F. Alamin, et al. (2006). "Low-pressure positive Discography in subjects asymptomatic of significant low back pain illness." Spine 31 (5): 505-9.
Cohen, S.P., T.M. Larkin, et al. (2005). "Lumbar discography: a comprehensive review of outcome studies, diagnostic accuracy, and principles." Reg Anesth Pain Med 30(2): 163-83.
Coppes, M.H., E. Marani, et al. (1997). "Innervation of "painful" lumbar discs." Spine 22(20): 2342-49.
Cunningham CH, Vigneron DB, Chen AP, Xu D, Hurd RE, Sailasuta N, Pauly JM. "Design of symmetric-sweep spectral-spatial RF pulses for spectral editing." Magn Reson Med 2004; 52: 147-153.
Derby, R., R.M. Baker, et al. (2008). "Analgesic Discography: Can Analgesic Testing Identify a Painful Disc?" SpineLine (Nov.-Dec.): 17-24.
Diamant, B., J. Karlsson, et al. (1968). "Correlation between lactate levels and pH in discs of patients with lumbar rhizopathies." Experientia 24(12): 1195-6.
Jiru, F., "Introduction to Post-Processing Techniques," Europeant Journal of Radialogy 67, (2008) 202-217.
Frahm J, Bruhn H, Gyngell ML, Merboldt KD, Hanicke W, Sauter R. "Localized high-resolution proton NMR spectroscopy using stimulated echoes: initial applications to human brain in vivo." Magn Reson Med 1989; 9:79-93.
Freemont, A.J., A. Watkins, et al. (2002). "Nerve growth factor expression and innervation of the painful intervertebral disc." J Pathol 197(3): 286-92.
Freemont, A.J., T.E. Peacock, et al. (1997). "Nerve ingrowth into diseased intervertebral disc in chronic back pain." Lancet 350(9072): 178-81.
Grunhagen, T., G. Wilde, et al. (2006). "Nutrient supply and intervertebral disc metabolism." J Bone Joint Surg Am 88 Suppl 2: 30-5.
Guyer, R.D. and D.D. Ohnmeiss (2003). "Lumbar discography." Spine J 3(3 Suppl): 11S-27S.
Immke, D. C. and E.W. McCleskey (2001). "Lactate enhances the acid-sensing Na+ channel on ischemia-sensing neurons." Nat Neurosci 4(9): 869-70.
Ishihara, H. and J.P. Urban (1999). "Effects of low oxygen concentrations and metabolic inhibitors on proteoglycan and protein synthesis rates in the intervertebral disc." J Orthop Res 17(6): 829-35.
Jain, A., S.M Brady-Kalnay, et al. (2004). "Modulation of Rho GTPase activity alleviates chondroitin sulfate proteoglycan-dependent inhibition of neurite extension." J Neurosci Res 77(2): 299-307.
Jones, L.L., D. Sajed, et al. (2003). "Axonal regeneration through regions of chondroitin sulfate proteoglycan deposition after spinal cord injury: a balance of permissiveness and inhibition." J Neurosci 23(28): 9276-88.

(56) References Cited

OTHER PUBLICATIONS

Keshari, K. R., A. S. Zektzer, et al. (2005). "Characterization of intervertebral disc degeneration by high-resolution magic angle spinning (HR-MAS) spectroscopy." Magn Reson Med 53(3): 519-27.

Keshari, K.R., J.C. Lotz, et al. (Dec. 1, 2005). "Correlation of HR-MAS spectroscopy derived metabolite concentrations with collagen and proteoglycan levels and Thompson grade in the degenerative disc." Spine 30(23): 2683-88.

Keshari, K.R., J.C. Lotz, et al. (2008). "Lactic acid and proteoglycans as metabolic markers for discogenic back pain." Spine 33(3): 312-317.

Klapka, N. and H. W. Muller (2006). "Collagen matrix in spinal cord injury." J Neurotrauma 23(3-4): 422-35.

Molliver, D. C., D. C. Immke, et al. (2005). "ASIC3, an acid-sensing ion channel, is expressed in metaboreceptive sensory neurons." Mol Pain 1: 35.

Nachemson, A. (1969). "Intradiscal measurements of pH in patients with lumbar rhizopathies." Acta Orthop Scand 40(1): 23-42.

Naves, L. A. and E. W. McCleskey (2005). "An acid-sensing ion channel that detects ischemic pain." Braz J Med Biol Res 38(11): 1561-9.

O'Neill, C. and M. Kurgansky (2004). "Subgroups of positive discs on discography." Spine 29(19): 2134-9.

Pauly J, Le Roux P, Nishimura D, Macovski A. "Parameter relations for the Shinnar-Le Roux selective excitation pulse design algorithm [NMR imaging]." IEEE Trans Med Imaging 1991; 10: 53-65.

Properzi, F., R. A. Asher, et al. (2003). "Chondroitin sulphate proteoglycans in the central nervous system: changes and synthesis after injury." Biochem Soc Trans 31(2): 335-6.

Roberts, S., H. Evans, et al. (2006). "Histology and pathology of the human intervertebral disc." J Bone Joint Surg Am 88 Suppl 2: 10-14.

Roughley, P. J., M. Alini, et al. (2002). "The role of proteoglycans in aging, degeneration and repair of the intervertebral disc." Biochem Soc Trans 30(Pt 6): 869-74.

Rukwied, R., B. A. Chizh, et al. (2007). "Potentiation of nociceptive responses to low pH injections in humans by prostaglandin E2." J Pain 8(5): 443-51.

Scuderi, G. J., G. V. Brusovanik, et al. (2008). "A critical evaluation of discography in patients with lumbar intervertebral disc disease." Spine J 8(4): 624-9.

Star-Lack J, Nelson SJ, Kurhanewicz J, Huang LR, Vigneron DB. "Improved water and lipid suppression for 3D PRESS CSI using RF bank selective inversion with gradient dephasing (BASING)." Magn Reson Med 1997; 38: 311-321.

Sutherland, S. P., C. J. Benson, et al. (2001). "Acid-sensing ion channel 3 matches the acid-gated current in cardiac ischemia-sensing neurons." Proc Natl Acad Sci U S A 98(2): 711-6.

Urban, J. P., S. Smith, et al. (2004). "Nutrition of the intervertebral disc." Spine 29(23): 2700-9.

Wichman, H. J. (2007). "Discography: over 50 years of controversy." Wmj 106(1): 27-9.

Wolfer, L. R., R. Derby, et al. (2008). "Systematic review of lumbar provocation discography in asymptomatic subjects with a meta-analysis of false-positive rates." Pain Physician 11(4): 513-38.

Mari Garseth et al. "Metabolic changes in the cerebrospinal fluid of patients with lumbar disc herniation or spinal stenosis." Journal of Neuroscience Research, vol. 69, No. 5, Sep. 1, 2002, pp. 692-695.

Henning A. et al. "Spinal cord MRS in and beyond the cerival spine", Proceedings of the International Society for Magnetic Resonance in Medicine, May 6, 2006, p. 889.

Zuo, J., D. Neubauer, et al. (1998). "Degradation of chondroitin sulfate proteoglycan enhances the neurite-promoting potential of spinal cord tissue." Exp Neurol 154(2): 654-62.

Zuo, J., Y. J. Hernandez, et al. (1998). "Chondroitin sulfate proteoglycan with neurite-inhibiting activity is up-regulated following peripheral nerve injury." J Neurobiol 34(1): 41-54.

Zuo, J., et al. "MR Spectroscopy in intervertebral disc and correlation with biochemical analysis." Proceedings of the International Society for Magnetic Resonance in Medicine, Apr. 18, 2009, p. 2002.

Zuo, J. et al. "Quantification of relaxation times of metabolite resonance in intervertebral disc using MR Spectroscopy", Proceedings of the International Society for Magnetic Resonance in Medicine, Apr. 18, 2009, p. 2001.

Haro, H. et al. "Matrix metalloproteinase-7-dependent release of tumor necrosis factor in a model of herniated disc resorption," Jour. of Clinical Inv., vol. 105, No. 2, Jan. 2000, pp. 143-150.

Mow, V.C. et al. "Basic Orthopaedic Biomechanics—Chapter 10—Bomechanics of the Human Spine," 1997, pp. 353-393.

Thompson, J. et al. "Preliminary Evaluation of a Scheme for Grading the Gross Morphology of the Human Intervertebral Disc," Spine, vol. 15, 1990, pp. 411-415.

Iatridis, J. et al. "Alterations in the Mechanical Behavior of the Human Lumbar Nucleas Pulposus with Degeneration and Aging," Jour. of Ortho Research, vol. 15, 1997, pp. 318-322.

Beall, et al. "NMR Data Handbook for Biomedical Applications," New York, Pergamon Press, 1984, 11 pages.

Boos, N. et al.—Quantitative Magnetic Resonance Imaging of the Lumbar Spine, Spine, vol. 20, No. 21, pp. 2358-2366.

Bottomley, P. et al. "A review of normal tissue hydrogen NMR relaxation times and relaxation mechanisms from 1-100 MHz: Dependence on tissue type, NMR frequency, temperature, species, excision and age," Med. Phys., vol. 11, No. 4, Jul./Aug. 1984, pp. 425-448.

Lyons, G. et al. "Biochemical Changes in Intervertebral Disc Degeneration," Biochimica Biophys Acta, vol. 673, 1981, pp. 443-453.

Maroudas, A.—"The Biology of the Intervertebral Disc"—In: Ghosh, P. el. The Biology of the Intervertebral Disc, vol. II, Chapter 9, 1988.

Pearce, R. et al.—"Degeneration and the Chemical Composition of the Human Lumbar Intervertebral Disc"—Jour. of Ortho. Research, vol. 5, 1987, pp. 198-205.

Tertti, M. et al.—"Disc Degeneration in Magnetic Resonance Imaging: A Comparative Biochemical, Histologic, and Radiologic Study in Cadaver Spines"—Spine, 1991, pp. 629-634.

Chiu, E. et al.—"Magnetic Resonance Imaging Measurement of Relaxation and Water Diffusion in the Human Lumbar Intervertebral Disc Under Compression in Vitro"—Spine, vol. 26, No. 19, 2001, pp. E437-E444.

Gundry, C. et al.—"Magnetic Resonance Imaging of the Musculoskeletal System, Part 8. The Spine, Section 1", Clinical Ortho, and Related Research, vol. 338, May 1997, pp. 275-287.

Gunzburg, R. et al.—"A Cadaveric Study Comparing Discography, Magnetic Resonance Imaging, Histology, and Mechanical Behavior of the Human Lumbar Disc"—Spine, 1991, pp. 417-426.

Modic, M. et al.—"Magnetic Resonance Imaging of Intervertebral Disk Disease"—Radiology, vol. 152, 1984, pp. 103-111.

Modic, M. et al.—"Lumbar Herniated Disk Disease and Canal Stenosis: Prospective Evaluation by Surface Coil MR, CT, and Myelography"—AJR, vol. 147, Oct. 1986, pp. 757-765.

Modic, M. et al.—"Imaging of Degenerative Disk Disease"—Radiology, vol. 168, 1988, pp. 177-186.

Sether, L. et al.—"Intervertebral Disk: Normal Age-related Changes in MR Signal Intensity"—Radiology, vol. 177, 1990, pp. 385-388.

Pfirrmann, C. et al.—"Magnetic Resonance Classification of Lumbar Intervertebral Disc Degeneration"—Spine, vol. 26, No. 17, pp. 1873-1878.

Nieminen, M. et al.—"Spatial Assessment of Articular Cartilage Proteoglycans with Gd-DTPA-Enhanced T1 Imaging"—Mag. Res, in Med., vol. 48, 2002, pp. 640-648.

Mosher, T. et al.—"Human Articular Cartilage: Influence of Aging and Early Symptomatic Degeneration on the Spatial Variation of T2-Preliminary Findings at 3 TI"—Radiology, vol. 214, 2000, pp. 259-266.

Burstein, D. et al.—"Diffusion of Small Solutes in Cartilage as Measured by Nuclear Magnetic Resonance (NMR) Spectroscopy and Imaging"—Jour. of Ortho. Res., vol. 11, 1993, pp. 465-478.

(56) References Cited

OTHER PUBLICATIONS

Abdulkarim, J. et al.—"Magnetic Resonance Imaging of the Cervical Spine: Frequency of Degenerative Changes in the Intervertebral Disc With Relation to Age"—Clinical Radiology, vol. 58, 2003, pp. 980-984.
Swanson, M. et al.—"Proton HR-MAS Spectroscopy and Quantitative Pathologic Analysis of MRI/3D-MRSI-Targeted Postsurgical Prostate Tissues"—Mag. Resonance in Med., vol. 54, 2003, pp. 944-954.
Schiller, J., et al. "H and C-13 HR-MAS NMR Investigations on Native and Enzymatically Digested Bovine Nasal Certilage." Magnetic Resonance Materials in Physics 2001; 13:19-27.
Carr, H. et al.—"Effects of Diffusion on Free Precession in Nuclear Magnetic Resonance Experiments"—Phys. Review, vol. 94, No. 3, May 1, 1954, pp. 630-638.
Kupce, E.—"Applications of Adiabatic Pulses in Biomolecular Nuclear Magnetic Resonance"—Methods in Enzymology, vol. 338, 2001, pp. 82-111.
Mucci, A. et al.—"1 Hand 13C nuclear magnetic resonance identification and characterization of components of chondroitin sulfates of various origin"—Carbohydrate Polymers, vol. 41, 2003, pp. 37-45.
Groupille, P. et al.—"Matrix Metalloproteinases: The Clue to Intervertebral Disc Degeneration?"—Spine, vol. 23, No. 14, Jul. 1998, pp. 1612-1626.
Kang, J. et al.—"Towards a Biochemical Understanding of Human Intervertebral Disc Degeneration and Herniation: Contributions of Nitric Oxide, Interleukins, Prostaglandin E2, and Matrix Metalloproteinases"—spine, vol. 22, No. 10, May 15, 1997, pp. 1065-1073.
Weiler, C. et al.—"2002 SSE Award Competition in Basic Science: Expression of major matrix metalloproteinases is associated with intervertebral disc degradation and resorption"—Eur. Spine Jour., vol. 11, 2002, pp. 308-320.
Urban, J. et al.—"The Nucleus of the Intervertebral Disc from Development to Degeneration"—American Zoologist, vol. 40, No. 1, Feb. 2000, pp. 53-61.
Weidenbaum, M. et al.—"Correlating Magnetic Resonance Imaging with the Biochemical Content of the Normal Human Intervertebral Disc"—Jour. of Ortho. Research, vol. 10, 1992, pp. 552-561.
Boos, N. et al.—"Quantitative MR Imaging of Lumbar Intervertebral Disks and Vertebral Bodies: Influence of Diurnal Water Content Variations"—Radiology, vol. 188, 1993, pp. 351-354.
Boos, N. et al.—"Quantitative MR Imaging of Lumbar Intervertebral Discs and Vertebral Bodies: Methodology, Reproducibility, and Preliminary Results"—Mag. Res. Imaging, vol. 12, No. 4, 1994, pp. 577-587.
Keshari, K et al.—Poster and Abstract—"Identification of Chondroitin Sulfate as a Marker for Human Intervertebral disc Degeneration Using Proton High Resolution Magic Angle Spinning *HR-MAS) Spectroscopy"—The 44th ENC, Mar. 30-Apr. 4, 2003, 22 pages.
Majumdar, S.—Abstract—"Spectroscopic Markers of Disc Degeneration."—downloaded from CRISP website Nov. 23, 2004, 2 pages.
Petrantonaki, M., et al. "MRI Techniques for the Examination of Trabecular Bone Structure." Current Medical Imaging Reviews 2005, 1:35-41.
Ford, J. C., et al. "In Vivo Quantitative Characterization of Trabecular Bone by NMR Interferometry and Localized Proton Spectroscopy." Magnetic Resonance in Medicine 1991; 17:543-551.
Schiller, J., et al. "Evaluation of Cartilage Composition and Degradation by High-Resolution Magic-Angle Spinning Nuclear Magnetic Resonance." Methods in Molecular Medicine 2004; 101:267-285.
Chung, C. T., et al. "Single photon emission computed tomography (SPECT) for low back pain induced by extension with no root sign." J. Chin. Med. Assoc, vol. 67, pp. 349-354 (2004).
Lusins, J. O., et al. "SPECT and lumbar MRI in back pain with emphasis on changes in end plates in association with disc degeneration (abstract)." J. Neuroimaging, vol. 8, No. 2, pp. 78-82 (1998).

McDonald, M., et al. "Use of computer tomography—single-photon emission computed tomography fusion for diagnosing painful facet arthropathy." Neurosurg. Focus, vol. 22, No. 1, E2 (2007).
Mulconrey, D. S., et al. "Interobserver reliability in the interpretation of diagnostic lumbar MRI and Nuclear imaging." The Spine Journal, vol. 6, pp. 177-184 (2006).
Keshari, K., et al. "Potential metabolic markers for intervertebral disc pain." Proc. Intl. Soc. Mag. Reson. Med. 14, p. 1710. May 9, 2006.
Savvopoulou, V., et al. "Degenerative Endplate Changes of the Lumbosacral Spine: Dynamic Contrast-Enhanced MRI Profiles Related to Age, Sex, and Spinal Level." Journal of Magnetic Resonance Imaging 33:382-389 (2011).
Hassler, O. "The Human Intervertebral Disc: A Micro-Angiographical Study on Its Vascular Supply at Various Ages." Acta Orthop. Scandinav. 40, 765-772, 1970.
Niinimaki, J., et al. "Association of lumbar artery narrowing, degenerative changes in disc and endplate and apparent diffusion in disc on postcontrast enhancement of lumbar intervertebral disc." Magn. Reson. Mater Phy. 22:101-109 (2009).
Rajasekaran, S., et al. "ISSLS Prize Winner: A Study of Diffusion in Human Lumbar Discs: A Serial Magnetic Resonance Imaging Study Documenting the Influence of the Endplate on Diffusion in Normal and Degenerate Discs." SPINE vol. 29, No. 23, pp. 2654-2667 (2004).
Liu, Y., et al. "Intervertebral Disk Degeneration Related to Reduced Vertebral Marrow Perfusion at Dynamic Contrast-Enhanced MRI." AJR:192: 974-979, Apr. 2009.
Bolan, Patrick J., et al., "Measurement and Correction of Repiration-Induced Bo Variations in Breast 1H MRS at 4 Tesla," Magnetic Resonance in Medicine 52:000-000 (2004).
Lorenz, C., et al. "3D Statistical Shape Models for Medical Image Segmentation," pp. 414-423, Second International Conference on 3-D Imaging and Modeling (3DIM '99), 1999.
Lin C S et al: "2D CSI proton MR spectroscopy of human spinal vertebra: feasibility studies.", Journal of Magnetic Resonance Imaging : JM RI Mar. 2000, vol. II, No. 3, Mar. 2000, pp. 287-293.
"Spectroscopy reconstruction" and "Spectroscopy processing" In: "Intera Spectroscopy—Instructions for Use", Jul. 2002 (Jul. 2002), Philips Medical Systems, Netherlands, pp. 6-1 to 7-6.
Dubey P. et al.: "Proton MR Spectroscopic Imaging of the Human Cervical Spine at 3 Tesla", Proceedings of the International Society for Magnetic Resonance in Medicine, 13th Meeting Proceedings, May 7, 2005 (May 7, 2005), p. 812.
Majumdar, "Review Article Magnetic resonance imaging and spectroscopy of the intervertebral disc," NMR in Biomed (2006) 19: 894-903.
Carragee et al., "Prospective Controlled Study of the Development of Lower Back Pain in Previously Asymptomatic Subjects Undergoing Experimental Discography." SPINE vol. 29, No. 10, pp. 1112-1117 (2004).
Carrino et al., "Prospective evaluation of contrast-enhanced MR imaging after uncomplicated lumbar discography." Skeletal Radiol (2007) 36:293-299.
Derincek et al., "Discography: can pain in a morphologically normal disc be due to an adjacent abnormal disc?" Arch Orthop Trauma Surg (2007) 127:699-703.
Boden et al., "Abnormal magnetic-resonance scans of the lumbar spine in asymptomatic subjects. A prospective investigation." The Journal of Bone & Joint Surgery (1990) 72:403-408.
Boos et al., "Natural History of Individuals With Asymptomatic Disc Abnormalities in Magnetic Resonance Imaging; Predictors of Low Back Pain-Related Medical Consultation and Work Incapacity." SPINE vol. 25, No. 12, pp. 1484-1492 (2000).
Borenstein et al., "The Value of Magnetic Resonance Imaging of the Lumbar Spine to Predict Low-Back Pain in Asymptomatic Subjects: A Seven-Year Follow-up Study." The Journal of Bone & Joint Surgery (2001) 83:1306-1311.
Carragee et al., "2004 Outstanding Paper Award: Nonoperative Science; Discographic, MRI and psychosocial determinants of low back pain disability and remission: a prospective study in subjects with benign persistent back pain." The Spine Journal 5 (2005) 24-35.

(56) References Cited

OTHER PUBLICATIONS

Cherkin et al., "Physician Variation in Diagnostic Testing for Low Back Pain." Arthritis & Rheumatism, vol. 37, Nubmer 1, Jan. 1994, pp. 15-22.
Freeborn et al., Primary Care Physicians' Use of Lumbar Spine Imaging Tests: Effects of Guidelines and Practice Pattern Feedback. JGIM, vol. 12, Oct. 1997, pp. 619-625.
Peng Z, "Automated Vertebra Detection and Segmentation from the Whole Spine MR Images," Proceedings of the 2005 IEEE Engineering in Medicine and Biology 27$^{th}$ Annual Conference, Shanghai, China, Sep. 1-4, 2005.
Wu M et al., "Quantitative comparison of AIR, SPM, and the fully deformable model for atlas-based segmentation of functional and structural MR images." Hum Brain Mapp. Sep. 2006; 27(9):747-54.
Liu J et al., "Rigid model-based 3D segmentation of the bones of joints in MR and CT images for motion analysis." Med Phys. Aug. 2008;35(8):3637-49.
Liu J et al., "Oriented active shape models." IEEE Trans Med Imaging. Apr. 2009; 28(4):571-84.
Chevrefils C et al., "Texture analysis for automatic segmentation of intervertebral disks of scoliotic spines from MR images." IEEE Trans Inf Technol Biomed. Jul. 2009; 13(4):608-20.
Huang SH et al., "Learning-based vertebra detection and iterative normalized-cut segmentation for spinal MRI." IEEE Trans Med Imaging. Oct. 2009; 28(10):1595-605.
Michopoulou SK et al., "Atlas-based segmentation of degenerated lumbar intervertebral discs from MR images of the spine." IEEE Trans Biomed Eng. Sep. 2009; 56(9):2225-31.
Kadoury S et al., "Personalized X-ray 3-D reconstruction of the scoliotic spine from hybrid statistical and image-based models." IEEE Trans Med Imaging. Sep. 2009; 28(9):1422-35.
Koh J et al., "Automatic segmentation of the spinal cord and the dural sac in lumbar MR images using gradient vector flow field." Conf Proc IEEE Eng Med Biol Soc. 2010; 2010:3117-20.
Hao S et al., "[Spine disc MR image analysis using improved independent component analysis based active appearance model and Markov random field]." Sheng Wu Yi Xue Gong Cheng Xue Za Zhi. Feb. 2010;27(1):6-9, 15.
Horsfield MA et al., "Rapid semi-automatic segmentation of the spinal cord from magnetic resonance images: application in multiple sclerosis." Neuroimage. Apr. 1, 2010; 50(2):446-55.
Bechara BP et al., "Application of a semiautomated contour segmentation tool to identify the intervertebral nucleus pulposus in MR images." AJNR Am J Neuroradiol. Oct. 2010; 31(9):1640-4.
Ben Ayed I et al., "Graph cuts with invariant object-interaction priors: application to intervertebral disc segmentation." Inf Process Med Imaging. 2011 ;22:221-32.
Dalca A et al., "Segmentation of nerve bundles and ganglia in spine MRI using particle filters." Med Image Comput Comput Assist Interv. 2011; 14(Pt 3):537-45.
Michopoulou S et. al., "Texture-based quantification of lumbar intervertebral disc degeneration from conventional T2-weighted MRI," Acta Radiologica 2011; 52: 91-98.
Neubert A, "Automated 3D Segmentation of Vertebral Bodies and Intervertebral Discs from MRI," 2011 International Conference on Digital Image Computing: Techniques and Applications.
Strickland CG et al., "Development of subject-specific geometric spine model through use of automated active contour segmentation and kinematic constraint-limited registration." J Digit Imaging. Oct. 2011; 24(5):926-42.
Giulietti G et al., "Semiautomated segmentation of the human spine based on echoplanar images," Magn Reson Imaging. Dec. 2011; 29(10):1429-36.
Stern D et al., "Parametric modelling and segmentation of vertebral bodies in 3D CT and MR spine images." Phys Med Biol. Dec. 7, 2011; 56(23):7505-22.
Neubert A et. al., "Automated detection, 3D segmentation and analysis of high resolution spine MR images using statistical shape models." Phys Med Biol. Dec. 21, 2012; 57(24):8357-76.
Egger J et al., "Square-cut: a segmentation algorithm on the basis of a rectangle shape." PLoS One. Dated Feb. 2012. 7(2).
Vrtovec T et al., "Automated curved planar reformation of 3D spine images." Phys Med Biol. Oct. 7, 2005; 50(19):4527-40.
Bandettini, Patricia et al., "MultiContrast Delayed Enhancement (MCODE) improves detection of subendocardial myocardial infarction by late gadolinium enhancement cardiovascular magnetic resonance: a clinical validation study", Journal of Cardiovascular Magnetic Resonance, vol. 14, No. I, Nov. 30, 2012 (Nov. 30, 2012).
Comments Regarding U.S. Appl. No. 12/579,371, filed Oct. 14, 2009 and PCT Patent Application No. PCT/US2010/052737 (Filed Oct. 14, 2010).
Vos T, Flaxman AD, Naghavi M, et al. Dec. 2012. Years lived with disability (YLDs) for 1160 sequelae of 289 diseases and injuries 1990-2010: a systematic analysis for the Global Burden of Disease Study 2010. Lancet 380(9859):2163-96.
Thompson KJ, Dagher AP, Eckel TS, et al. Mar. 2009. Modic changes on MR images as studied with provocative diskography: clinical relevance—a retrospective study of 2457 disks. Radiology 250(3):849-55.
Modic MT, Steinberg PM, Ross JS, et al. Jan. 1988. Degenerative disk disease: assessment of changes in vertebral body marrow with MR imaging. Radiology 166(1 Pt 1): 193-9.
Jensen TS, Karppinen J, Sorensen JS, et al. Sep. 12, 2008. Vertebral endplate signal changes (Modic change): a systematic literature review of prevalence and association with non-specific low back pain. Eur. Spine J. 17(11): 1407-22.
Jensen OK, Nielsen CV, Sorensen JS, Stengaard-Pedersen K. Nov. 1, 2014. Type 1 Modic changes was a significant risk factor for 1-year outcome in sick-listed low back pain patients: a nested cohort study using magnetic resonance imaging of the lumbar spine. Spine J. 14(11):2568-81.
Schistad El, Espeland A, Rygh LJ, et al. Jun. 26, 2014. The association between Modic changes and pain during 1-year follow-up in patients with lumbar radicular pain. Skeletal Radiol. 43(9):1271-9.
Järvinen J, Karppinen J, Niinimäki J, et al. Apr. 22, 2015. Association between changes in lumbar Modic changes and low back symptoms over a two-year period. BMC Musculoskelet. Disord. 16(1):98.
Albert HB, Lambert P, Rollason J, et al. Feb. 10, 2013. Does nuclear tissue infected with bacteria following disc herniations lead to Modic changes in the adjacent vertebrae? Eur. Spine J. 22(4):690-6.
Vowels BR, Yang S, Leyden JJ. Aug. 1995. Induction of proinflammatory cytokines by a soluble factor of Propionibacterium acnes: implications for chronic inflammatory acne. Infect. Immun. 63(8):3158-65.
McDowell A, Barnard E, Nagy I, et al. Jul. 2012. An expanded multilocus sequence typing scheme for propionibacterium acnes: investigation of "pathogenic", "commensal" and antibiotic resistant strains. PLoS One 7(7):e41480.
Valanne S, McDowell A, Ramage G, et al. May 2005. CAMP factor homologues in Propionibacterium acnes: A new protein family differentially expressed by types I and II. Microbiology 151(5):1369-1379.
Stirling A, Worthington T, Rafiq M, et al. Jun. 23, 2001. Association between sciatica and Propionibacterium acnes. Lancet 357(9273):2024-5.
Rollason J, McDowell A, Albert HB, et al. Aug. 2013. Genotypic and antimicrobial characterisation of Propionibacterium acnes isolates from surgically excised lumbar disc herniations. Biomed Res. Int. 2013:530382.
Albert HB, Sorensen JS, Christensen BS, Manniche C. Feb. 13, 2013. Antibiotic treatment in patients with chronic low back pain and vertebral bone edema (Modic type 1 changes): a double-blind randomized clinical controlled trial of efficacy. Eur. Spine J. 22(4):697-707.
Fritzell P, Bergstrom T, Welinder-Olsson C. May 8, 2004. Detection of bacterial DNA in painful degenerated spinal discs in patients without signs of clinical infection. Eur. Spine J. 13(8):702-6.
Wedderkopp N, Thomsen K, Manniche C, et al. Jul. 9, 2009. No evidence for presence of bacteria in modic type I changes. Acta Radiol. 50(1):65-70.

(56) References Cited

OTHER PUBLICATIONS

Arndt J, Charles YP, Koebel C, et al. Oct. 2012. Bacteriology of degenerated lumbar intervertebral disks. J. Spinal Disord. Tech. 25(7):E211-6.
Bhanji S, Williams B, Sheller B, et al. Jul.-Aug. 2002. Transient bacteremia induced by toothbrushing a companson of the Sonicare toothbrush with a conventional toothbrush. Pediatr. Dent. 24(4):295-9.
Urquhart DM, Zheng Y, Cheng AC, et al. Jan. 22, 2015. Could low grade bacterial infection contribute to low back pain? A systematic review. BMC Med. 13(1):13.
Weiner BK, Vilendecic M, Ledic D, et al. 2015. Published online Dec. 28, 2014. Endplate changes following discectomy: natural history and associations between imaging and clinical data. Eur. Spine J. 24(11):2449-57.
Kerttula L, Luoma K, Vehmas T, et al. Jan. 17, 2012. Modic type I change may predict rapid progressive, deforming disc degeneration: a prospective 1-year follow-up study. Eur. Spine J. 21 (6):1135-42.
Holm S, Baranto A, Kaigle Holm A, et al. 2007. Reactive changes in the adolescent porcine spine with disc degeneration due to endplate injury. Vet. Comp. Orthop. Traumatol. 20(1):12-7.
McDowell A, Valanne S, Ramage G, et al. Jan. 2005. Propionibacterium acnes types I and II represent phylogenetically distinct groups. J. Clin. Microbial. 43(1):326-34.
Nadkarni MA, Martin FE, Jacques NA, Hunter N. Jan. 2002. Determination of bacterial load by real-time PCR using a broad-range (universal) probe and primers set. Microbiology 148(1):257-266.
Mühl H, Kochem A-J, Disqué C, Sakka SG. Jan. 2010. Activity and DNA contamination of commercial polymerase chain reaction reagents for the universal 16S rDNA real-time polymerase chain reaction detection of bacterial pathogens in blood. Diagn. Microbial. Infect. Dis. 66(1):41-9.
Burke J, Watson R, McCormack D, et al. Feb. 21, 2003. Endplate changes are associated with increased disc inflammatory mediator production. J Bone Jt. Surg Br 85-B(Supp II): 164.
Klawitter M, Hakozaki M, Kobayashi H, et al. Jul. 5, 2014. Expression and regulation of toll-like receptors (TLRs) in human intervertebral disc cells. Eur. Spine J. 23(9):1878-91.
Quero L, Klawitter M, Schmaus A, et al. Aug. 22, 2013. Hyaluronic acid fragments enhance the inflammatory and catabolic response in human intervertebral disc cells through modulation of toll-like receptor 2 signaling pathways. Arthritis Res. Ther. 15(4):R94.
Ellman MB, Kim J-S, An HS, et al. Jun. 10, 2012. Toll-like receptor adaptor signaling molecule MyD88 on intervertebral disk homeostasis: In vitro, ex vivo studies. Gene 505(2):283-90.
Wang J, Tian Y, Phillips KLE, et al. Mar. 2013. Tumor necrosis factor α- and interleukin-1β-dependent induction of CCL3 expression by nucleus pulposus cells promotes macrophage migration through CCR1. Arthritis Rheum. 65(3):832-42.
Le Maitre CL, Hoyland JA, Freemont AJ. Aug. 9, 2007. Catabolic cytokine expression in degenerate and herniated human intervertebral discs: 1L-1β and TNFα expression profile. Arthritis Res. Ther. 9(4):R77.
Burke JG, G Watson RW, Conhyea D, et al. Dec. 2003. Human nucleus pulposis can respond to a pro-inflammatory stimulus. Spine (Phila. Pa. 1976). 28(24):2685-93.
Li B, Dong Z, Wu Y, et al. Jul. 2016. Association between Lumbar Disc degeneration and Propionibacterium Acnes Infection: Clinical Research and Preliminary Exploration of Animal Experiment. Spine (Phila. Pa. 1976). [Epub ahead of print].
Ferguson SJ, Ito K, Nolte LP. Feb. 2004. Fluid flow and convective transport of solutes within the intervertebral disc. J. Biomech. 37(2):213-21.
Mirantes C, Passegué E, Pietras EM. Aug. 19, 2014. Pro-inflammatory cytokines: Emerging players regulating HSC function in normal and diseased hematopoiesis. Exp. Cell Res. :1-7.

Dudli S, Sing D, Burch S, et al. Mar. 2, 2016. Molecular and Cellular Changes in Vertebral Bone Marrow Lesions. In: Annual Meeting American Academy of Orthopaedic Surgeons. Orlando; Paper 454.
Dudli S, Haschtmann D, Ferguson SJ. 2012. Published online Oct. 24, 2011. Fracture of the vertebral endplates, but not equienergetic impact load, promotes disc degeneration in vitro. J. Orthop. Res. 30(5):809-16.
Torkki M, Majuri M-L, Wolff H, et al. Mar. 27, 2015. Osteoclast activators are elevated in intervertebral disks with Modic changes among patients operated for herniated nucleus pulposus. Eur. Spine J. [Epub ahead of print].
Perilli E, Parkinson IH, Truong L-H, et al. Jul. 26, 2014. Modic (endplate) changes in the lumbar spine: bone micro-architecture and remodelling. Eur. Spine J. 24(9):1926-34.
Mackiewicz Z, Salo J, Konttinen YT, et al. Mar.-Apr. 2009. Receptor activator of nuclear factor kappa B ligand in an experimental intervertebral disc degeneration. Clin. Exp. Rheumatol. 27(2):299-306.
Laasonen LS, Karvonen SL, Reunala TL. May 1994. Bone disease in adolescents with acne fulminans and severe cystic acne: radiologic and scintigraphic findings. AJR. Am. J. Roentgenol. 162(5):1161-1165.
Ziegler P, Boettcher S, Takizawa H, et al. 2016. Published online Nov. 11, 2015. LPS-stimulated human bone marrow stroma cells support myeloid cell development and progenitor cell maintenance. Ann. Hematol. 95(2): 173-8.
Wan Y, Chong L-W, Evans RM. Dec. 2007. PPAR-gamma regulates osteoclastogenesis in mice. Nat. Med. 13(12):1496-503.
Piccinini AM, Midwood KS. Jul. 2010. DAMPening inflammation by modulating TLR signalling. Mediators Inflamm. 2010.
Oegema TR, Johnson SL, Aguiar DJ, Ogilvie JW. Nov. 2000. Fibronectin and its fragments increase with degeneration in the human intervertebral disc. Spine (Phila. Pa. 1976). 25(21):2742-7.
Patel KB, Poplawski MM, Pawha PS, et al. Aug. 2014. Diffusion-weighted MRI "claw sign" improves differentiation of infectious from degenerative modic type 1 signal changes of the spine. AJNR. Am. J. Neuroradiol. 35(8):1647-52.
Di Martino A, Merlini L, Faldini C. Aug. 30, 2013. Autoimmunity in intervertebral disc herniation: from bench to bedside. Expert Opin. Ther. Targets 17(12):1461-70.
Ulrich JA, Liebenberg EC, Thuillier DU, et al. Dec. 2007. ISSLS prize winner: repeated disc injury causes persistent inflammation. Spine (Phila. Pa. 1976). 32, 2812-9.
Bendix T, Sorensen JS, Henriksson GAC, et al. Sep. 15, 2012. Lumbar modic changes—a comparison between findings at low- and high-field magnetic resonance imaging. Spine (Phila. Pa. 1976). 37, 1756-62.
McDowell A, Perry AL, Lambert PA, er al. Feb. 2008. A new phylogenetic group of Propionibacterium acnes. J. Med. Microbial. 57, 218-24.
Sharif, H. S. Role of MR imaging in the management of spinal infections. Jun. 1992. AJR Am J Roentgenol 158, 1333-1345.
Bertok L. Apr. 2005. Natural immunity, First Edit. Elsevier Science; 291 p.
Inagawa H, Kohchi C, Soma G-1. Jul. 2011. Oral administration of lipopolysaccharides for the prevention of various diseases: benefit and usefulness. Anticancer Res. 31(7):2431-6.
Chen Z, Zheng Y, Yuan Y, et al. (Jan. 26, 2016) Modic Changes and Disc Degeneration Caused by Inoculation of Propionibacterium acnes inside Intervertebral Discs of Rabbits: A Pilot Study. Biomed Res Int 2016:9612437.
Zuo, Assessment of Intervertebral Disc Degeneration With Magnetic Resonance Single-Voxel Spectroscopy, Magnetic Resonance in Medicine, 62: 1140-1146 (Sep. 24, 2009).
Freemont, A J., The cellular pathobiology of the degenerate intervertebral disc and discogenic back pain, (2009) Rheumatology; 48:5-10. (Advanced access publication Oct. 14, 2008).
Dudli, S. et al. "Propionibacterium acnes infected intervertebral discs cause vertebral bone marrow lesions consistent with Modic changes." J. Orthop. Res. Aug. 2016. 34(8):1447-55.

(56) References Cited

OTHER PUBLICATIONS

Urban, Winlove, "Pathophysiology of the Intervertebral Disc and the Challenges for MRI." J. Magnetic Resonance Imaging. 25(2):419-32. Feb. 2007.

Gornet, Matthew et al., "Magentic Resonance Spectroscopy (MRS) can identify painful lumbar dics and may facilitate improved clinical outcomes of lumbar surgeries for discogenic pain", European Spine Journal, Jan. 4, 2019.

Magnitsky, Sergey et al., "Quantification of Propionic Acid in the Bovine Spinal Disk After Infection of the Tissue With Propionibacteria acnes Bacteria", Spine Journal, vol. 43, No. 11, pp. E634-E638, Jun. 2018.

"Solving Low Back Pain: If We Can't Measure It, We Can't Improve It," Jeffrey C. Lotz, PhD, presented on Nov. 10, 2015 at the International Philadelphia Spine Research Symposium.

International Search Report and Written Opinion dated Jul. 27, 2011 issued to international application No. PCT/US2010/052737.

International Search Report and Written Opinion dated Jul. 26, 2013 for international application No. PCT/US2013/036014.

International Search Report and Written Opinion dated Aug. 1, 2012 for PCT Application No. PCT/US2011/062137.

International Search Report and Written Opinion dated Sep. 25, 2014 for PCT Application No. PCT/US2014/022845.

International Search Report and Written Opinion dated Aug. 18, 2017 for PCT Application No. PCT/US2017/038034.

Cheng et al., "Quantitative neuropathology by high resolution magic angle spinning proton magnetic resonance spectroscopy." PNAS Jun. 10, 1997: 94(12) 6408-6413.

* cited by examiner

Using Pain='+' to be the positive level
Area Under Curve = 0.99121

| "Pre-Processed" Combined Channel Spectrum | Signal | Noise | SNR dB (Log₁₀(RMS)*10) |
|---|---|---|---|
| Range of Interest | 215-247 | 420-452 | |
| Sum of Squares Along the Range | 3717963 | 811206 | |
| Mean of Sum of Squares | 92949.08 | 20280.15 | |
| Root Mean Square | 304.8755 | 142.4084 | 6.611793 |

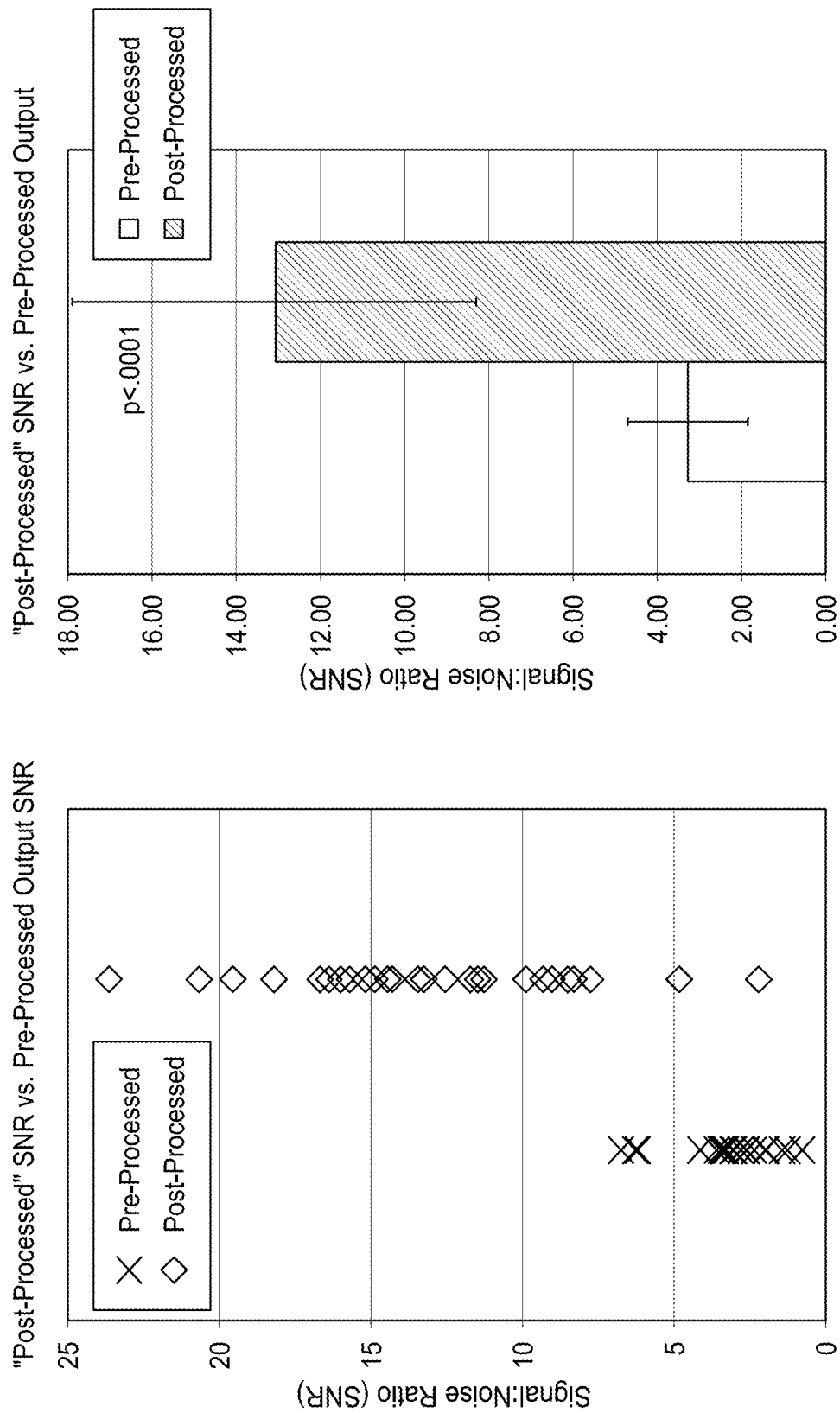

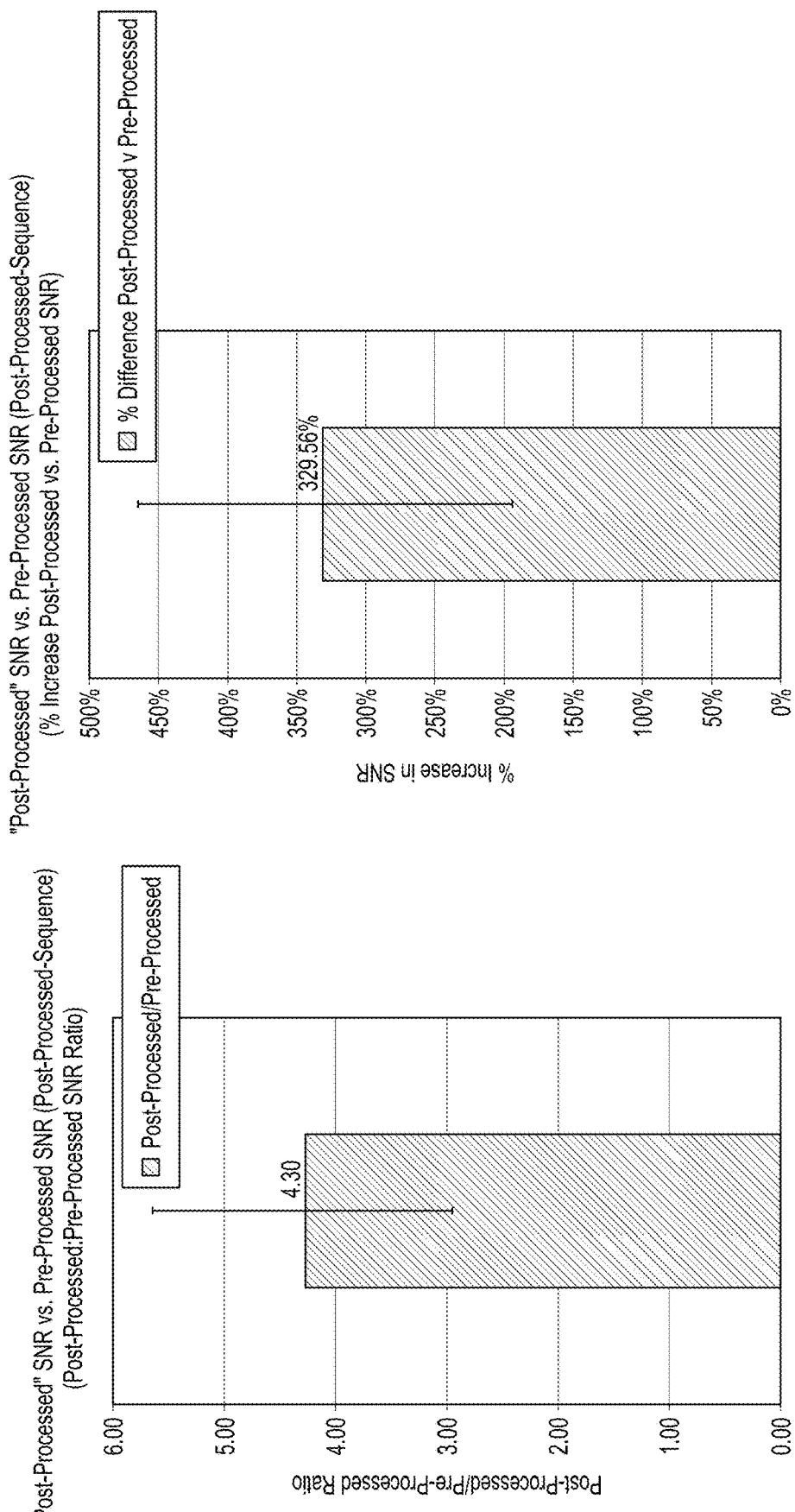

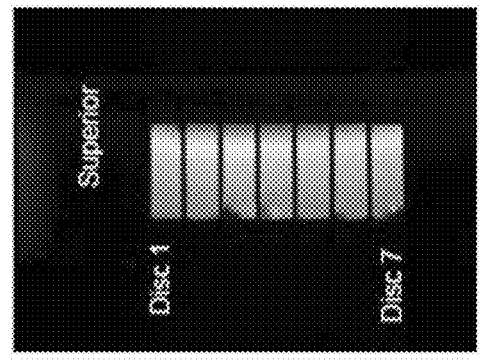
FIG. 40B
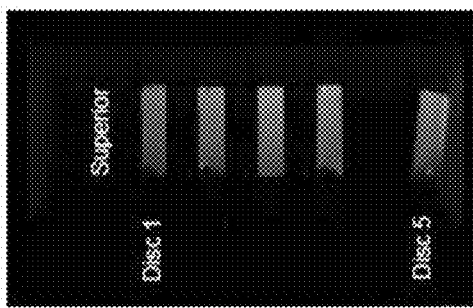
FIG. 40A
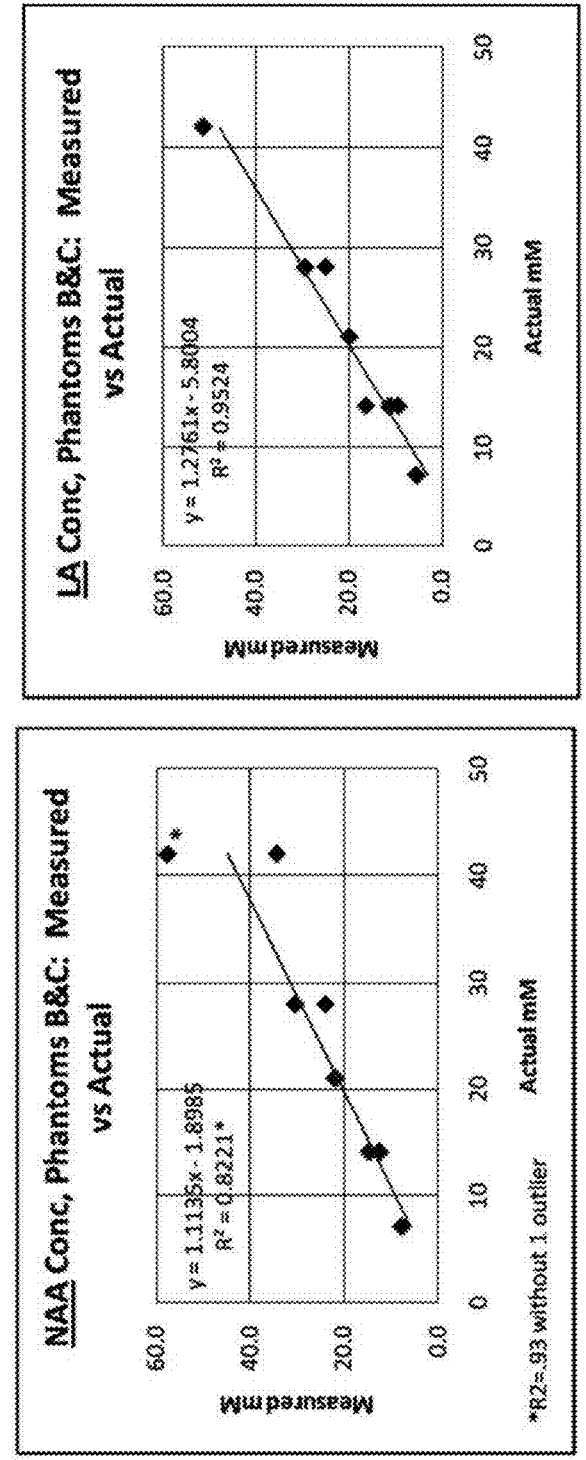
FIG. 40D
FIG. 40C

Patient DDD-MRS Example

| MARKERS | DISC | | | | |
|---|---|---|---|---|---|
| | L12 | L23 | L34 | L45 | L51 |
| LA | | | | | |
| LA/PG | 0.00 | 0.00 | 0.00 | 0.00 | 0.41 |
| LA/CA | 0.00 | 0.00 | 0.00 | 0.00 | 0.70 |
| ALPAmax | | | | | |
| ALPAmax/PG | 0.22 | 0.00 | 0.25 | 0.00 | 0.41 |
| ALPAmax/CA | 0.57 | 0.00 | 0.50 | 0.00 | 0.70 |
| ALPAsum | | | | | |
| ALPAsum/PG | 0.15 | 0.00 | 0.17 | 0.00 | 0.27 |
| ALPAsum/CA | 0.35 | 0.00 | 0.31 | 0.00 | 0.44 |

| | | | | | |
|---|---|---|---|---|---|
| Total Score (max=6) | 1.29 | 0.00 | 1.23 | 0.00 | 2.93 |
| Normalized Score | 0.44 | 0.00 | 0.42 | 0.00 | 1.00 |

FIG. 42

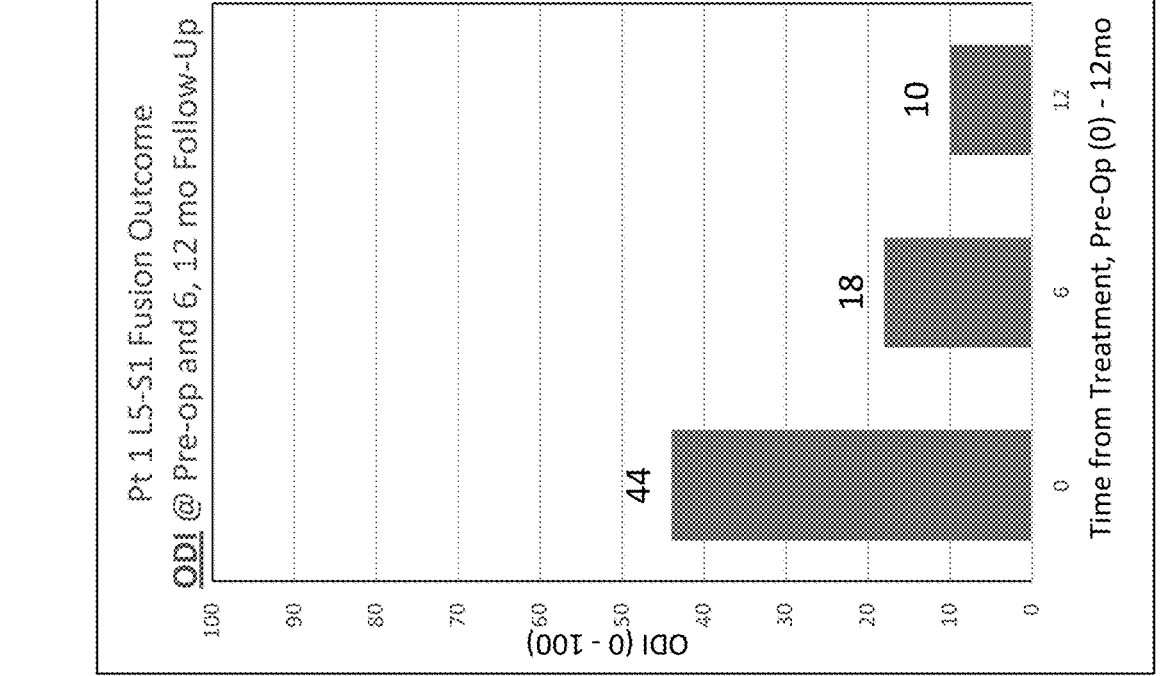
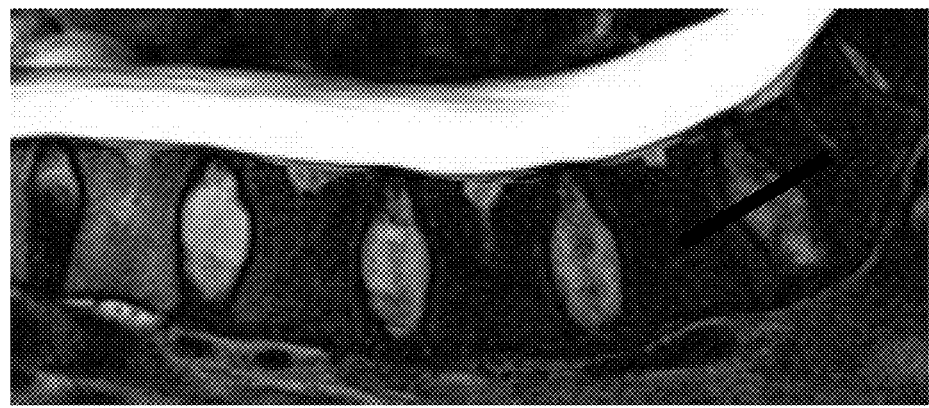
FIG. 43A: Example 5, Patient 1: Herniated L5S1, no evidence instability, Posterior annular tear @ L5-S1 → Fusion, Significant Pain Reduction @ 12mo post-op follow-up

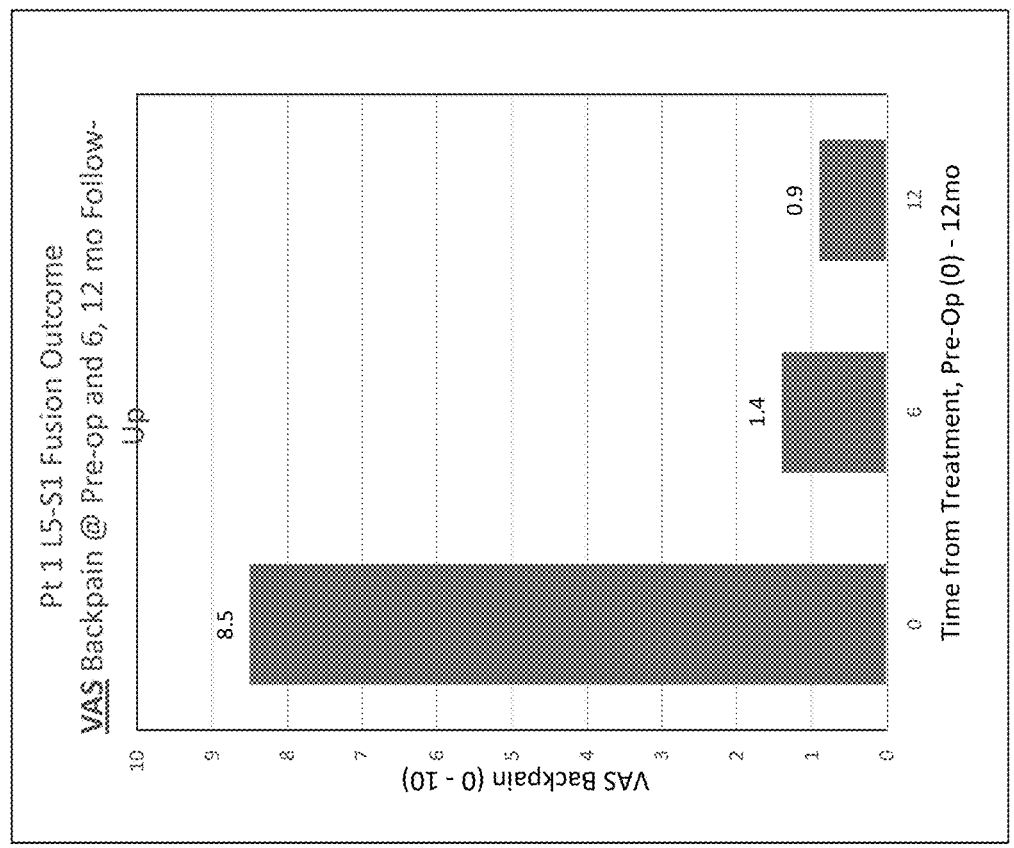
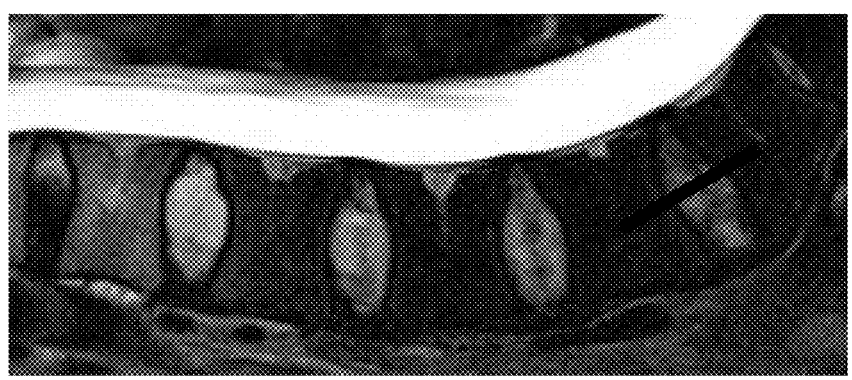
FIG. 43B: Example 5, Patient 1: Herniated L5S1, no evidence instability, Posterior annular tear @ L5-S1 → Fusion, Significant Pain Reduction @ 12mo post-op follow-up

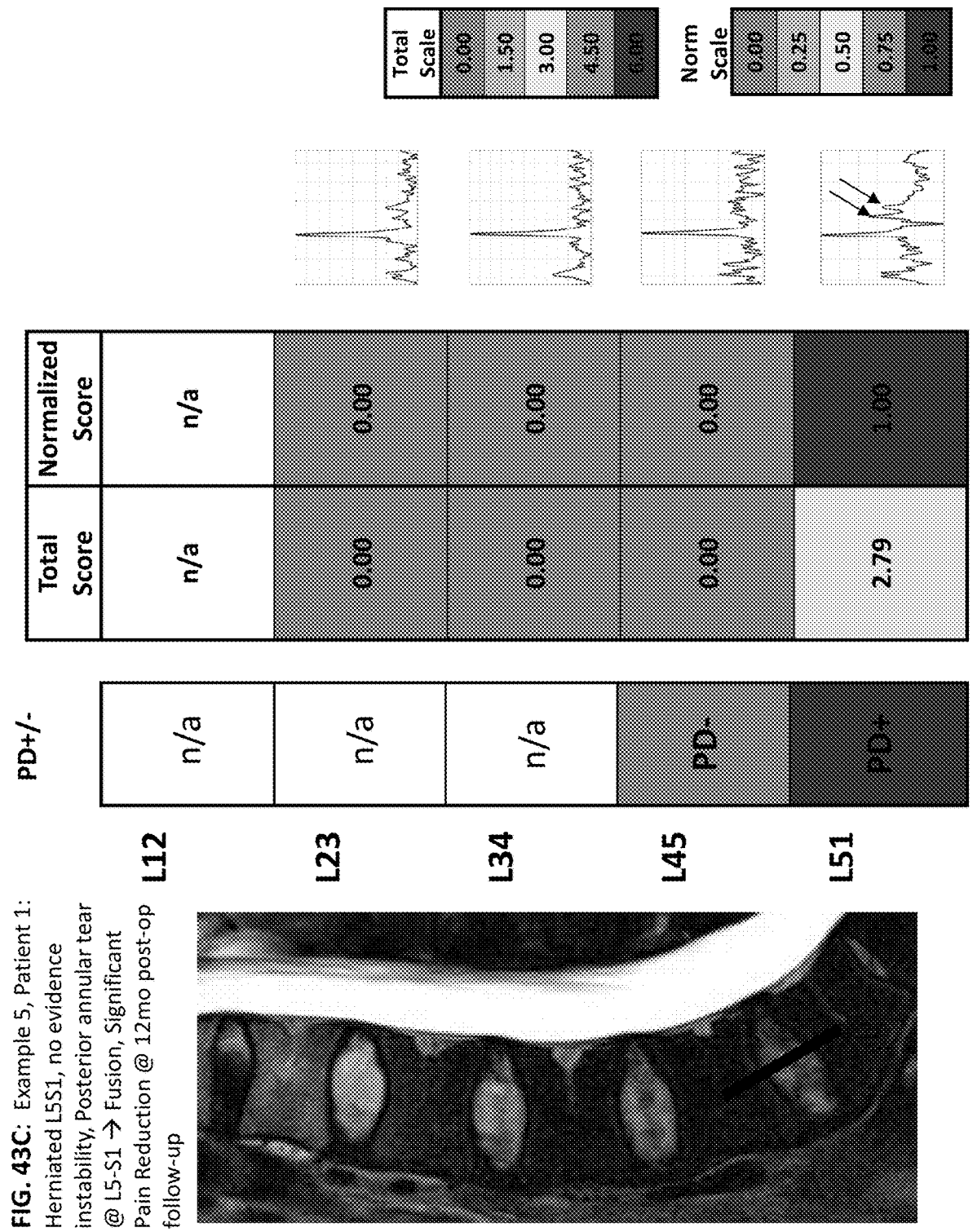
FIG. 43C: Example 5, Patient 1: Herniated L5S1, no evidence instability, Posterior annular tear @ L5-S1 → Fusion, Significant Pain Reduction @ 12mo post-op follow-up

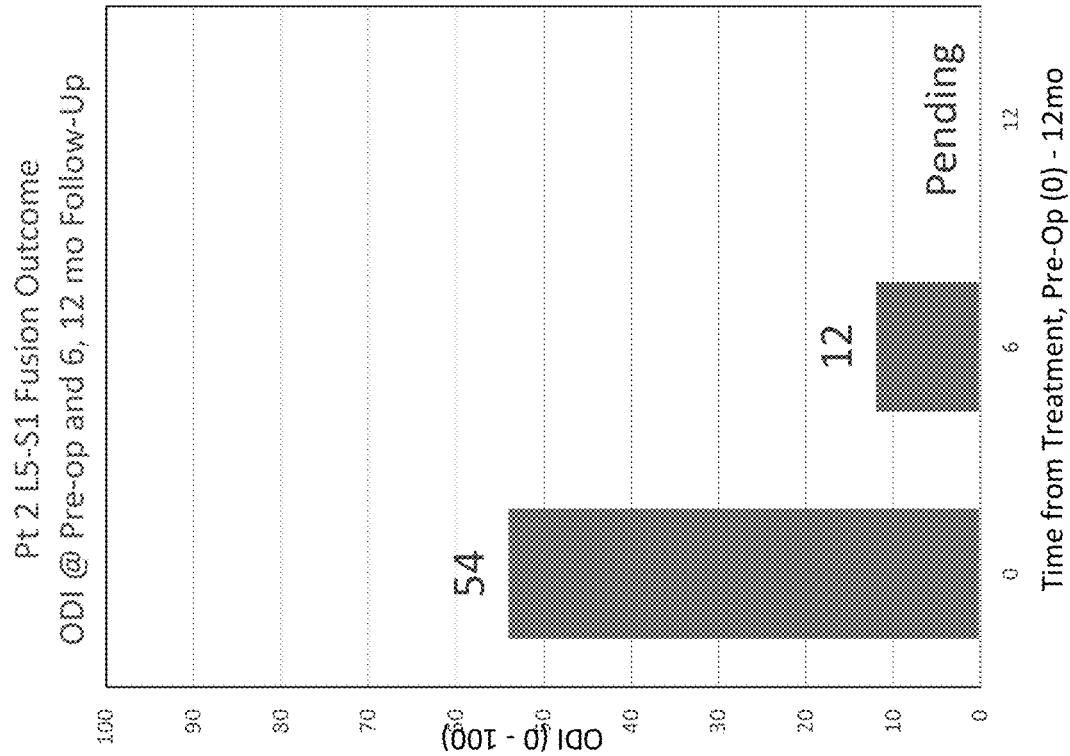
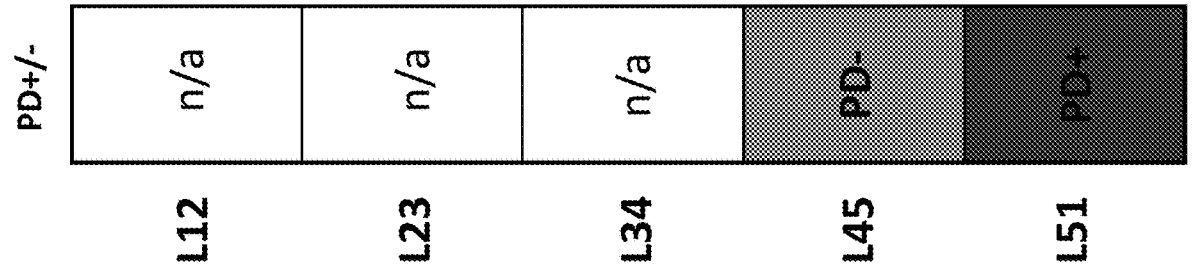
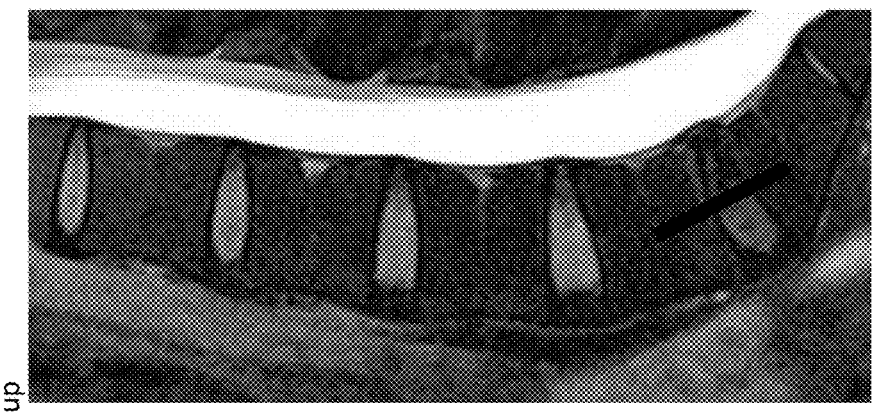
FIG. 44A: Example 5, Patient 2: L5S1 herniation, posterior annular tear, no evidence of instability → L5-S1 Fusion, Significant Pain Reduction @ 6mo post-op follow-up.

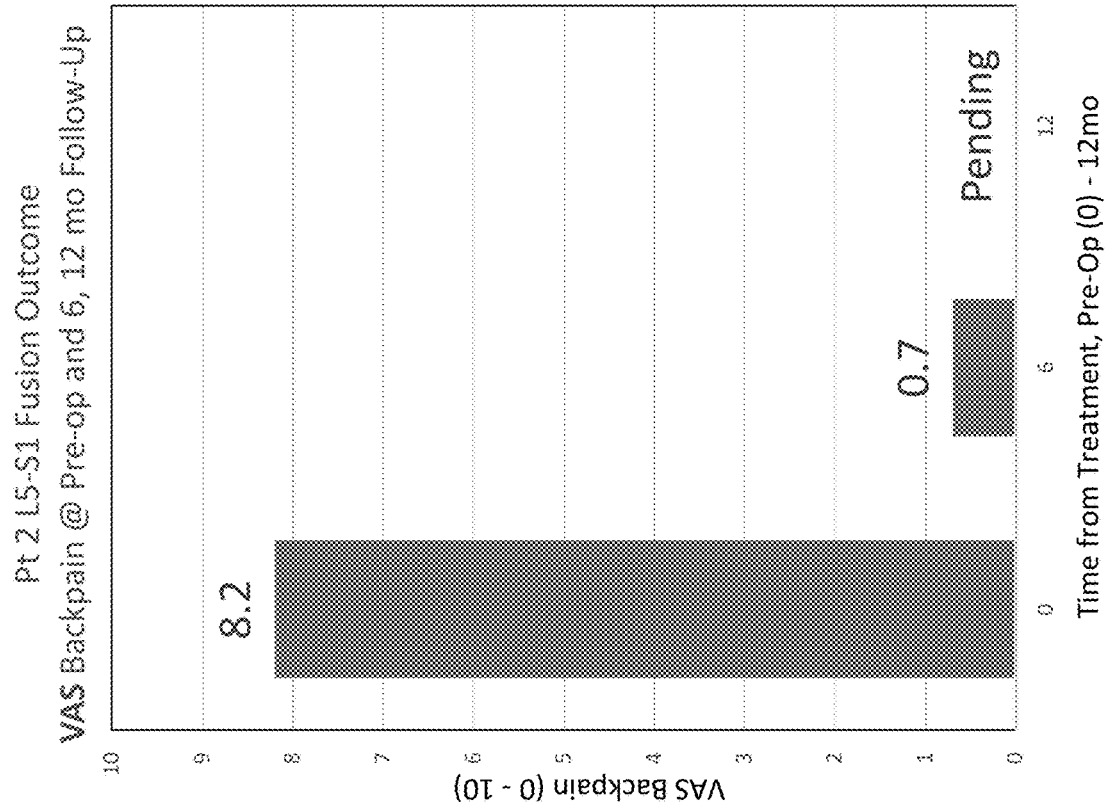
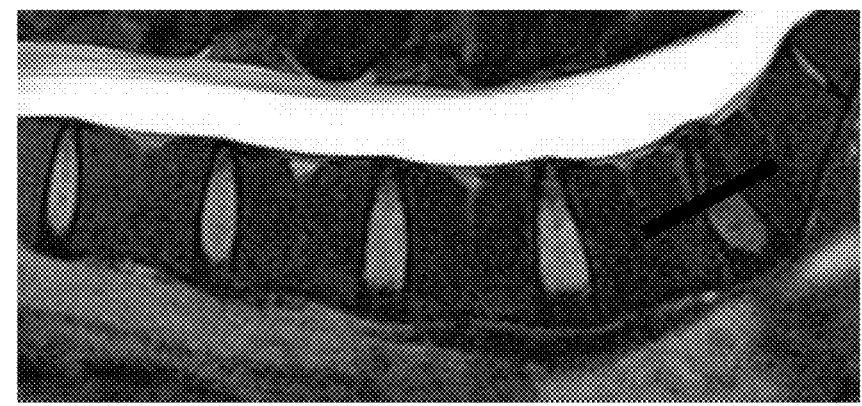
FIG. 44B: Example 5, Patient 2: L5S1 herniation, posterior annular tear, no evidence of instability → L5-S1 Fusion, Significant Pain Reduction @ 6mo post-op follow-up

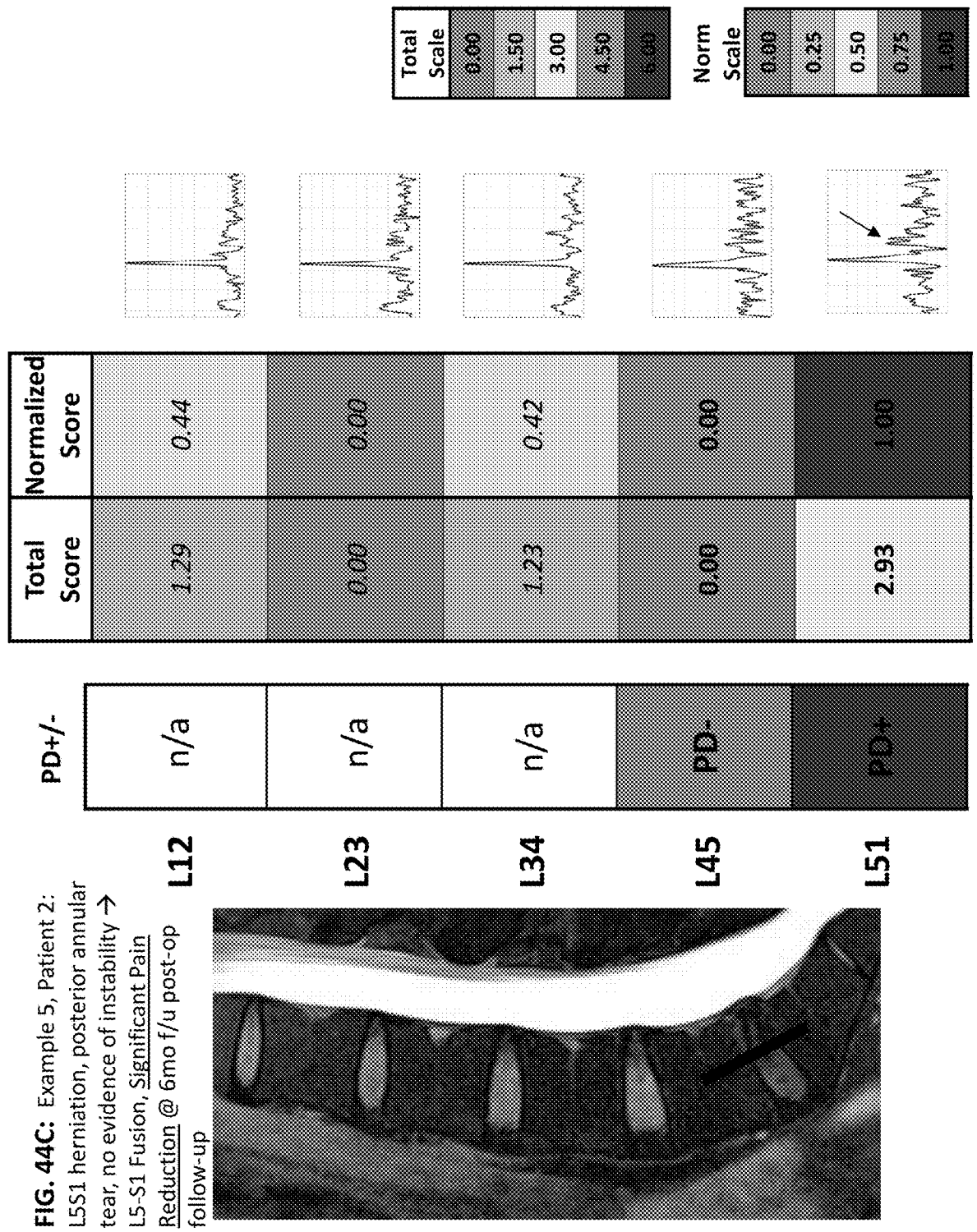
FIG. 44C: Example 5, Patient 2: L5S1 herniation, posterior annular tear, no evidence of instability → L5-S1 Fusion, Significant Pain Reduction @ 6mo f/u post-op follow-up

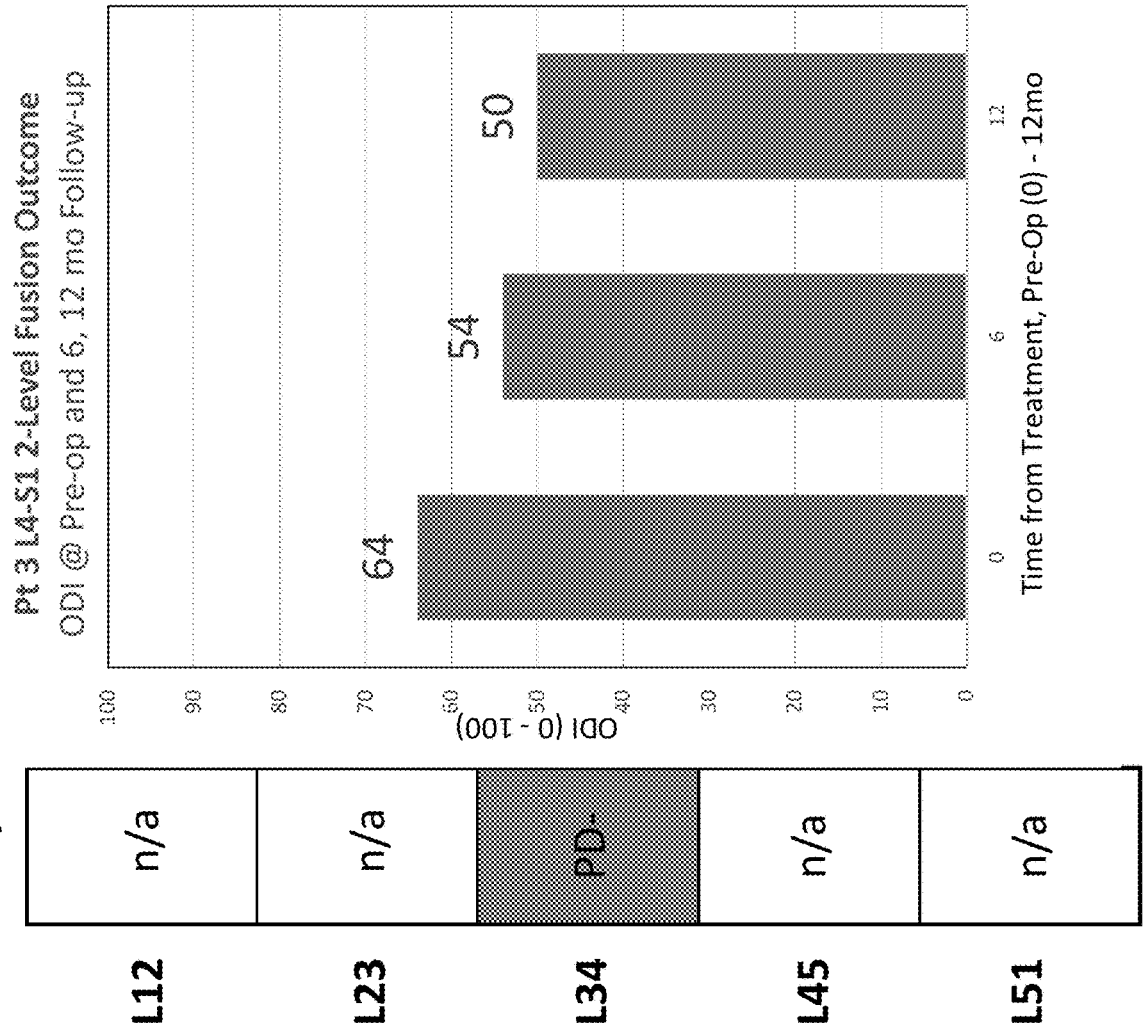
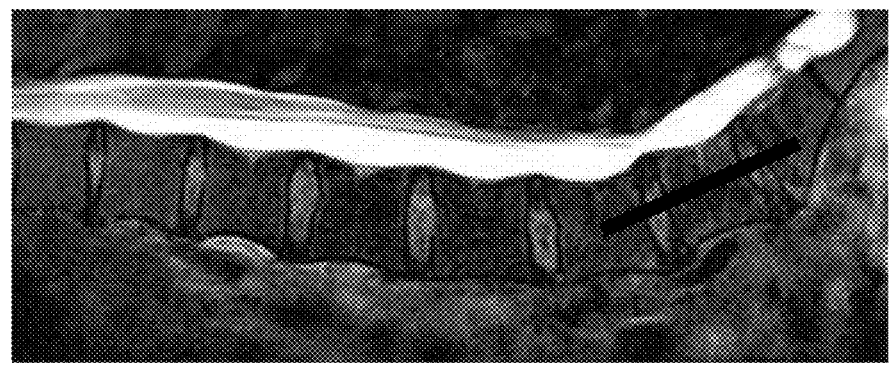
FIG. 45A: Example 5, Patient 3: L4-L5 Spondylolysthesis, suspected potential adjacent level L3-L4 discogenic back pain (PD-) → L3-S1 Fusion, Not Significantly Improved @ 6,12mo post-op follow-up

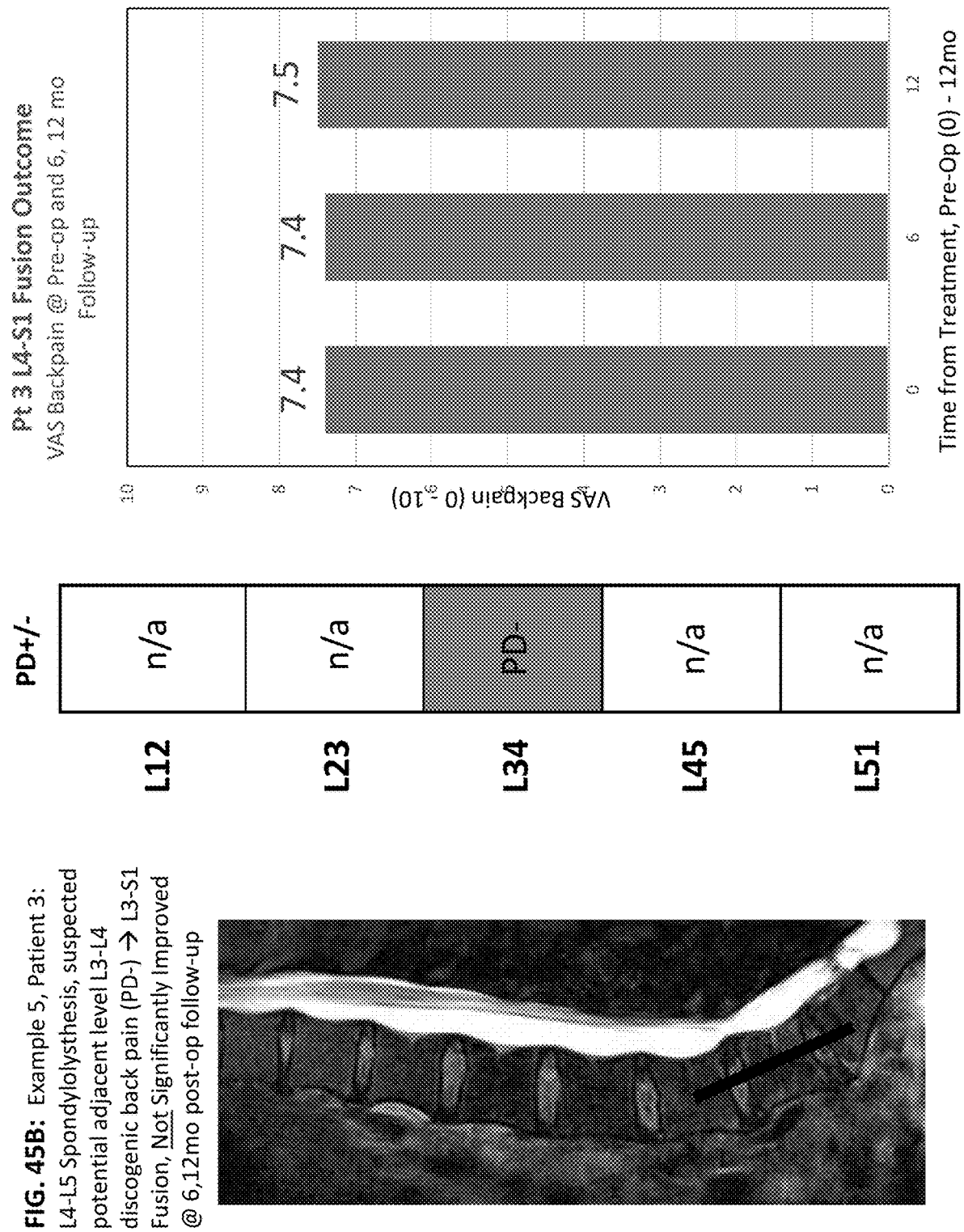
FIG. 45B: Example 5, Patient 3: L4-L5 Spondylolysthesis, suspected potential adjacent level L3-L4 discogenic back pain (PD-) → L3-S1 Fusion, Not Significantly Improved @ 6,12mo post-op follow-up

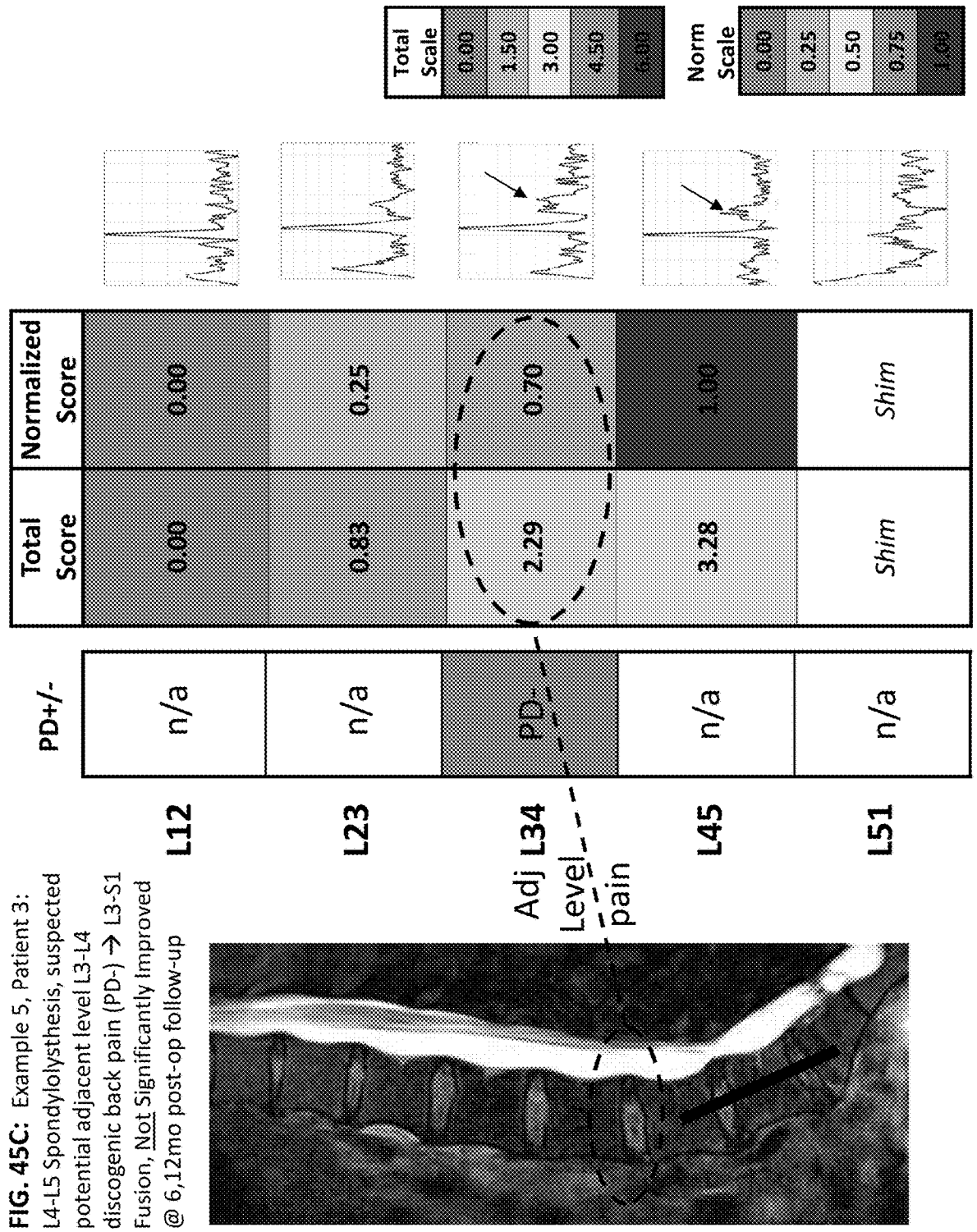
FIG. 45C: Example 5, Patient 3: L4-L5 Spondylolysthesis, suspected potential adjacent level L3-L4 discogenic back pain (PD-) → L3-S1 Fusion, Not Significantly Improved @ 6,12mo post-op follow-up

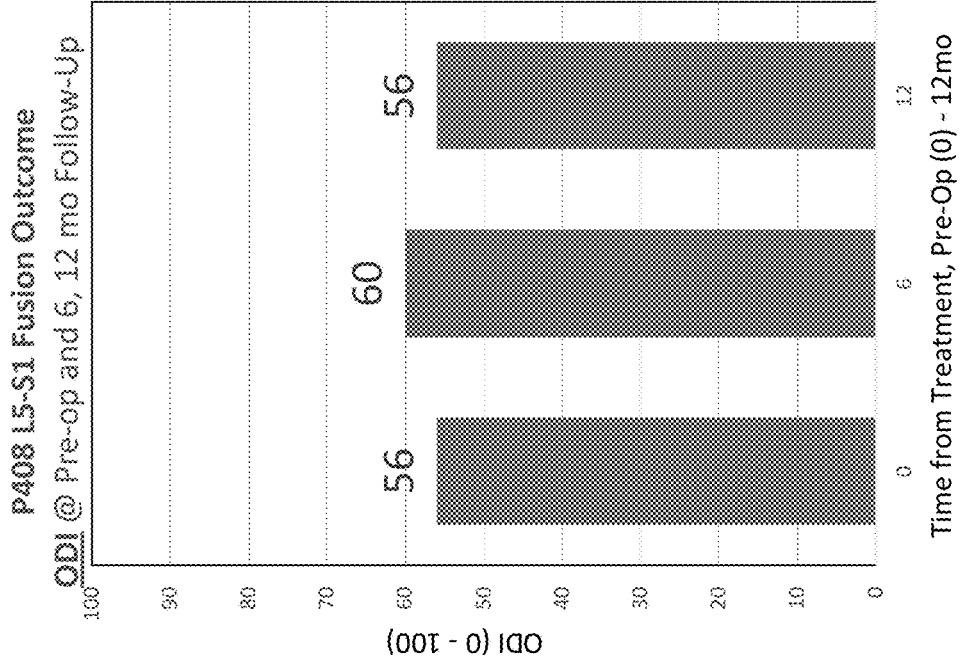
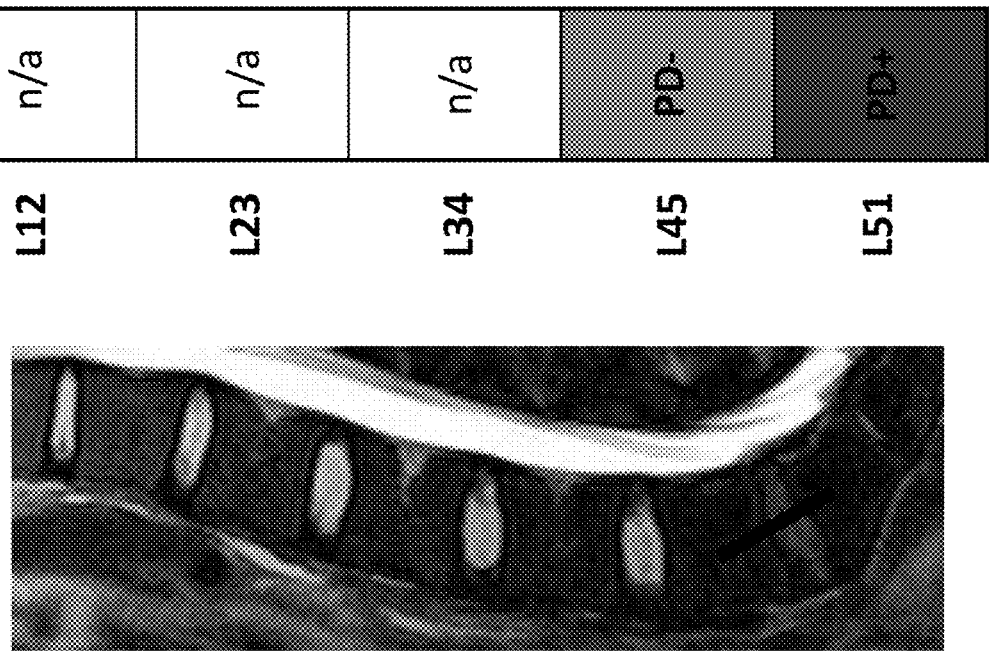
FIG. 46A: Example 5, Patient 4: L5-S1 herniation, radiculopathy; L5-S1 Fusion, Not Sig. Improved @ 6,12mo post-operative follow-up

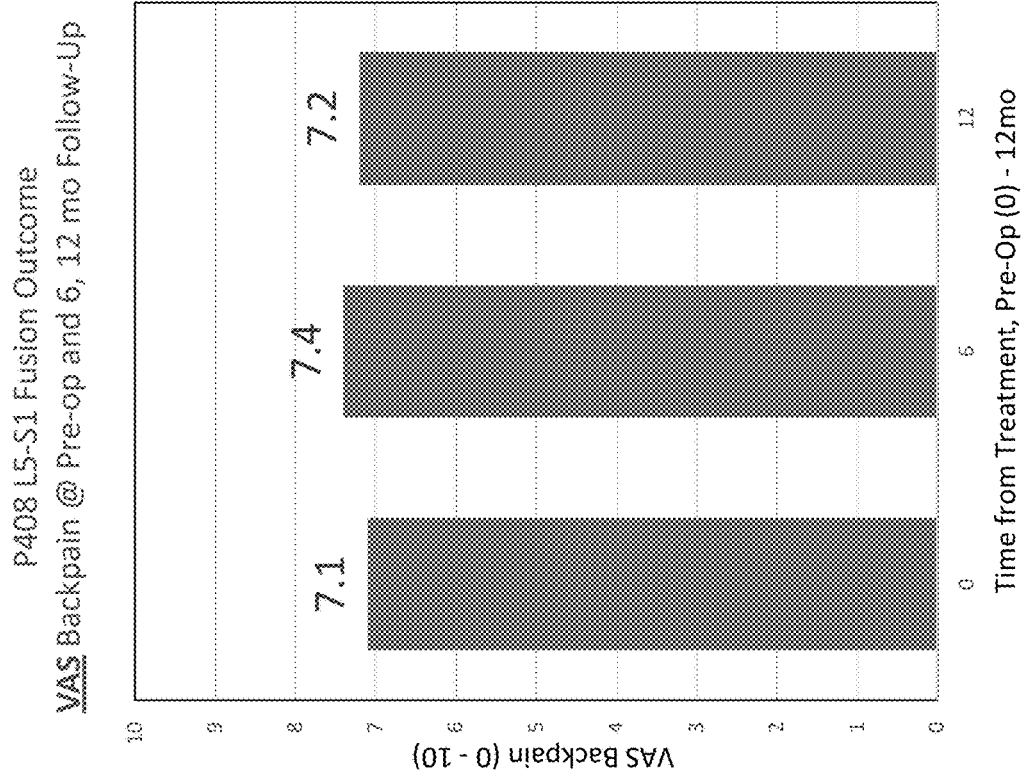
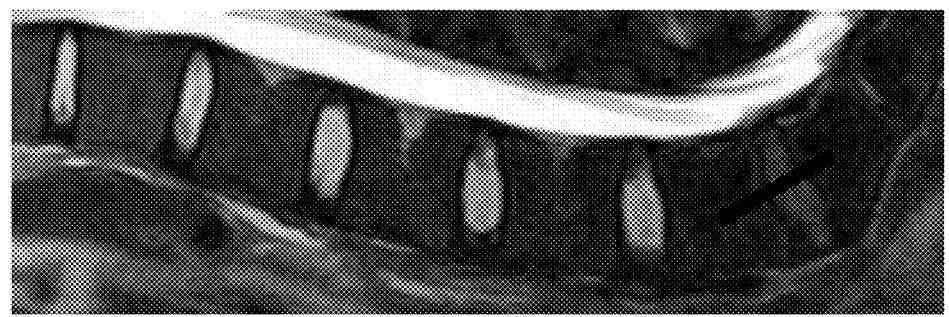
FIG. 46B: Example 5, Patient 4: L5-S1 herniation, radiculopathy; L5-S1 Fusion, <u>Not Sig. Improved</u> @ 6,12mo post-operative follow-up

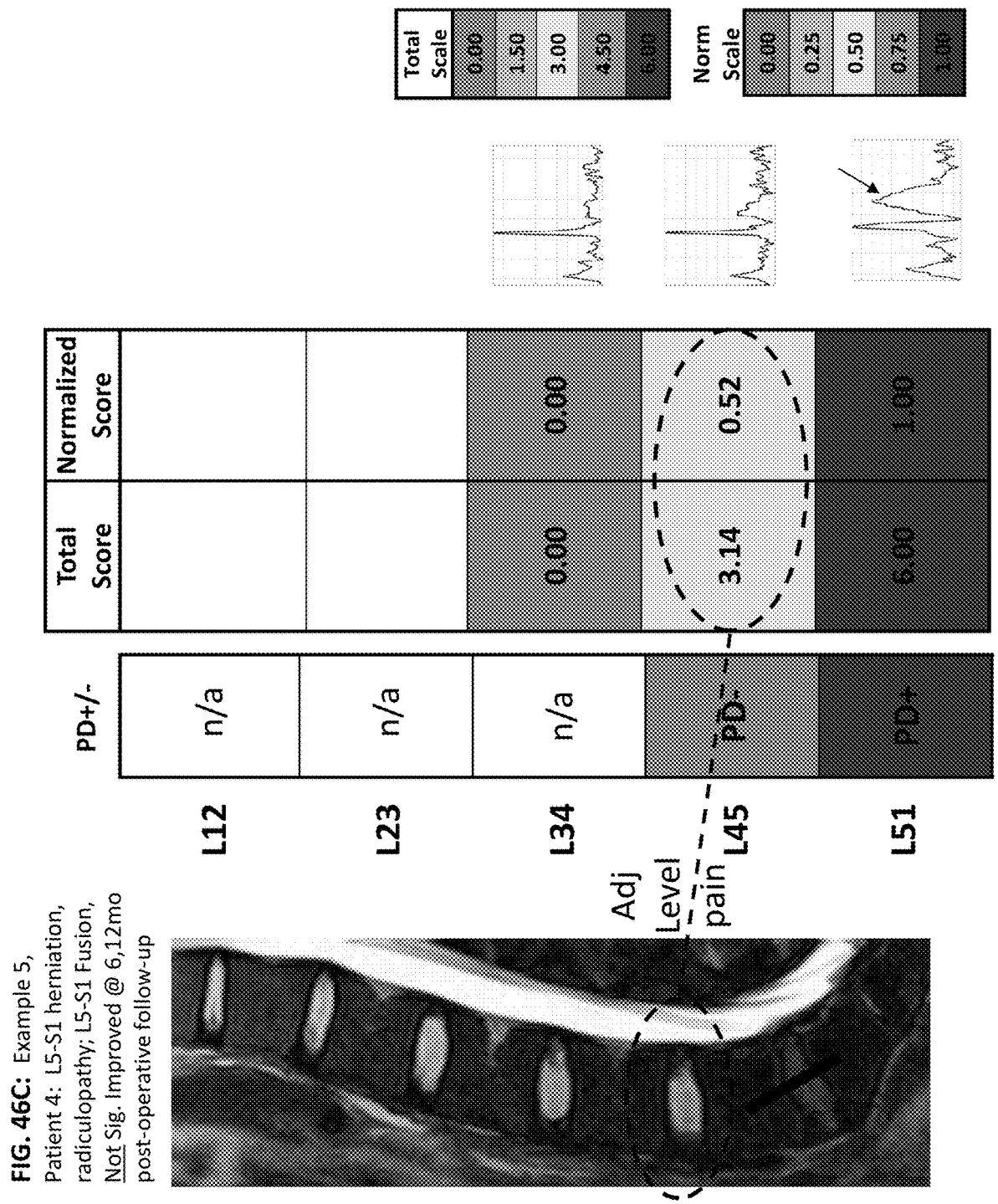
FIG. 46C: Example 5, Patient 4: L5-S1 herniation, radiculopathy; L5-S1 Fusion, Not Sig. Improved @ 6,12mo post-operative follow-up

|  | Test + | Test - | TOTAL |
|---|---|---|---|
| True + | 64 | 15 | 79 |
| True - | 7 | 76 | 83 |
| TOTAL | 71 | 91 | 162 |

| | | |
|---|---|---|
| Sensitivity | 81% | 64/79 |
| Specificity | 92% | 76/83 |
| PPV | 90% | 64/71 |
| NPV | 84% | 76/91 |
| Overall | 86.4% | 140/162 |

FIG. 49

|         | Test + | Test - | TOTAL |
|---------|--------|--------|-------|
| True +  | 12     | 2      | 14    |
| True -  | 3      | 61     | 64    |
| TOTAL   | 15     | 63     | 78    |

| | | |
|---|---|---|
| Sensitivity | 86% | 12/14 |
| Specificity | 95% | 61/64 |
| PPV | 80% | 12/15 |
| NPV | 97% | 61/63 |
| Overall | 94% | 73/78 |

FIG. 51

MAGNETIC RESONANCE SPECTROSCOPY SYSTEM AND METHOD FOR DIAGNOSING PAIN OR INFECTION ASSOCIATED WITH PROPIONIC ACID

CROSS-REFERENCE TO RELATED APPLICATIONS

This application is a continuation of International Patent Application No. PCT/US2017/038034, filed on Jun. 16, 2017, and titled MAGNETIC RESONANCE SPECTROSCOPY SYSTEM AND METHOD FOR DIAGNOSING PAIN OR INFECTION ASSOCIATED WITH PROPIONIC ACID, which designates the United States, and which claims the benefit of U.S. Provisional Patent Application No. 62/351,963, filed Jun. 19, 2016, and titled MAGNETIC RESONANCE SPECTROSCOPY SYSTEM AND METHOD FOR DIAGNOSING PAIN OR INFECTION ASSOCIATED WITH PROPIONIC ACID. Each of the above-identified application(s) is hereby incorporated by reference in its entirety and made a part of this specification for all that it discloses.

STATEMENT REGARDING FEDERALLY SPONSORED RESEARCH OR DEVELOPMENT

This invention was made with government support under grant no. R01 AR063705 awarded by the National Institutes of Health. The government has certain rights in the invention.

BACKGROUND

Field of the Disclosure

This disclosure relates to systems, processors, devices, and methods for measuring chemical constituents in tissue for diagnosing medical conditions. More specifically, it relates to systems, pulse sequences, signal and diagnostic processors, diagnostic displays, and related methods using novel application of nuclear magnetic resonance, including magnetic resonance spectroscopy, for diagnosing pain such as low back pain, and/or bacterial infection, associated with degenerative disc disease.

Description of the Related Art

While significant effort has been directed toward improving treatments for discogenic back pain, relatively little has been done to improve the diagnosis of painful discs.

Magnetic resonance imaging (MRI) is the primary standard of diagnostic care for back pain. An estimated ten million MRIs are done each year for spine, which is the single largest category of all MRIs at an estimated 26% of all MRIs performed. MRI in the context of back pain is sensitive to changes in disc and endplate hydration and structural morphology, and often yields clinically relevant diagnoses such as in setting of spondylolisthesis and disc herniations with nerve root impingement (e.g. sciatica). In particular context of axial back pain, MRI is principally useful for indicating degree of disc degeneration. However, degree disc degeneration has not been well correlated to pain. In one regard, people free of back pain often have disc degeneration profiles similar to those of people with chronic, severe axial back pain. In general, not all degenerative discs are painful, and not all painful discs are degenerative. Accordingly, the structural information provided by standard MRI exams of the lumbar spine is not generally useful for differentiating between painful and non-painful degenerative discs in the region as related to chronic, severe back pain.

Accordingly, a second line diagnostic exam called "provocative discography" (PD) is often performed after MRI exams in order to localize painful discs. This approach uses a needle injection of pressurized dye in awake patients in order to intentionally provoke pain. The patient's subjective reporting of pain level experienced during the injection, on increasing scale of 0-10, and concordancy to usual sensation of pain, is the primary diagnostic data used to determine diagnosis as a "positive discogram"—indicating painful disc—versus a "negative discogram" for a disc indicating it is not a source of the patient's chronic, severe back pain. This has significant limitations including invasiveness, pain, risks of disc damage, subjectivity, lack of standardization of technique. PD has been particularly challenged for high "false+" rates alleged in various studies, although recent developments in the technique and studies related thereto have alleged improved specificity of above 90%. (Wolfer et al., Pain Physician 2008; 11:513-538, ISSN 1533-3159). However, the significant patient morbidity of the needle-based invasive procedure is non-trivial, as the procedure itself causes severe pain and further compromises time from work. Furthermore, in another recent study PD was shown to cause significant adverse effects to long term disc health, including significantly accelerating disc degeneration and herniation rates (on the lateral side of needle puncture). (Carragee et al., SPINE Volume 34, Number 21, pp. 2338-2345, 2009). Controversies around PD remain, and in many regards are only growing, despite the on-going prevalence of the invasive, painful, subjective, harmful approach as the secondary standard of care following MRI. PD is performed an estimated 400,000 times annually world-wide, at an estimated total economic cost that exceeds $750 Million Dollars annually. The need for a non-invasive, painless, objective, non-significant risk, more efficient and cost-effective test to locate painful intervertebral discs of chronic, severe low back pain patients is urgent and growing.

A non-invasive radiographic technique to accurately differentiate between discs that are painful and non-painful may offer significant guidance in directing treatments and developing an evidence-based approach to the care of patients with lumbar degenerative disc disease (DDD).

SUMMARY OF CERTAIN EMBODIMENTS

One aspect of the present disclosure is a MRS pulse sequence configured to generate and acquire a diagnostically useful MRS spectrum from a voxel located principally within an intervertebral disc of a patient. An MR Spectroscopy (MRS) system and approach is provided for measuring spectral information corresponding with propionic acid (PA), either alone or in combination with other measurements corresponding with other chemicals, to diagnose and/or monitor at least one of bacterial infection, such as associated with *P. acnes*, or conditions related thereto such as nociceptive pain associated with tissue acidity. Certain applications include diagnosing painful and non-painful discs in chronic, severe low back pain patients (DDD-MRS). An applied DDD-MRS pulse sequence generates and acquires DDD-MRS spectra within intervertebral disc nuclei for later signal processing and diagnostic analysis. An interfacing DDD-MRS signal processor receives output signals of the DDD-MRS spectral information to produce a post-processed spectrum, with spectral regions corresponding with certain chemicals, including PA, then measured as biomarkers. A diagnostic processor derives a diagnostic value for each disc, and performs certain normalizations, based upon ratios of the spectral regions related to chemicals implicated in degenerative painful tissue pathology, such as PA and hypoxia markers of lactic acid (LA) and alanine (AL), and structural chemicals of proteoglycan (PG) and collagen or carbohydrate (CA). This information is then presented and used in a manner that is helpful for distinguishing degenerative painful vs. non-painful discs. A diagnostic display provides a scaled, color coded legend and indication of results for each disc analyzed, which is shown with and/or as an overlay onto an MRI image of the lumbar spine region for the patient being evaluated. Clinical application of the embodiments provides a non-invasive, objective, pain-free, reliable approach for diagnosing painful vs. non-painful discs by simply extending and enhancing the utility of otherwise standard MRI exams of the lumbar spine, and/or monitoring such chemicals (such as for purpose of evaluating response to therapies—e.g. PA as a biomarker to monitor bacterial infection response to antibiotics).

Another aspect of the present disclosure is an MRS signal processor that is configured to select a sub-set of multiple channel acquisitions received contemporaneously from multiple parallel acquisition channels, respectively, of a multi-channel detector assembly during a repetitive-frame MRS pulse sequence series conducted on a region of interest within a body of a subject.

Another aspect of the present disclosure is an MRS signal processor comprising a phase shift corrector configured to recognize and correct phase shifting within a repetitive multi-frame acquisition series acquired by a multi-channel detector assembly during an MRS pulse sequence series conducted on a region of interest within a body of a subject.

Another aspect of the present disclosure is a MRS signal processor comprising a frequency shift corrector configured to recognize and correct frequency shifting between multiple acquisition frames of a repetitive multi-frame acquisition series acquired within an acquisition detector channel of a multi-channel detector assembly during a MRS pulse sequence series conducted on a region of interest within a body of a subject.

Another aspect of the present disclosure is a MRS signal processor comprising a frame editor configured to recognize at least one poor quality acquisition frame, as determined against at least one threshold criterion, within an acquisition channel of a repetitive multi-frame acquisition series received from a multi-channel detector assembly during a MRS pulse sequence series conducted on a region of interest within a body of a subject.

Another aspect of the present disclosure is an MRS signal processor that comprises an apodizer to reduce the truncation effect on the sample data. The apodizer can be configured to apodize an MRS acquisition frame in the time domain otherwise generated and acquired by via an MRS aspect otherwise herein disclosed, and/or signal processed by one or more of the various MRS signal processor aspects also otherwise herein disclosed.

Another aspect of the present disclosure is an MRS diagnostic processor configured to process information extracted from an MRS spectrum for a region of interest in a body of a subject, and to provide the processed information in a manner that is useful for diagnosing a medical condition or chemical environment associated with the region of interest.

Another aspect of the present disclosure is an MRS system comprising an MRS pulse sequence, MRS signal processor, and MRS diagnostic processor, and which is configured to generate, acquire, and process an MRS spectrum representative of a region of interest in a body of a patient for providing diagnostically useful information associated with the region of interest.

Still further aspects of the present disclosure comprise various MRS method aspects associated with the other MRS system, sequence, and processor aspects described above.

Each of the foregoing aspects, modes, embodiments, variations, and features noted above, and those noted elsewhere herein, is considered to represent independent value for beneficial use, including even if only for the purpose of providing as available for further combination with others, and whereas their various combinations and sub-combinations as may be made by one of ordinary skill based upon a thorough review of this disclosure in its entirety are further contemplated aspects also of independent value for beneficial use.

Some aspects of this disclosure can relate to a diagnostic system for providing diagnostic information for a medical condition associated with a region of interest (ROI) in a patient. The diagnostic system can include a magnetic resonance spectroscopy (MRS) system configured to generate and acquire an MRS spectral acquisition series of data for a voxel located within the region of interest (ROI) using an MRS pulse sequence, and an MRS signal processor configured to process the MRS spectral acquisition series of data to produce a processed MRS spectrum. The system can include an MRS diagnostic processor configured to process the processed MRS spectrum to identify a spectral feature along a spectral peak region of the processed MRS spectrum corresponding at least in part with propionic acid (PA), calculate a measurement for the spectral feature, and generate the diagnostic information for the medical condition using the calculated measurement.

Some aspects of the present disclosure can relate to a method for providing diagnostic information for a medical condition of a region of interest (ROI) in a patient. The method can include generating and acquiring a magnetic resonance spectroscopy (MRS) spectral acquisition series of data for a voxel located within the region of interest (ROI) using an MRS system with an MRS scanner comprising a magnet and operated according to an MRS pulse sequence to generate the series of data and a detector assembly configured for receiving said series of data, and signal processing the MRS spectral acquisition series of data to produce a processed MRS spectrum, and identifying a spectral feature along a spectral peak region of the processed MRS spectrum that corresponds at least in part with propionic acid (PA), and calculating a measurement for the spectral feature, and generating the diagnostic information for the medical condition using the calculated measurement.

Some aspects of the present disclosure can relate to a magnetic resonance spectroscopy (MRS) processing system configured to process a multi-frame MRS spectral acquisition series generated and acquired for a voxel principally located within a region of interest (ROI) within a tissue in a body of a subject via an MRS pulse sequence and in order to provide diagnostic information for a medical condition associated with the ROI. The system can include an MRS signal processor configured to receive and process the MRS spectral acquisition series to produce a processed MRS spectrum, an MRS diagnostic processor configured to process the processed MRS spectrum to identify a spectral feature along a spectral peak region that comprises a region corresponding at least in part with propionic acid (PA), and calculate a measurement for the spectral feature, and generate the diagnostic information for the medical condition using the calculated measurement.

Some aspects of this disclosure can relate to a magnetic resonance spectroscopy (MRS) processing method for processing a multi-frame MRS spectral acquisition series generated and acquired for a voxel principally located within a region of interest (ROI) via an MRS pulse sequence, and for providing diagnostic information associated with the ROI. The method can include receiving the MRS spectral acquisition series, and signal processing the MRS acquisition series to produce a processed MRS spectrum, and diagnostically processing the processed MRS spectrum by identifying at least one identifiable feature along a chemical region in the processed MRS spectrum, the chemical region corresponding at least in part with propionic acid (PA), calculating a measurement for the feature, and processing the calculated measurement in a manner that provides MRS-based diagnostic information for diagnosing a medical condition or chemical environment associated with the ROI.

Some aspects of this disclosure can relate to a medical diagnostic system, which can include a signal processor configured to process a multi-frame MRS pulse sequence acquisition series of MRS spectra frames received from an acquisition channel of a detector assembly during a MRS pulse sequence series conducted on a region of interest (ROI) within a tissue in a body of a subject and to generate a processed MRS spectrum for the series, and a diagnostic processor configured to calculate a measurement for a spectral feature along a spectral region of the processed MRS spectrum, wherein the region corresponds with propionic acid (PA).

Some aspects of this disclosure can relate to a medical diagnostic system, which can include a diagnostic processor configured to provide diagnostic information for diagnosing a medical condition or chemical environment associated with a region of interest (ROI) in a tissue in a body of a subject based at least in part upon a calculated measurement derived from information extracted from the ROI corresponding with at least one chemical factor in the ROI comprising propionic acid (PA).

Some aspects of this disclosure can relate to a medical diagnostic system, which can include a diagnostic processor configured to provide diagnostic information for diagnosing a medical condition or chemical environment associated with a region of interest (ROI) in a tissue in a body of a subject based at least in part upon a calculated measurement derived from information extracted from the ROI and corresponding with at least one chemical factor comprising propionic acid (PA) in the ROI.

The calculated measurement can be adjusted by an adjustment factor that comprises at least one of a volume-related adjustment factor based upon a volume of the ROI, and a subject-related adjustment factor associated with a known value or condition of a subject-dependent variable for the subject.

Some aspects of the disclosure relate to a medical diagnostic method, which can include using a computing system for signal processing a multi-frame MRS pulse sequence acquisition series of MRS spectra frames received from an acquisition channel of a detector assembly during a MRS pulse sequence series conducted on a region of interest (ROI) within a tissue in a body of a subject and to generate a processed MRS spectrum for the series, calculating a measurement for a spectral feature along a spectral region of the processed MRS spectrum corresponding with propionic acid (PA), determining a chemical condition of the ROI or medical condition of the subject based at least in part on the calculated measurement.

Some aspects of this disclosure can relate to a medical diagnostic method, which can include using a computing system to execute executable code to operate a diagnostic processor for providing diagnostic information for diagnosing a medical condition or chemical environment associated with a region of interest (ROI) in a tissue in a body of a subject based at least in part upon a calculated measurement derived from information extracted from the ROI corresponding with at least one chemical factor in the ROI comprising a combination of (i) propionic acid (PA), and (ii) at least one of lactate (LA) and alanine (AL), chemicals.

Some aspects of this disclosure can relate to a medical diagnostic method, which can include using a computing system to execute executable code to operate a diagnostic processor for providing diagnostic information for diagnosing a medical condition or chemical environment associated with a region of interest (ROI) in a tissue in a body of a subject based at least in part upon a calculated measurement derived from information extracted from the ROI corresponding with at least one chemical factor in the ROI comprising propionic acid (PA), wherein the calculated measurement is adjusted by an adjustment factor that comprises at least one of a volume-related adjustment factor that is based upon a volume of the ROI, and a subject-related adjustment factor associated with a known value or condition of a subject-dependent variable for the subject.

Some aspects of this disclosure can relate to a method, which can include measuring a level of propionic acid (PA) in a region of tissue of a subject, and diagnosing or determining a medical condition of the subject or chemical environment of the tissue based upon the measurement.

Some aspects of this disclosure can relate to a diagnostic system for providing diagnostic information for diagnosing whether a region of interest (ROI) in an intervertebral disc in a spine of a patient is infected with bacteria (e.g., *Propionibacteria acnes* (*P. acnes*)). The diagnostic system can include a magnetic resonance (MR) system configured to generate and acquire an MRS spectral acquisition series of data for a voxel located within the region of interest (ROI) using an MRS pulse sequence and obtain one or more MRI images associated with the ROI. The system can include an MRS signal processor configured to process the MRS spectral acquisition series of data to produce a processed MRS spectrum. The system can include a diagnostic processor configured to identify a spectral feature along a spectral peak region of the processed MRS spectrum that corresponds with propionic acid (PA), and calculate a measurement for the spectral feature, and process the one or more MRI images to extract an MRI signature of Modic change (MC) in the spine, and generate the diagnostic information for the medical condition using the calculated measurement and the MRI signature.

Some aspects of this disclosure can relate to a method for providing diagnostic information for diagnosing whether a region of interest (ROI) in an intervertebral disc in a spine of a patient is infected with bacteria (e.g., *Propionibacteria acnes* (*P. acnes*)). The method can include generating and acquiring a magnetic resonance spectroscopy (MRS) spectral acquisition series of data for a voxel located within the region of interest (ROI) using an MRS system with an MRS scanner comprising a magnet and operated according to an MRS pulse sequence to generate the series of data and a detector assembly configured for receiving said series of data, and signal processing the MRS spectral acquisition series of data to produce a processed MRS spectrum, and identifying a spectral feature along a spectral peak region of the processed MRS spectrum that corresponds with propionic acid (PA), and calculating a measurement for the spectral feature, and obtaining one or more MRI images associated with the ROI, and processing the one or more MRI images to extract an MRI signature of Modic change (MC) in the spine, and generate the diagnostic information for the medical condition using the calculated measurement and the MRI signature.

Some aspects of this disclosure can relate to a method for providing diagnostic information associated with bacterial infection in a tissue region within a body of a patient. The method can include generating an image for a first region of interest (ROI) in the patient, and identifying a signature in the image that corresponds with bacterial infection in the first ROI, and extracting chemical-related information from a second ROI in the patient, and calculating a measurement from the chemical-related information that corresponds with an amount or concentration of propionic acid (PA) in the second ROI, and providing the diagnostic information based upon a combination of each of the identified signature and calculated measurement for PA.

Some aspects of the disclosure can relate to a system for providing diagnostic information associated with bacterial infection in a tissue region within a body of a patient. The system can include an image generation system configured to generate an image for a first region of interest (ROI) in the patient, and a chemical analysis system configured to extract chemical-related information from a second ROI in the patient, and a processing system configured to identify a signature in the image that corresponds with bacterial infection in the first ROI, and calculate a measurement from the chemical-related information that corresponds with an amount or concentration of propionic acid (PA) in the second ROI, and provide the diagnostic information based upon a combination of each of the identified signature and calculated measurement for PA.

BRIEF DESCRIPTION OF THE DRAWINGS

These and other features, aspects, and advantages of the present disclosure will now be described with reference to the drawings of embodiments, which embodiments are intended to illustrate and not to limit the disclosure.

FIG. 31C shows a scatter plot histogram of signal-to-noise ratio (SNR) for standard "all channels, non-corrected" frame averaged MRS spectra (absorption) produced by the 3T MR system for a subset of discs evaluated using the DDD-MRS pulse sequence in the clinical study of Example 1, and the SNR of MRS spectra (in phase real power) for the same series acquisitions for the same discs post-processed by the DDD-MRS signal processor configured according to various of the present aspects of this disclosure, as such SNR data was derived for example as illustrated in FIGS. 31A-B.

FIG. 31D shows the same data shown in FIG. 31C, but as bar graph showing mean values and standard deviation error bars for the data within each pre-processed and post-processed groups.

FIGS. 31G-H respectively show the mean and standard deviation for absolute improvement between pre- and post-processed SNR (FIG. 31F), the mean ratio improvement of post-processed/pre-processed SNR (FIG. 31G), and the mean % improvement of post-processed vs. pre-processed SNR (FIG. 31H).

FIGS. 40A-B show MRI images of two lumbar spine phantoms according to another Example 4 of the disclosure.

FIGS. 40C-D show graphical plots of n-acetyl (NAA) and lactic acid (LA) concentrations in discs from phantoms shown in FIGS. 40A-B as measured according to certain DDD-MRS aspects of the present disclosure, versus known amounts, per Example 4.

FIG. 42 shows an example of a 'heat map' of combined biomarker measurements related to six spectral chemical measurement ratios for each of five lumbar discs from a DDD-MRS exam conducted in a lumbar spine of a patient according to Example 5 of this disclosure.

FIGS. 43A-C show various aspects of the results of a DDD-MRS clinical patient study for a Patent Example 1 of Example 5 of this disclosure that had a successful outcome after fusion surgery following provocative discogram diagnostic guidance.

FIGS. 44A-C show various aspects of the results of a DDD-MRS clinical patient study for a Patent Example 2 of Example 5 of this disclosure that also had a successful outcome after fusion surgery following provocative discogram diagnostic guidance.

FIGS. 45A-C show various aspects of the results of a DDD-MRS clinical patient study for a Patent Example 3 of Example 5 of this disclosure that did not have a successful outcome and without significant pain relief after fusion surgery following provocative discogram diagnostic guidance.

FIGS. 46A-C show various aspects of the results of a DDD-MRS clinical patient study for a Patent Example 4 of Example 5 of this disclosure that also did not have a successful outcome and without significant pain relief after fusion surgery following provocative discogram diagnostic guidance.

FIG. 49 shows certain correlation results of the data shown in FIGS. 48A-B according to the classifications shown in FIG. 48B, and related diagnostic performance measures against control test data.

FIG. 51 shows similar diagnostic correlation and performance data as shown in FIG. 49, except for the filtered data shown in FIGS. 50A-B.

DETAILED DESCRIPTION OF CERTAIN EMBODIMENTS

Figure 1A:
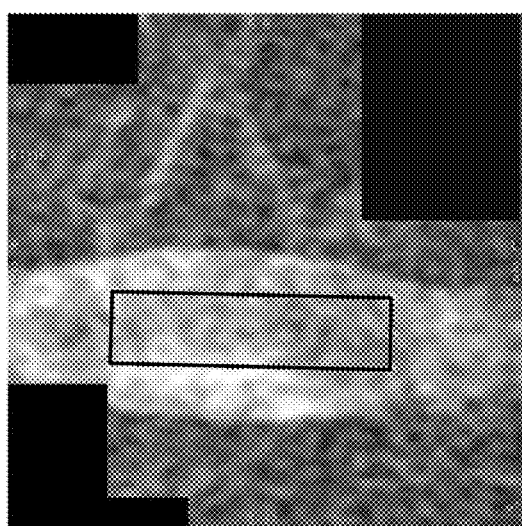
FIGS. 1A-C show respective MRI images of an intervertebral disc region of a lumbar spine with overlay features representing a voxel prescription within a disc for performing a DDD-MRS exam according to one aspect of the disclosure, in coronal, sagittal, and axial imaging planes, respectively.

Previously reported lab experiments used 11T HR-MAS Spectroscopy to compare chemical signatures of different types of ex vivo disc nuclei removed at surgery. (Keshari et al., SPINE 2008) These studies demonstrated that certain chemicals in disc nuclei, e.g. lactic acid (LA) and proteoglycan (PG), may provide spectroscopically quantifiable metabolic markers for discogenic back pain. This is consistent with other studies that suggest DDD pain is associated with poor disc nutrition, anaerobic metabolism, lactic acid production (e.g. rising acidity), extracellular matrix degradation (e.g. reducing proteoglycan), and increased enervation in the painful disc nuclei. In many clinical contexts, ischemia and lowered pH cause pain, likely by provoking acid-sensing ion channels in nociceptor sensory neurons.

The previous disclosures evaluating surgically removed disc samples ex vivo with magnetic resonance spectroscopy (MRS) in a laboratory setting is quite encouraging for providing useful diagnostic tool based on MRS. However, an urgent need remains for a reliable system and approach for acquiring MRS signatures of the chemical composition of the intervertebral discs in vivo in a readily adoptable clinical environment, and to provide a useful, clinically relevant diagnostic tool based on these acquired MRS signatures for accurately diagnosing discogenic back pain. A significant need would be met by replacing PD with an alternative that, even if diagnostically equivalent, overcomes one or more of the significant shortcomings of the PD procedure by being non-invasive, objective, pain-free, risk-free, and/or more cost-effective. Magnetic resonance spectroscopy (MRS) is a medical diagnostic platform that has been previously developed and characterized for a number of applications in medicine. Some of these have been approved such as for example for brain tumors, breast cancer, and prostate cancer. Some MRS platforms disclosed have been multi-voxel, and others single voxel. None of these have been adequately configured or developed for in vivo clinical application to reliably diagnose medical conditions or chemical environments associated with nociceptive pain, and/or with respect to intervertebral discs such as may be associated with disc degeneration and/or discogenic back pain (including in particular, but without limitation, with respect to the lumbar spine).

Various technical approaches have also been alleged to enhance the quality of MRS acquisitions for certain purposes. However, these approaches are not considered generally sufficient to provide the desired spectra of robust, reliable utility for many intervertebral discs in vivo, at least not at field strengths typically employed for in vivo spectroscopy, e.g. from about 1.2 tesla (T) or about 1.5 T to about 3.0 T or even up to about 7 T. Furthermore, while individual techniques have been disclosed for certain operations that might be conducted in processing a given signal for potentially improved signal:noise ratio (SNR), an MRS signal processor employing multiple steps providing significant MRS signal quality enhancement, in particular with respect to improved SNR for multi-channel single voxel pulse sequence acquisitions, have yet to be sufficiently automated to provide robust utility for efficient, mainstream clinical use, such as in primary radiological imaging centers without sophisticated MR spectroscopists required to process and interpret MRS data. This is believed to be generally the case as a shortcoming for many such in vivo MRS exams in general. Such shortcomings have also been observed in particular relation to the unique challenge of providing a robust MRS diagnostic system for diagnosing medical conditions or otherwise chemical environments within relatively small voxels, areas of high susceptibility artifact potential, and in particular with respect to unique challenges of performing MRS in voxels within intervertebral discs (including with further particularity, although without necessary limitation, of the lumbar spine). In solving many of these challenges according to certain aspects of the present disclosure, such as those providing particular utility for diagnosing discogenic low back pain and/or chemical environments within discs, additional beneficial advances have also been made that are also considered more broadly applicable to MRS in general, and as may become adapted for many specific applications, as are also herein disclosed.

Certain aspects of the current disclosure therefore relate to new and improved system approaches, techniques, processors, and methods for conducting in vivo clinical magnetic resonance spectroscopy (MRS) on human intervertebral discs, in particular according to a highly beneficial mode of this disclosure for using acquired MRS information to diagnose painful and/or non-painful discs associated with chronic, severe axial lumbar (or "low") back pain associated with degenerated disc disease (or "DDD pain"). For purpose of helpful clarity in this disclosure, the current aspects, modes, embodiments, variations, and features disclosed with particular benefits for this purposed are generally assigned the label "DDD-MRS." However, other descriptors may be used interchangeably as would be apparent to one of ordinary skill in context of the overall disclosure. It is also further contemplated within the scope of this present disclosure that, while this disclosure is considered to provide particular benefit for use involving such human intervertebral discs (and related medical indications and purposes), the novel approaches herein described are also considered more broadly and applicable to other regions of interest and tissues within the body of a subject, and various medical indications and purposes. For purpose of illustration, such other regions and purposes may include, without limitation: brain, breast, heart, prostate, GI tract, tumors, degeneration and/or pain, inflammation, neurologic disorders, Alzheimer's, etc.

Various aspects of this disclosure relate to highly beneficial advances in each of three aspects, and their various combinations, useful in particular for conducting a DDD-MRS exam: (1) MRS pulse sequence for generating and acquiring robust MRS spectra; (2) signal processor configured to improve signal-to-noise ratio (SNR) of the acquired MRS spectra; and (3) diagnostic processor configured to use information from the acquired and processed MRS spectra for diagnosing painful and/or non-painful discs on which the MRS exam is conducted in a DDD pain patient.

Several configurations and techniques related to the DDD-MRS pulse sequence and signal processor have been created, developed, and evaluated for conducting 3 T (or other suitable field strength) MRS on human intervertebral discs for diagnosing DDD pain. A novel "DDD" MRS pulse sequence was developed and evaluated for this purpose, and with certain parameters specifically configured to allow robust application of the signal processor for optimal processed final signals in a cooperative relationship between the pulse sequence and post-signal processing conducted. These approaches can be used, for example, with a 3 Tesla (3 T) "Signa" MR system commercially available from General Electric (GE). Highly beneficial results have been observed using the current disclosed application technologies on this particular MR platform, as has been demonstrated for illustration according to Examples provided herein, and it is to be appreciated that applying the present aspects of this present disclosure in combination with this one system alone is considered to propose significant benefit to pain management in patients requiring diagnosis. Accordingly, various aspects of the present disclosure are described by way of specific reference to configurations and/or modes of operation adapted for compatible use with this specific MR system, and related interfacing components such as spine detector coils, in order to provide a thorough understanding of the disclosure. It is to be appreciated, however, that this is done for purpose of providing useful examples, and though significant benefits are contemplated per such specific example applications to that system, this is not intended to be necessarily so limited and with broader scope contemplated. The current disclosure contemplates these aspects broadly applicable according to one of ordinary skill to a variety of MR platforms commercially available that may be different suitable field strengths or that may be developed by various different manufacturers, and as may be suitably adapted or modified to become compatible for use with such different systems by one of ordinary skill (with sufficient access to operating controls of such system to achieve this). Various novel and beneficial aspects of this present disclosure are thus described herein, as provided in certain regards under the Examples also herein disclosed.

Figure 1B:
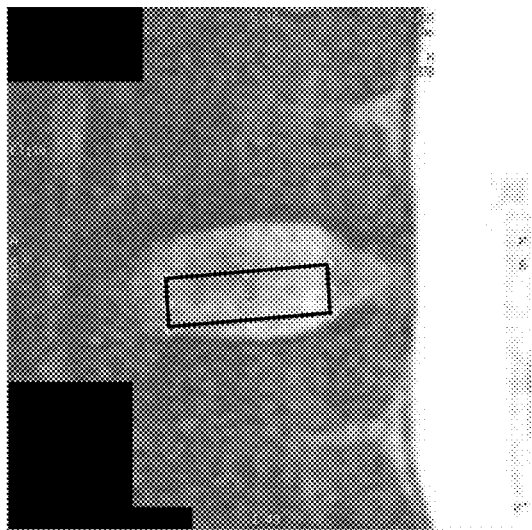
Figure 1C:
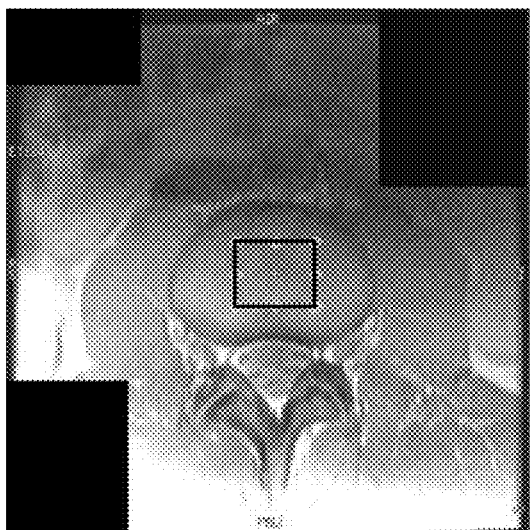

A DDD-MRS sequence exam is conducted according to one example overview description as follows. A single three dimensional "voxel," typically a rectangular volume, is prescribed by an operator at a control consul, using 3 imaging planes (mid-sagittal, coronal, axial) to define the "region of interest" (ROI) in the patient's body, such as shown in FIGS. 1A-C, for MR excitation by the magnet and data acquisition by the acquisition channel/coils designated for the lumbar spine exam within the spine detector coil assembly. The DDD-MRS pulse sequence applies a pulsing magnetic and radiofrequency to the ROI, which causes single proton combinations in various chemicals within the ROI to resonate at different "signature resonant frequencies" across a range. The amplitudes of frequencies at various locations along this range are plotted along a curve as the MRS "spectrum" for the ROI. This is done iteratively across multiple acquisitions for a given ROI, typically representing over 50 acquisitions, often 100 or more acquisitions, and often between about 200 and about 600 acquisitions, such as between 300 and 400 acquisitions for a given exam of a ROI. One acquisition spectrum among these iterations is called a "frame" for purpose of this disclosure, though other terms may be used as would be apparent to one of ordinary skill. These multiple acquisitions are conducted in order to average their respective acquired spectra/frames to reduce the amplitudes of acquired signal components representing noise (typically more random or "incoherent" and thus reduced by averaging) while better maintaining the amplitudes of signal components representing target resonant chemical frequencies of diagnostic interest in the ROI (typically repeatable and more "coherent" and thus not reduced by averaging). By reducing noise while maintaining true target signal, or at least resulting in less relative signal reduction, this multiple serial frame averaging process is thus conducted for the primary objective to increase SNR. These acquisitions are also conducted at various acquisition channels selected at the detector coils, such as for example 6 channels corresponding with the lumbar spine area of the coil assembly used in the Examples (where for example 2 coils may be combined for each channel).

The 3T MRI Signa system ("Signa" or "3T Signa"), in standard operation conducting one beneficial mode of DDD-MRS sequence evaluated (e.g. Examples provided herein), is believed to be configured to average all acquired frames across all acquisition channels to produce a single averaged MRS curve for the ROI. This unmodified approach has been observed, including according to the various Figures and Examples provided herein, to provide a relatively low signal/noise ratio, with low confidence in many results regarding data extraction at spectral regions of diagnostic interest, such as for example and in particular regions associated with proteoglycan or "PG" (n-acetyl) and lactate or lactic acid (LA). Sources of potential error and noise inherent in this imbedded signal acquisition and processing configuration of the typical MR system, for example were observed in conducting the DDD-MRS pulse sequence such as according to the Examples. These various sources of potential error or signal-to-noise ratio (SNR) compromise were determined to be mostly correctable—either by altering certain structures or protocols of coil, sequence, or data acquisition, or in post-processing of otherwise standard protocols and structures used. Among these approaches, various post-acquisition signal processing approaches were developed and observed to produce significantly improved and highly favorable results using otherwise un-modified operation pre-processing. In particular, various improvements developed and applied under the current post-signal processor disclosed herein have been observed to significantly improve signal quality and SNR.

Certain such improvements advanced under the post-signal processor configurations disclosed herein include embodiments related to the following: (1) acquisition channel selection; (2) phase error correction; (3) frequency error correction; (4) frame editing; and (5) apodization. These modules or steps are typically followed by channel averaging to produce one resulting "processed" MRS spectrum, when multiple channels are retained throughout the processing (though often only one channel may be retained). These may also be conducted in various different respective orders, though as is elsewhere further developed frame editing will typically precede frequency error correction. For illustration, one particular order of these operations employed for producing the results illustrated in the Examples disclosed herein are provided as follows: (1) acquisition channel selection; (2) phase correction; (3) apodization; (4) frame editing; (5) frequency correction; and (6) averaging.

While any one of these signal processing operations is considered highly beneficial, their combination has been observed to provide significantly advantageous results, and various sub-combinations between them may also be made for beneficial use and are also contemplated. Various illustrative examples are elsewhere provided herein to illustrate sources of error or "noise" observed, and corrections employed to improve signal quality. Strong signals typically associated with normal healthy discs were evaluated first to assess the signal processing approach. Signals from the Signa that were considered more "challenged" for robust data processing and diagnostic use were evaluated for further development to evaluate if more robust metabolite signal can be elicited from otherwise originally poor SNR signals from the Signa.

Additional description further developing these aspects according to additional embodiments, and other aspects, is provided below.

Spine Detector Coil and Patient Positioning

Figure 2:
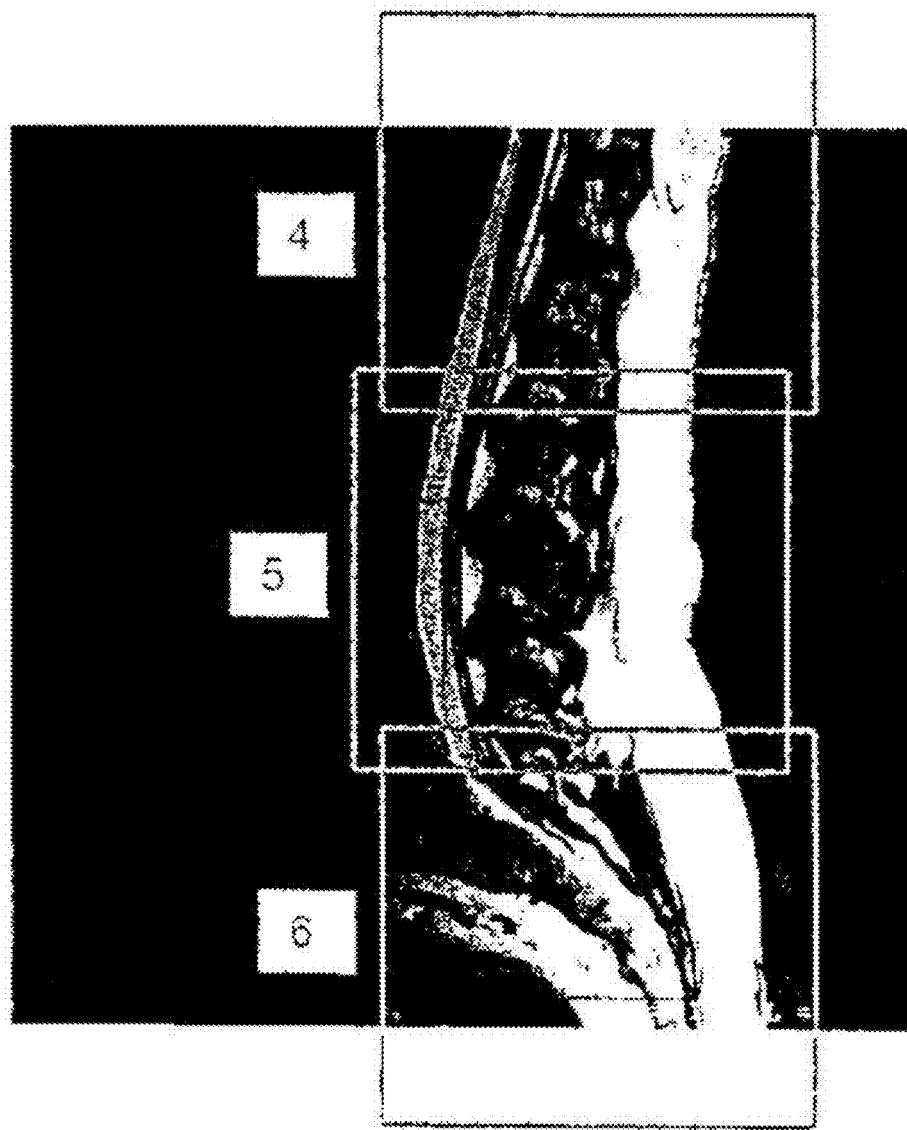
FIG. 2 shows an example of the sectional deployment in one commercially available MR spine detector coil assembly, and with which certain aspects of the present disclosure may be configured to interface for cooperative operation and use, and have been so configured and used according to certain Examples provided elsewhere herein.

A typical DDD-MRS exam according to the present embodiments will be conducted in an MR scanner in which the patient lies still in a supine position with a spine detector coil underneath the patient's back and including the lower spine. While this scanner applies the magnetic and RF fields to the subject, the spine detector coil functions as an antenna to acquire signals from resonating molecules in the body. The primary source of MRS signals obtained from a Signa 3T MR scanner, according to the physical embodiments developed and evaluated in the Examples herein this disclosure, are from the GE HD CTL 456 Spine Coil. This is a "receive-only" coil with sixteen coils configured into eight channels. Each channel contains a loop and saddle coil, and the channels are paired into sections. For lumbar (and thoracic) spine coverage, such as associated with lumbar DDD pain diagnosis, sections 4, 5, and 6 are typically deployed to provide six individual channel signals, as shown for example in FIG. 2.

Defining the Voxel (Voxel Prescription)

Certain embodiments of this disclosure relates principally to "single voxel" MRS, where a single three dimensional region of interest (ROI) is defined as a "voxel" (VOlumetric piXEL) for MRS excitation and data acquisition. The spectroscopic voxel is selected based on T2-weighted high-resolution spine images acquired in the sagittal, coronal, and axial planes, as shown for example in FIGS. 1A-C. The patient is placed into the scanner in a supine position, head first. The axial spine images acquired are often in a plane oriented with disc angle (e.g. may be oblique) in order to better encompass the disc of interest. This voxel is prescribed within a disc nucleus for purpose of using acquired MRS spectral data to diagnose DDD pain, according to the present preferred embodiments. In general for DDD-MRS applications evaluating disc nucleus chemical constituents, the objective for voxel prescription is to capture as much of the nuclear volume as possible (e.g. maximizing magnitude of relevant chemical signals acquired), while restricting the voxel borders from capturing therewithin structures of the outer annulus or bordering vertebral body end-plates (the latter being a more significant consideration, where lipid contribution may be captured and may shroud chemical spectral regions of interest such as lactate or alanine, as further developed elsewhere herein). In fact, the actual operation may not exactly coincide with acquiring signal from only within the voxel, and may include some bordering region contribution. Thus some degree of spacing between the borders and these structures is often desired. These typical objectives may be more difficult to achieve for some disc anatomies than others, e.g. relatively obliquely angled discs. For example, L5-S1 may be particularly challenging because in some patients it can frequently be highly angulated, irregularly shaped, and collapsed as to disc height.

In certain voxel prescriptions, the thickness is limited by the scanner's ability to generate the magnetic gradient that defines the Z-axis (axial plane) dimension. For example, a minimum thickness limit is pre-set to 4 mm on the GE Signa 3T. While such pre-set limits of interfacing, cooperative equipment and related software may result in limits on the current application's ability to function in that environment outside of these limits, the broad aspects of the current disclosure should not be considered necessarily so limited in all cases, and functionality may flourish within other operating ranges perhaps than those specifically indicated as examples herein, such as in cases where such other imparted limitations may be released.

These usual objectives and potential limitations in mind, typical voxel dimensions and volumes (Z-axis, X-axis, Y-axis, Vol) may be for example 5 mm (thick) by 14 mm (width) by 16 mm (length), and 1.12 cc, though one may vary any or all of these dimensions by operator prescription to suit a particular anatomy or intended application. The Z-axis dimension is typically limited maximally by disc height (in order to exclude the end-plates, described further herein), and minimally by either the set minimum limitations of the particular MR scanner and/or per SAR safety considerations, in many disc applications (such as specific indication for pain diagnosis or other assessment of disc chemistry described herein). This Z-axis dimension will typically be about 3 mm to about 6 mm (thick), more typically between about 4 mm to about 6 mm, and most typically will be suitable (and may be required to be, per anatomy) between about 4 mm to about 5 mm. The other dimensions are typically larger across the disc's plane, and may be for example between about 15 mm to about 20 mm (width and/or length), as have been observed suitable ranges for most observed cases (e.g. per the Examples herein). While the higher dimension of these ranges is typically limited only by bordering tissues desirable to exclude, the opportunity for patient motion to alter the relative location of the target voxel relative to actual anatomy may dictate some degree of "spacing" from such bordering structures to ensure exclusion. The smaller dimensions of the ranges are more related to degraded signal quality that comes with excessively small voxel volume, whereas signal amplitude will typically be directly related to voxel dimension and volume. Accordingly, voxels within discs will generally provide robust results, at least with respect to signal quality, at volumes of at least about 0.5 cc, and in many cases at least about 0.75 cc or 1 cc. This typically will be limited by bordering anatomy to up to about 2 ccs, or in some less typical cases up to about 3 ccs for exceptionally large discs. These voxel volume ranges will typically be achieved with various combinations of the typical axis dimensions as also stated above.

Also according to the typical voxel prescription objectives and limitations stated above, an initial prescription may not be appropriate for achieving acceptable results, though this may not be known until a sequence is begun to allow observation of acquired signal quality. Accordingly, further aspects of the present disclosure contemplate a voxel prescription protocol which prescribes a first prescription, monitors results (either during scan or after completion, or via a "pre-scan" routine for this purpose), and if a lipid signature or other suspected signal degradation from expected results is observed, re-prescribe the voxel to avoid suspected source of contaminant (e.g. make the voxel smaller or adjust its dimensions, tilt, or location) and re-run an additional DDD-MRS acquisition series (retaining the signal considered more robust and with least suspected signal degradation suspected to be voxel error). According to still a further mode, a pre-set protocol for re-prescribing in such circumstances may define when to accept the result vs. continue re-trying. In one embodiment, the voxel may be re-prescribed and acquisition series re-run once, or perhaps twice, and then the best result is to be accepted. It is to be appreciated, as with many technology platforms, that operator training and techniques in performing such user-dependent operations may be relevant to results, and optimal (or conversely sub-optimal) results may track skill levels and techniques used.

To further illustrate this current aspect of the present disclosure, the example of a single voxel prescription according to the typical three planar slice images is shown in FIGS. 1A-1C as follows. More specifically, FIG. 1A shows a coronal view oriented aspect of the voxel prescription. FIG. 1B shows a sagittal view oriented aspect of the voxel prescription. FIG. 1C shows an axial view oriented aspect of the voxel prescription.

The "DDD" MRS Pulse Sequence—PRESS

The DDD-MRS pulse sequence according to one embodiment shares certain similarities, though with certain differences and modifications defined herein, with another MRS pulse sequence called "PROSE". PROSE is primarily intended for use for diagnosing prostate cancer, and is approved for use and sale and available from GE on 1.5T GE MR systems. The DDD-MRS pulse sequence of the present embodiments, and PROSE for further reference, employ a sequence approach called Point RESolved Spectroscopy (PRESS). This involves a double spin echo sequence that uses a 90° excitation pulse with two 180° slice selective refocusing radio frequency (RF) pulses, combined with 3D chemical shift imaging (CSI) phase encoding gradients to generate 3-D arrays of spectral data or chemical shift images. Due to the small size, irregular shape, and the high magnetic susceptibility present when doing disc spectroscopy for DDD pain, the 3D phase encoding option available under PROSE is not an approach typically to be utilized under the current disclosed version of DDD-MRS sequence, and single voxel spectra are acquired by this version embodiment of DDD-MRS pulse sequence. This unique relative configuration for the DDD-MRS pulse sequence can be accomplished by setting the user control variables (CVs) for the matrix acquisition size of each axis to 1 (e.g., in the event the option for other setting is made available). Further aspects of pulse sequence approaches contemplated are disclosed elsewhere herein. It is to be appreciated that while the modified PRESS approach herein described is particularly beneficial, other approaches may be taken for the pulse sequence according to one of ordinary skill consistent with other aspects and objectives herein described and without departing from the broad aspects of intended scope herein.

Water and Lipid Signal Suppression—CHESS

In another sequence called "PROBE" also commercially available from GE, and which is a CSI sequence used for brain spectroscopy, the lipid/fat signals are believed to be resolved through the use of long TE (144 ms) periods and 2 dimensional transformations (2DJ). These acquisition and signal processing techniques are believed to be facilitated by the large voxel volumes prescribed in the brain as well as the homogeneity of the brain tissue resulting in relatively narrow spectral line widths. In the prostate region targeted by the different pulse sequence of PROSE, however, the voxel prescriptions are much smaller and it is often impossible to place the voxel so as to assuredly exclude tissues that contain lipid/fat. Therefore, two water and lipid suppression approaches are available and may be used, if warranted, in the PROSE sequence: "BASING" and "SSRF" (Spectral Spatial Radio Frequency). An even more challenging environment of bordering lipid and reduced homogeneity has been observed with the current DDD pain application of the lumbar intervertebral discs where the current ROI within disc nuclei are closely bordered by vertebral bodies with bone marrow rich in lipid content. However, due both to the desire to use short TE times (e.g. 28 ms) for the current DDD pain application in lumbar spine, and the desire to observe MRS signatures of other chemicals within disc nuclei that may overlap with lipid signal contribution along the relevant DDD-MRS spectrum, these water/lipid suppression approaches as developed for brain and prostate application are not necessarily optimized for DDD-MRS application in many circumstances. While a SSRF suppression approach for lipid resonances may be employed in the DDD-MRS sequence, the narrow band RF pulse required for this may require a long RF period and amplitude that will exceed the SAR level for many MR systems.

Water suppression is also provided by a CHESS sequence interleaved or otherwise combined in some manner with the PRESS sequence in order to provide appropriate results. Optimization of the residual water spectral line for frequency correction is done, according to one highly beneficial further aspect of the present disclosure, with the setting prescribed for the third flip angle. The angle is lowered to reduce the water suppression function which increases the residual water spectral line amplitude. Conversely higher relative third flip angles will increase water suppression for reduced water signal in an acquired MRS spectrum. A particular flip angle for this purpose may be for example about 125, though may be according to other examples between about 45 degrees and about 125 degrees (or as much as about 145 degrees). Accordingly, in one aspect, the flip angle may be for example at least about 45 degrees. In another aspect, the flip angle may be up to 125 degrees or even up to 145 degrees. Notwithstanding these examples, an expanded experimental data set of 79 discs in 42 subjects represented under Example 3 included robust, reliable results across this population with an average flip angle of about 120 or 121 degrees+/−about 33 degrees. Moreover, a later component of that population conducted with further refinements revealed a majority of cases suitable at a flip angle between about 65 degrees and about 125 degrees, and in fact with most found to be sufficient at about 85 degrees. It is to be appreciated that despite these specific number and range examples, and robust results observed therefrom, it is also believed that flip angles within about 5 or 10 degrees apart are likely to produce substantially similar results for purposes intended herein.

This flip angle aspect of the present disclosure is another example where some degree of customization may be required, in order to optimize water signal for a given disc, in a given particular MR system. As some discs may be more dehydrated or conversely more hydrated than others, the water suppression may be more appropriate at one level for one disc, and at another level for another disc. This may require some iterative setting and acquisition protocol to optimize, whereas the angle example described herein is considered appropriate for most circumstances and may be a pre-defined starting place for "first try."

Figure 3A:
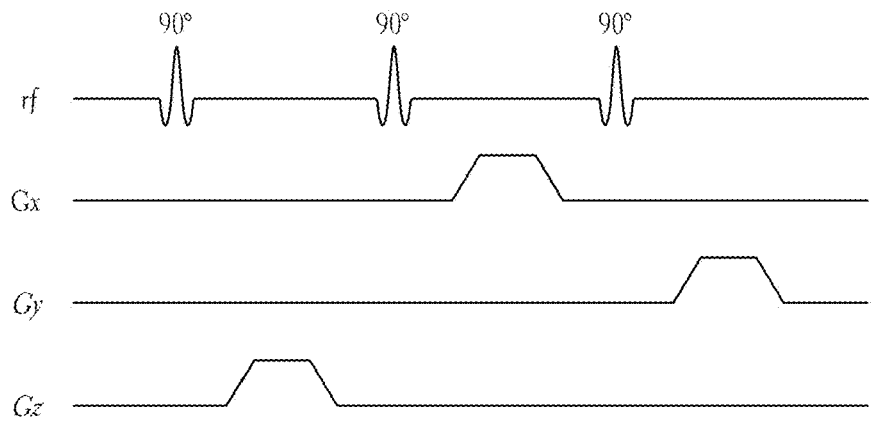
FIG. 3A shows an example of a CHESS water suppression pulse sequence diagram representing certain pulse sequence aspects contemplated by certain aspects of the present disclosure.
Figure 3B:
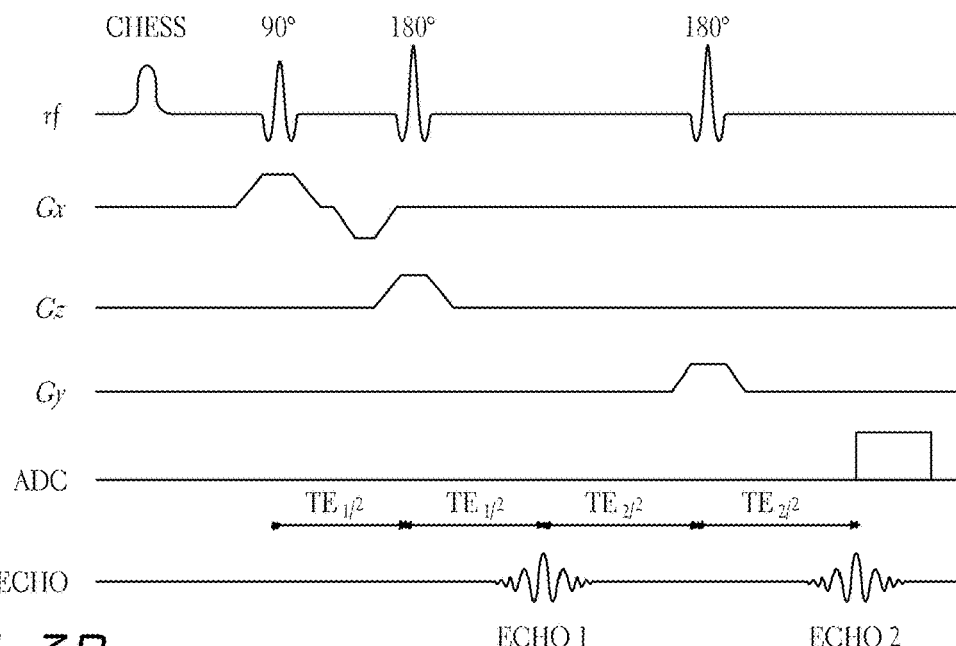
FIG. 3B shows certain aspects of a combined CHESS-PRESS pulse sequence diagram also consistent with certain aspects of the present disclosure.

For further clarity and understanding of the present DDD-MRS pulse sequence embodiments introduced above and also elsewhere herein described, FIG. 3A shows an example of a CHESS water suppression pulse sequence diagram, whereas FIG. 3B shows an example of a combined CHESS-PRESS pulse sequence diagram.

Very Selective Saturation (VSS) Bands

The volume excitation achieved using PRESS takes advantage of three orthogonal slices in the form of a double spin echo to select a specific region of interest. In some embodiments, the range of chemical shift frequencies (over 400 Hz for proton at 3.0 T) is not insignificant relative to the limited band width of most excitation pulses (1000-2000 Hz). The result can be a misregistration of the volume of interest for chemical shift frequencies not at the transmitter frequency. Thus, when a PRESS volume is resolved by MRS, the chemical levels may be not only dependent on tissue level, T1 and T2, but also dependent on location within the volume of interest. In some embodiments, due to imperfections in the RF pulse, out of volume excitation may occur which can present signals from chemicals that are not in the frequency/location range of interest.

Accordingly, another feature that is contemplated according to a further mode of the DDD-MRS sequence is the use of very selective saturation (VSS) pulses. This is often beneficial to deploy for example for removal of signal contamination that may arise from chemical shift error due to the presence of lipids within the voxel as well as outside the selected ROI or voxel in the disc nuclei. In the default operating mode of one DDD-MRS sequence approach, in some regards sharing some similarities with PROSE, for example, multiple pairs of VSS RF suppression bands are placed symmetrically around the prescribed DDD-MRS voxel. In certain embodiments, the voxel in this approach is oversized, such as for example by 120% (e.g. PRESS correction factor=about 1.2). The DDD-MRS sequence according to this mode uses the VSS bands to define the actual DDD-MRS volume. It is believed that up to about six additional VSS bands may be prescribed (each consisting of three VSS RF pulses) graphically in PROSE, with the goal of reducing the chemical shift error that can occur within the voxel as well as suppress excitation of out of voxel tissue during the PRESS localization of the voxel. According to some observations in applying DDD-MRS to disc spectroscopy, these additional graphic VSS pulses were found to not significantly improve the volume selection. In other observations, some benefit is suspected to have resulted. Accordingly, while they may provide benefit in certain circumstances, they also may not be necessary or even desired to be used in others.

Figure 3C:
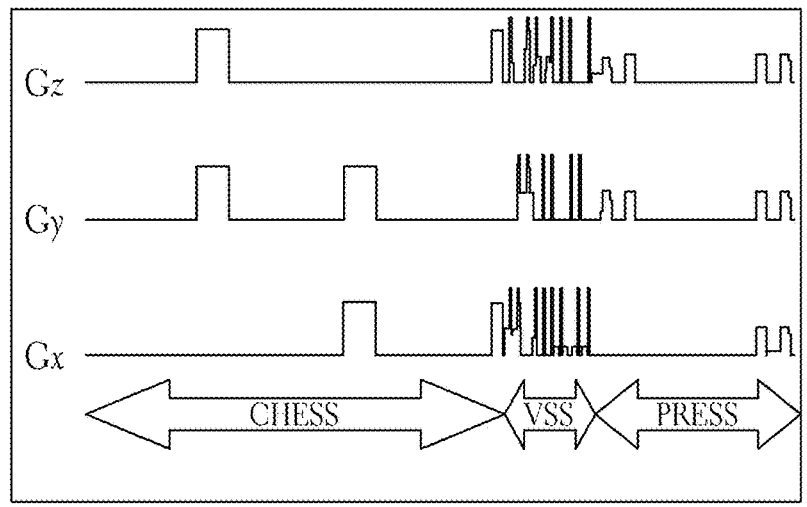
FIG. 3C shows various different aspects of a combined CHESS-VSS-PRESS pulse sequence diagram also illustrative of certain aspects of the present disclosure.
Figure 4A:
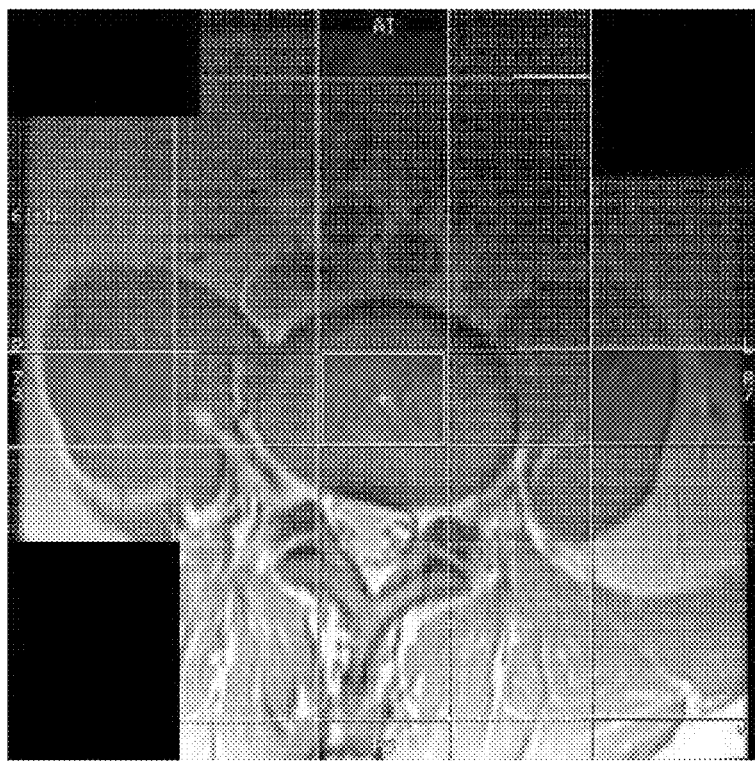
FIGS. 4A-B show two examples of respective planar views of a very selective saturation (VSS) prescription for a voxelated acquisition series in an intervertebral disc to be conducted via a DDD-MRS pulse sequence according to further aspects herein.
Figure 4B:
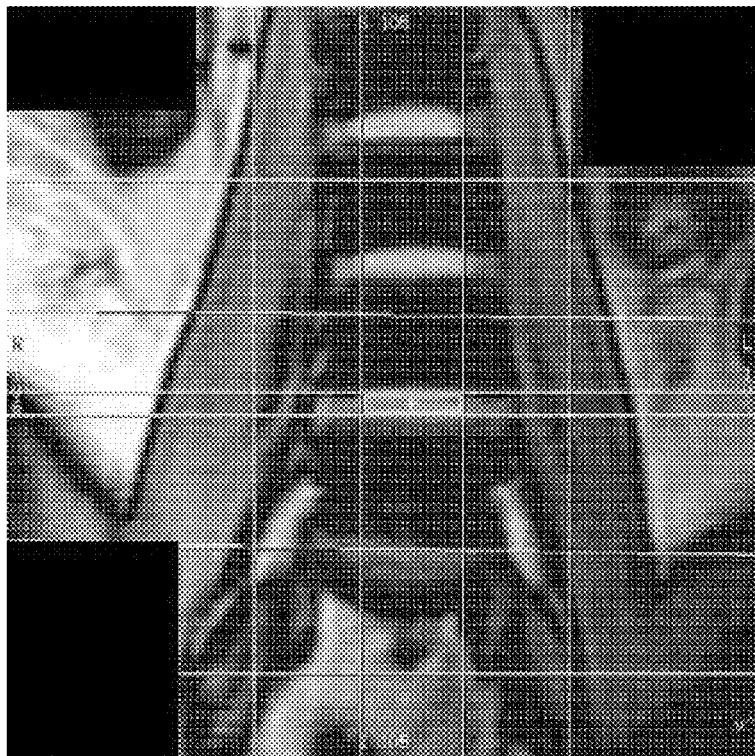

FIG. 3C shows a schematic diagram of certain aspects of a combined CHESS-VSS-PRESS pulse sequence diagram also consistent with certain aspects of the present disclosure. As also shown for further illustration in multiple respective image planes in FIGS. 4A-B, multiple VSS bands are placed around the voxel prescription in each plane to reduce out of voxel excitation and chemical shift error present during the PRESS localization of the voxel.

PRESS Timing Parameters

For purpose of comparative reference, the echo time (TE) of about 130 ms is believed to be the default selection typically used for PROSE data acquisitions. This echo time is typically considered too long for DDD-MRS pulse sequence applications for acquiring robust disc spectra due to the small voxel volume and shorter $T_2$ relaxation times of the chemical constituents of lumbar intervertebral discs, leading to a dramatic decrease in signal to noise in long echo PRESS spectra. Therefore a shorter echo time setting for the scanner, such as for example about 28 milliseconds, is generally considered more appropriate and beneficial for use in the current DDD-MRS sequence and DDD pain application (though this may be varied as would be apparent to one of ordinary skill based upon review of this total disclosure and to suit a particular situation). A frame repetition time (TR) of for example about 1000 ms provides sufficient relaxation of the magnetic dipoles in the ROI and leads to reasonable acquisition times and is believed to represent a beneficial compromise between short acquisition times and signal saturation at shorter values of TR (though this may also be varied, as also elsewhere herein described). Other appropriately applicable operating parameter settings for PRESS spectra suitably applicable to the DDD-MRS sequence may be, for example: number of data points equal to about 1024, number of repetitions equal to about 300, and example typical voxel size of about 4 mm×18 mm×16 mm (1.12 cc). Furthermore, first, second, and third flip angles of PRESS for the current DDD-MRS sequence embodiment may be for example 90, 167, and 167, respectively (though these may slightly vary, and user-defined settings may not always reflect actual angle—for example the latter two values may be exchanged with or represent one example of an actual result of a 180 degree setting).

Summary of User Control Variable (CV) Examples for DDD-MRS Sequence

The foregoing disclosure describes various user controllable sequence settings observed to be appropriate and of particular benefit for use in an example DDD-MRS sequence according to the current disclosure and for use for diagnosing DDD pain, as contemplated under the preferred embodiments herein. These are further summarized in Table 1 appended herewith at the end of this disclosure.

One or more of these CVs may comprise modifications from similar settings that may be provided for another CHESS-PRESS or CHESS-VSS-PRESS pulse sequence, such as for example PROSE, either as defaults or as user defined settings for a particular other application than as featured in the various aspects herein this disclosure. These CV settings, in context of use as modifications generally to a sequence otherwise sharing significant similarities to PROSE, are believed to result in a highly beneficial resulting DDD-MRS sequence for the intended purpose of later signal processing, according to the DDD-MRS signal processor embodiments herein described, and performing a diagnosis of DDD pain in discs examined (the latter according for example to the DDD-MRS diagnostic processor aspects and embodiments also herein disclosed). However, it is also appreciated that these specific settings may be modified by one of ordinary skill and still provide highly beneficial results, and are also contemplated within the broad intended scope of the various aspects of this present disclosure.

Data Acquisition of DDD-MRS Pulse Sequence

Figure 5:
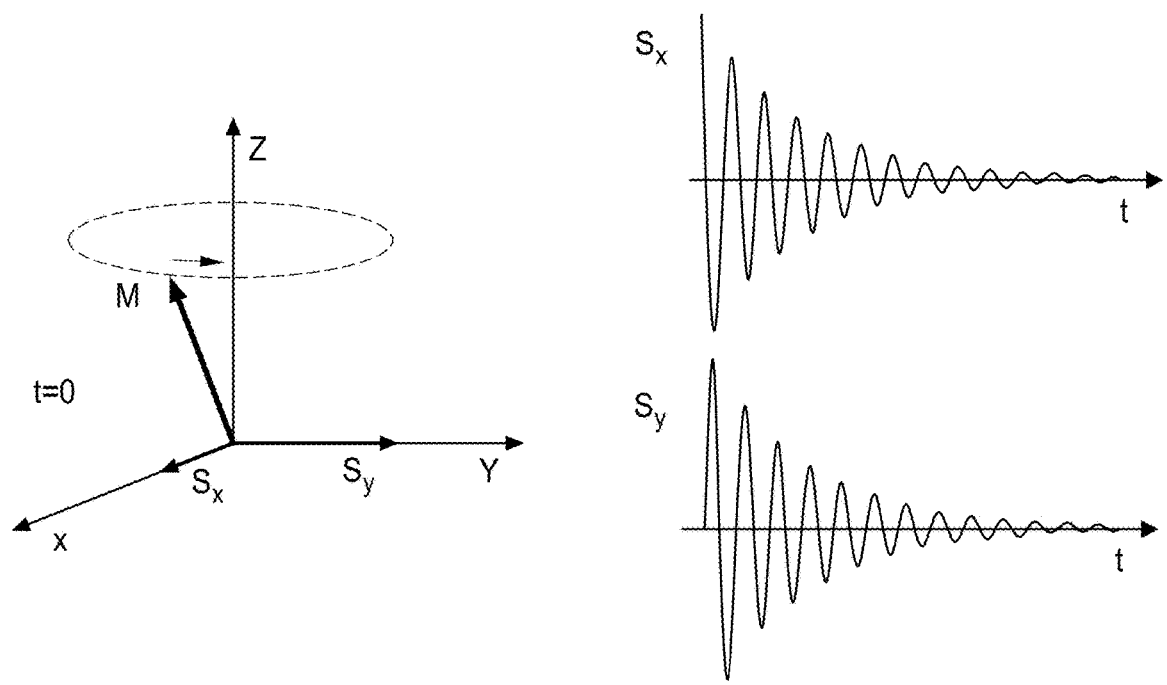
FIG. 5 shows Real (Sx) and imaginary (Sy) parts of an FID (right) that correspond to x and y components of the rotating magnetic moment M (left).

The signal detected in the MR spectrometer in the receiving "detector" coil assembly, after exposing a sample to a radio frequency pulse, is called the Free Induction Decay (FID) for purpose of this disclosure. In modern MR spectrometers the MR signal is typically detected using quadrature detection. As a result, the acquired MR signal is composed of two parts, often referred as real and imaginary parts of the FID. A schematic example of the time domain FID waveform is shown in FIG. 5, which shows the real (Sx) and imaginary (Sy) parts of an FID (right) that correspond to x and y components of the rotating magnetic moment M (left).

FIDs are generated at the period defined by TR. Thus a TR of about 1000 milliseconds, according to the example embodiment described above, equals a rate of about 1 Hz (about one FID per second). The FID signal received from each coil channel is digitized by the scanner to generate a 1024 point complex number data set or acquisition frame. An MRS scan session consists of a number of frames of unsuppressed water FIDs (such as for example may be about 16 frames) and up to 368 or more (as may be defined by an operator or setting in the pulse sequence) frames of suppressed water FIDs, which together are considered an acquisition series. The unsuppressed water FIDs provide a strong water signal that is used by the signal processing to determine which coils to use in the signal processing scheme as well as the phase information from each coil (and in certain embodiments may also be used for frequency error correction). However, due to gain and dynamic range in the system these high water content unsuppressed frames do not typically provide appropriate resolution in the target biomarker regions of the associated spectra to use them for diagnostic data purposes. The suppressed water FIDs are processed by the DDD-MRS processor to obtain this spectral information, although the unsuppressed frames may be used for certain processing approaches taken by the processor.

Figure 6:
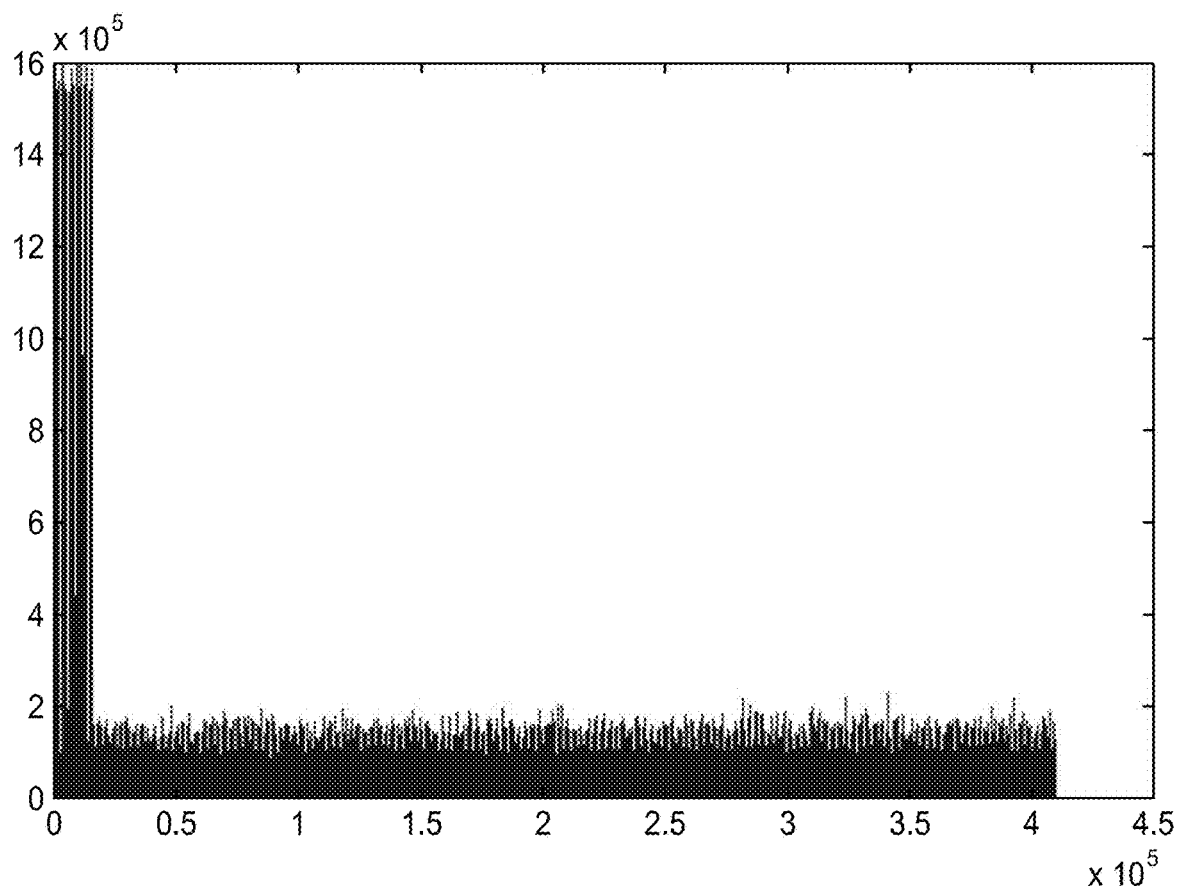
FIG. 6 shows an amplitude plot of complex data from a standard MRS series acquisition of multiple frame repetitions typically acquired according to certain present embodiments, and shows amplitude of signal on the y-axis and time on the x-axis.

For further illustration, FIG. 6 shows a plot of all the FIDs obtained in a DDD-MRS pulse sequence scan according to certain present illustrative embodiments, and is an amplitude plot of complex data from a standard DDD-MRS acquisition with the y-axis representing the magnitude of FID data and the x-axis representing serial frame count over time.

DDD-MRS Pulse Sequence Data Transfer from MR System to Post-Processor

The MR scanner generates the FIDs using the defined sequences to energize the volume of interest (VOI), digitizes them according to the defined data acquisition parameters, and stores the data, typically as floating point numbers. While this data may be packaged, e.g. in "archive file," and communicated in various formats and methods, one example is provided here. A data descriptor header file (DDF) with all the aforementioned parameters along with voxel prescription data is appended to the data to generate the archive file. Examples of certain parameters provided in a DDF, are as follows: studyID (String); seriesNum (Integer for assigned Series Number); studyDate (String date code); seriesDesc (String for series description); rootName (String); nSamps (Integer for number of complex samples, typically 1024); nFrames (Integer for number of frames or reps); coilName (String); pulseSeqName (String); Te (Float, echo time, in ms); Tr (Float, repetition time, in ms); TxFreq (Float, in MHz); nSatBands (Integer, number of saturation bands); voxTilt (Float, voxel tilt about x-axis, in degrees); voxVol (Float, Voxel volume in cc); voxX (Float, Voxel X dimension, in mm); voxY (Float, Voxel Y dimension, in mm); voxZ (Float, Voxel Z dimension, in mm). The archive file can include data received from the MR scanner that is representative of the anatomy of a patient (e.g., representative of the chemical makeup of tissue inside the area of interest inside an intervertebral disc of the patient's spine).

The archive file may then be transferred to another computer running an application written in a language, such as for example Matlab® R2009a (e.g. with "Image Processing Toolbox" option, such as to generate time-intensity plots such as shown in various Figures herein), which opens the archive file. The Matlab application may be user-configurable, or may be configured as full or partial executables, and is configured to signal process the acquired and transferred DDD-MRS information contained in the archive file, such as according to the various signal processing embodiments herein. Other software packages, such as "C," "C+," or "C++" may be suitably employed for similar purposes. This application, subsequently referred to as the DDD-MRS signal processor, parses information pertinent to the signal processing of the data from the data description header, and imports the FID data acquired at each detector coil for subsequent signal processing. It will be understood that the DDD-MRS signal processor can be implemented in a variety of manners, such as using computer hardware, firmware, or software, or some combination thereof. In some embodiments, the DDD-MRS signal processor can comprise a computer processor configured to execute a software application as computer-executable code stored in a non-transitory computer-readable medium. In some embodiments, the computer processor can be part of a general purpose computer. In some embodiments, the DDD-MRS signal processor can be implemented using specialized computer hardware such as integrated circuits instead of computer software. It will be understood that the DDD-MRS signal processor, as well as other components described herein that may be implemented by a computer, can be implemented by multiple computers connected, for example, by a network or the internet. Thus, algorithms, processes, sequences, calculations, and tasks, etc. described herein can be divided into portions to be performed by multiple computer processors or other hardware located on multiple physically distinct computers. Also, some tasks that are described herein as being performed by distinct computers or systems may be performed by a single computer or a single integrated system.

The archive file and related MRS data may be communicated via a number of available networks or methods to external source for receipt, processing, or other form of use. In one particular typical format and method, the information is communicated via picture archiving and communication system (PACS) that has become ubiquitous for storing and communicating radiologic imaging information. In addition to the archive file with DDF and stored MRS data, accompanying MRI images may also be stored and communicated therewith, e.g. in standardized "digital imaging and communications in medicine" or "DICOM" format.

The data transfer described may be to a local computer processor for processing, or more remotely such as via the web (typically in secure format). In alternative to data transfer of acquired MRS data pre-processing to an external system for post-processing as described above, e.g. MRS signal processor and diagnostic processor aspects of this disclosure, all or a portion of the various aspects of the present embodiments may be installed or otherwise integrated within the MR system itself, e.g. a computer based controller or processor embedded therewithin or otherwise connected thereto, for operation prior to packaging results for output (and any remaining portions might be performed peripherally or more remotely).

DDD-MRS Signal Processing

Figure 7:
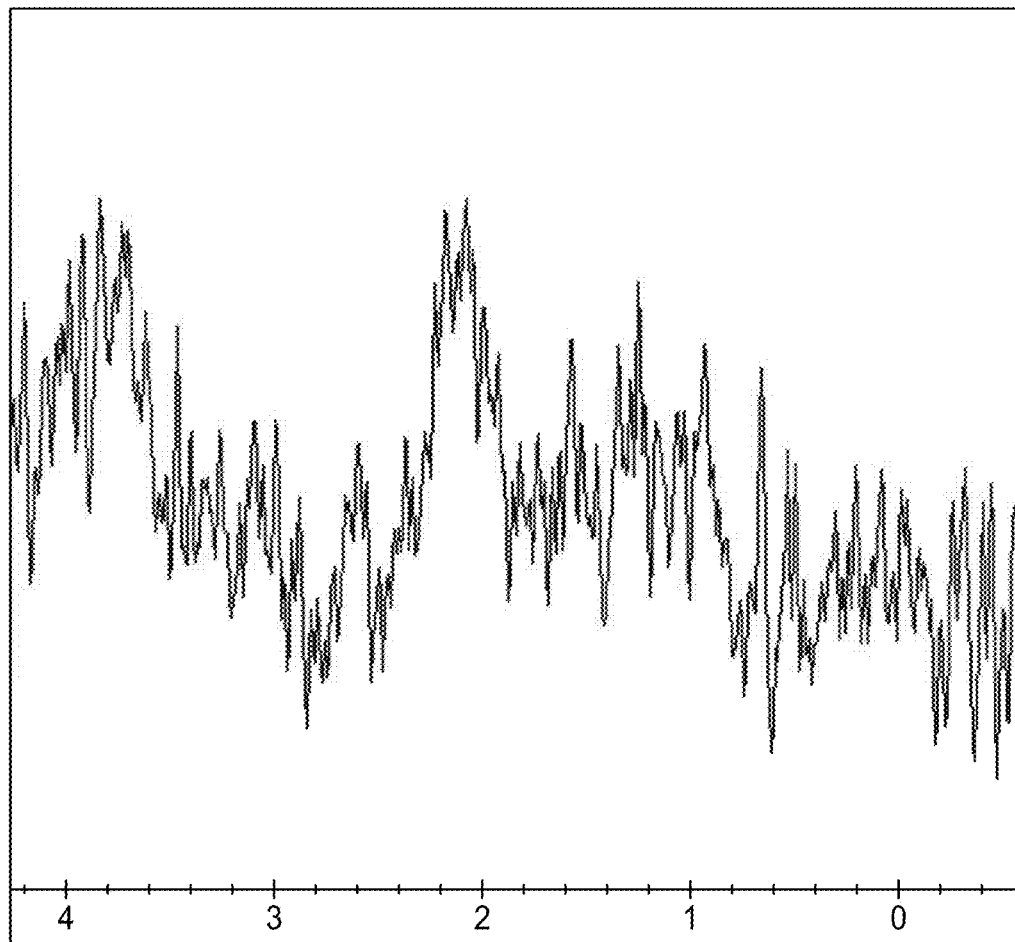
FIG. 7 shows a graphical plot of an MRS absorption spectrum from an MRS pulse sequence acquisition from a lumbar disc using a 3T MR system, and which is produced from the transform of the complex data as the output average after combining all of 6 activated acquisition channels and averaging all frames, such as typically provided in display by a commercially available MRS system, and is generated without applying the various signal processing approaches of the present disclosure.
Figure 8:
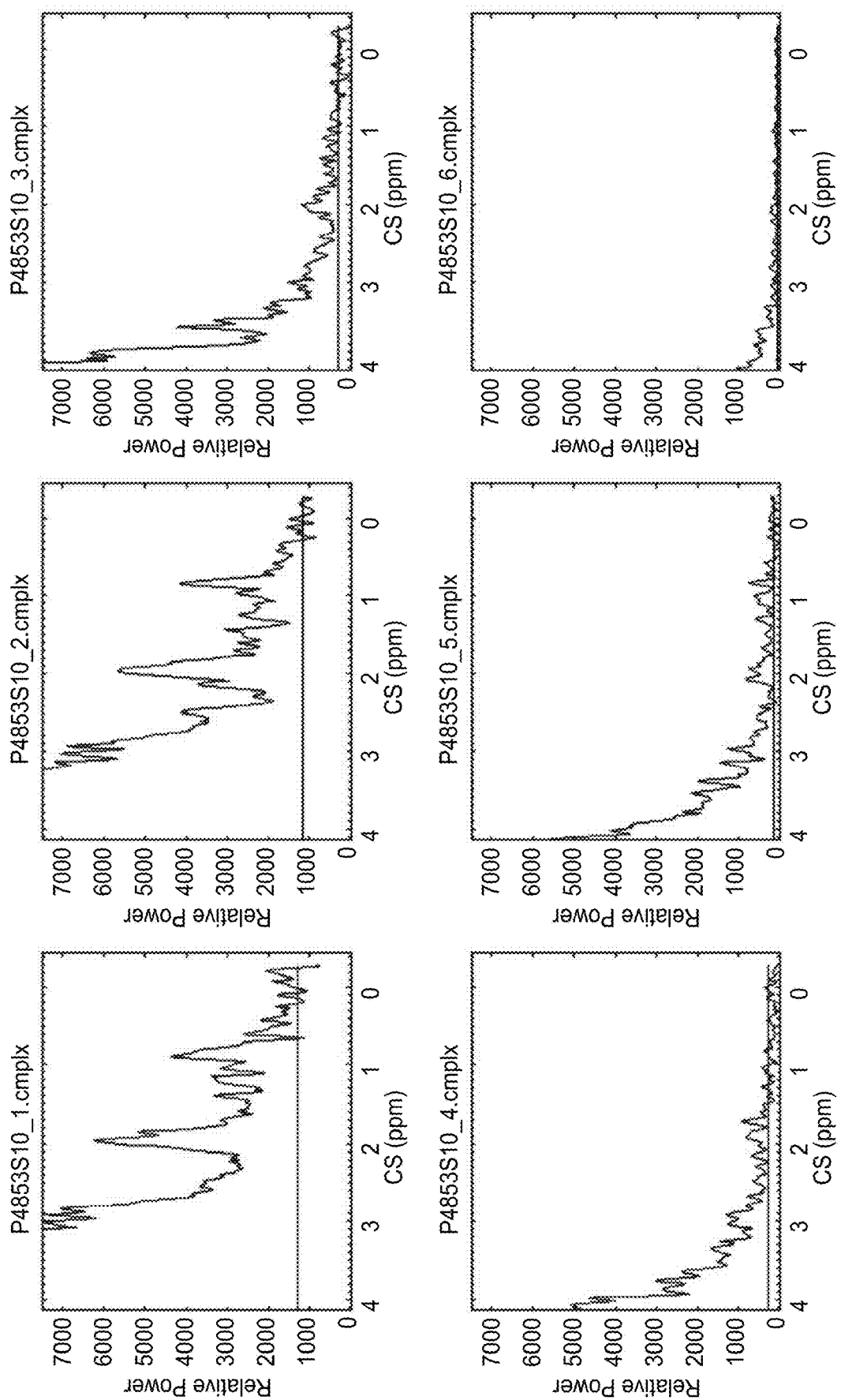
FIG. 8 shows a graphical display of individual channel MRS spectra of all uncorrected channels of the same MRS acquisition featured in FIG. 7, and is shown as "real part squared" representation of the acquired MRS spectral data prior to combining the channels, and is also prior to pre-processing according to the signal processing approaches of the present disclosure.

Upon the acquisition of all MRS data from a DDD-MRS pulse sequence exam, according to certain aspects of the present embodiments, the MR scanner system will typically provide the operator with a spectral image that is the averaged combination of all frames across all the 6 detection channels (coils). An example of such a waveform from an MRS pulse sequence exam acquired for an ROI in a disc nucleus via a GE Signa 3T MR system is shown in FIG. 7, which shows a typical scanner-processed spectral signal plot of combined, averaged channels. FIG. 8 shows the magnitude only (no correction) MRS spectral images of each of the six channels which are aggregated to form the output from the example MR system as shown in FIG. 7, and thus this raw uncorrected individual channel spectral data output provides the input to the DDD-MRS signal processor of the present embodiments.

Figure 9A:
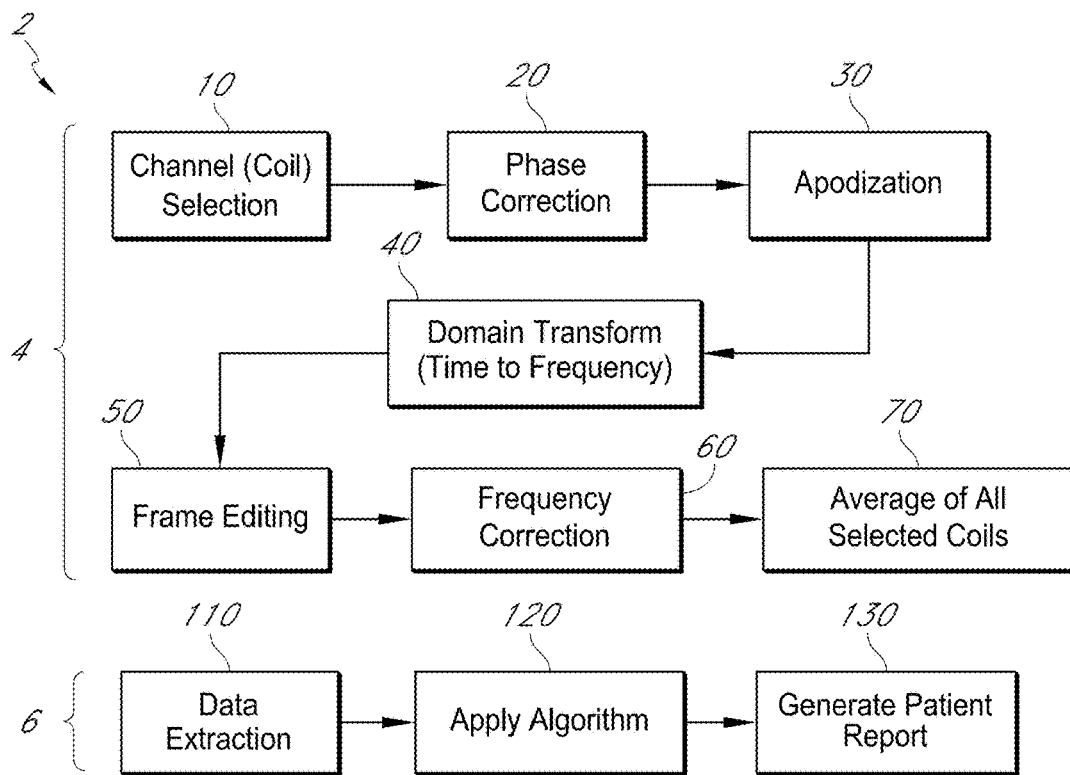
FIG. 9A shows a schematic flow diagram of one DDD-MRS processor configuration and processing flow therein, first operating in DDD-MRS signal processor mode by conducting optimal channel (coil) selection, phase correcting, then apodizing, then transforming domain (from time to frequency), then frame editing (editing out poor quality frames while retaining higher quality), then frequency error correction (correcting for frequency shifts), then averaging of all selected coils, and then followed by a DDD-MRS diagnostic processor and processing flow that comprises data extraction related to MRS spectral regions of diagnostic interest, then applying the diagnostic algorithm, then generating a diagnostic patient report.
Figure 9B:
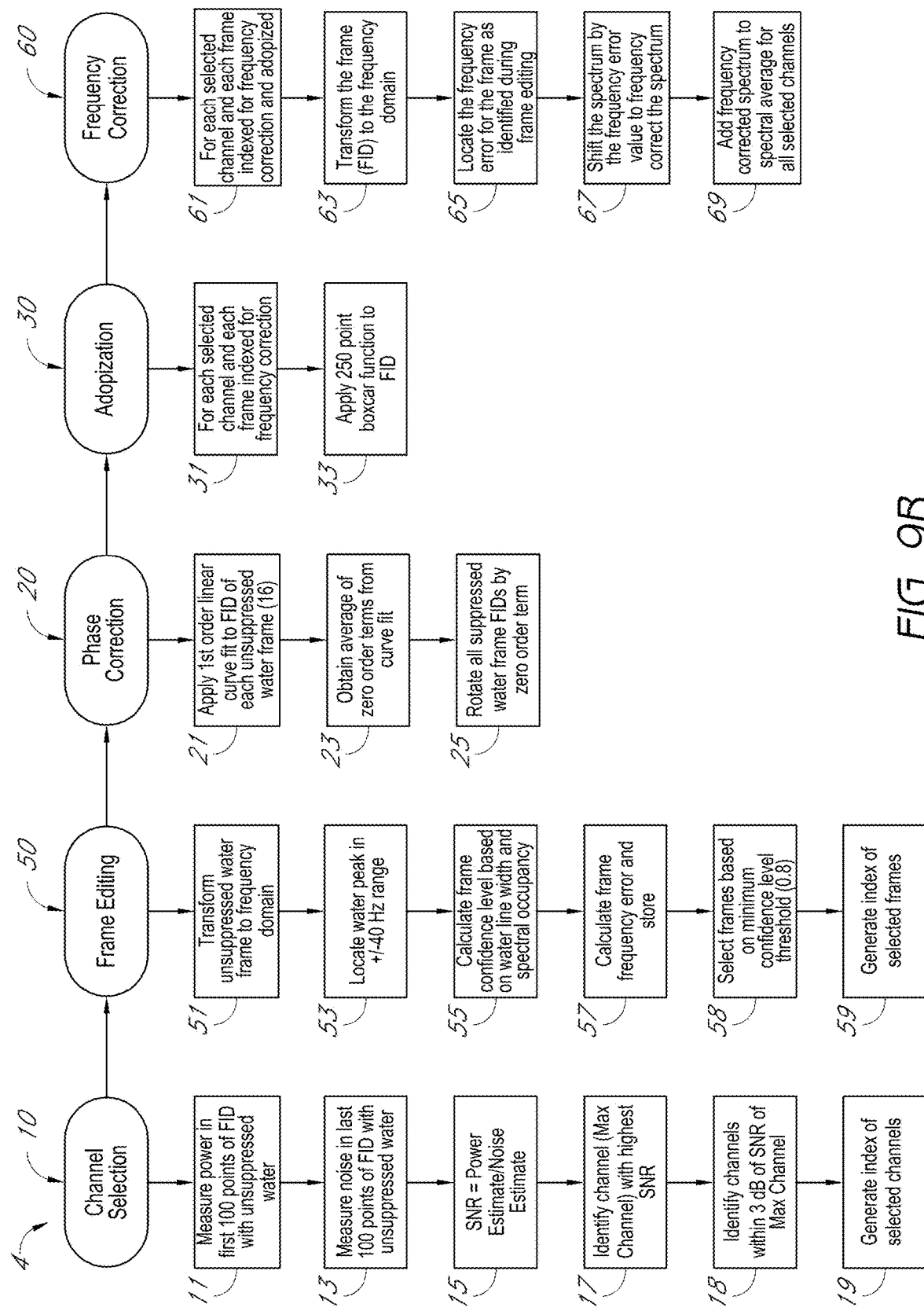
FIG. 9B shows a schematic flow diagram of further detail of various component parts of the DDD-MRS signal processor and respective steps taken thereby as shown more generally in FIG. 9A.
Figure 9C:
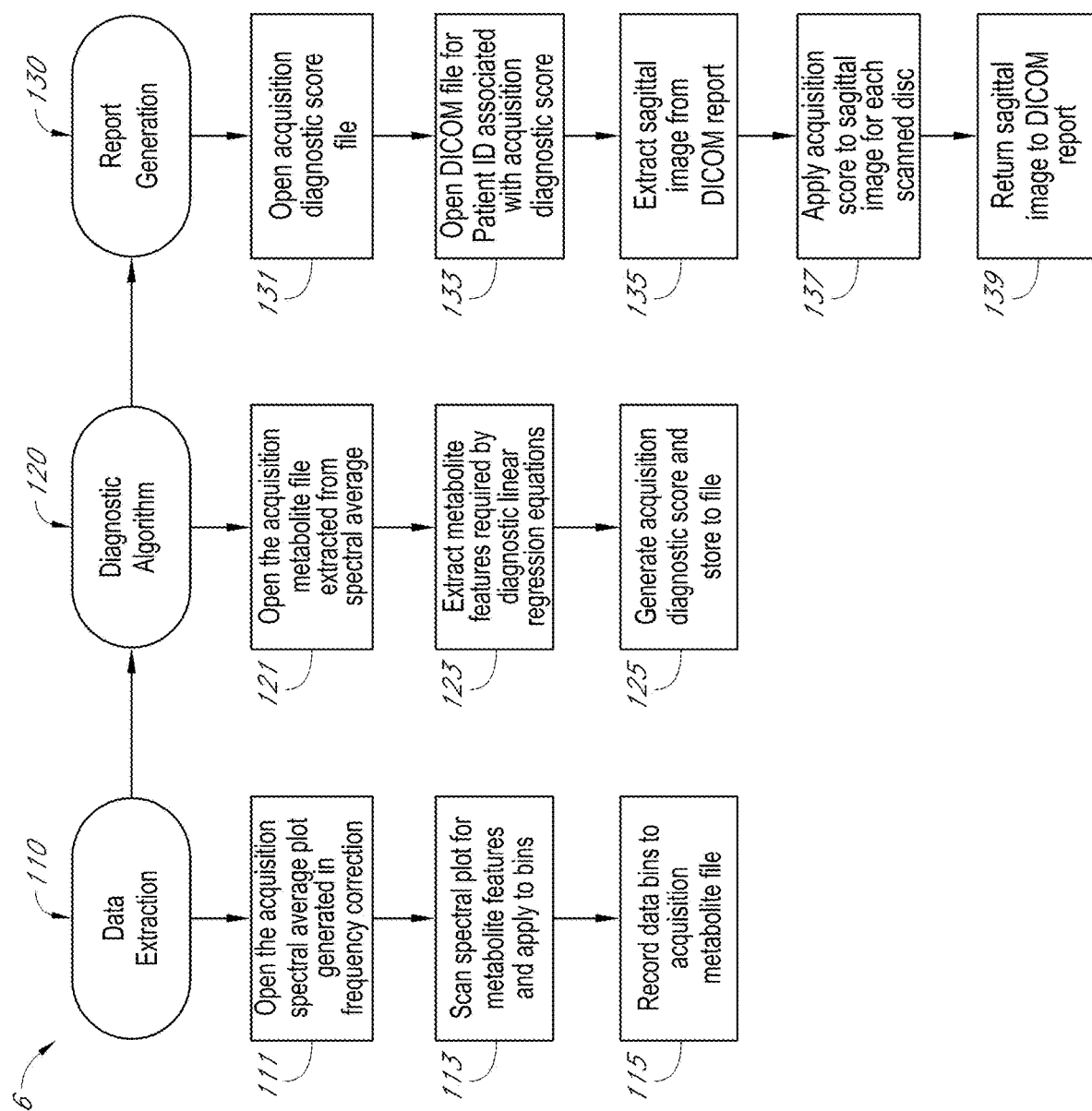
FIG. 9C shows a schematic flow diagram of further detail of various component parts of the DDD-MRS diagnostic processor and processing flow taken thereby as also shown more generally in FIG. 9A.

According to one highly beneficial mode, the DDD-MRS signal processor is configured to conduct a series of operations in temporal fashion as described herein, and as shown according to the present detailed embodiments in the flow charts illustrated in general to increasing detail for the various component modes and operable steps in FIGS. 9A-C. More specifically, FIG. 9A shows a general schematic overview for the flow of a diagnostic system 2 that includes a signal processor 4 and a diagnostic processor 6. Signal processor includes various sub-components and processors that carry out certain steps, such as a channel selector that conducts channel or "coil" selection step 10, phase corrector that does phase correction step 20, apodizer that conducts apodizer step 30, domain transformer that conducts the domain transform step 44 such as from time domain to frequency domain, frame editor that conducts frame editing steps 50, frequency corrector that conducts frequency correction steps 60, and channel combiner that conducts combining or averaging steps 70 to aggregate retained channels into one final post-processed spectral results (not shown). Following signal processing steps 6, a diagnostic processor conducts diagnostic processing of the signal processed signals through data extraction steps 110, diagnostic algorithm application steps 120, and patient or diagnostic report generation 130. While this configuration is considered highly beneficial, these same or similar tasks may be performed in different order, as would be apparent to one of ordinary skill.

For illustration, FIGS. 9B-C show further details regarding some of these specific steps, and also illustrate a different order than has been shown and referenced to FIG. 9A. More specifically, the signal processor 4 in shown to include the main primary steps shown in FIG. 9A, but in finer detail and different order. It some embodiments, the steps shown in FIGS. 9A-C may be performed in an order different than those shown in FIGS. 9A-C. Also, in some embodiments, steps that are shown in FIGS. 9A-C can be omitted, combined with other steps, or divided into additional sub-steps. Additionally, in some cases, additional steps not specifically shown in FIGS. 9A-C can be performed in addition to the steps shown in FIGS. 9A-C.

Channel selection includes the following steps: signal power measurement step 11 measures signal power for SNR calculation, as shown here in the specific embodiment in first 100 points of FID with unsuppressed water. Noise power measurement step 13 measures noise in the last 100 points, for example, of the FID with unsuppressed frames. SNR estimate 15 is then conducted, at which point thereafter channel selection step 17 is conducted per the channel with the maximum or highest signal. Channel selection includes an additional step 18 where additional channels are selected if within range of the strongest, e.g. about 3 dB. Upon completing channel selection, an index of selected channels is generated (step 19).

Frame editing operation 50 is also shown, with transformation of unsuppressed water frame to frequency domain 51, locate water peak in +/−40 Hz per peak location step 53, frame confidence level calculation 55, frame frequency error and store 57, and actual frame selection step 59 based upon minimum confidence level threshold (e.g. 0.8) Phase correction 20 is also done per applying 21 $1^{st}$ order linear curve fit to the FID of each unsuppressed water frame (e.g. n=16), obtaining average of zero order terms from the curve fit 23, and rotate 25 all suppressed water frame FIDs by zero order term. Apodization 30 includes for each selected channel and each frame indexed for frequency correction 31, then apply 250 point boxcar function to the FID (step 33). In addition, frequency correction 60 entails for each selected channel and each frame indexed for frequency correction and apodization 61, transform 63 the frame (FID) to the frequency of domain, and locate the frequency error 65 for the frame as identified during frame editing. The spectrum is shifted 67 by the frequency error value to frequency correct the spectrum. Step 69 adds frequency corrected spectrum to many to spectral average for all selected channels.

As also shown in FIG. 9C for the diagnostic processor 6, data extraction 110 involves opening 111 the acquisition spectral average lot generated in frequency correction, scan step 113 of spectral plot for metabolite features and apply to bins, and record data bins to acquisition metabolite 115. The diagnostic algorithm 120 itself involves opening the acquisition metabolite file extracted from spectral average 121, extract 123 metabolite features required by diagnostic linear regression equations, and generate 125 acquisition diagnostic score and store to file. Report generation 130 includes open acquisition diagnostic score fill 131, open DICOM file 133 for Patient ID associated with acquisition diagnostic score, extract 135 sagittal image from the DICOM report, apply 137 acquisition score to sagittal image for each scanned disc, and return sagittal image to DICOM report 139.

According to the current example embodiment, a first operation of the DDD-MRS processor assesses the SNR of each channel. This is done to determine which channels have acquired sufficiently robust signal to use for data processing and averaging. The result may produce one single channel that is further processed, or multiple channels that are later used in combination under multi-channel averaging. In the majority of acquired signals observed according to the Examples disclosed herein, only a subset of the 6 lumbar acquisition channels were determined to be sufficiently robust for use. However, the standard system output averages all 6 channels. Accordingly, this filtering process alone—removing poor signal channels and working with only stronger signal channels—has been observed to dramatically improve processed spectra for diagnostic use in some cases. While various techniques may be suitable according to one of ordinary skill, and thus contemplated herein, according to the present illustrative embodiment the SNR is calculated by obtaining the average power in the first 100 data points (the signal) and the last 100 points (the noise) of the unsuppressed water FID. The unsuppressed water FIDs signals are used because of the strong water signal. The channel with the greatest SNR, and channels within a predetermined threshold variance of that strongest one, e.g. within about 3 dB for example, are preserved for further processing and as candidates for multi-channel averaging—other channels falling below this range are removed from further processing (though may be used for further processing, yet removed from final results).

Further examples and embodiments for evaluating relative channel quality are provided as follows. One additional indication of channel quality that may be observed and used is the line width of the unsuppressed water signal based on the averaged frequency and phase corrected FFTs of the coil channels with the highest SNRs. This is computed to serve as a general indicator of signal quality as determined by the quality of the shimming process and to provide an estimate of the resolution we should expect in the chemical shift spectrum. Another indication of channel quality is the degree of water suppression. This has utility in determining the optimum degree of water suppression to apply in the acquisition protocol. The water suppression should leave enough residual water signal to use as a reference to reliably perform frame-by-frame frequency correction but not so much that water signal artifacts affect the chemical shift spectrum in the metabolite areas of interest. Such artifacts include simple spectral leakage as well as phase modulation sidebands due to gradient vibration induced $B_o$ modulation.

Further to the present embodiments and per further reference to FIGS. 9A-B, a second operation conducted by the DDD-MRS processor is phase alignment, or phase error correction. This is performed to support coherent summation of the signals from the selected channels and the extraction of the absorption spectra. This is often necessary, or at least helpful, because in many cases a systemic phase bias is present in the different channels. This systemic phase bias is best estimated by analysis of the data frames (e.g. about 16 frames in the DDD-MRS pulse sequence of the current illustrative detailed embodiments) collected at the beginning of each scan without water suppression. This operation, according to one mode for example, analyzes the phase sequence of the complex samples and fits a polynomial to that sequence. A first-order (linear) fit is used in one further illustrative embodiment. This is believed to provide a better estimate of the offset than simply using the phase of the first sample, as is often done. This is because eddy current artifacts, if present, will be most prominent in the first part of the frame. The offset of the linear fit is the initial phase. Observation has indicated that the first 150 samples (75 mS at the typical 2000 samples-per-second rate) typically provide reliable phase data. The fit is performed on each of the water-unsuppressed frames for each channel and the mean phase of these is used to phase adjust the data for the corresponding channel. This is accomplished by performing a phase rotation of every complex sample in each frame to compensate for the phase offset as estimated above, setting the initial phase to zero.

Figure 10:
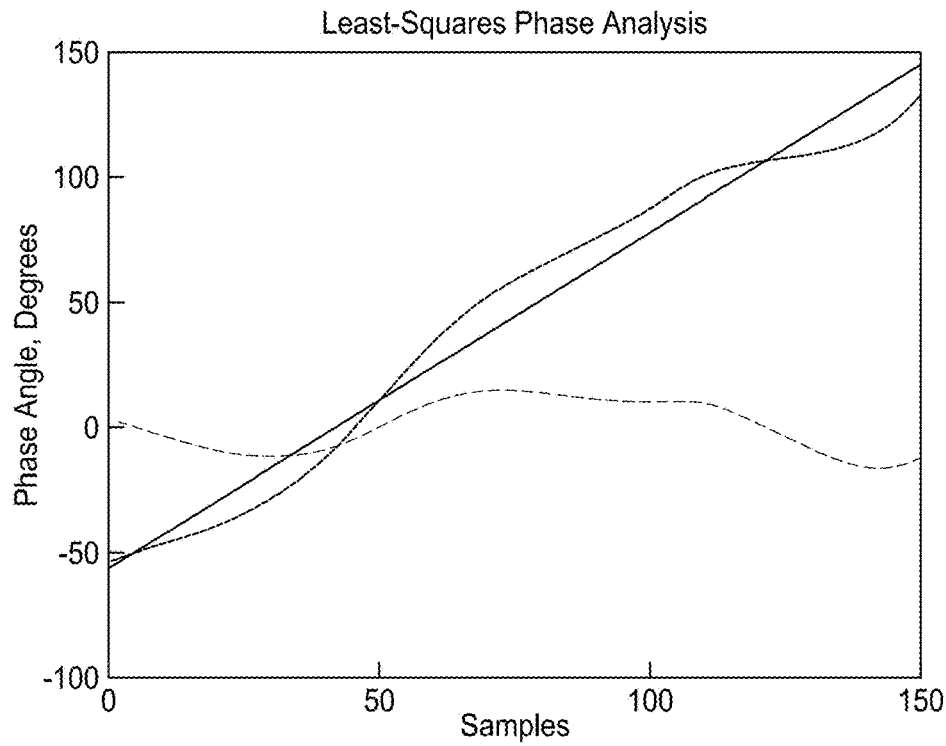
FIG. 10 shows a plot of phase angle pre- and post-phase correction for an acquisition series example, and as is similarly applied for a DDD-MRS acquisition such as for a disc according to certain aspects of the present disclosure.

The offset of the linear fit is the phase bias with respect to zero and the slope is the frequency error with respect to perfect center-tuning on the water signal. Only the offset portion of the curve fit is used to phase correct the data. An illustrative example of this is shown in schematic form in FIG. 10, which shows phase angle before and after phase correction. The phase angle signal is shown as the dotted line. The solid line is the least squares fit estimate. The dashed line is the phase and frequency corrected signal, though the offset component is used to phase correct and frequency correction is performed subsequently in the temporal process according to the present DDD-MRS processor embodiment.

Figure 11:
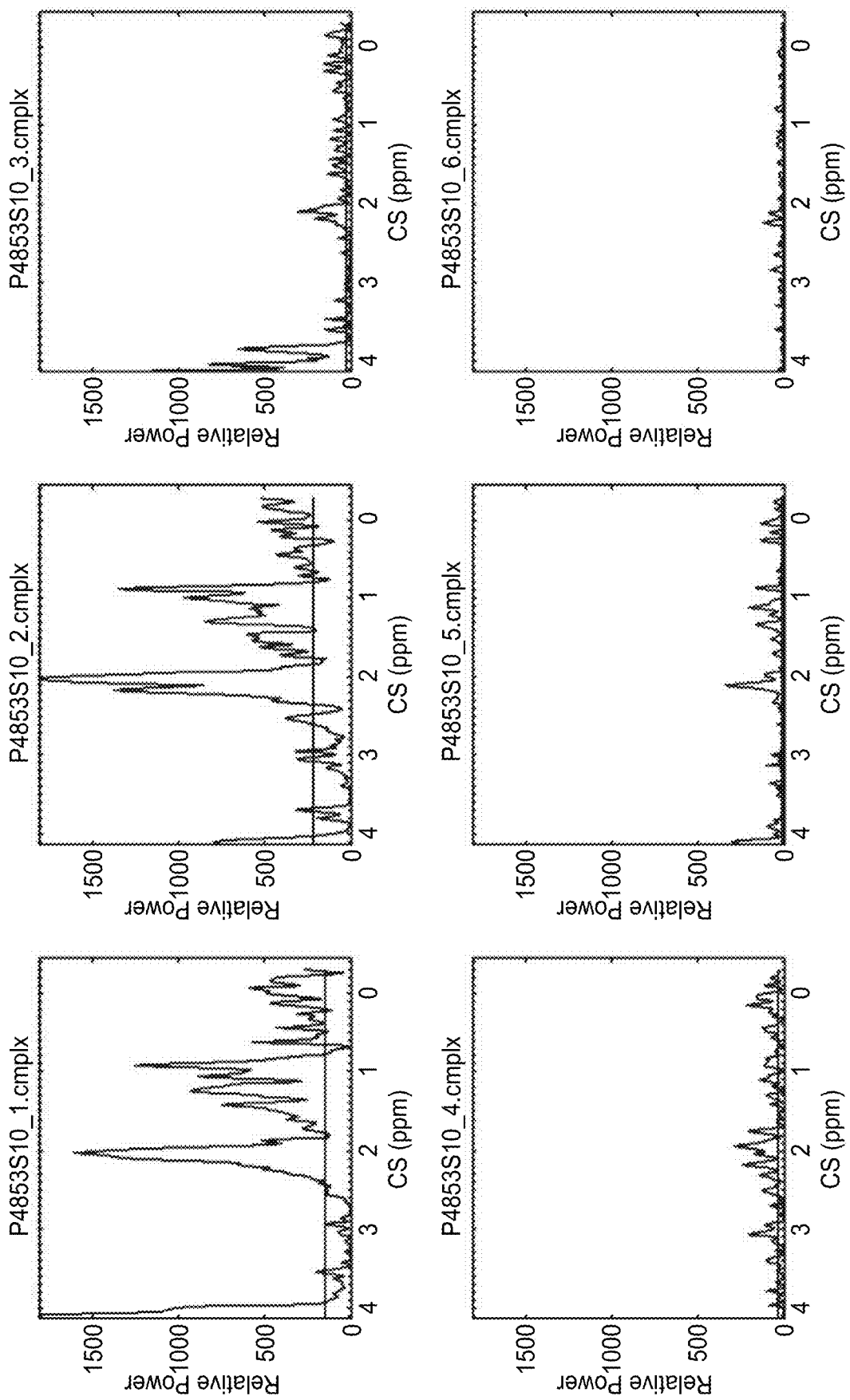
FIG. 11 shows the serial acquisition frame averages for each of 6 individual acquisition channels as shown in FIG. 8, but after phase correction consistent with the signal processing flow shown in FIGS. 9A-B and phase-correction approach illustrated in FIG. 10.
Figure 12:
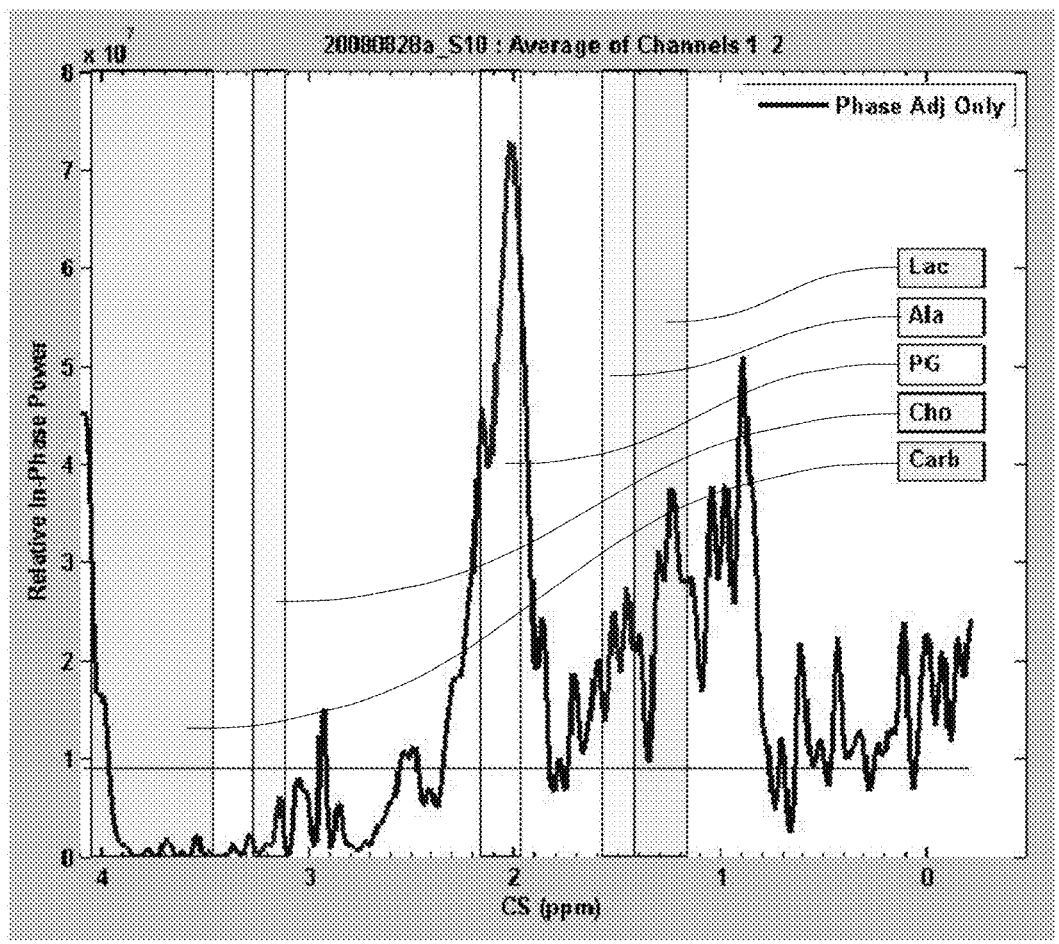
FIG. 12 shows the frame-averaged real part squared MRS spectrum after combining the strongest two channels (channels 1 and 2) selected among the 6 phase-corrected frame-averaged channel spectra shown in FIG. 11 using a channel selection approach and criterion according to a further aspect of the current disclosure, but without frequency correction.

The real-part squared MRS spectral results of phase correction for each of all the six channels shown prior to correction in FIG. 8 is shown in FIG. 11, with channels 1-3 indicated from left to right at the top, and channels 4-6 indicated from left to right at the bottom of the figure. The averaged spectrum of the selected, phase corrected channels (channels 1 and 2) is shown in FIG. 12, which reflects significant SNR improvement versus the uncorrected all channel average spectrum shown in FIG. 7.

Frame Editing

While it is contemplated that in some circumstances individual MRS acquisition frames may provide some useful information, frame averaging is prevalently indicated in the vast majority of cases to achieve a spectrum with sufficient SNR and interpretable signal at regions of interest for pathology assessment. It is, at most, quite rare that an individual frame will have sufficient SNR for even rudimentary metabolite analysis to the extent providing reliable diagnostic information. Often individual frames along an acquisition series will have such low SNR, or possess such artifacts, that they make no improvement to the average—and in fact may even degrade it. To the extent these "rogue" frames may be recognized as such, they may be excluded from further processing—with only robust frames remaining, the result should improve.

Accordingly, a further mode of the present DDD-MRS processor embodiment utilizes a frame editor to conduct frame editing to identify those frames which vary sufficiently from the expected or otherwise observed acquisition results such that they should be excluded, as is also represented schematically in the flow diagram examples of FIGS. 9A-B. In one aspect of the underlying concern, certain patient motions during an acquisition may result in signal drop-out as well as frequency shifts (e.g. magnetic susceptibility artifact). While involuntary motion, e.g. respiration, is a common cause of frequency shifts, these are typically sufficiently minor and within a range that they are not believed to implicate signal quality other than the shift itself (which can be significant source of SNR degradation, but correctable per the present disclosure). However, other more significant movements (e.g. voluntary) may cause sufficiently significant shifts to seriously degrade the acquired spectrum, beyond merely correctable spectral shifts. For example, such activity may move the voxelated region to include adjacent tissues versus only the intended VOI upon prescription prior to the motion. If the salient artifact is frequency shift, a correction may be applied and the frame can be used to make a positive contribution to the averaged spectrum. If a frame is discarded its contribution is lost, and across sufficient number of discarded frames across a series the result may not include a sufficient number of frames in the average for a reliable SNR in the resulting spectrum. The DDD-MRS processor, according to the current embodiment, analyzes the residual water signal in each frame to determine if it is of sufficient quality to support frequency correction.

Figure 13:
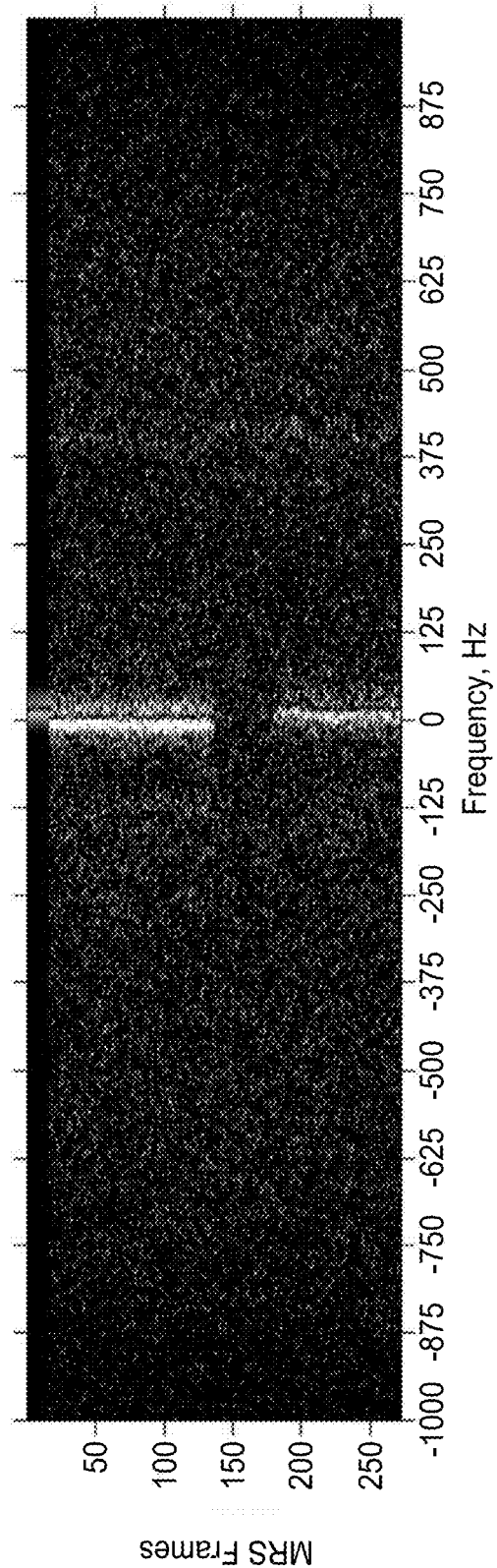
FIG. 13 shows an example of a time-intensity plot for a DDD-MRS acquisition similar to that shown in FIG. 17D for the acquisition shown in FIGS. 7-8 and 11-12, except that the plot of FIG. 13 relates to another MRS pulse sequence acquisition series of another lumbar disc in another subject with corrupted frames midway along the temporal acquisition series in order to illustrate frame editing according to other aspects of the disclosure.

FIG. 13 shows a time-intensity plot which illustrates a scan series with frequency shifts and "drop outs" with SNR changes considered to represent corrupted frames due to patient motion. More specifically, this shows 1 dimensional horizontal lines for each frame, with signal amplitude reflected in "brightness" or intensity (e.g. higher values are whiter, lower are darker), with time across the serial acquisition of the series progressing top to bottom vertically in the Figure. A vertical band of brightness is revealed to the left side of the plot. However, in this particular example, there is a clear break in this band as "drop out" frames. After excluding the "drop out" frames (center of time sequence between about 75 and 175 MRS frames, it was still possible to obtain a high quality final averaged spectrum from this scan using the remaining robust frames, as further developed immediately below.

Figure 14A:
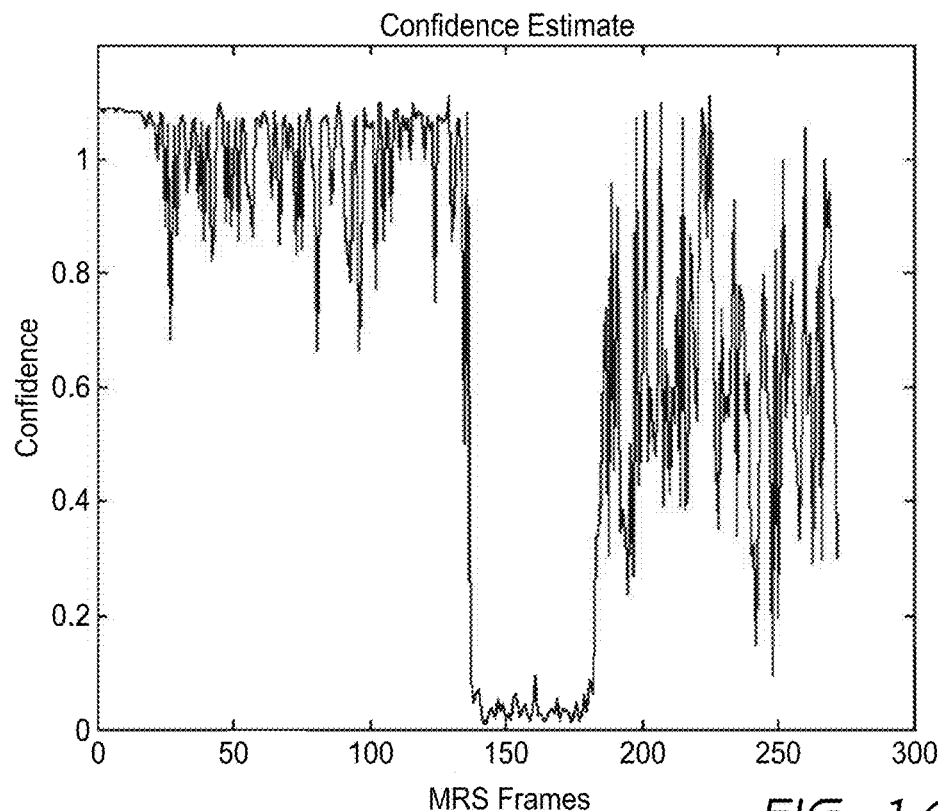
FIG. 14A shows confidence in frequency error estimate vs. MRS frames temporally acquired across an acquisition series for a disc, as plotted for the DDD-MRS series acquisition shown in different view in FIG. 13.
Figure 14B:
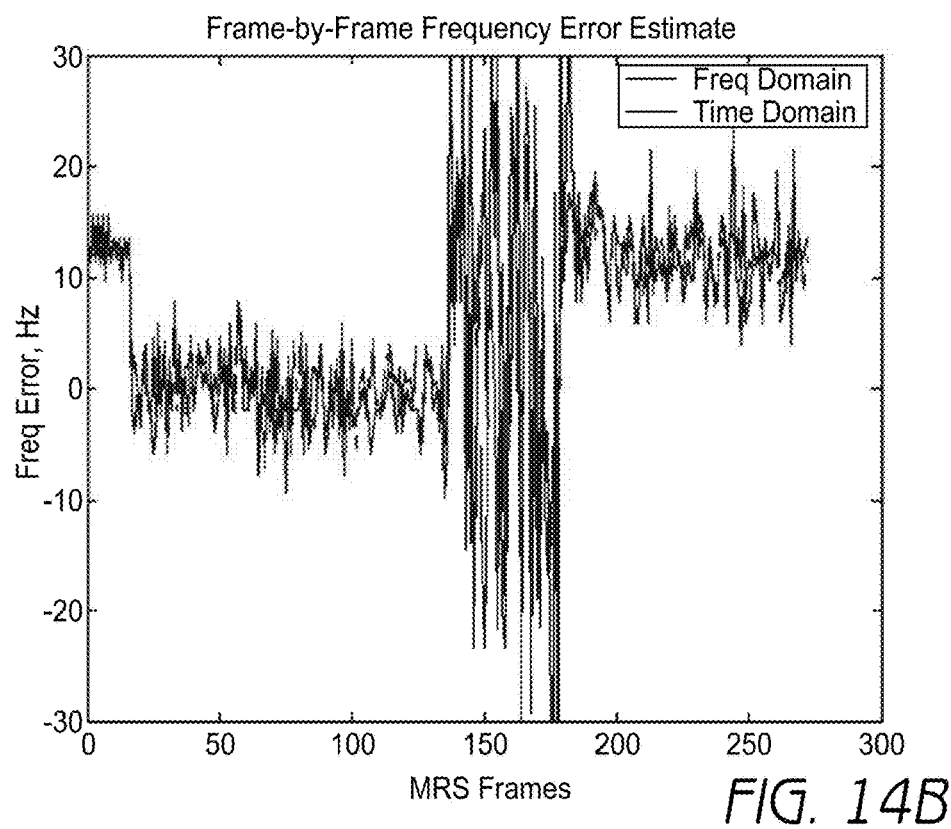
FIG. 14B shows a frame by frame frequency error estimate of the acquisition series featured in FIG. 14A.

FIGS. 14A and 14B show the confidence level estimate and the frame by frame frequency error estimate, respectively, which are used according to the present embodiment for frame editing according to this acquisition series example of FIG. 13. More specifically, FIG. 14A shows the frame by frame confidence level, with confidence level on the Y-axis, and the sequential series of frame acquisitions along a scan indicated along the X-axis. FIG. 14B shows the actual frequency error along the Y-axis, for the same frame series along the X-axis. This is based on analyzing the characteristics of the residual water peak and the noise in a band 80 Hz wide (for 3 T processing, the band would be 40 Hz wide at 1.5 T) around the center-tuned frequency. The largest peak is assumed to be the water signal and the assumption is qualified by the confidence estimate. For the purpose of this example, if the confidence value is above a threshold, i.e. 0.8, the frame is flagged as a candidate for frequency correction and thus "retained." As seen from the plots in FIGS. 14A-B, when the confidence is low, the variance of the frequency error estimate is greatly increased. The final qualification step, per this example, is to determine if there are enough qualified candidate frames to achieve sufficient SNR improvement when averaged. This threshold limit for proceeding with frequency correction (and thus frame editing therefore) has been empirically established as 90 frames meeting the criteria. According to the present embodiments, this has been observed to provide sufficiently robust results per the Examples described herein. It is to be appreciated, however, that other limits may be appropriate in various circumstances. The number of frames required will be based upon the SNR levels achievable from the completed signal processing. This will be paced by SNR of input signal acquisitions to begin with, and performance of other signal processing modes and steps taken with those signals. According to the acquisitions under the Examples disclosed herein, SNR is believed to increase over about 150 frames, and then with little gained typically thereafter, though the 90 frame minimum limit has been observed to provide sufficient results when reached (in rare circumstances). In the event the result drops below the 90 frame limit, the DDD-MRS processor is still configured to proceed with other modes of signal processing, signal quality evaluation, and then diagnostic processor may be still employed—just without the added benefit of the frame editing and frequency error correction.

Further description related to acceptable confidence level estimate approach according to the present disclosure is provided as follows, for further illustration of this embodiment for the frame editing and frequency correction modes of the disclosure. The discrete amplitude spectrum can be analyzed in the range of the center-tuned frequency ±40 Hz for example in the case of a 3T system acquisition, and half this bounded range (e.g. ±20 Hz) for a 1.5T system acquisition. The highest peak is located to determine its width at the half-amplitude point. Next, the total spectral width of all parts of the spectrum which exceed the half-amplitude point of the highest peak are determined. The confidence estimate is formed by taking the ratio of the spectral width of the greatest peak divided by the total spectral width which exceeds the threshold. If there is only a single peak above the threshold, the confidence estimate will be 1.0, if there are many other peaks or spectral components which could be confused with the greatest one, then the estimate will approach 0.0. This provides a simple and robust estimate of the randomness or dispersal of energy in the vicinity of the water peak. Like another approach using entropy measurement, e.g. as described below, this current approach provides at least one desirable characteristic in that it's performance is substantially invariant with amplitude.

Yet another system and method to compute a confidence estimate that also can be appropriate is provided as follows. The spectral entropy is computed by normalizing the spectrum to take the form of a probability mass function. The Shannon entropy or uncertainty function, H, is then computed as follows:

$$H = -\Sigma p_i \log_2 p_i$$

where p=probability, and i=frequency index value (e.g. −40 to +40 hz).

It is to be appreciated that other approaches to quantify randomness or uncertainty of the spectrum may also be suitable for use with the various DDD_MRS signal processor aspects of the present disclosure.

Figure 15:
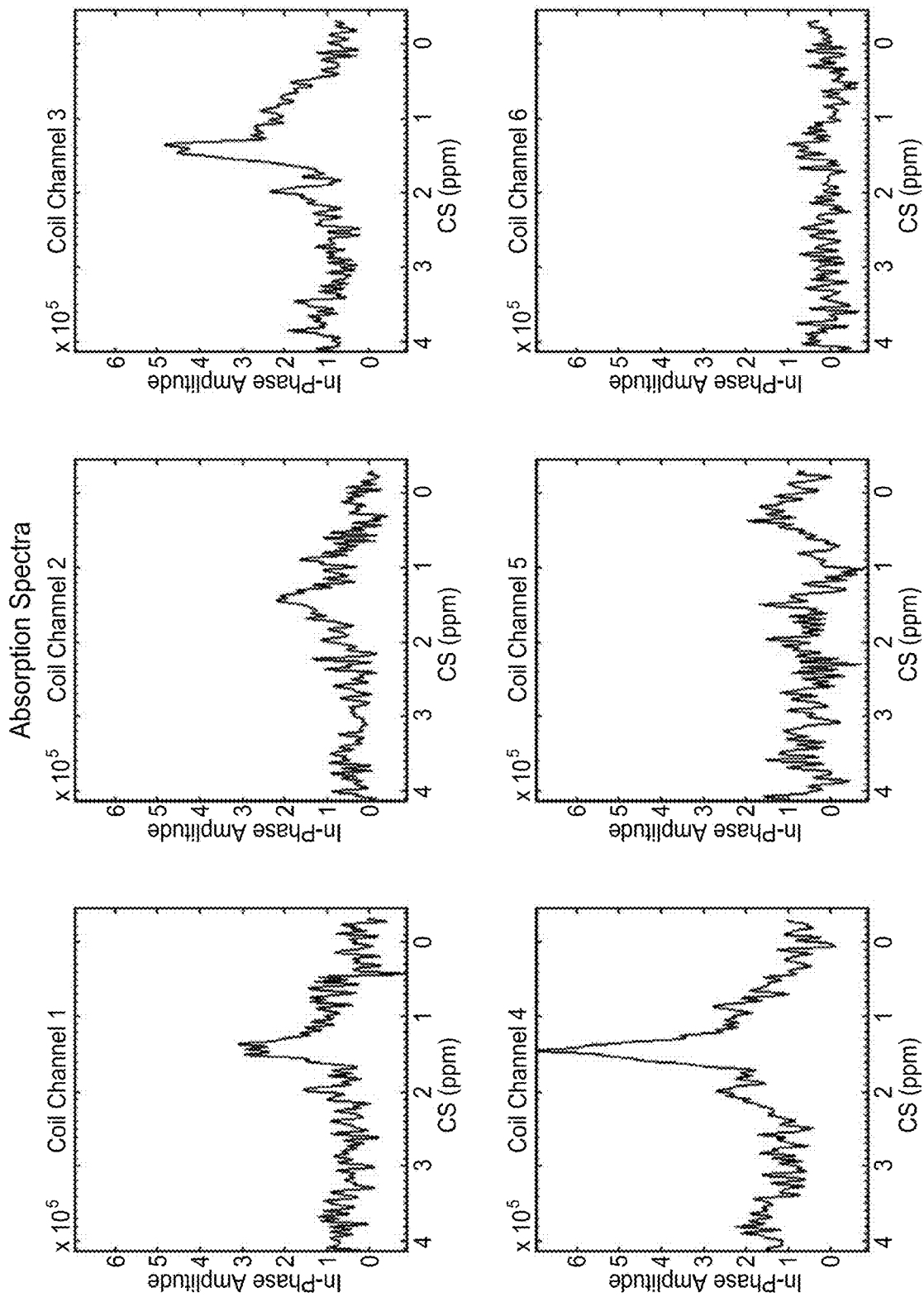
FIG. 15 shows all 6 frame-averaged acquisition channels for the series acquisition conducted on the disc featured in FIGS. 13-14B, prior to correction.
Figure 16A:
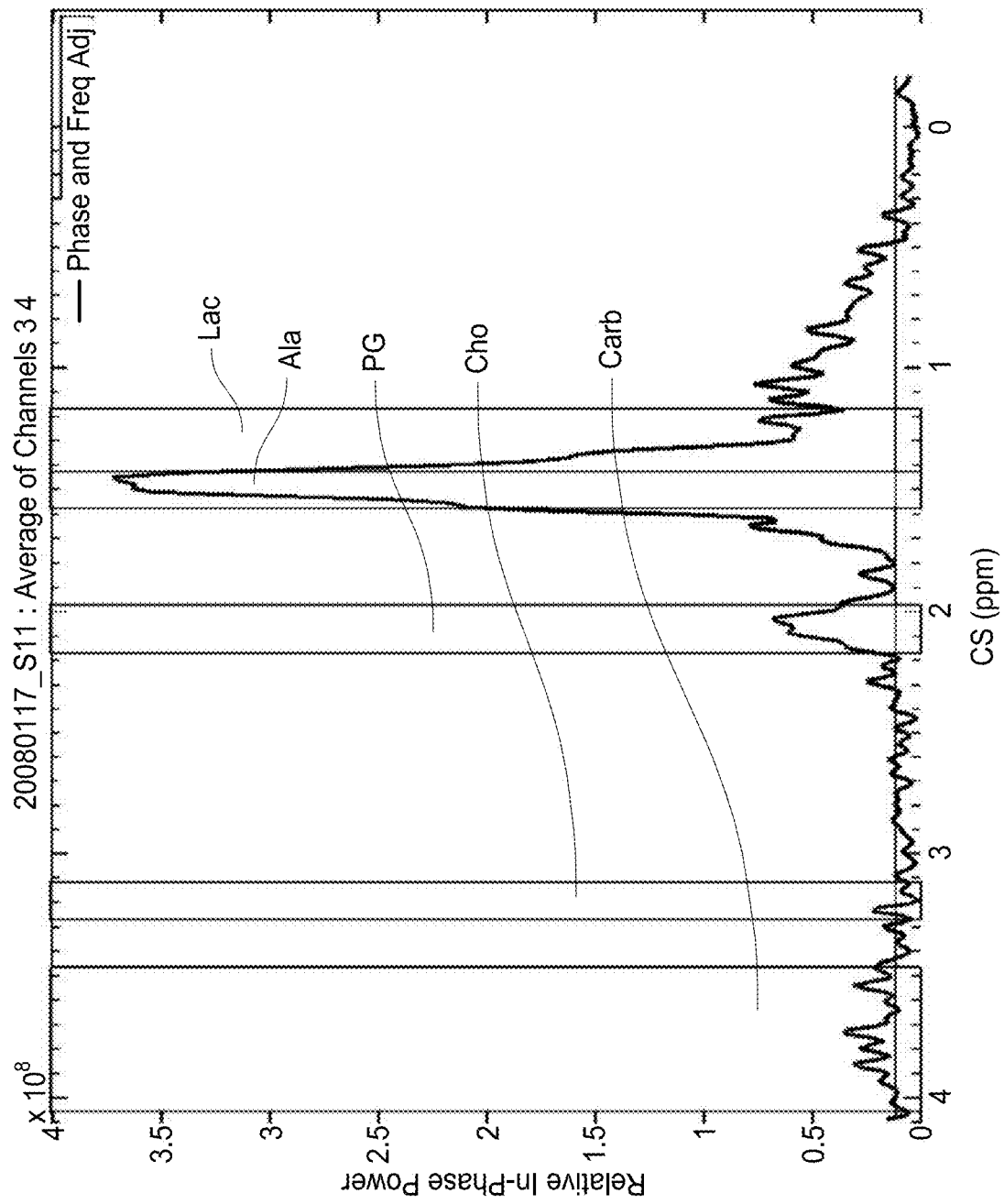
FIG. 16A shows phase corrected, frequency corrected, but not frame edited spectral average combining all of acquired series frames for channels 3 and 4 as combined after optimal channel selection, for the same series acquisition featured in FIGS. 13-15.
Figure 16B:
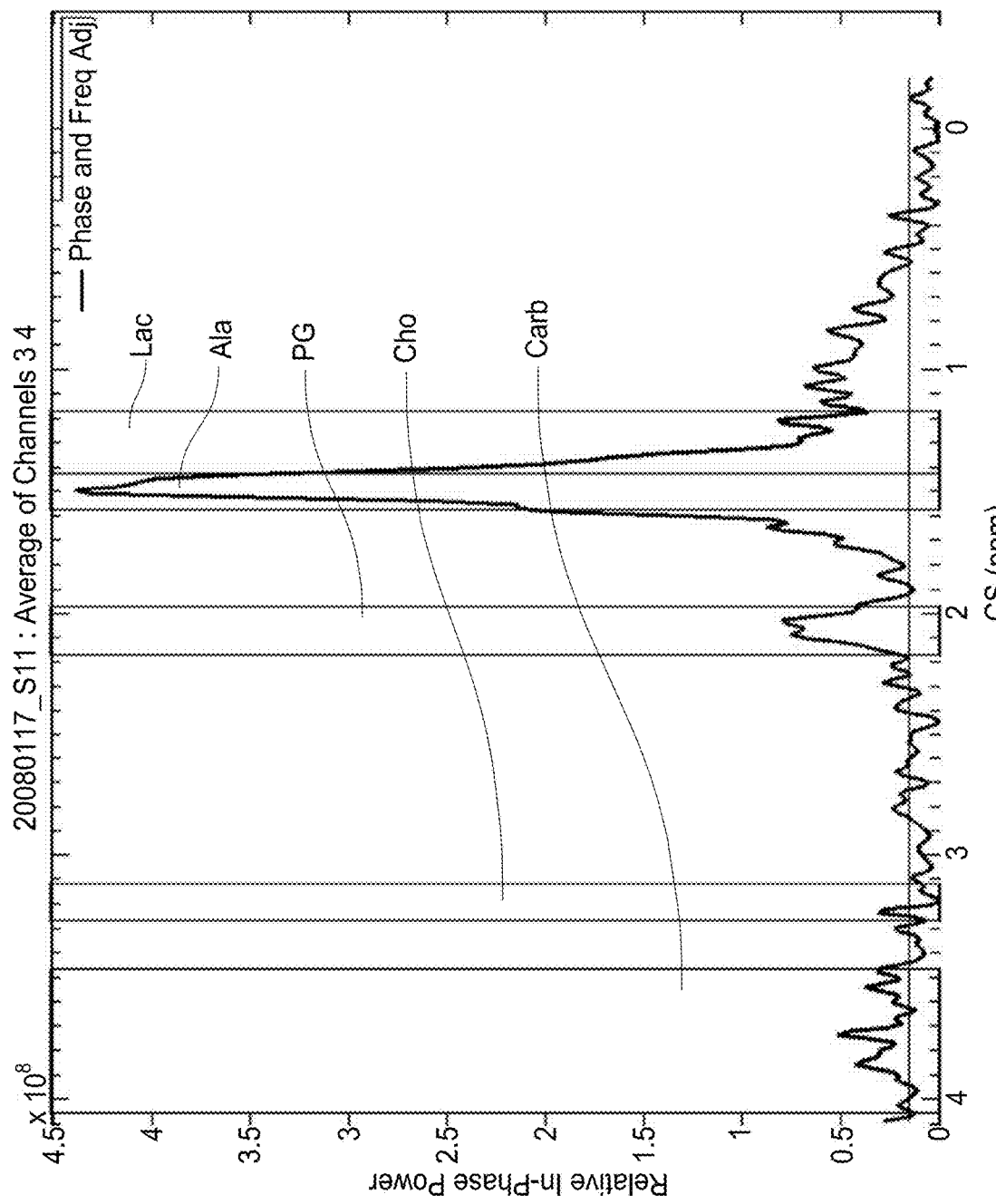
FIG. 16B shows phase corrected, frequency corrected, and frame edited spectral average combining the partial retained frames not edited out from the acquired series for channels 3 and 4 as combined after optimal channel selection, also for the same series acquisition featured in FIGS. 13-15.

For further understanding and clarity re: the ultimate impact frame editing as described herein, the unprocessed absorption spectrum plot for all six channels from the patient (with the compromised frames included as aggregated in the respective channel spectra) in various views in prior Figures is shown for each respective channel in the six indicated panes shown in FIG. 15. The phase and frequency corrected spectrum averaged for selected channels 3 and 4, and for all 256 acquired frames aggregated/averaged per channel, without applying frame editing and thus including the corrupted frames, is shown in FIG. 16A. In contrast, FIG. 16B shows a similar phase and frequency error corrected spectrum averaged for the same selected channels 3 and 4, but for only 143 of the 256 acquired frames aggregated/averaged per channel (the remaining 113 frames edited out), per frame editing applied according to the present embodiments prior to frequency error correction. The peak value in the combined lactate-alanine (LAAL) region of the frame edited spectrum of FIG. 16B is significantly increased—with corresponding increase in SNR—relative to the peak value in the same LAAL region of the non-frame edited spectrum in FIG. 16A (e.g. the peak value increases from about $3.75 \times 10^8$ to about $4.4 \times 10^8$), a nearly 20% SNR increase despite about 40% corresponding reduction in the number of FID frames used.

Figure 17B:
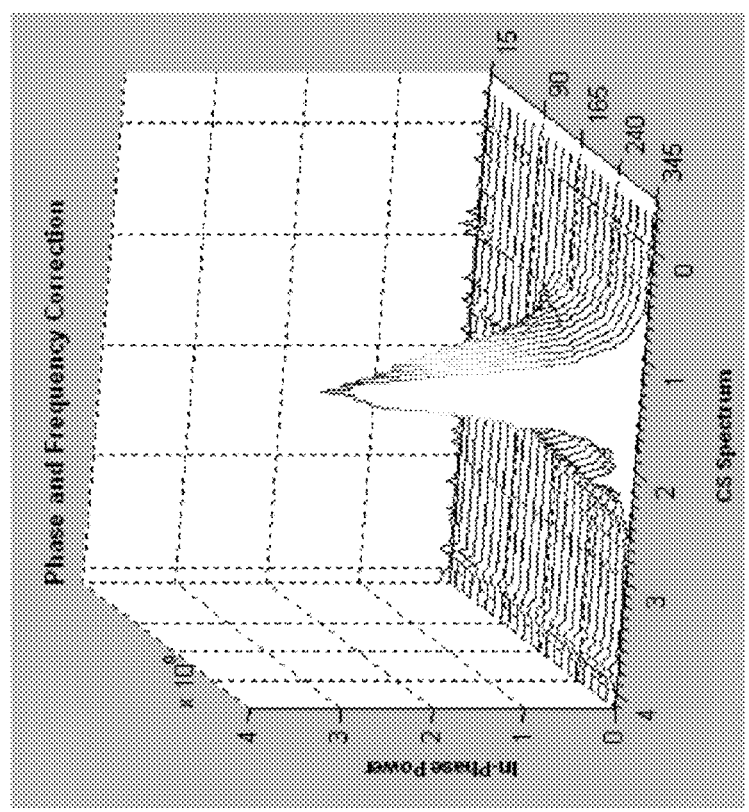
FIG. 17B shows a waterfall plot in 3-dimensions for the DDD-MRS acquisition series shown in FIG. 17A, and shows the chemical shift spectrum as a running cumulative average at discrete points over time of serial frames acquired, with spectral amplitude on the vertical axis.
Figure 17A:
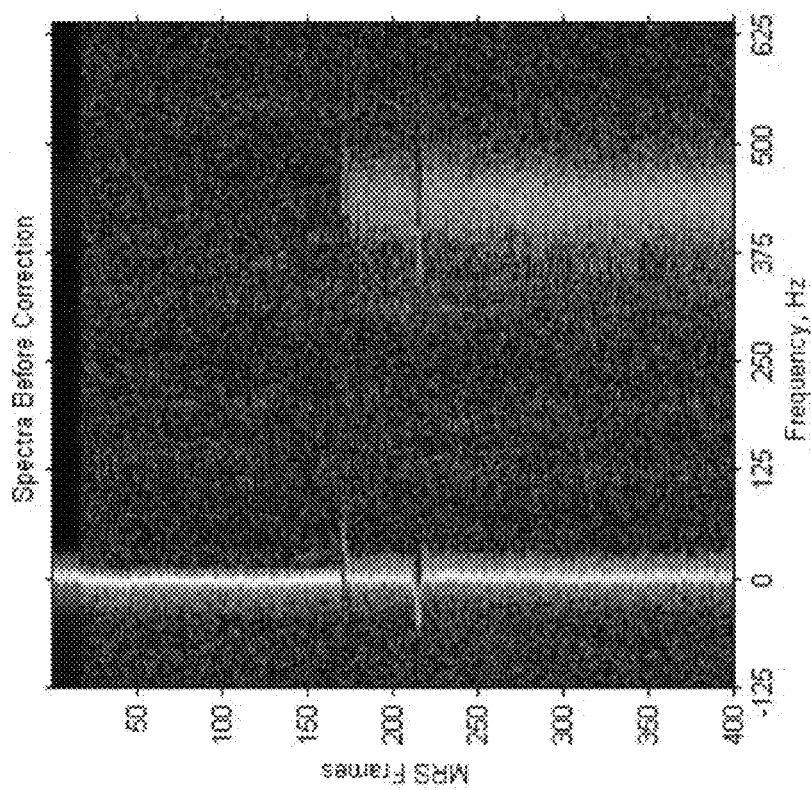
FIG. 17A shows a 2-dimensional time-intensity plot similar to that shown in FIG. 13, but for yet another DDD-MRS acquisition series of another disc in another subject and to illustrate another mode of frame editing aspects of the present disclosure.
Figure 17C:
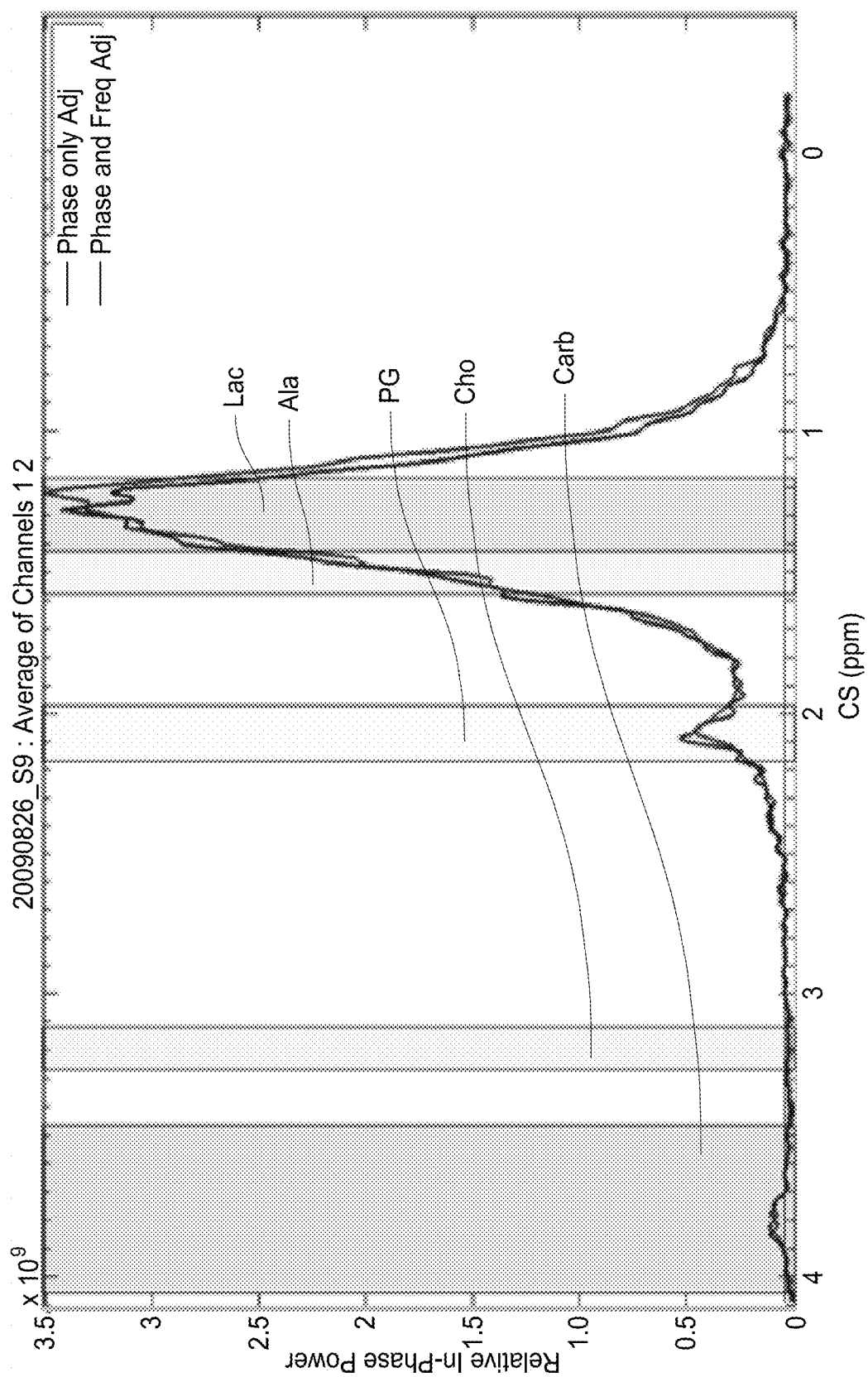
FIG. 17C shows an average DDD-MRS spectrum across the full acquisition series shown in FIGS. 17A-B, without frame editing, and plots both phase only and phase+frequency corrected formats of the spectrum.

While the examples addressed above by reference to FIGS. 13-16B address a highly beneficial embodiment for frame editing based upon water signal, other frame editing embodiments are also contemplated, and many different features of acquired DDD-MRS signals may be used for this purpose. One such further embodiment is shown for example by reference to another DDD-MRS pulse sequence acquisition for another disc in another subject by reference to FIGS. 17A-F. More specifically, per the time-intensity plot shown for this acquisition in FIG. 17A, while the water signal region of the acquired spectral series (bright vertical band on left side of plot) reveals some shift artifact, another bright band appears at a broader region on the right side of the spectra, between about 150 and 200 FID frames into the exam. This region is associated with lipid, and also overlaps with lactic acid (LA) and alanine (AL) regions of diagnostic interest according to the present detailed embodiments and Examples. This is further reflected in FIG. 17B which shows a waterfall plot of running cumulative average of acquired frames in series, where signal amplitude rises in this lipid-related spectral region during this portion of the exam. A resulting average spectral plot for channels 1 and 2 of this acquisition, post phase and frequency correction (again noting water signal did not prompt frame editing to remove many frames) is shown for reference in FIG. 17C. This resulting spectrum has significant signal peak intensity and line width commensurate with lipid signal, and which shrouds an ability to assess underlying LA and/or AL chemicals overlapping therewith in their respective regions. Accordingly, an ability to measure LA and AL being compromised may also compromise an ability to make a diagnostic assessment of tissue based upon these chemicals (as if un compromised by overlapping lipid). However, as this lipid contribution clearly only occurs mid-scan, an ability to edit it out to assess signal without that portion of the exam may provide a robust result for LA and AL-based evaluation nonetheless.

Figure 17D:
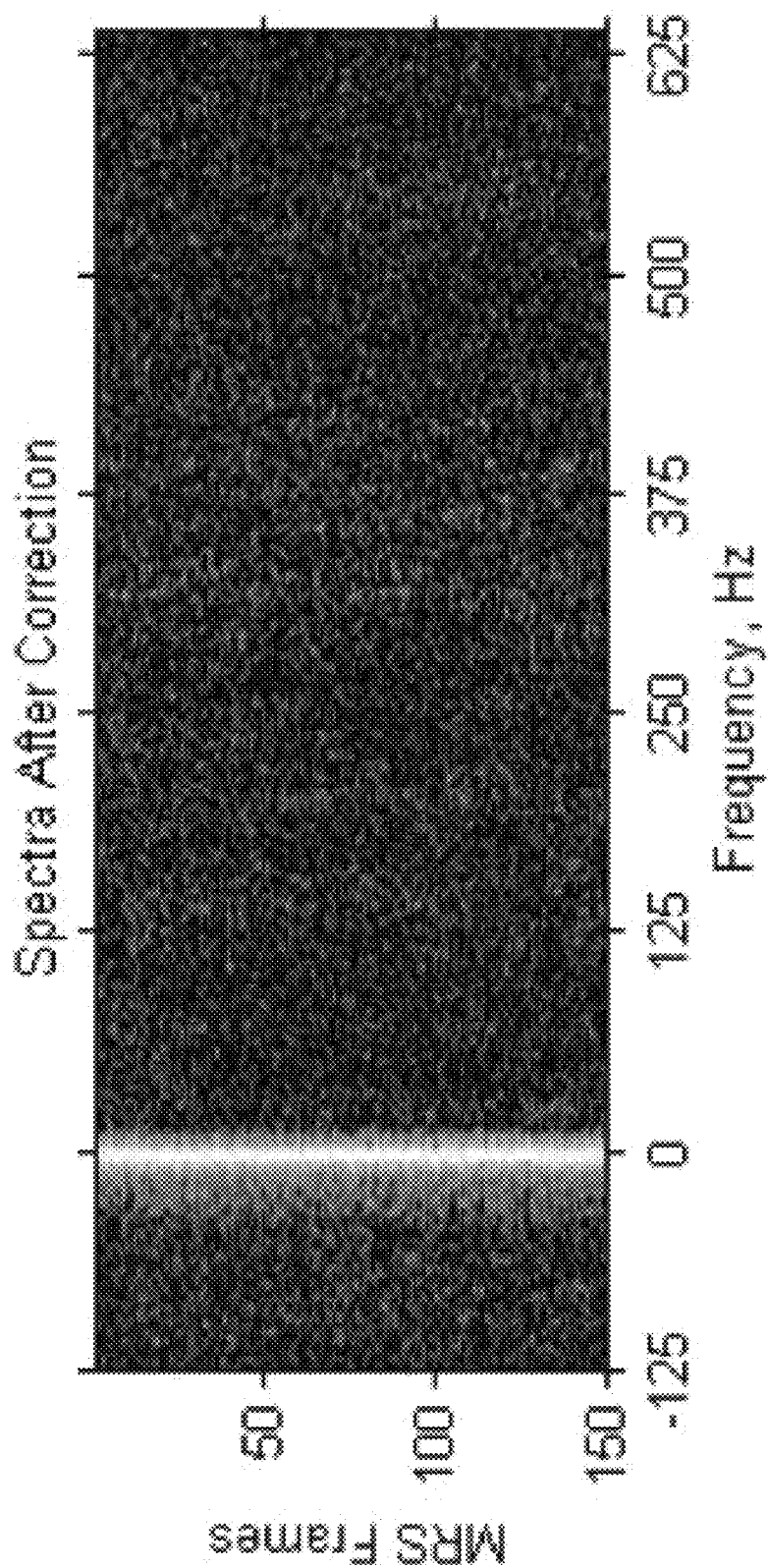
FIG. 17D shows a 2-dimensional time-intensity plot similar to that shown and for the same DDD-MRS acquisition series of FIG. 17A, but only reflecting retained frames after editing out other frames according to the present aspect of the disclosure and referenced to FIGS. 17A-C.
Figure 17E:
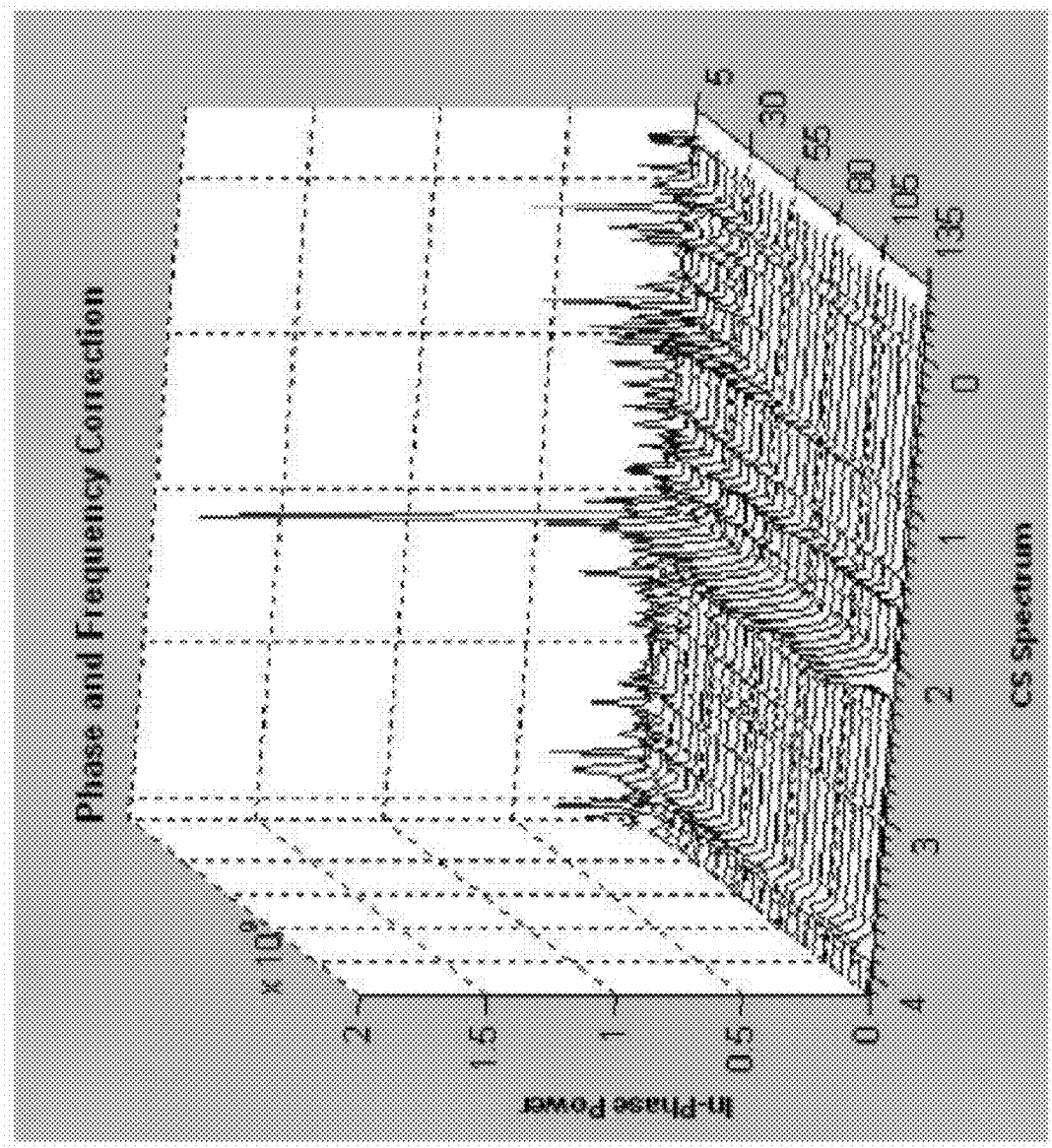
FIG. 17E shows a similar waterfall plot of cumulative spectral averages and for the same DDD-MRS acquisition series shown in FIG. 17B, but according to only the retained frames after frame editing as shown in FIG. 17D.
Figure 17F:
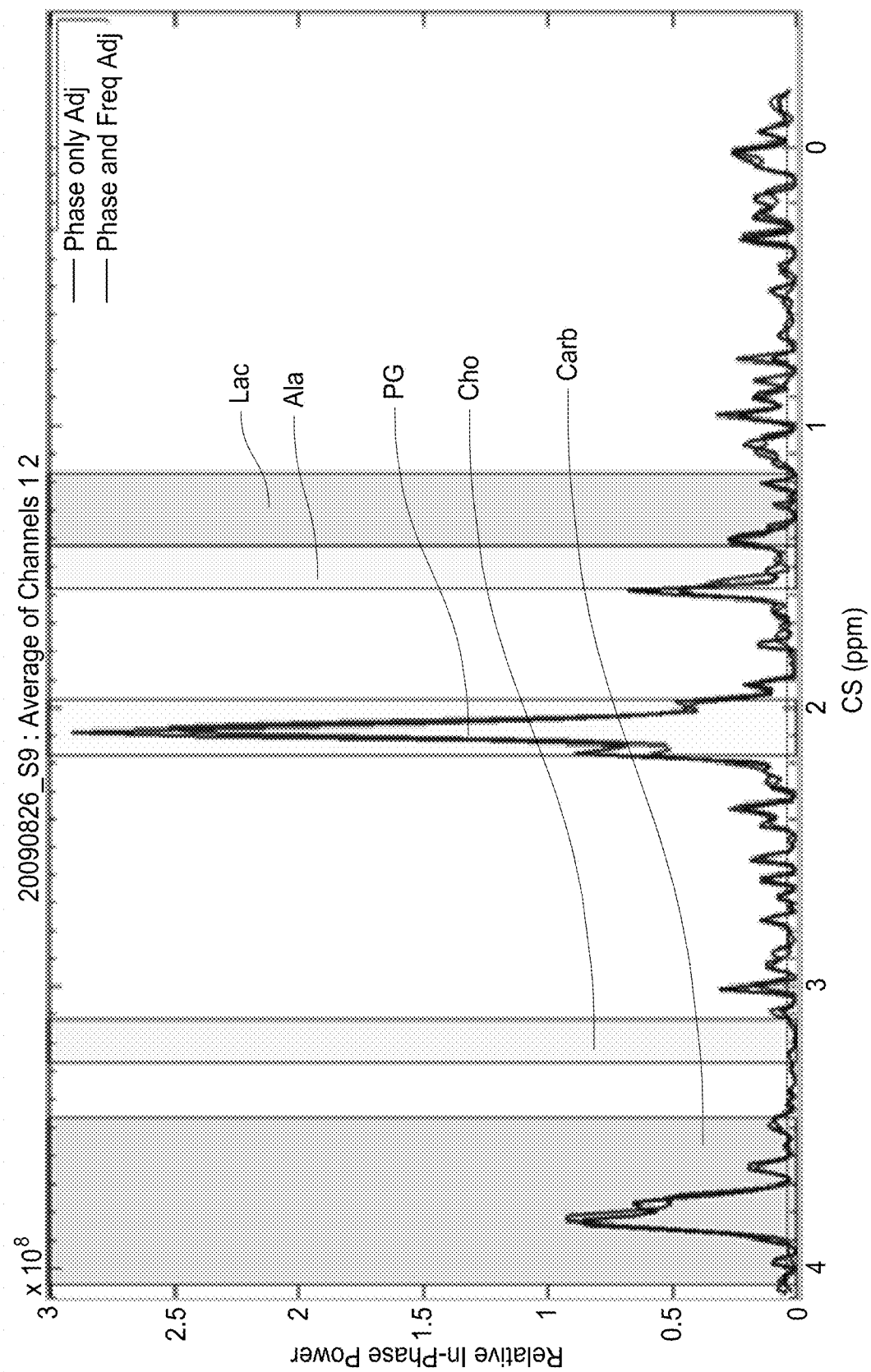
FIG. 17F shows a similar average DDD-MRS spectrum and for the same acquisition series shown in FIG. 17C, but only for the retained frames after frame editing as shown in various modes in FIGS. 17D-E.

This is shown in FIGS. 17D-F where only the first 150 frames of the same acquisition are evaluated, which occur prior to the lipid contribution arising in the acquired signals. As is shown here, no lipid signal is revealed in the time intensity plot of FIG. 17D, or waterfall plot of FIG. 17E, or resulting final spectrum of FIG. 17F, though strong proteoglycan peak is shown with very little (if any) LA or AL in the signal of otherwise high SNR (e.g. per the PG peak). As this example illustrates a DDD-MRS processed acquisition for a non-painful control disc, strong PG signal and little to no LA and/or AL signal is typically expected, and this thus represents a diagnostically useful, robust signal for intended purpose (whereas the prior spectra without editing out the lipid frames may have erroneously biased the results). Accordingly, it is contemplated that a lipid editor may also be employed as a further embodiment for frame editing, with approaches for recognizing lipid signal taken as elsewhere herein described (or as may be otherwise available to one of ordinary skill and appropriately applicable to this applied use).

Frequency Correction

As noted elsewhere herein, during the course of a typical single voxel DDD-MRS series acquisition cycle according to the pulse sequence aspects of the present embodiments (e.g. about 2-4 minutes, depending upon settings chosen for TR and number of frames), frequency errors can occur due to patient motion and changes in magnetic susceptibility (respiration, cardiac cycle etc). In this environment where the acquired spectral signals "shift" along the x-axis between multiple sequential frames in an exam series, their subsequent averaging becomes "incoherent"—as they are mis-aligned, their averaging compromises signal quality. Unless this is corrected to "coherently" align the signals prior to averaging, this error can result in an increase in line width, split spectral peaks and reduced peak amplitudes for diminished spectral resolution relative between signal peaks themselves (as well as reduced SNR). Accordingly, the DDD-MRS processor according to further aspects of this disclosure comprises a frequency error corrector that performs frequency correction, such as for example prior to averaging frames, as also represented schematically in the flow diagrams of FIGS. 9A-B.

This is performed according to one embodiment in the frequency domain. This is done by transforming the time domain data for each frame into frequency domain absorption spectra, locating the water absorption peaks, and shifting the spectrum to align them to an assigned center reference location or bin. Once shifted, the frame spectra are averaged in the frequency domain to generate the corrected or "coherent" channel spectra. In another embodiment, the desired frequency shift correction for a frame may be applied to the time domain data for that frame. The time domain data for all the frames would then be averaged with the final average then transformed back to spectra. While the processes are linear and thus not dependent upon sequence of operation, it is believed in some circumstances that the latter embodiment may present slightly increased spectral resolution. In difficult signal acquisition situations, some of the frames do not have sufficient signal quality to support frequency correction. More specifically, water signal in some frames may be insufficiently robust to accurately "grab" its peak with high degree of confidence. This circumstance is addressed by another operation of the DDD-MRS processor, frame editing in which the frames are omitted if the water peak cannot be identified with sufficient confidence, also described herein (though may be performed independent of frame editing, which may not necessarily be required to be performed, despite the distinct benefits believed and observed to result therefrom).

The frame editing can be performed distinct from the frequency correction process (e.g., performed beforehand), or the frame editing and frequency correction can be performed simultaneously. The DDD-MRS processor can attempt to identify the water peak, calculate a level of confidence that the identified peak is water. If the confidence level is below a threshold, the frame can be disregarded. If the confidence level is above a threshold, the water peak, as well as the rest of the spectrum, can be shifted to its proper alignment. The DDD-MRS processor can then proceed to the next frame in the sequence.

Frequency error can be visualized using a time-intensity plot of the absorption spectra of all the frames in an acquisition cycle. An example process and related results of frequency error correction according to this present embodiment is shown and described by reference to FIGS. 18A-21 for the same DDD-MRS series acquisition featured in FIGS. 7-8 (prior to any correction) and FIGS. 11-12 (per prior DDD-MRS signal processing step of phase error correction). As shown in FIGS. 18A-19B (and similarly for prior FIGS. 13 and 17A), each acquisition frame is represented by a horizontal line, with amplitude of signal intensity across the frequency spectrum indicated by brightness in grey scale (brighter shade/white designates higher amplitude, darker signal intensity indicates lower relative amplitude). The horizontal lines representing individual acquisition frames are displayed in vertically "stacked" arrangement that follows their temporal sequence as acquired, e.g. time zero is in the upper left corner and frequency incremented from left to right. The top 16 lines represent unsuppressed water frames, with the remainder below representing suppressed water acquisitions. The brightest portion of each line (left side of the time-intensity plots) is reliably recognized as the water peak absorption, typically the strongest signal of acquired MRS spectra in body tissues.

Figure 18B:
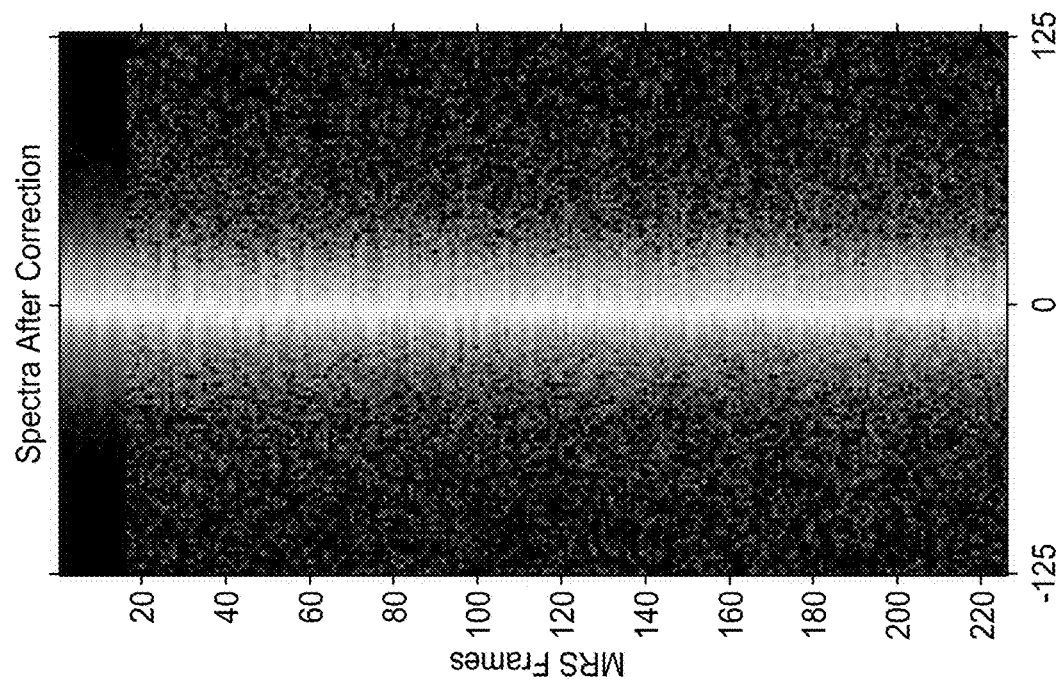
FIGS. 18A-B show time-intensity plots of the same MRS series acquisition for the same disc featured in FIGS. 7-8 and 11-12 as pre- (FIG. 18A) and post-(FIG. 18B) frequency correction according to a further aspect of the present disclosure, and shows each acquisition frame as a horizontal line along a horizontal frequency range with brightness indicating signal amplitude (bright white indicating higher amplitude, darker indicating lower), and shows the series of related repetitive frames in temporal relationship stacked from top to bottom, e.g. top is time zero).
Figure 18A:
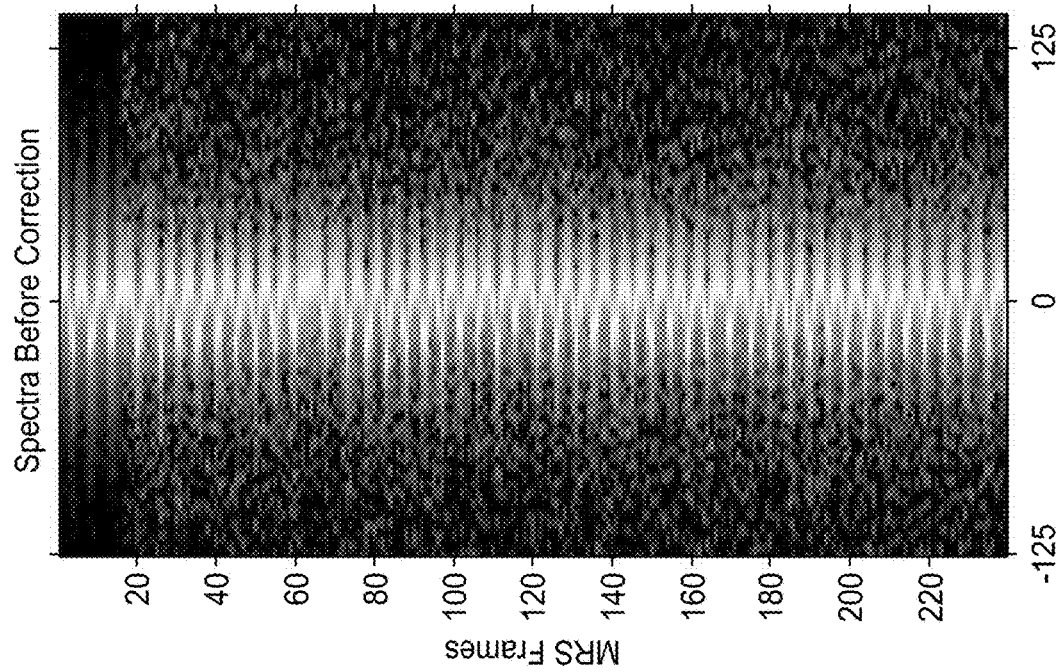
Figure 19B:
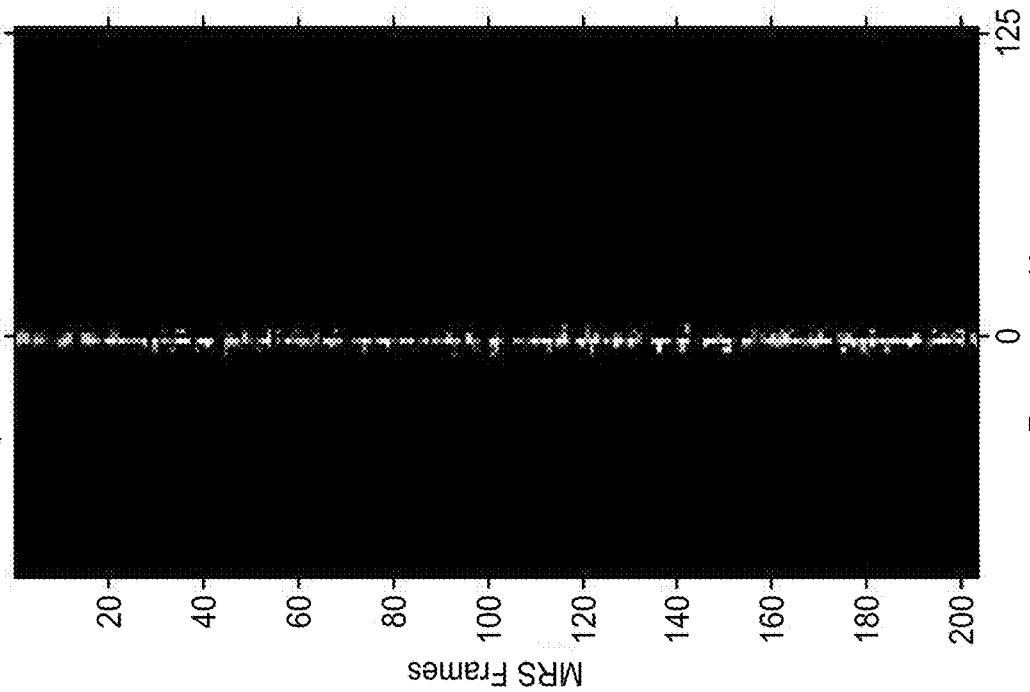
FIGS. 19A-B show the same respective time-intensity plots shown in FIG. 19A (pre-) and FIG. 19B (post-) frequency correction, but in enhanced contrast format.
Figure 19A:
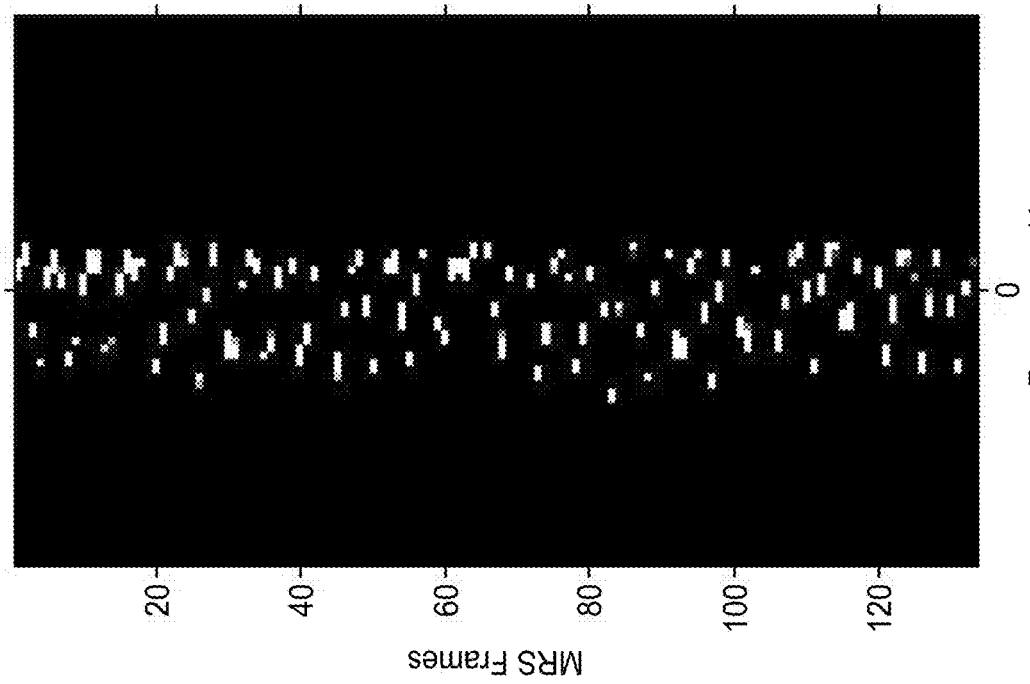

Further to FIG. 18A, this plot for the original acquired sequence of frames from an acquisition series intended to be averaged is shown pre-frequency correction (e.g. with original frequency locations), and similar view but post-frequency correction is shown in FIG. 18B. Shifting of the location of this bright white water peak region, as observed between vertically stacked frames, indicates frequency shift of the whole MRS spectrum between those frames—including thus the peaks of spectral regions of interest related to chemicals providing markers for pain. The rhythmic quality observed in this frequency shifting, per the alternating right and left shifts seen around a center in the uncorrected plot (left side of figure) shift, remarkably approximates frequency of respiration—and thus is believed to represent respiration-induced magnetic susceptibility artifact. The contrasted plots seen in the pre and post frequency corrected time intensity plots shown in FIGS. 18A-B reveal the process to achieve corrected "alignment" of the previously shifted signals for coherent averaging. For further clarity, each of two similar views of an enhanced contrast image (FIGS. 19A-B)(though FIG. 19B reveals wider range of MRS Frames acquired in the series), shows the original frequency shifted, incoherent misalignment (FIG. 19A) and frequency corrected, coherent alignment (FIG. 19B) of the water peaks from this same acquisition series. In this example case shown in FIGS. 18A-B and FIGS. 19A-B, all of the frames were of sufficient quality to support frequency correction.

Figure 20:
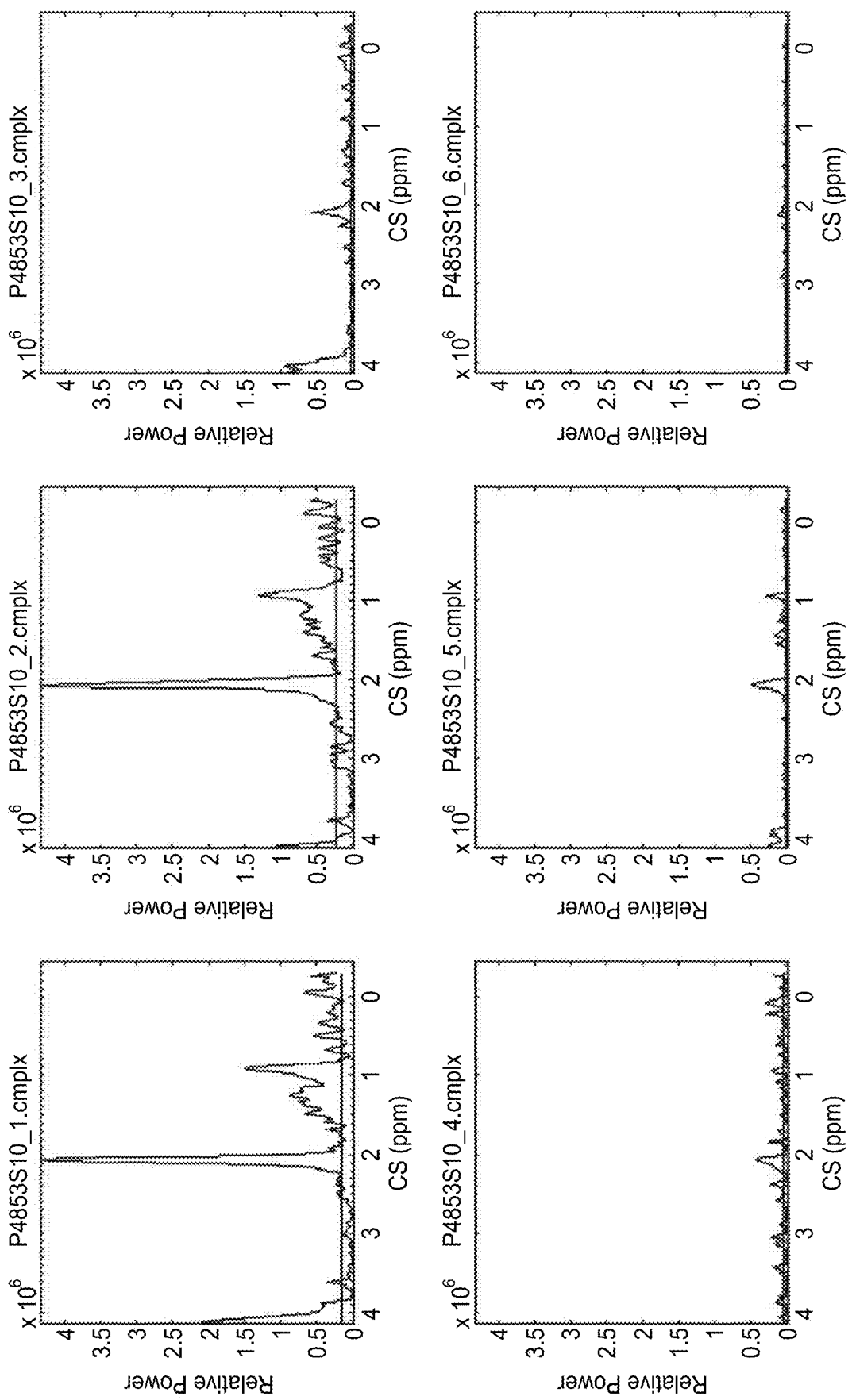
FIG. 20 shows spectral plots for 6 frame-averaged acquisition channels for the same acquisition shown in FIGS. 7-8 and 11-12, except post phase and frequency correction and prior to optimal channel selection and/or combination channel averaging.
Figure 21:
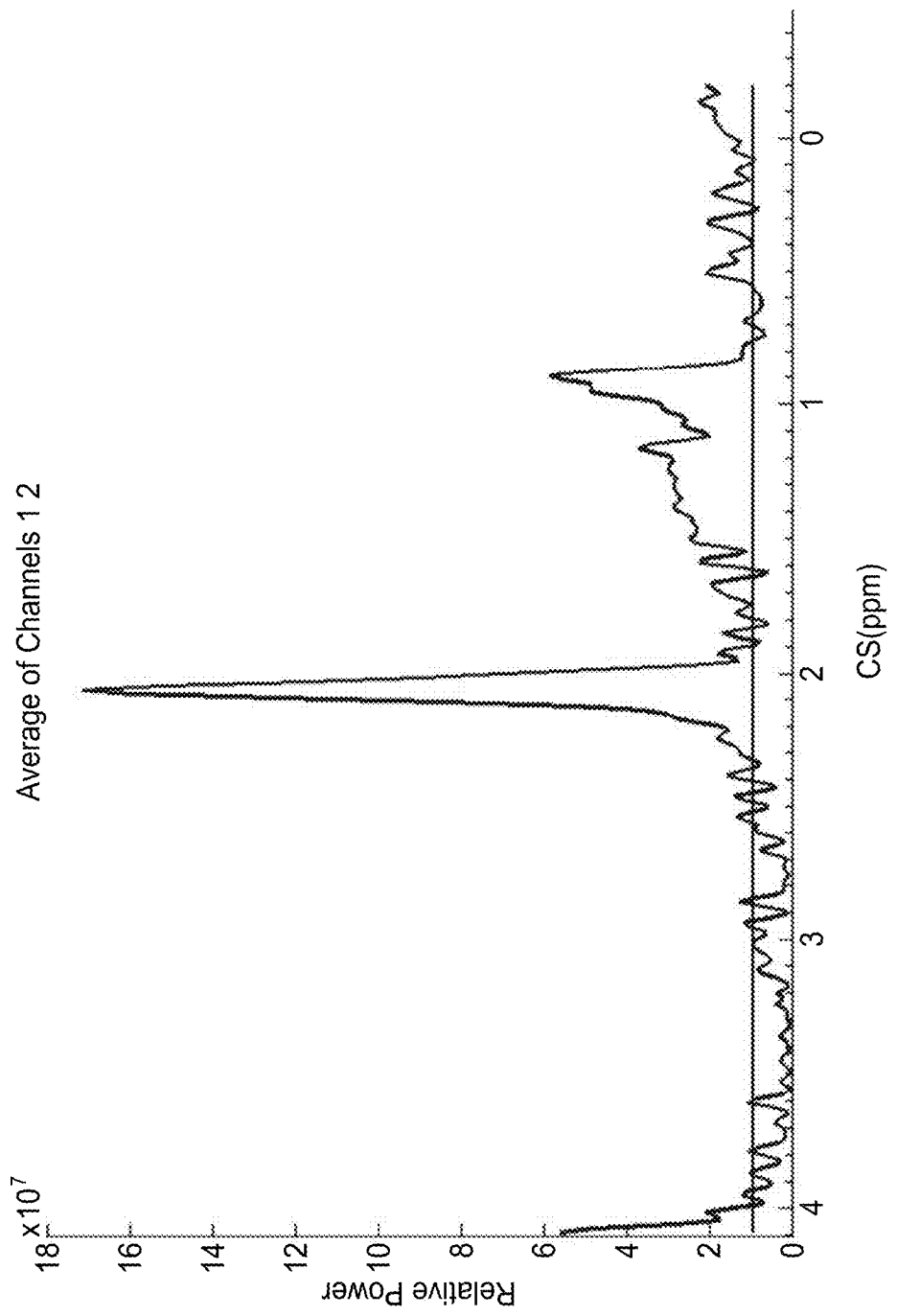
FIG. 21 shows a spectral plot for phase and frequency error corrected channels 1 and 2 selected from FIG. 20 as averaged, according to a further aspect of the disclosure.

The frequency corrected absorption spectra for each acquisition cycle are averaged to generate an average frequency (and phase) corrected spectra for each channel, as is shown in FIG. 20. The selected channels (channels 1 and 2) are then averaged to produce the final spectra (FIG. 21) used for extraction of data along spectral regions of interest that are considered relevant to DDD pain diagnosis. In comparing the phase+frequency error result of FIG. 21 against the phase error corrected-only result for the same acquisition series in FIG. 12, a significant increase in SNR and general signal quality is revealed in the latter more fully processed case—showing for example an increase from slightly more than $11\times10^7$ peak intensity with clear doublet in the PG region in FIG. 12 (where a doublet is not typically found, and likely reflective result of incoherent averaging of the PG peak) to nearly $18\times10^7$ or an 80% peak intensity increase with narrower band and no doublet in FIG. 21, and also clearly higher PG/LA and/or PG/LAAL ratio, as are signal qualities elsewhere revealed herein to be of diagnostic relevance in some highly beneficial applications. Still further comparison against the fully unprocessed spectral output from the MR scanner in FIG. 7 for the same acquisition series reveals even more dramatic signal quality, and in particular SNR, improvement.

The following documents are herein incorporate in their entirety by reference thereto:
1. Bottomley P A. Spatial localization in NMR spectroscopy in vivo. Ann N Y Acad Sci 1987; 508:333-348.
2. Brown T R, Kincaid B M, Ugurbil K. NMR chemical shift imaging in three dimensions. Proc. Natl. Acad. Sci. USA 1982; 79:3523-3526.
3. Frahm J, Bruhn H, Gyngell M L, Merboldt K D, Hanicke W, Sauter R. Localized high-resolution proton NMR spectroscopy using stimulated echoes: initial applications to human brain in vivo. Magn Reson Med 1989; 9:79-93.
4. Star-Lack J, Nelson S J, Kurhanewicz J, Huang L R, Vigneron D B. Improved water and lipid suppression for 3D PRESS CSI using RF band selective inversion with gradient dephasing (BASING). Magn Reson Med 1997; 38:311-321.
5. Cunningham C H, Vigneron D B, Chen A P, Xu D, Hurd R E, Sailasuta N, Pauly J M. Design of symmetric-sweep spectral-spatial RF pulses for spectral editing. Magn Reson Med 2004; 52:147-153.
6. Pauly J, Le Roux P, Nishimura D, Macovski A. Parameter relations for the Shinnar-Le Roux selective excitation pulse design algorithm [NMR imaging]. IEEE Trans Med Imaging 1991; 10:53-65.

7. F. Jim, Europeant Journal of Radialogy 67, (2008) 202-217

The following U.S. Patent Application Publications are herein incorporated in their entirety by reference thereto: US2008/0039710 to Majumdar et al.; and US2009/0030308 to Bradford et al.

DDD-MRS Diagnostic Processor and Use for Diagnosing DDD Pain

Development, application, and evaluation of a DDD-MRS diagnostic processor configured for use for diagnosing DDD pain based upon DDD-MRS acquisition series acquired from discs according to a DDD-MRS pulse sequence and DDD-MRS signal processor applications is disclosed by reference to the Examples and other disclosure provided elsewhere herein.

The diagnostic processing aspects of the present disclosure is also represented schematically in the flow diagrams of FIGS. 9A and 9C, and generally includes multiple individual steps or operations: (1) regional MRS spectral data extraction; and (2) diagnostic algorithm application. In addition, the diagnostic results will be typically displayed or otherwise produced in an appropriate fashion intended to satisfy an intended use. Furthermore, despite the many significant benefits of the DDD-MRS signal processor aspects herein disclosed for producing reliably robust MRS spectra from such DDD-MRS pulse sequence exams of disc nuclei, certain results will nonetheless provide insufficient signal quality, such as due to low SNR below a threshold (e.g. 2 or 3), water "washout" of signal, lipid artifact, or obviously out of phase outer voxel artifact, for making reliable measurements in spectral regions of diagnostic interest (e.g. considered to represent certain chemical biomarker regions). In the event such poor quality signals were to enter the diagnostic process of extracting data for diagnostic algorithm purposes, the results would be much more likely to be corrupted by noise artifact vs. real signal basis of the measured values, and could potentially yield diagnostically incorrect results.

Accordingly, the present disclosure according to further aspects includes a spectrum quality analyzer which determines which signals otherwise passed through the DDD-MRS signal processor modules have sufficient signal quality to perform diagnostic algorithm, and which do not. As for the latter, these may be considered "indeterminate" or otherwise "failed test" results and thus not used diagnostically. This may prompt a repeat exam, perhaps with modified parameters intended to counteract the underlying cause of such poor quality (e.g., low SNR or lipid artifacts), such as by re-voxelating according to a different prescription (e.g., increasing voxel size, or decreasing voxel size, or moving its location), adjusting water suppression, etc. In order to assist in appropriately directing such corrections in a re-exam, the spectrum quality analyzer may compare certain aspects of the subject signal against known features associated with such corruptions, determine the potential source of corruption, and flag and/or identify to a user a suspected cause (and may further recommend one or more courses of action to attempt correcting in a re-exam).

As this spectrum quality analyzer assesses the result of signal processing, it may be considered a part of the overall DDD-MRS signal processor. However, as it also comprises one of potentially multiple analysis algorithms to determine "procedural failures" from the processed DDD-MRS acquisition and filter them out from further diagnostic processing to an affirmative result, it may also in some regards be considered a portion of the diagnostic processor.

As still another embodiment of the diagnostic processor of the present disclosure, spectral data may be acquired for diagnostic purposes, such as processing through a diagnostic algorithm, and thus a data extractor is also provided and as featured in FIGS. 9A and 9B. The data extraction or acquisition can typically involve recognizing regions along the spectrum generally associated with certain specific biomarker chemicals of diagnostic interest (e.g. spectral regions of diagnostic interest or "SRDI"), and extracting target data from such SRDIs. These SRDI's will typically have known ranges, with upper and lower bounds, along the x-axis of the spectrum, and thus making up "bins" that are defined for respective data extraction. Examples of such bins are shown between adjacent vertical overlay lines in spectra shown in FIGS. 16A-B, 17C, and 17F (where top to bottom direction of a legend on the right of FIGS. 17C and 17F corresponds with right to left direction of "bins" in those FIGS., though as also alternatively reflected with lead lines to respective chemical bin regions in FIGS. 16A-B). The typical SRDIs of various biomarkers of interest are elsewhere described herein, and as may be otherwise known in the literature and applicable for a given application of the present aspects in practice. In some cases, it is to be appreciate that such bins may provide only an ability to find a certain feature of the spectrum, e.g. a regional "peak", and this information can then be used to determine and extract other information (e.g. power under a peak region, which may be determined to include spectral power around the peak that extends outside of the respective "bin"). Furthermore, certain artifacts may cause chemical shift error in the spectra despite corrections provided in the signal processing. This data extractor may recognize a certain feature in one respective SRDI bin, e.g. PG peak, and then adjust the location for another target SRDI from where it might otherwise be sought (e.g. based upon a prescribed distance from the first recognized target peak, vs. fixed relative locations for the SRDIs along the x-axis). In some embodiments, to compensate for slight shifts in the spectrum (e.g., chemical shift errors) after a regional peak is identified in a specified bin, the bin and/or the spectrum can be shifted to align the regional peak with the center of the bin, and an area under the curve can be taken for a region (e.g., in the shifted bin) centered on the located regional peak.

Once processed signal quality is confirmed, and spectral data extraction is performed, diagnostic processing based upon that extracted data may then be performed, as also per schematic flow diagrams of FIGS. 9A-C. Such approaches are further developed below by way of the present Examples, though it is to be appreciated that various different specific diagnostic approaches, algorithms, uses, etc. may be performed by one of ordinary skill without departing from the other broad intended scopes of the current disclosure. Nonetheless, for purpose of understanding of the present detailed embodiments, the following bin region "limits" were used for certain aspects of data extraction in the LA, AL, and PG regions of acquired and processed DDD-MRS spectra for general purpose of most data extracted and processed in the Examples: LA: 1.2 to 1.45; AL: 1.45 to 1.6; PG: 2.0 to 2.2.

It will also be understood that the DDD-MRS diagnostic processor can be implemented in a variety of manners, such as using computer hardware, software, or firmware, or some combination thereof. In some embodiments, the DDD-MRS diagnostic processor can include one or more computer processors configured to execute a software application as computer-executable code stored in a non-transitory computer-readable medium. In some embodiments, the computer processor can be part of a general purpose computer. The computer processor(s) used by the DDD-MRS diagnostic processor can be the same computer processor(s) used by the DDD-MRS signal processor, or it can be one or more separate computer processors. In some embodiments, the DDD-MRS diagnostic processor can be implemented using specialized computer hardware such as integrated circuits instead of computer software. The DDD-MRS signal processor may also be implemented by multiple computers connected, for example, through a network or the internet.

EXAMPLES

Example 1

A DDD-MRS pulse sequence and signal processor were constructed to incorporate various aspects of the present embodiments disclosed herein and were used and evaluated in clinical experience across a population of discs in chronic, severe low back pain patients and asymptomatic control volunteers. Various data extracted from features of interest along the acquired and processed DDD-MRS acquisition series for discs evaluated in these subjects were compared against control diagnoses for severe disc pain vs. absence severe disc pain, in order to develop and characterize a DDD-MRS diagnostic processor with the highest possible correlation to the control diagnoses.

Methods:

Clinical Study Population:

The study included 65 discs from 36 total subjects. Thirty-eight discs were from 17 patients with a clinical diagnosis of chronic, severe low back pain (LBP group), and 27 discs were from 19 asymptomatic volunteers (ASY Group). 25 discs in 12 of the LBP patients also received PD (PD Group) sufficiently contemporaneous with the DDD-MRS exam to provide appropriate comparison basis. All 65 discs were evaluated for single voxel magnetic resonance spectroscopy pulse sequence and data acquisition (DDD-MRS), and signal processor parameter development of the new DDD-MRS approach. 52 discs from 31 subjects were considered appropriate and used as controls for developing and assessing the DDD-MRS diagnostic processor for diagnostic application of the overall DDD-MRS system and approach. Thirteen discography positive (PD+) discs from the PD Group were used as positive control (PC) discs, and 12 discography negative (PD−) discs from the PD Group plus all the ASY discs were used as negative control (NC) discs. A breakdown summary analysis of demographics among and between these groups under this Example is shown in Table 2.

Figure 22:
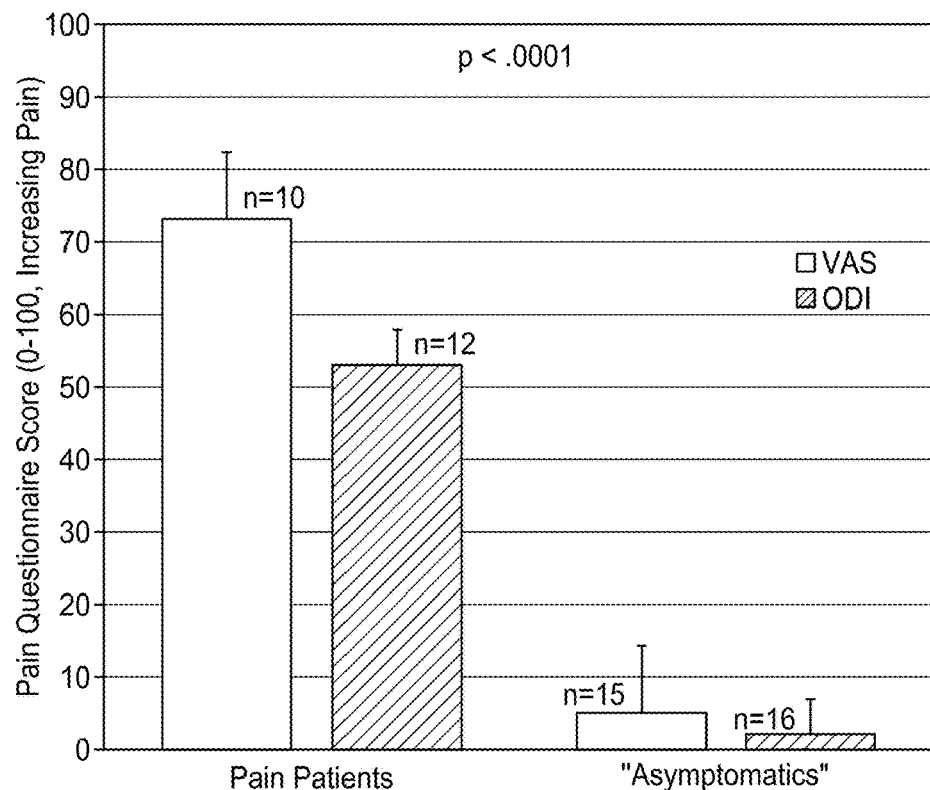
FIG. 22 shows a bar graph of mean values, with standard deviation error bars, of Visual Analog Scale (VAS) and Oswestry Disability Index (ODI) pain scores calculated for certain of the pain patients and asymptomatic volunteers evaluated in a clinical study of Example 1 and conducted using certain physical embodiments of a diagnostic system constructed according to various aspects of the present disclosure.

Study Design:

Standard lumbar MRI was performed on all subjects. PD performed within the PD Group was conducted by discographers per their discretionary techniques, and in all cases was performed blinded to DDD-MRS exam information. However, the PD+ criteria included a pain intensity score of greater than or equal to 6 concordant to typical back pain on PD; less than or equal to 50 psi above opening pressure (where measured); and a negative control PD− disc in the same patient (except one). All PD− discs had less than 6 pain intensity scores per PD. Pain questionnaires, including Oswestry Disability Index (ODI) and Visual Analog Scale (VAS), were completed by all subjects, and the PD Group scored significantly higher than the ASY Group according to both measures as shown in FIG. 22 (PD Group VAS and ODI on left side of graph, ASY Group VAS and ODI on right side of graph; VAS shown to left, ODI shown on right, within each group). The DDD-MRS pulse sequence and signal processor constructed according to the various present embodiments herein was used for each series acquisition for each disc, with data extracted from voxels prescribed at regions of interest within nuclei of all discs included in the study. A 3.0T GE Signa MRI system and 8-channel local spine detector coil were used with the DDD-MRS package and approach (lower 6 of the 8 channels activated for lumbar signal acquisition). Information along spectral regions of the acquired DDD-MRS signals and associated with various chemicals of interest were evaluated against control diagnoses across the PC and NC groups.

Figure 23:
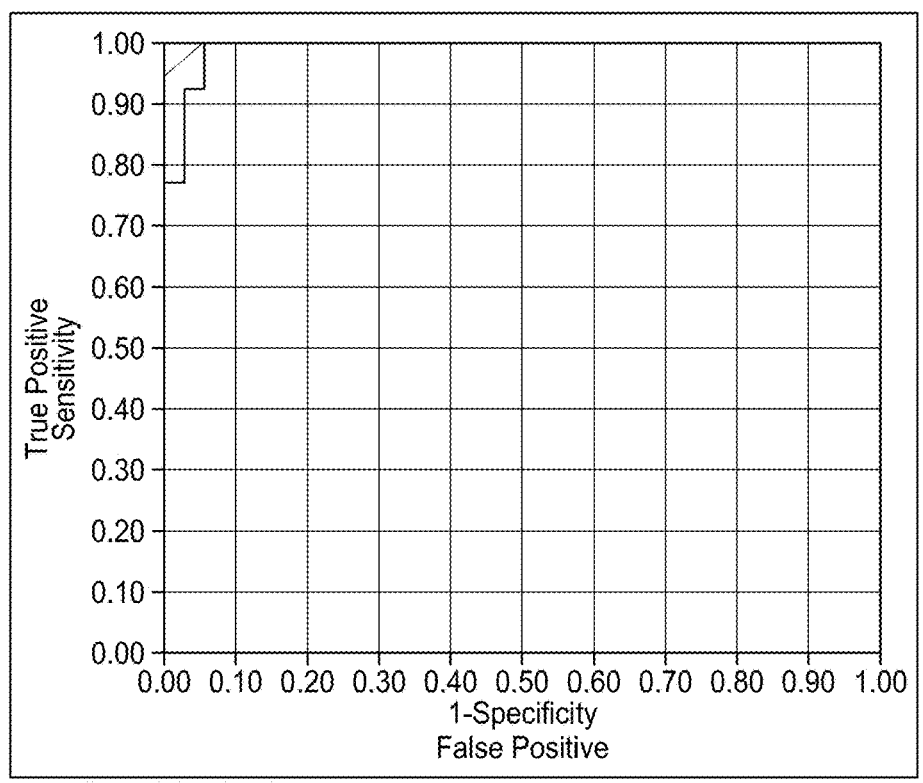
FIG. 23 shows a Receiver Operator Characteristic (ROC) curve representing the diagnostic results of the DDD-MRS diagnostic system used in the clinical study of Example 1 with human subjects featured in part in FIG. 22, as compared against standard control diagnostic measures for presumed true diagnostic results for painful vs. non-painful discs.
Figure 24:
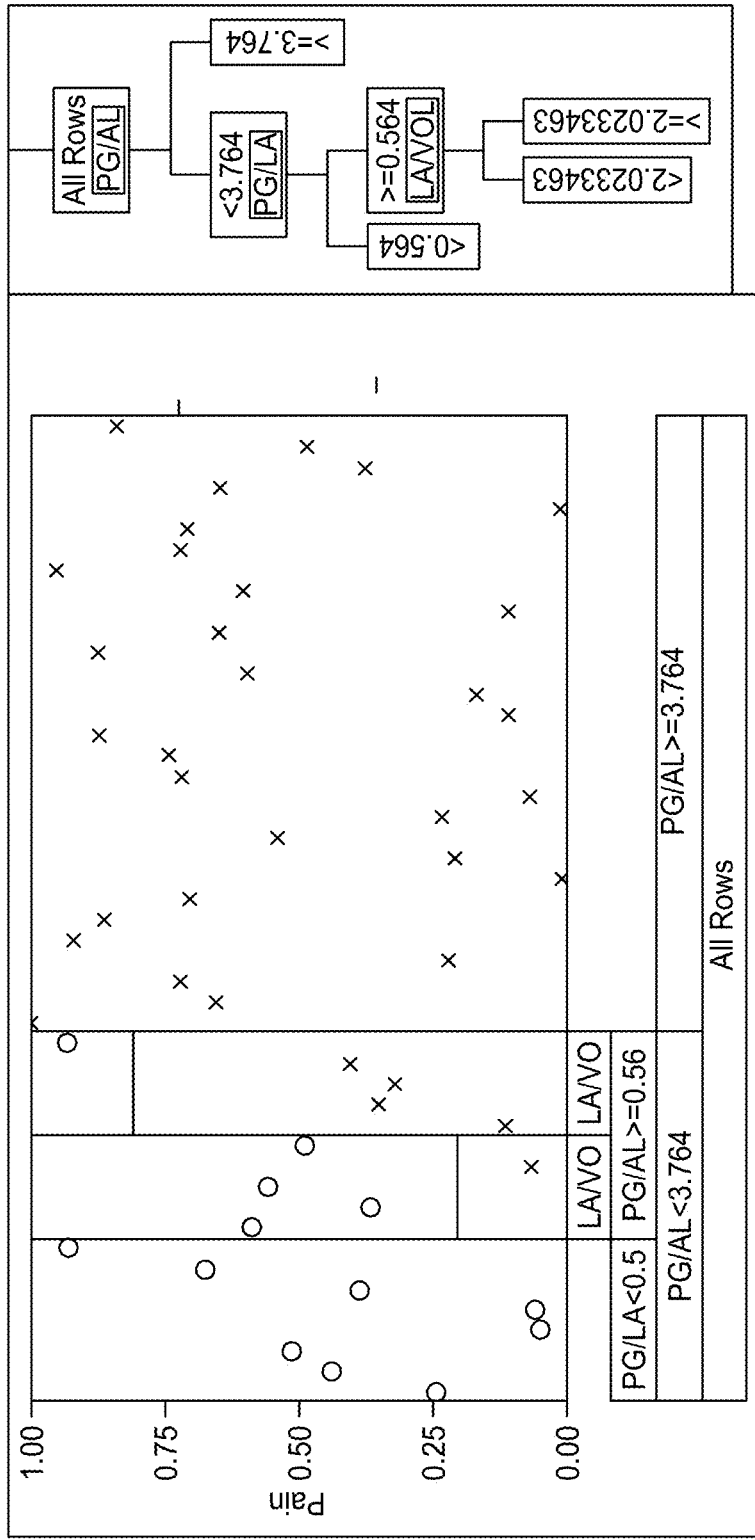
FIG. 24 shows a partition analysis plot for cross-correlation of a portion of the clinical diagnostic results of the DDD-MRS system under the same clinical study of Example 1 and also addressed in FIGS. 22-23, based on partitioning of the data at various limits attributed to different weighted factors used in the DDD-MRS diagnostic processor, with "x" data point plots for negative control discs and "o" data point plots for positive control discs, also shows certain statistical results including correlation coefficient ($R^2$).

Multi-variate logistic regression analyses were performed to fit the dicotomous response (PC vs NC) to the continuous spectral measures and develop a binary DDD-MRS diagnostic set of criteria and threshold for determining positive (MRS+) and negative (MRS−) pain diagnoses. A receiver operator characteristic (ROC) curve was generated, and area under the curve (AUC) was calculated to assess the accuracy of the developed test (FIG. 23). Five-fold cross-validation was performed to assess the generalizability of the predictive relationship (FIG. 24).

DDD-MRS diagnostic outcomes for each disc were based on a single number calculated via the developed set of criteria based upon four weighted factors derived from regions of the acquired MRS signals and associated with three chemicals—PG, LA, and alanine (AL). It is noted, however, that LA and AL regions are relatively narrow and immediately adjacent to each other, and in some cases the true respective signals representing these actual chemical constituents may overlap with each other and/or into the adjacent region's location. Furthermore, either or both of the LA and AL regions may also overlap with possible lipid contribution, which was believed to be observed in some cases (which may include signal from adjacent tissues such as bone marrow of bordering vertebral body/s). Positive numerical threshold results were assigned "MRS+" as severely painful, and negative results were assigned "MRS−" as not severely painful. Accordingly, the threshold for severely painful vs. otherwise non-painful diagnostic result is zero (0). The set of diagnostic criteria used to determine MRS+vs. MRS-diagnostic values around this threshold with the most robust statistical correlation and fit to the control data observed across the disc population evaluated for this purpose is summarized as follows:

$$\text{Threshold} = -[\log(PG/LA*(0.6390061) + PG/AL*(1.45108778) + PG/vol*(1.34213514) + LA/vol*(-0.5945179) - 2.8750366)];$$

wherein:

PG=peak measurement in PG region, AL=peak measurement in AL region, LA=peak measurement in LA region, and vol=volume of prescribed voxel in disc used for MRS data acquisition.

The distribution of DDD-MRS results according to these calculated thresholds were compared against all PC and NC diagnoses, PD results alone, and portion of the NC group represented by the ASY group alone. Sensitivity, specificity, and positive (PPV) and negative (NPV) predictive values were also calculated per control comparisons.

Further aspects of the statistical methods herein applied, with respect to identifying diagnostic algorithm and also evaluating resulting data, are described in more detail below with respect to similar approaches also taken in subsequent Examples 2 and 3.

Results:

DDD-MRS data demonstrated a strong correlation with the clinical diagnoses ($R^2$=0.89, p<0.00001), with Receiver Operator Characteristic (ROC) analysis yielding an area under the curve (AUC) of 0.99 (FIG. 23) and cross-validation through partition analysis resulting in only deminimus variance in the $R^2$ (FIG. 24). Tables 3 and 4, and FIGS. 25A-27, show various aspects of the resulting clinical comparison data for DDD-MRS vs. control diagnostic data, which data and comparisons are further described as follows.

Figure 25A:
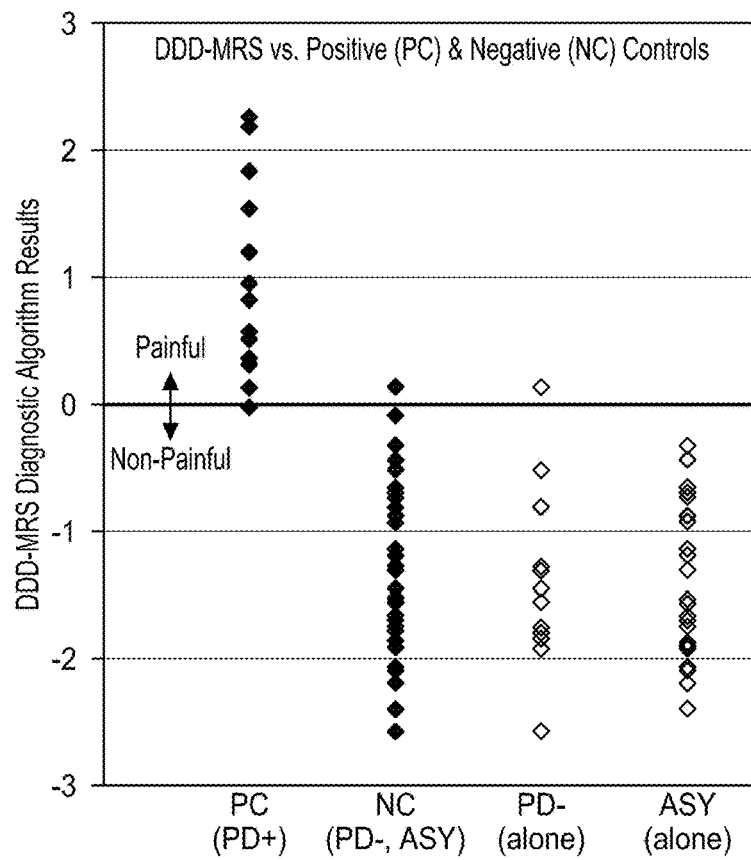
FIG. 25A shows a scatter plot histogram of DDD-MRS diagnostic results for each disc evaluated in the clinical study of Example 1 and also addressed in FIGS. 22-24, and shows the DDD-MRS results separately for positive control (PC) discs (positive on provocative discography or "PD+"), negative control (NC) discs (negative on provocative discography or "PD−", plus discs from asymptomatic volunteers or "ASY"), PD− alone, and ASY alone.
Figure 25B:
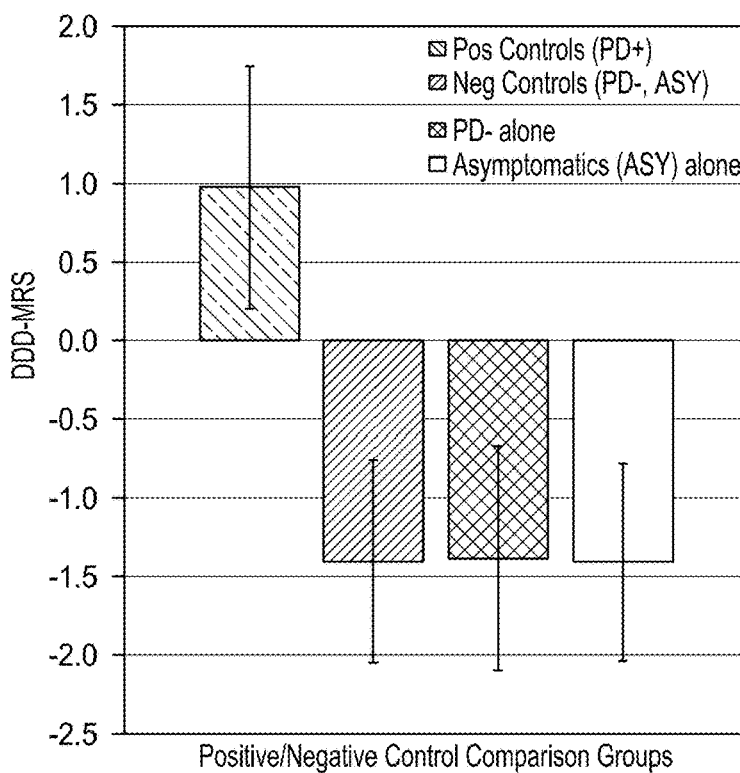
FIG. 25B shows a bar graph of the same DDD-MRS diagnostic results shown in FIG. 25A across the same subject groups of Example 1, but shows the mean values with standard deviation error bars for the data.
Figure 26:
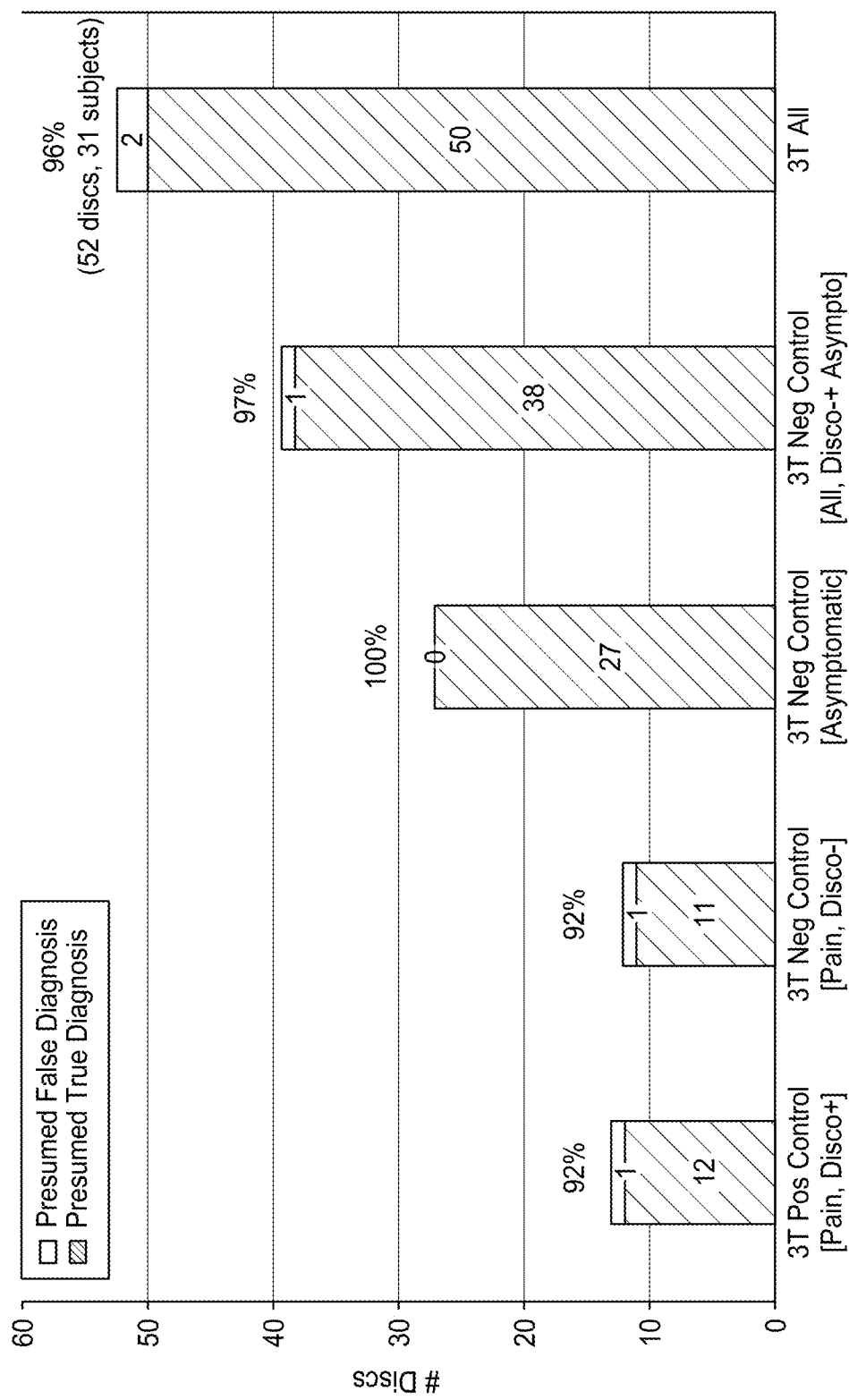
FIG. 26 shows a bar graph of presumed true and false binary "positive" and "negative" diagnostic results produced by the DDD-MRS system for painful and non-painful disc diagnoses in the clinical study of Example 1, as compared against standard control diagnostic measures across the positive controls, negative controls (including sub-groups), and all discs evaluated in total in the study.
Figure 27:
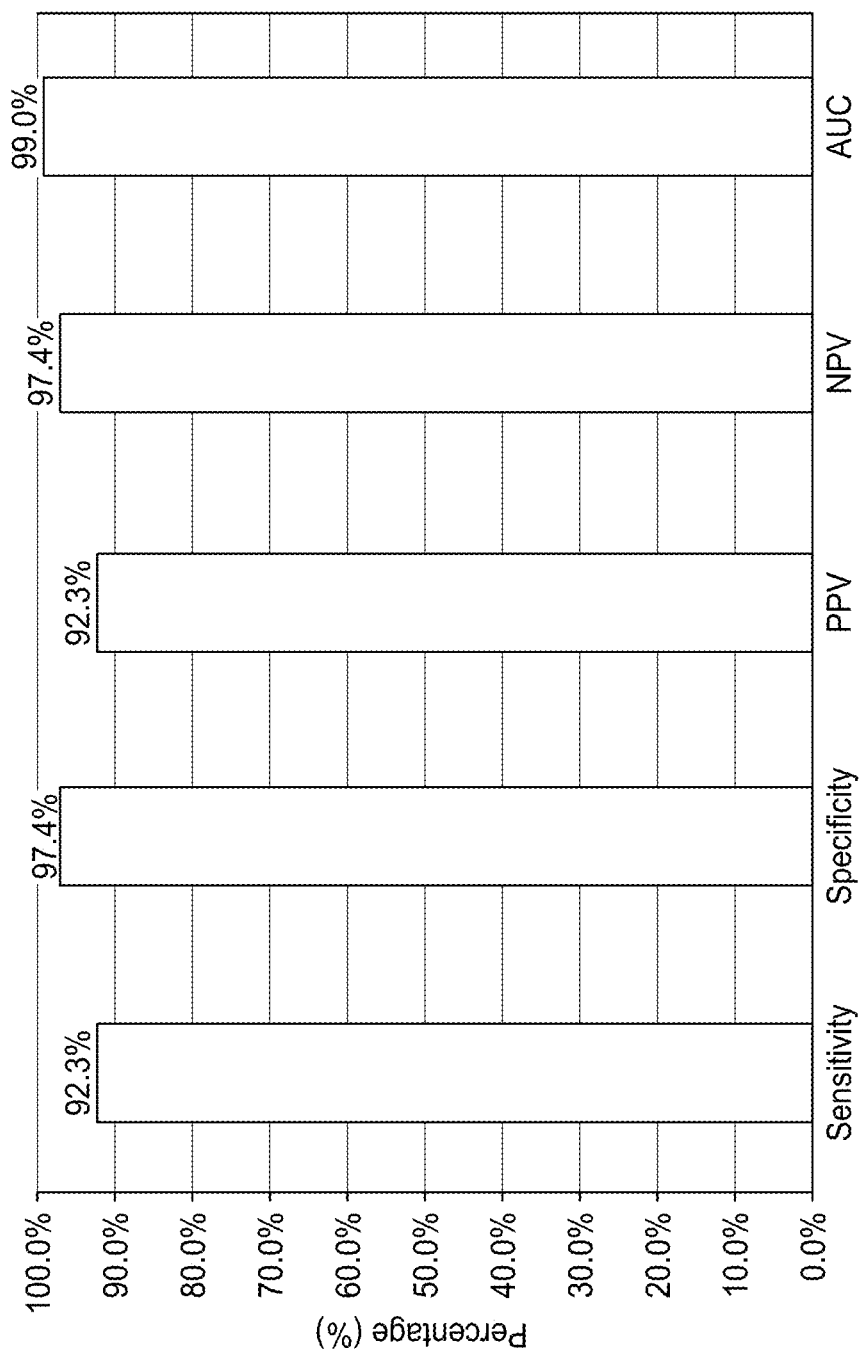
FIG. 27 shows diagnostic performance measures of Sensitivity, Specificity, Positive Predictive Value (PPV), Negative Predictive Value (NPV), and area under the curve (AUC) which in this case is equivalent to Global Performance Accuracy (GPA) for the DDD-MRS diagnostic results in the clinical study of Example 1.

DDD-MRS results, with respect to binary MRS+ and MRS− diagnoses, correctly matched binary PC and NC diagnoses of painful/non-painful for 50/52 (96.2%) discs evaluated across the PD and ASY groups. Of the 13 MRS+ discs, 12 discs were from the PC group (PPV=92%). Of the 40 discs that were MRS−, 39 were from the NC group (NPV=97%). DDD-MRS sensitivity was about 92% and specificity was about 97%. Mean DDD-MRS results for the PC and NC groups were 0.97±0.77 and −1.40±0.65 ($R^2$=0.89, p<0.00001, FIG. 25B). As shown in FIG. 26, DDD-MRS results matched PD results in 23/25 (92.0%) discs of the PD Group: 12/13 (96.2%) of PD+ and 11/12 (91.7%) of PD−. Mean DDD-MRS algorithm results for PD+ and PD− groups were 0.97±0.77 and −1.39±0.72 (p<0.00001)(FIG. 25B). DDD-MRS results also correlated with PD pain intensity scores ($R^2$=0.73)(not shown). DDD-MRS results matched all 27/27 (100%) NC results represented by the ASY group (FIG. 26). The mean DDD-MRS algorithm results for the ASY group were −1.4±0.63, which differed significantly vs. PD+(p<0.0001), but were not significantly distinguishable vs. PD-results (p=0.46)(FIGS. 25A-B).

Figure 28:
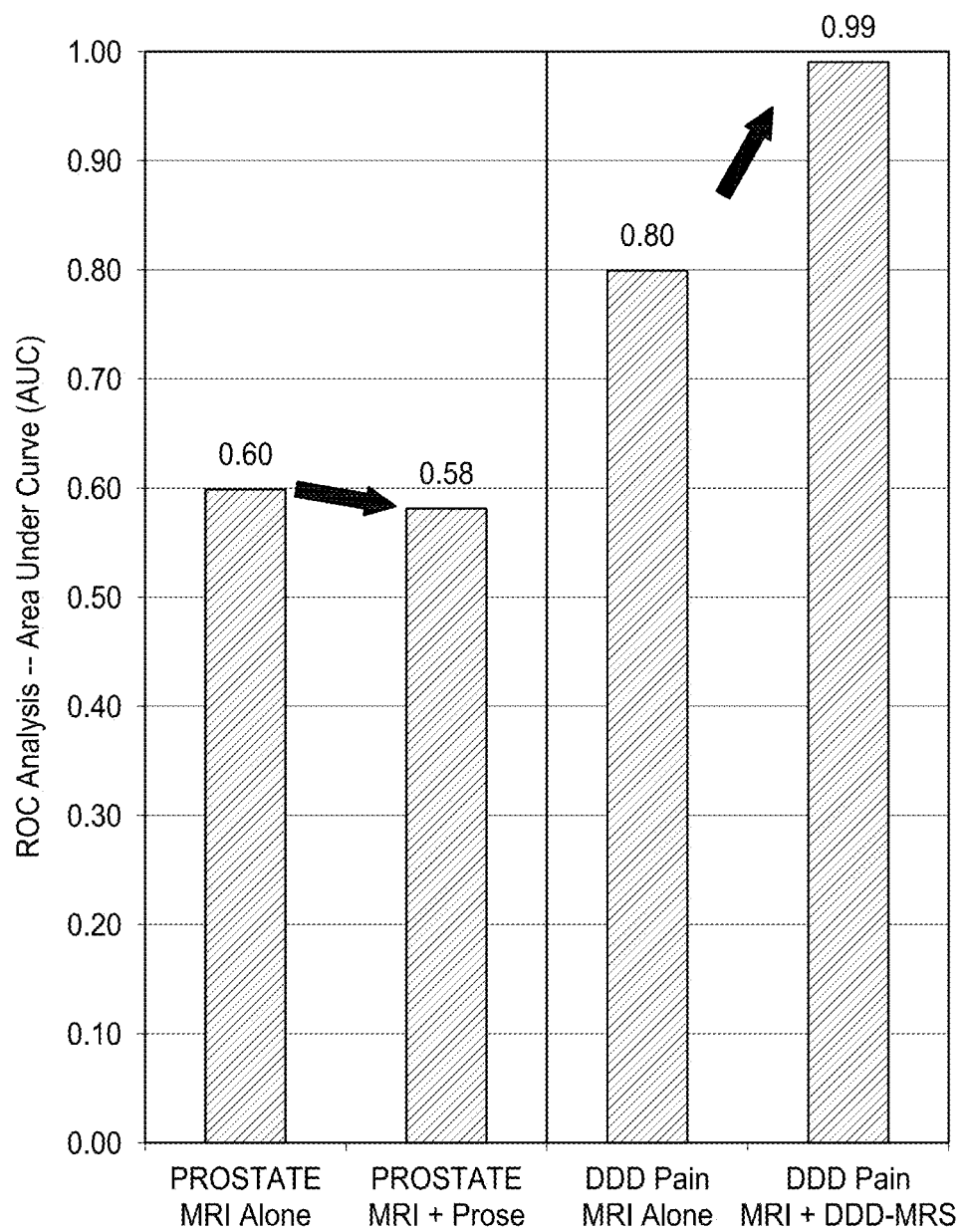
FIG. 28 shows a bar graph comparing areas under the curve (AUC) per ROC analysis of MRI alone (for prostate cancer diagnosis), MRI+ PROSE (MRS package for prostate cancer diagnosis), MRI alone (for discogenic back pain or DDD pain), and MRI+DDD-MRS (for discogenic back pain or DDD pain), with bold arrows showing relative impact of PROSE vs. DDD-MRS on AUC vs. MRI alone for the respective different applications and indications, with DDD-MRS results shown as provided under Example 1.
Figure 29:
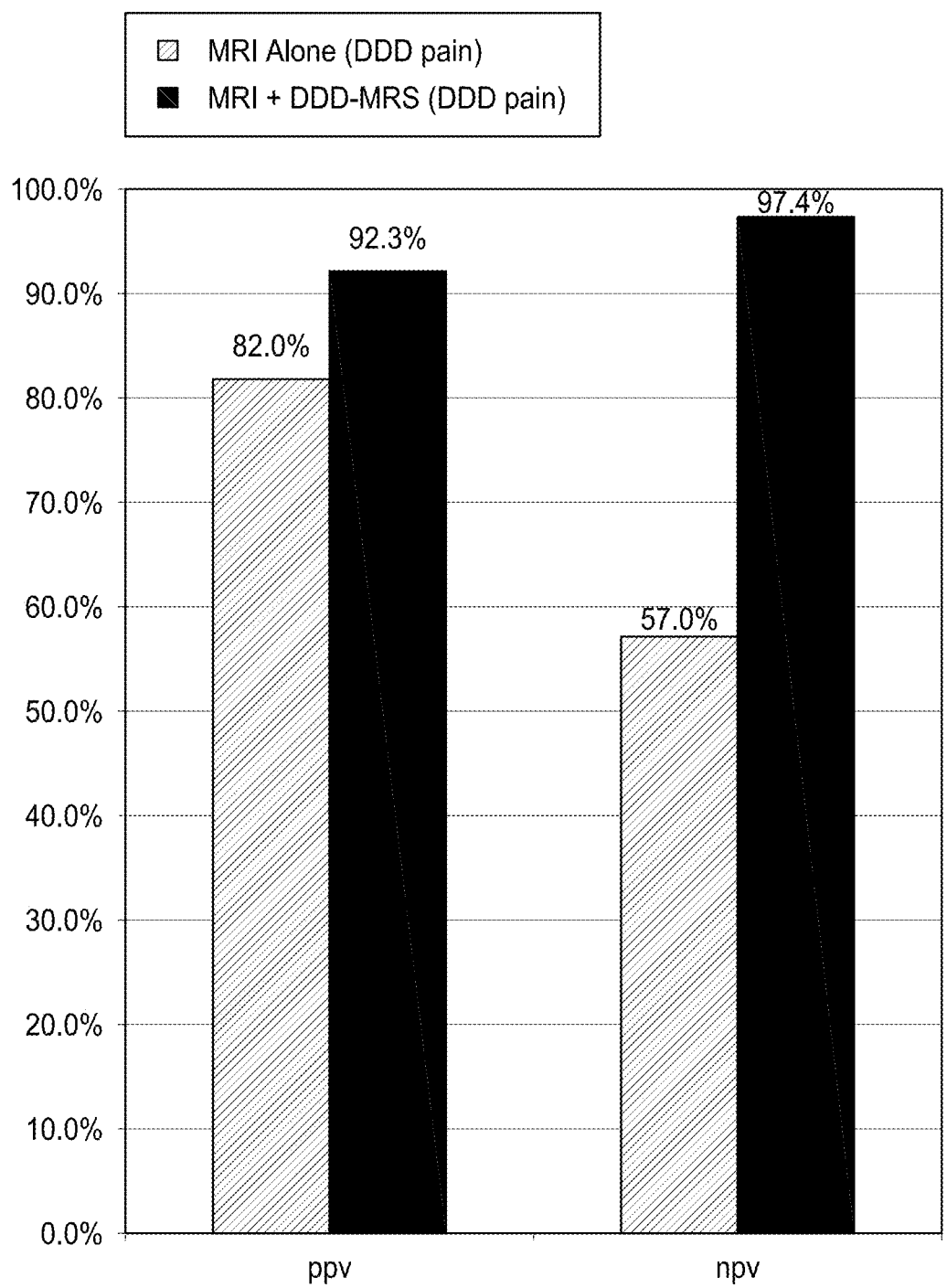
FIG. 29 shows positive predictive value (PPV) and negative predictive value (NPV) for MRI alone and for MRI+ DDD-MRS (per Example 1 results), both as applied for diagnosing DDD pain, vs. standard control measures such as provocative discography.

As shown in FIGS. 28-29, the DDD-MRS results according to this study of this Example provided highly favorable improvement vs. the diagnostic accuracy typically attributed to MRI alone for diagnosing painful vs. non-painful DDD. More specifically, FIG. 28 (two bars on right side of graph) shows a comparison of the AUC for MRI alone vs. MRI+ DDD-MRS, per meta analysis of previously reported AUC data for MRI for this indication. This is further compared in the graph against a recent study reporting AUC for MRI alone vs. MRI+PROSE for prostate cancer diagnosis (as compared to histopathological diagnosis of biopsy samples), where no significant improvement was shown by the additional inclusion of PROSE application of MRS within the MR-based diagnostic regimen. While the prostate data reflected within the graph reflects a larger relative population of samples in multi-center study, and the DDD-MRS pain diagnostic results shown reflects a smaller population within single center experience, the dramatic relative improvement presented by the DDD-MRS approach in the single center experience is expected to carry over to a significant degree into larger, multi-center context for this application. Further to FIG. 29, the results of this study additionally show improvement to positive and negative predictive values by enhancing standard MRI alone with the addition of the DDD-MRS diagnostic—per meta analysis of the current data vs. previously published data for MRI for this purpose.

Figure 30A:
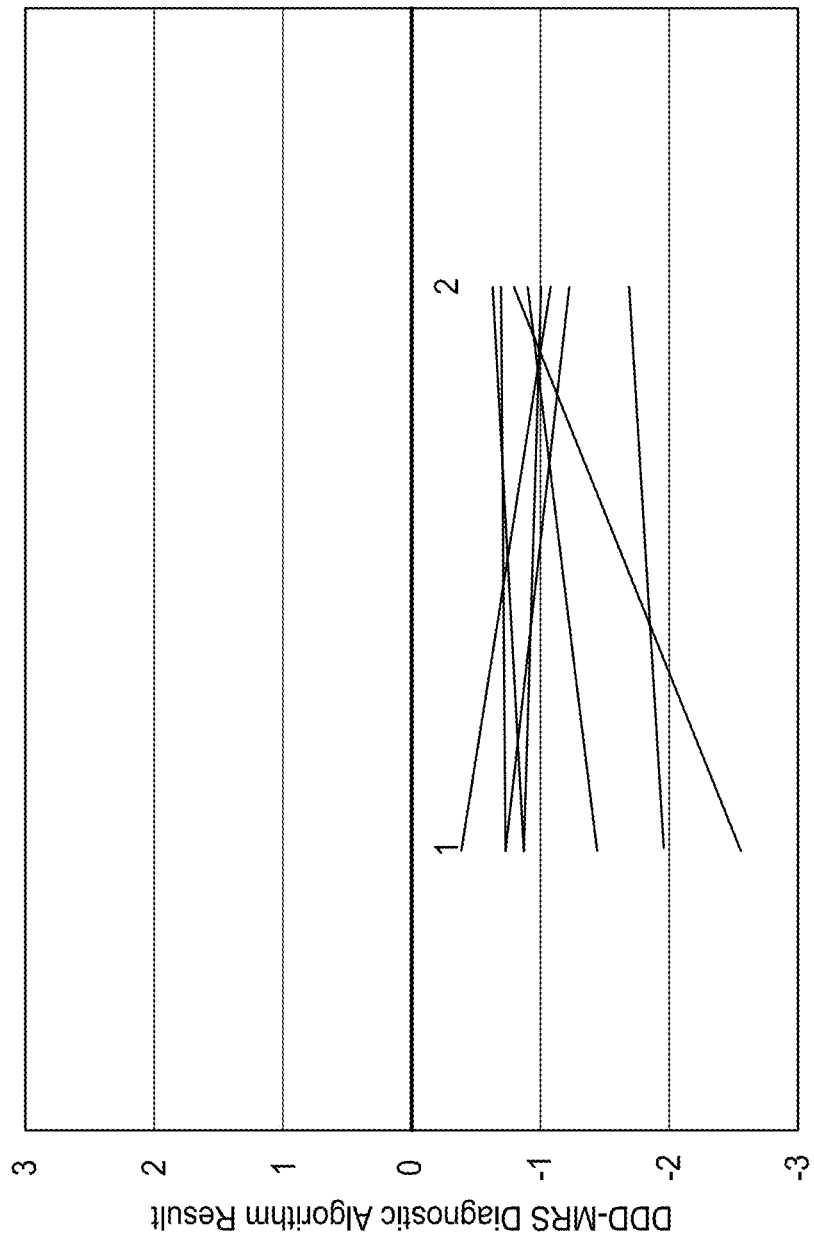
FIG. 30A shows a plot of DDD-MRS algorithm output data for a series of 8 L4-L5 lumbar discs in 8 asymptomatic human control subjects per clinically acquired and processed DDD-MRS exam under Example 1, and plots these results twice for each disc on first (1) and second (2) separate repeat scan dates in order to demonstrate repeatability of the DDD-MRS exam's diagnostic results.
Figure 30B:
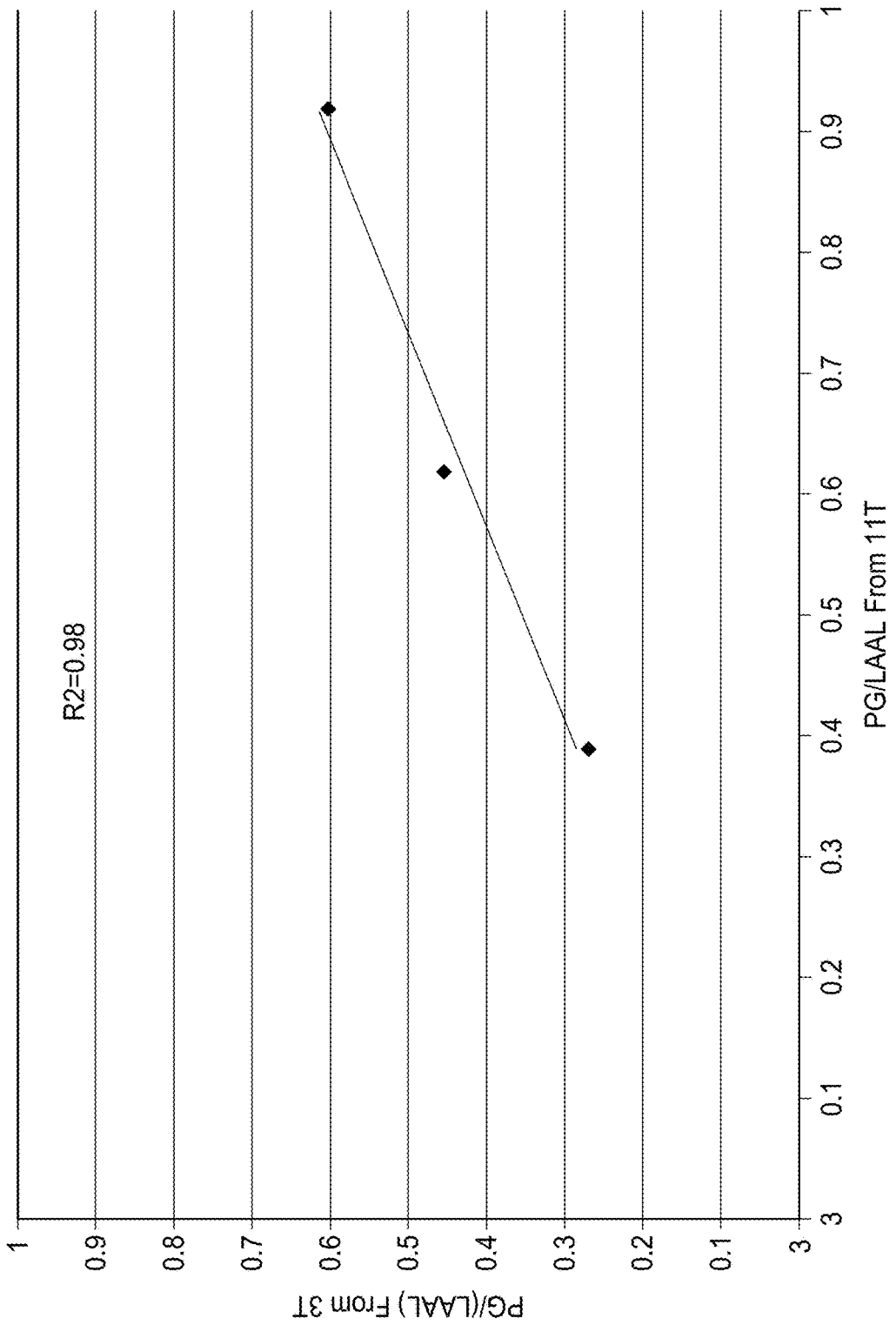
FIG. 30B shows a plot of PG/LAAL ratio data for 3 discs per DDD-MRS pulse sequence and signal processing data of Example 1, and shows the clinically acquired results via 3T DDD-MRS exams of the discs in vivo in pain patients (y-axis) against acquired measurements for the same chemicals in the same disc material but flash frozen after surgical removal and using 11T HR-MAS spectroscopy.

While the other information described herein is clearly sufficient to demonstrate the remarkable utility of the present embodiments in operation for the indicated purpose of this Example, further supportive information is also provided as follows. The DDD-MRS diagnostic exam was also evaluted for and demonstrated robust repeatability, as reflected in FIG. 30A. More specifically, FIG. 30A shows DDD-MRS diagnostic algorithmic results according to this Example for eight (8) L4-L5 discs in eight (8) asymptomatic pain free volunteers examined twice—each on 2 separate dates, with trend between sequential results for each disc shown in respective lines between columns (1) and (2) along the x-axis of the graph. These were all negative diagnostic results, indicating pain free diagnosis according to the exams, with relative repeatability and little variance between exams on average between the group and individually for the vast majority of the samples (with one obvious outlier demonstrating more variance than the others, though still nonetheless representing a repeatable diagnostic result as negative). In addition, as shown in FIG. 30B, the measured ratios between metabolite regions for PG and a combination of LA and AL (alanine) or "LAAL" were compared as per spectral acquisitions and extracted regional data measurements in vivo, against measurements taken for the same chemical regions but via 11T HR-MAS spectroscopy ex vivo after surgical removal for pain treatment. These comparisons were highly correlative, with $R^2$=0.98, demonstrating the robustness of the measurements taken in vivo by ex vivo validation measurements for the same disc material.

Certain benefits provided by the DDD-MRS processor for post-processing acquired MRS signals were also evaluated across a sub-set sampling of the DDD-MRS data derived from the clinical population under this study of this Example. In particular, for each series acquisition the SNR of the processed DDD-MRS signals ("DDD-MRS spectra/spectrum") was characterized, and compared against the 6 channel average, non-phase or frequency corrected, GE Signa output spectra as acquired "pre-processing" according to the present embodiments (e.g. "input combined spectra/spectrum"). This SNR characterization and comparison exercise was conducted as follows.

Figure 31A:
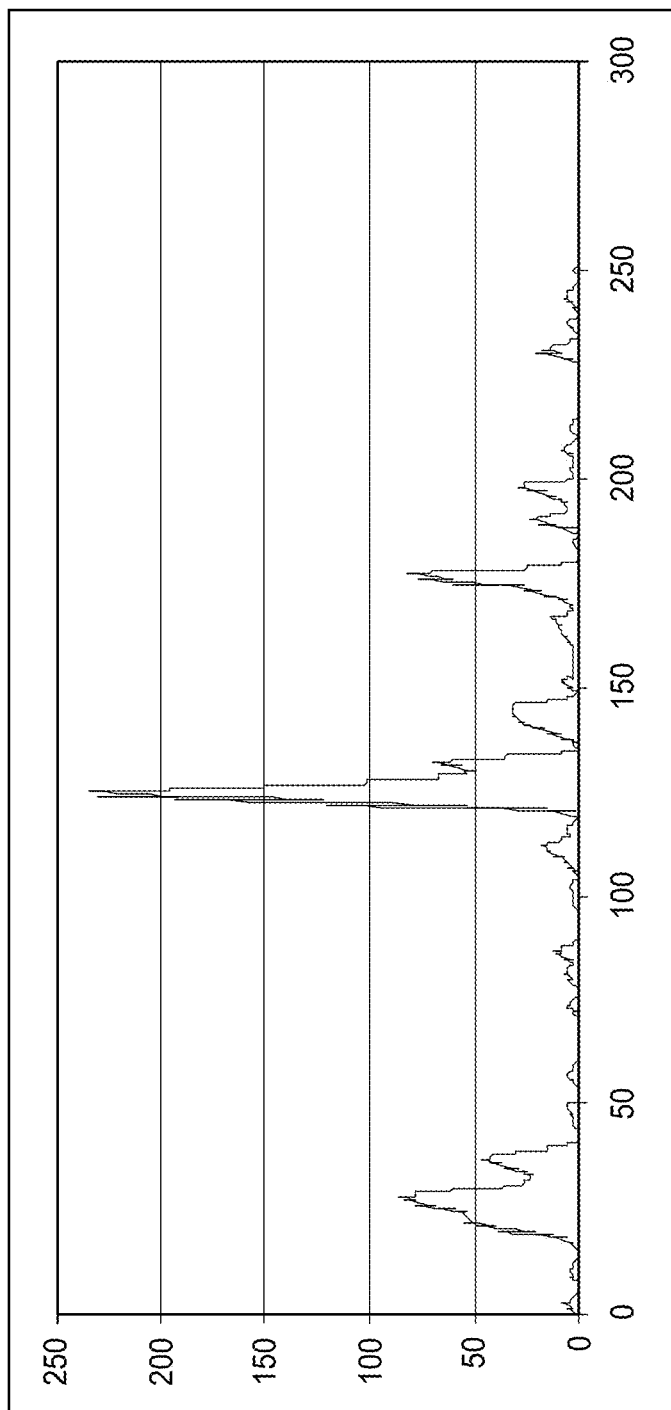
FIG. 31A shows a digitized post-processed DDD-MRS spectrum (in phase real power) as processed according to certain of the MRS signal processor aspects of the present disclosure, and certain calculated data derived therefrom as developed and used for calculated signal-to-noise ratio (SNR) of the processed result, as taken across a sub-set of samples evaluated under Example 1.
Figure 31B:
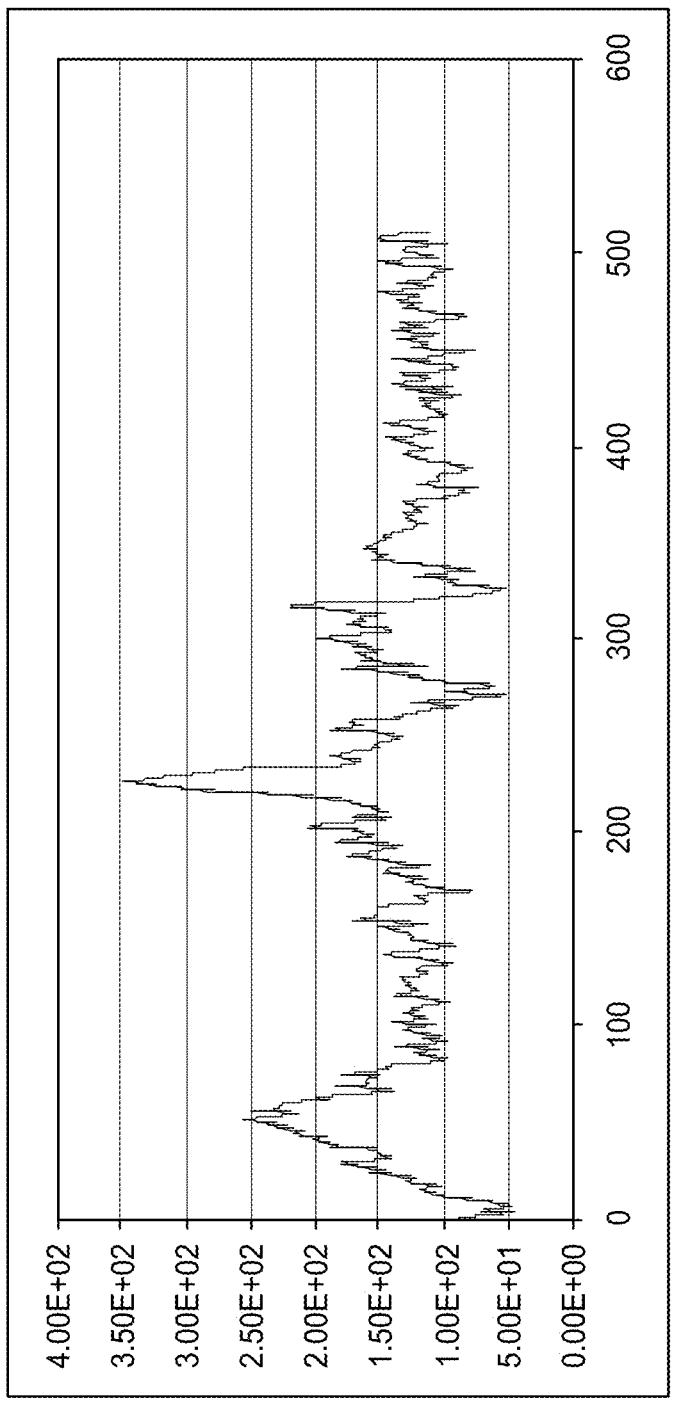
FIG. 31B shows a digitized pre-processed DDD-MRS spectrum (absorption) as 6 channel spectral average without deploying the MRS signal processing aspects of the present disclosure (e.g. "pre-processing"), and certain calculated data derived therefrom as developed and used for calculated signal-to-noise ratio (SNR) of the processed result.
Figures 31E, 31F:
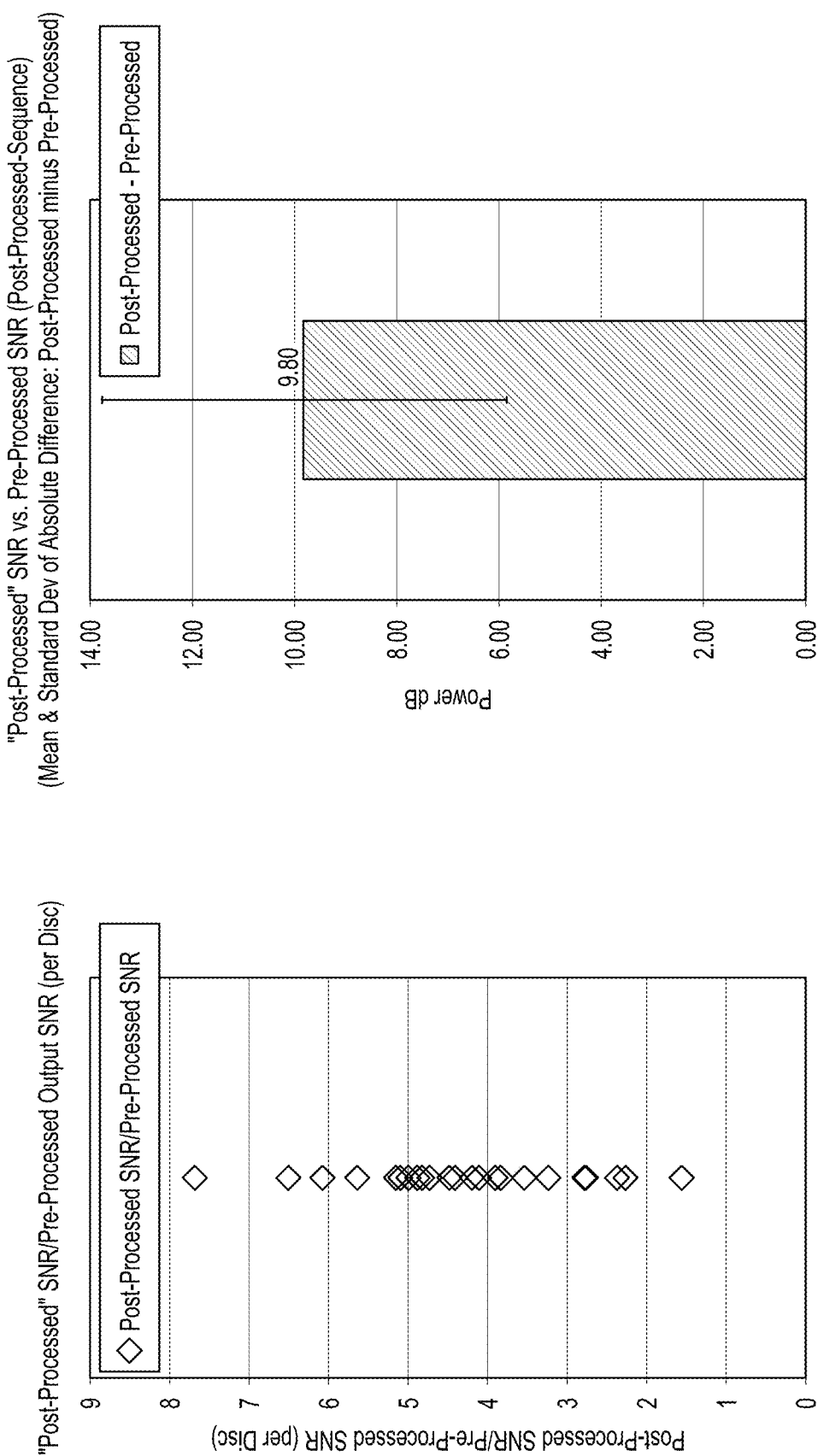
FIG. 31E shows a scatter plot histogram of the ratio of SNR values calculated post- versus pre-processing for each of the discs per the SNR data shown in FIGS. 31C-D.
FIG. 31F shows a bar graph of mean value and standard deviation error bar of the absolute difference between post- and pre-processed SNR values for each of the discs shown in different views in FIGS. 31C-E.

A freeware digitization program (WinDIG™, Ver 2.5, copyright 1996, D. Lovy)) was used to digitize both final DDD-MRS results and "screen shot" images. The "screen shot" images were reverse-imaged using MS Paint prior to digitization. The output of the digitizer program is an array of integers in a comma-separated values (CSV) file format. The CSV data files were imported to Microsoft™ Excel™ and re-plotted as shown in FIGS. 31A-B. A "region of interest" on the chemical shift (CS) axis (x-axis) pertaining to metabolite proteoglycan (PG, C S=2.11 PPM) was deemed to be the "signal". A region of interest to the far right (CS=0.5 PPM) which would not typically contain any spectral activity was deemed to be the "noise". In the event there was not a significant spectral peak in the PG region which is the often the case on pain patient discs, then the lactate/Lipid region of interest (CS=1.33 PP) was used as the signal. The "ranges of interest" were visually determined on both images resulting in sections of the data array. The SNR of a waveform is expressed as:

$$10*\log_{10}(RMS\ \text{signal}/RMS\ \text{noise}).$$

The RMS value was calculated by taking the sum of squares of the data section, calculating the mean of the sum of squares, and then taking the square root of the mean. Since the spectra are power amplitude plots, the log base 10 of the ratio of the RMS values is then multiplied by 10 to generate the SNR in dB.

For further understanding of this approach and examples of the digitized spectra and information extracted therefrom, FIG. 31A shows a digitized DDD-MRS spectral plot and accompanying SNR information, whereas FIG. 31B shows similar views for a digitized pre-processed all channel (n=6) averaged output spectral plot output from the respective MR system and related SNR information for the same acquisition series (without processing according to the present signal processing aspects of the present disclosure).

These pre- and post-processing SNR results are shown in FIGS. 31C-F. More specifically, FIG. 31C shows the calculated SNR for the pre- and post-processed spectra, with significant majority of the pre-processed spectral SNR shown on the left side histogram distribution of the plot falling below 5 (and also much of the data below 3), but with a significant majority of the post-processed spectral SNR shown on the right side histogram distribution of the plot falling above 3 (all but 1) and even above 5 (all but just 2). A typical accepted SNR range for confidently measuring chemical constituents from an MRS plot is in many cases over 5, though in many cases may be for any data over 3—such that below these thresholds may be "unquantifiable" or "immeasurable" at least per such standards (if applied). In such an application of these thresholds, it is clear that a significant portion of data acquired pre-processing according to the present embodiments is not generally useful for interpreting signal regions of interest, whereas these data as post-processed herein become quite consistently useful. In fact, as shown in FIG. 31D, the average SNR across the signals evaluated for this comparison exercise was: about 3 (e.g. well below 5) pre-processing, and about 13 (e.g. well above 5) post-processing ($p<0.001$). As per the ratio of post- vs. pre-processed signals further shown in FIG. 31E, in all cases compared the post-processed signals were higher SNR than pre-processing, generally along a range between 2 to 8 times higher SNR (with only one point falling below 2× improvement, though still about 50% improved). As further evaluated (e.g. FIGS. 31F-H), the mean absolute improvement was about 10 dB, the mean ratio improvement was over 4×, and the mean % improvement was well over 300% in converting from pre- to post-processed signals according to the present embodiments.

Figure 32A:
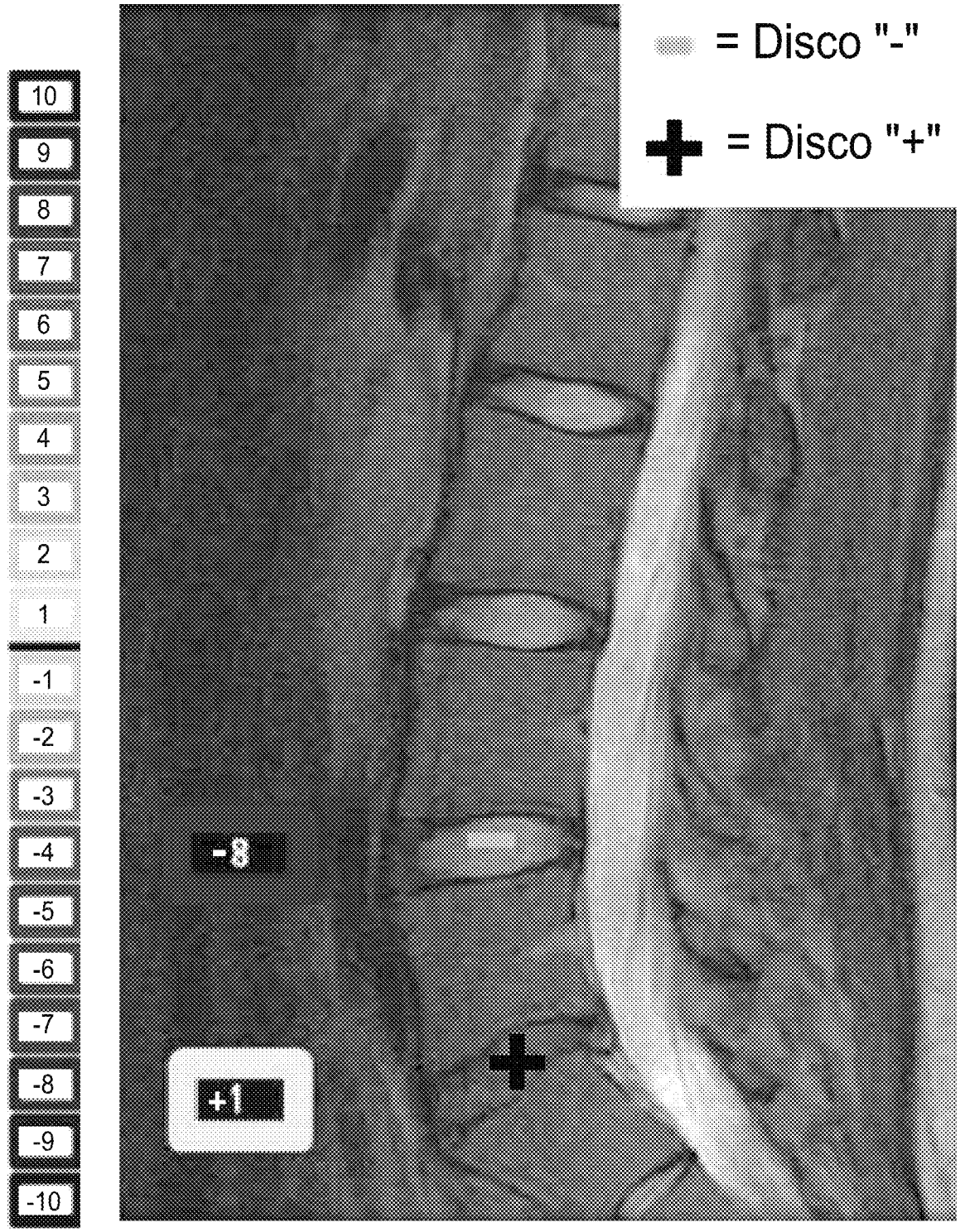
FIG. 32A shows a mid-sagittal T2-weighted MRI image of a patient evaluated under the clinical study of Example 1 and comparing the diagnostic results of the operating embodiment for DDD-MRS system developed according to various aspects herein against provocative discography results for the same discs, and shows a number-coded (and also may be color coded) diagnostic legend for the DDD-MRS results (on left of image) and discogram legend (top right on image) with overlay of the DDD-MRS results and discogram results on discs evaluated in the patient.
Figure 32B:
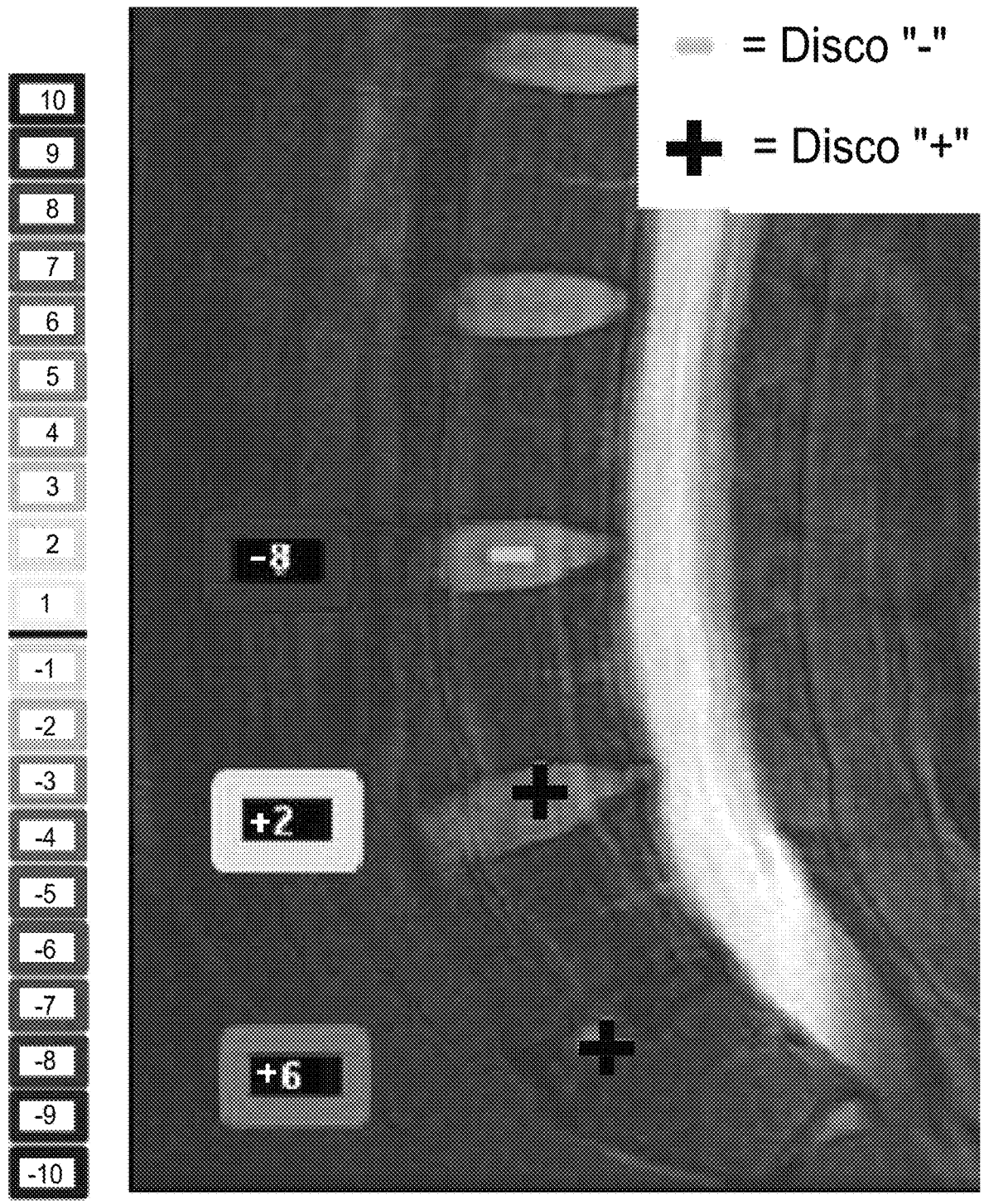
FIG. 32B shows a mid-sagittal T2-weighted MRI image of another patient evaluated under the clinical study of Example 1 and comparing the diagnostic results of the physical embodiment DDD-MRS system developed according to various aspects herein against provocative discography results for the same discs, and shows a number-coded (and also may be color coded) diagnostic legend for the DDD-MRS results (on left of image) and discogram legend (top right on image) with overlay of the DDD-MRS results and discogram results on discs evaluated in the patient.
Figure 33A:
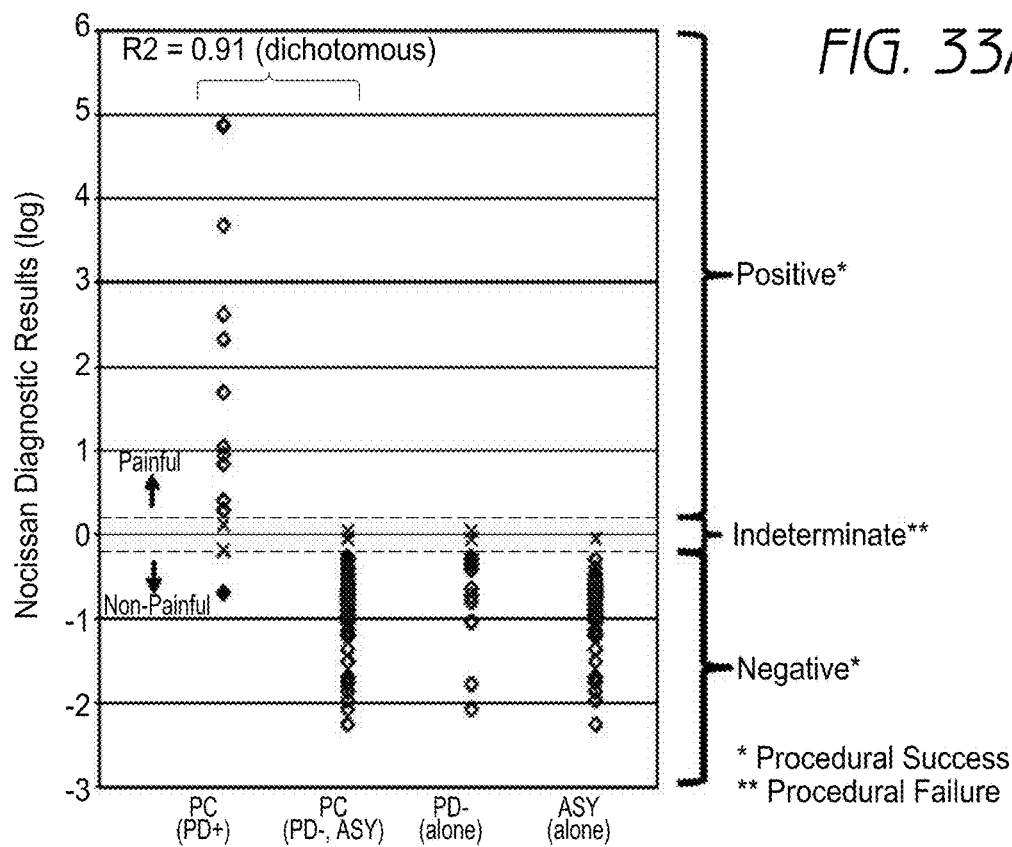
FIG. 33A shows a scatter plot histogram plot of DDD-MRS (or "Nociscan") diagnostic results against control groups for various discs evaluated in vivo according to the data set reviewed and processed under Example 2, as similarly shown for the data evaluated in Example 1 in FIG. 25A (plus the further addition of certain additional information further provided as overlay to the graph and related to another aspect of data analysis applied according to further aspects of the present disclosure under Example 2).
Figure 33B:
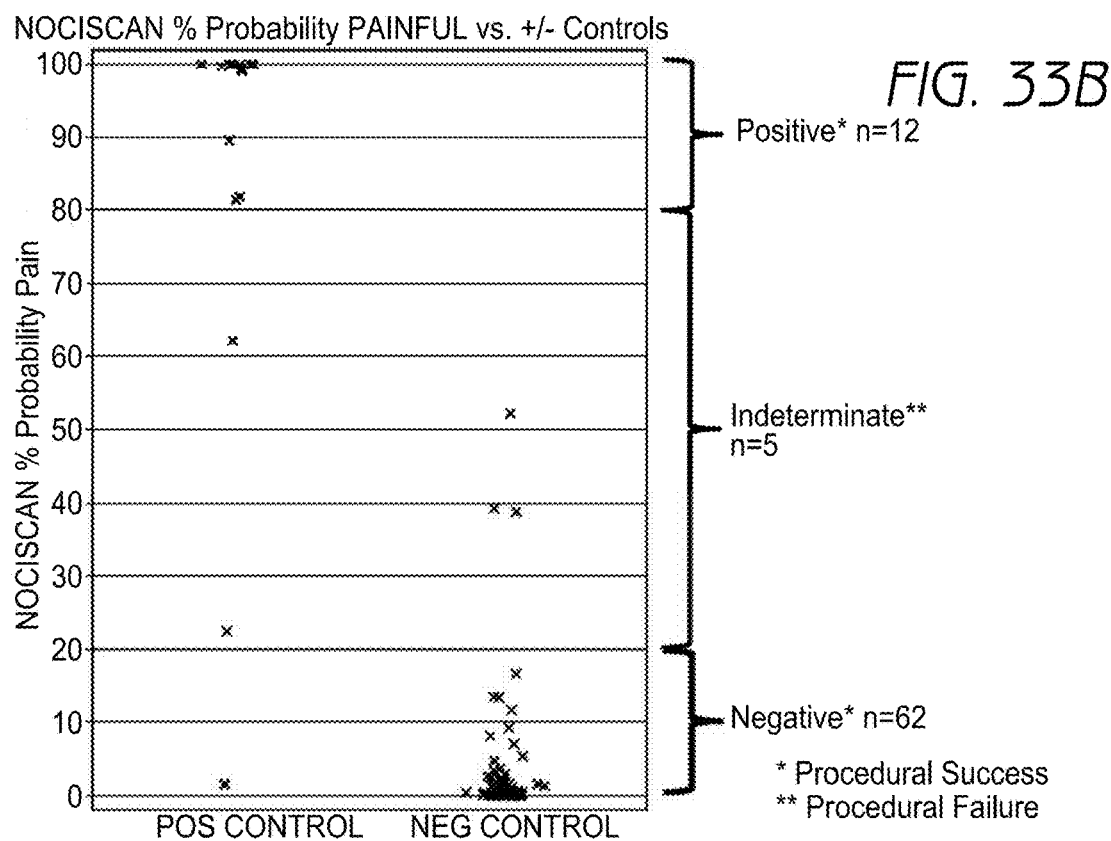
FIG. 33B shows another scatter plot histogram of another processed form of the DDD-MRS diagnostic results also shown in FIG. 33A and per Example 2, after transformation of the DDD-MRS diagnostic algorithm results for the discs into "% probability painful" assigned to each disc as distributed across the positive (POS) and negative (NEG) control group sub-populations shown.

For further illustration of the beneficial results demonstrated by the DDD-MRS diagnostic exam, FIGS. 32A and 32B show two different examples of DDD-MRS diagnostic display results for two different patients in the clinical study featured under this Example 1. These patients have similar disc degeneration profiles as seen on the MRI images, with dark disc at L5-S1 and relatively healthy discs revealed above at L4-L5 and L3-L4 in each patient. As also shown in each of these figures, both patients also had positive discogram results at L5-S1. However, as also shown in these two comparison Figures, the patient featured in FIG. 32A had a negative discogram result (e.g. non-painful diagnosis) at L4-L5, whereas the patient featured in FIG. 32B had a positive discogram result (e.g. painful diagnosis) at that level—despite having similar disc degeneration profile. As a consequence of both exams, with modern discography technique guidelines indicating requirement for a negative control disc before positive levels may be accepted results, the patients each had another negative discogram done at the L3-L4 (FIG. 32A) and L4-L5 (FIG. 32B) levels, respectively, to provide the required negative control level. As an awarded recent study has shown discography significantly increases disc degeneration and herniations rates, the result of both of these studies, if followed for directed intervention, would have resulted in treating the positive discogram levels, but not the negative discogram levels—leaving those untreated levels in place to potentially accelerate in degeneration and toward possible herniations. As shown in these Figures, the non-invasive DDD-MRS results matched these invasive discography results at all disc levels. The DDD-MRS approach provides the distinct benefit of providing the diagnostic information required, while leaving all discs uncompromised due to the non-invasive nature of the approach.

Discussion:

The differentiation of painful and non-painful lumbar degenerative discs is an important goal in the accurate assessment of pain generators, and in guiding clinical management of patients with lumbar degenerative disc disease. The novel application of Magnetic Resonance Spectroscopy developed and evaluated under this study proposes a non-invasive, objective, and quantifiable measure of the chemical composition of the lumbar intervertebral disc. The MRS diagnostic algorithm developed and used in this study demonstrates a high degree of sensitivity in identifying patients with a clinical assessment of lumbar discogenic pain and a positive discogram, and a high degree of specificity in identifying levels that are not painful, without any false positive results observed in asymptomatics. This study developing, uniformly applying, and characterizing the DDD-MRS diagnostic approach retrospectively across the study population evaluated herein is quite encouraging. Cross validation also performed on the results predicts the approach is generalizable to broader population, as may be readily confirmed in additional prospective study in more subjects, and as may be conducted by one of ordinary skill.

Example 2

The 52 disc clinical data set evaluated under the DDD-MRS system embodiments of the present disclosure and associated with Example 1 was further expanded with additional new subjects examined for a total of 74 discs, with additional signal processing developments performed and diagnostic algorithm development conducted to determine the optimal correlation to the expanded data set. The results of this algorithm development and analysis was then applied to an additional 5 discs in new asymptomatic control volunteers prospectively, for 79 total discs later evaluated.

Standard logistic regression procedures were used to develop a second generation linear regression model between disc variables obtained from DDD-MRS acquisitions and processed by the DDD-MRS signal processing engine, to disc pain status (pain/no-pain entered as a categorical variable based on provocative discography). MR spectra (in-phase real power format) from a population of 74 discs (15 painful and 59 asymptomatic) were used for classifier development and cross-validation partition analysis. The DDD-MRS data demonstrated a strong correlation with the clinical diagnoses ($R^2=0.76$, $p<0.00001$) with an ROC analysis yielding an AUC of 0.99. Cross-validation through partition analysis resulted in only small variance in $R^2$.

Materials and Methods

All statistical analyses were performed using JMP (version 7.0, SAS). Standard logistic regression procedures were used to relate the disc variables (proteoglycan, lactate, and alanine spectral peaks entered as continuous variables) to the disc pain status (pain/no-pain entered as a categorical variable). Discography performed according to ISIS Guidelines was used as the reference standard for pain status in low back pain patients. Discs from asymptomatic volunteers were assumed negative. The discography status and disc variables were entered into an excel spreadsheet and imported into JMP.

The DDD-MRS diagnostic algorithm was determined in a three-stage process.

First, the terms were limited to spectral features related to proteoglycan, lactate and alanine because these were shown to be important classifiers in prior studies (Keshari, 2008. "Lactic acid and proteoglycans as metabolic markers for discogenic back pain." *Spine* 33(3): 312-317), and fit with biologically-plausible theories for discogenic pain generation. In addition, normalized values for these factors were considered. To provide an estimate of metabolite concentration, the spectral measures were divided by the region of interest (ROI) volume. Also, given signal strength may vary with ROI depth, subject body mass index (BMI) was also considered as a normalizing factor. This was done by taking the BMI for a subject associated with a given disc sample being evaluated divided by the average BMI across the data set used for the logistic regression modeling. Also as raw signal region values represent "amounts" of respective chemicals associated such regions, dividing such values by voxel volume may provide a surrogate approach to more closely approximating "concentration" for such chemicals (amount/unit volume)—which as biomarkers as mediators to a pain cascade are likely more relevantly assessed as concentration. For example, lactic acid is more relevant to disc tissue acidity, which is believed to be a pain generator, on a concentration basis vs. total amount in the tissue. Accordingly, voxel volume adjustment for a signal measurement simply involved dividing the measured factor or parameter by the voxel volume.

In the second step, the form of the factor dependence was estimated using Screening Platform in JMP. Within the Screening Platform, the dependent variable was chosen to be pain status, and the candidate independent variables were chosen to be proteoglycan, lactate, and alanine (either raw values or values normalized by voxel volume and/or BMI). The Screening Platform then identified candidate terms with associated p-values. These would include either individual factors, or products of multiple factors. Terms with p-values less than 0.05 were selected as candidates for further consideration.

In the third step, candidate terms from the Screening Platform were entered as independent predictors in the Logistic Platform of JMP. This platform was used to conduct logistic regression analysis to identify statistically-significant terms plus their parameter estimates. The Logistic Platform fits the probabilities for the response category (pain/no-pain status) to a set of continuous predictors (metabolite terms). The fit quality was judged by the coefficient of determination $R^2$ and the p-value. In an ad-hoc stepwise fashion, candidate terms were brought into the Logistic model to judge their influence on model performance.

Because some metabolite data are not normally distributed, log and square-root transformations of the candidate terms were also considered. Candidate terms with p-values less than 0.05 were removed from the model. The Logistic regression output provided parameters that are multipliers for each term plus an intercept term. These formed an algorithm that provides a continuous number that, if greater than zero would indicate a painful status, and if less than zero would indicate a non-painful status.

As an additional summary of the discriminatory accuracy of the Nociscan diagnostic algorithm, generated standard Receiver-Operator curves (ROC) that are plots of sensitivity versus specificity across a rank ordered list of study discs. The area under the ROC curve (AUC) was used to judge the algorithm accuracy. The AUC is the probability that test results for a randomly-selected painful disc and non-painful disc will be rank ordered correctly. Additionally, continuous correlation procedures were used to judge whether the output of the diagnostic algorithm correlates with VAS score, disc degeneration grade, and the discography pain intensity.

Results/Data

Using the aforementioned procedures, a diagnostic algorithm was developed using a 74 disc (15 pain, 59 control) population. The best-fit linear regression equation result using this approach was as follows:

$$\text{Score} = -4.6010405 + 1.5875166(BLA) -$$
$$0.081991(VBLAAL - 29.3125) * (VBLAAL - 29.3125) +$$
$$0.01483355(PG/MAXLAAL - 7.14499) *$$
$$(PG/MAXLAAL - 7.14499) * (PG/MAXLAAL - 7.14499) +$$
$$0.1442603(MAXLAAL/vol - 16.1202) * (VBLAAL - 29.3125) -$$
$$0.0008879(VBLAAL - 29.3125)^2 * (MAXLAAL/VOL - 16.1202)$$

where BLA is the BMI corrected LA spectral peak, VBLAAL is the ROI volume and BMI normalized sum of the LA and AL spectral peaks, MAXLAAL is the maximum of either the LA or AL peaks, and PG is the n-acetyl spectral peak.

The present linear regression equation of this Example 2 uses similar features as its predecessor such as chemical peak values and peak ratios, but in addition uses features normalized for voxel volume and BMI (e.g. "VB" designating both). Increased body fat (increased BMI) will reduce chemical peak values because the voxel is physically further away from the RF coil resulting in reduced signal strength and chemical peak values. The BMI value is adjusted (normalized) by the mean BMI of the population. The adjusted BMI value thus applies a proportional "gain" to chemical peak values otherwise reduced by large BMI.

Similarly small voxel volumes will reduce the chemical peak values and the inverse of voxel volume is applied as a "gain" factor. In addition to normalization, the equation also defines a two new features. The first consists of combined regions of interest (ROI) lactate (LA) and alanine (AL) regions to create LAAL. The second is a region called MAXLAAL whose value is the greater of the two regions.

A final development to the diagnostic engine is the application of an indeterminate band to the classification process. This band lies between the highly probable pain and pain free states and is statistically determined from the distribution of the two disc populations. Diagnostic scores that fall within this band are determined to be procedural failures because of the low probability to diagnose either way. When applied this band results in one false negative (a positive discography disc diagnosed as pain free).

Results and Discussion

A second generation diagnostic classifier using DDD MRS acquisition data as processed by the Nociscan signal processing average has been developed using an increased disc population (from n=52 to n=74). The incorporation of BMI adjustment per each sample's BMI relationship to a mean population BMI, voxel volume adjustment to more closely approximate concentration aspects of the target biomarker metabolites, and the use of combined regions of interest (LAAL, MAXLAAL), has resulted in a linear regression equation with a significant improvement over the otherwise highly accurate first generation linear regression equation, with ($R^2$=0.89, p<0.00001) with an ROC analysis yielding an AUC of 0.99.

Figure 34B:
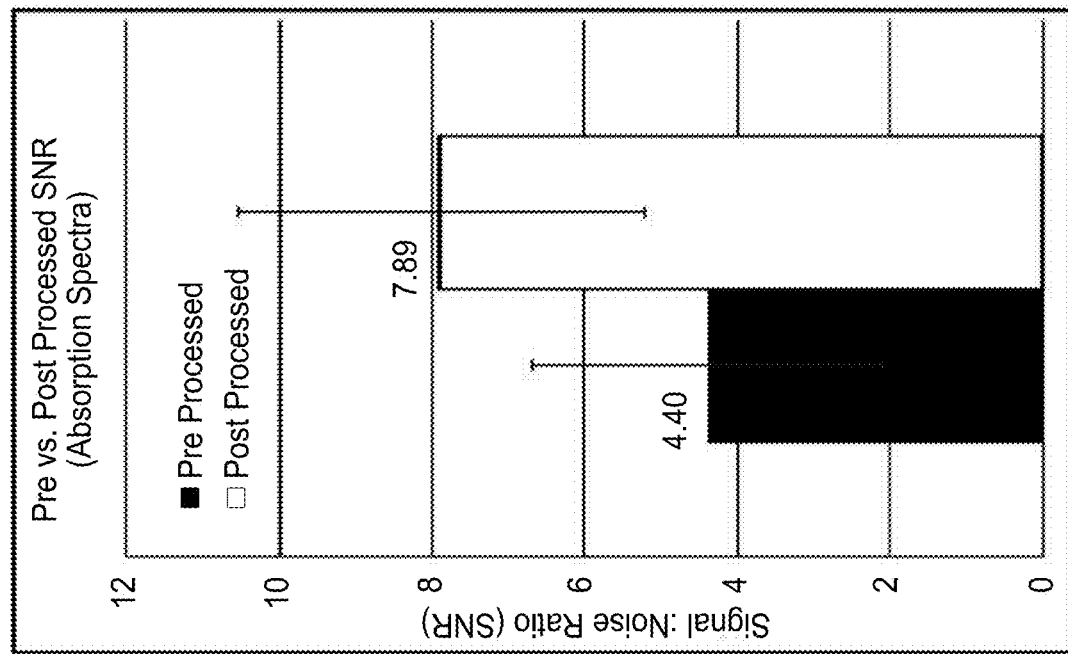
FIG. 34B shows the same data shown in FIG. 34A, but as bar graph showing mean values and standard deviation error bars for the data within each pre-processed and post-processed groups.
Figure 34A:
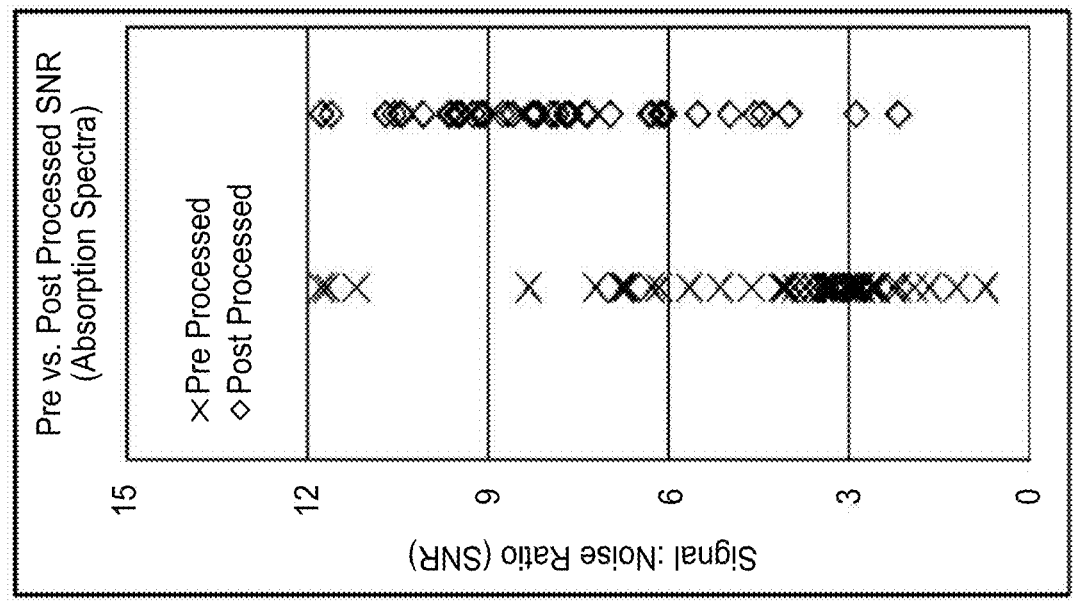
FIG. 34A shows a scatter plot histogram of signal-to-noise ratio (SNR) for standard "all channels, non-corrected" frame averaged MRS spectra (absorption) produced by the 3T MR system for a subset of discs evaluated using the DDD-MRS pulse sequence and signal processor in the clinical study of Example 2, and the SNR of spectra (absorption) for the same series acquisitions for the same discs post-processed by the DDD-MRS processor, as such SNR data was derived for example as illustrated in FIGS. 31A-B.

For further illustration, FIG. 34A shows the distribution of this algorithmic data across the combined data set via the formulaic algorithmic "score" for each disc plotted against designation of the discs as fitting within the positive controls (positive discogrammed discs, or PD+), negative controls (negative discogrammed discs in pain patients, or PD−, combined with discs from asymptomatic control volunteers or "ASY" discs), and versus these two negative control sub-populations alone. This also shows the application of the statistically guided "indeterminate" band bordering the "zero" line and where n=5 discs fall, with positive test results above the upper limit of that band (n=12), and negative results below the lower limit of that band (n=63, of which 62 were negative controls and 1 was a positive control disc). Excluding these indeterminates as "procedural failures" excludes 5/79 discs or only 6% of the test population, while remaining 94% are considered procedural successes for making a confident diagnosis. Among these 94% procedural successes, the results were 99% accurate with 73/74 overall match to controls (only 1 mismatch), $R^2$=0.91, p<0.0001, and AUC=0.99. These more detailed breakdown for the matches against controls (e.g. positive match to positive discogram, or negative match to negative discogram or discs from asymptomatic subjects) are as follows: 12/13 (92%) of Positive Discography; 13/13 (100%) of Negative Discography; 48/48 (100%) of Asymptomatics—thus there were no false positive results in 62 negative combined controls, and only 1/13 presumed false negative result among 13 positive control discs. These results further provide the following performance characteristics typically used to evaluate a diagnostic platform: 92% Sensitivity, 100% Specificity, 100% Positive Predictive Value, and 98% Negative Predictive Value.

For still further illustration of another highly beneficial view of these highly accurate results of this current approach of Example 2 to this test group, FIG. 34B shows another distribution of the same results for this same data set, but as converted to % probability prediction a disc is painful (as generated by rank ordering of the logistic regression analysis and results). As shown in this Figure, a region between about 80% probability and about 20% probability prediction of pain corresponds with capturing the same n=5 discs indeterminate zone discs of the other view of the data distribution in the prior Figure, with greater than about 80% probability criteria capturing all of the n=12 same positive test results (all matching positive controls), and less than about 20% probability criteria capturing all of the n=63 same negative test results (62 matching all of the negative controls, and 1 a positive control and thus representing the same single presumed false negative test result).

Example 3

Standard logistic regression procedures were used to relate disc variables obtained from DDD-MRS acquisitions and processed by the Nociscan signal processing engine to disc pain status (pain/no-pain entered as a categorical variable based on provocative discography). Acquired DDD-MRS spectra were processed, analyzed, and presented post-processing for diagnostic purposes in absorption mode—vs. real-part squared power format of prior Examples. The spectral acquisitions were the same and from the same population of 79 discs in 42 subjects (15 painful and 64 asymptomatic) as featured in Example 2, used here for further algorithmic classifier development. Certain signal quality criteria were also used in this Example 3 to determine each of three classifications of acquired results—namely recognizing the following sub-groups: (1) a first spectral group with clearly apparent lipid signal (then given its own logistic regression model and resulting algorithm), and (2) a second spectral group absent any obvious lipid signal that was still further sub-classified into still further sub-groups: (2)(a) spectra with significant PG/LAAL peak ratios over a determined criteria threshold, and (2)(b) the remaining non-lipid signals not meeting this criteria also given its own second logistic regression model and resulting algorithm. The three classifier equations that were developed resulted in 100% procedural success and 100% separation for differentiating painful from non-painful discs in all 79 discs evaluated.

Purpose

The purpose of this study was to evaluate still further potentially valuable approaches for developing a robust classifier, including as using features extracted from absorption spectra as opposed to features formerly extracted from in phase real power spectra, and also to evaluate a different approach for classifier modeling based upon a serial application of a limited few tests applied to what appeared to be unique sub-populations among data. Absorption power format is the traditional method of displaying spectra. In phase real power spectra are comprised of the square of the real component of each spectral point. This format presents only positive going spectra with minimal baseline shift. This mitigates the need to fit a spline curve to the baseline as well as makes the spectra appear more peaked. The overall effect is to enhance the apparent signal to noise ratio (SNR) and remove the variability associated with fitting a baseline to the spectral plot for the purpose of making spectral peak and area under the curve (AUC) measurements. Nonetheless, the current absorption spectra approach of this Example 3 is more common to typical MRS analysis in other applications, and may be more relevant for biomarker assessment in certain cases, vs. previous classifier development of prior Examples that has been done using spectra presented in in-phase, real power squared format.

Materials and Methods

A comparison of SNR for post-processed versus pre-processed DDD-MRS spectra acquired per this Example was performed similarly as featured above for Example 1 data set (e.g. FIGS. 31A-H), except using absorption spectra for both pre- and post-processed data, and per the expanded clinical data set represented in this Example 3. These were otherwise analyzed similarly as was done in those prior Figures for the prior Example 1.

All statistical analyses were performed using JMP (version 7.0, SAS). Standard logistic regression procedures were used to relate the disc variables (proteoglycan, lactate, and alanine spectral peaks entered as continuous variables) to the disc pain status (pain/no-pain entered as a categorical variable). A significant majority of the discography was performed according to ISIS Guidelines and was used as the reference standard for pain status of 'positive control' discs in low back pain patients. Discs from asymptomatic volunteers were assumed negative, and were combined with negative discography discs from the pain patients as the negative control group presumed to be non-painful. The discography status and disc variables were entered into an excel spreadsheet and imported into JMP.

The terms in each of the two sub-groups (1) and (2)(b) where logistic modeling was applied for algorithm development were determined in a three-stage process. The first step choosing spectral features of interest for analysis, and corresponding to the PG, LA, and AL biomarker chemicals, proceeded as per prior examples, and including BMI and voxel adjustment as described for Example 2, with the following difference in this Example 3 that absorption spectra were used for the data extraction and subsequent inputs into the diagnostic processor.

In the second step, the form of the factor dependence was estimated using Screening Platform in JMP. Within the Screening Platform, the dependent variable was chosen to be pain status, and the candidate independent variables were chosen to be proteoglycan, lactate, and alanine (either raw values or values normalized by ROI volume and/or BMI). The Screening Platform then identified candidate terms with associated p-values. These would include either individual factors, or products of multiple factors. Terms with p-values less than 0.05 were selected as candidates for further consideration.

In the third step, candidate terms from the Screening Platform were entered as independent predictors in the Logistic Platform of JMP. This platform was used to conduct logistic regression analysis to identify statistically-significant terms plus their parameter estimates. The Logistic Platform fits the probabilities for the response category (pain/no-pain status) to a set of continuous predictors (metabolite terms). The fit quality was judged by the coefficient of determination $R^2$ and the p-value. In an ad-hoc stepwise fashion, candidate terms were brought into the Logistic model to judge their influence on model performance.

Because some metabolite data are not normally distributed, log and square-root transformations of the candidate terms were also considered. Candidate terms with p-values less than 0.05 were removed from the model. The Logistic regression output provided parameters that are multipliers for each term plus an intercept term. These formed an algorithm that provides a continuous number that, if greater than zero would indicate a painful status, and if less than zero would indicate a non-painful status.

As an additional summary of the discriminatory accuracy of the Nociscan diagnostic algorithm, generated standard Receiver-Operator curves (ROC) that are plots of sensitivity versus specificity across a rank ordered list of study discs. The area under the ROC curve (AUC) was used to judge the algorithm accuracy. The AUC is the probability that test results for a randomly-selected painful disc and non-painful disc will be rank ordered correctly. Additionally, we used continuous correlation procedures to judge whether the output of the diagnostic algorithm correlates with VAS score, disc degeneration grade, and the discography pain intensity.

In context of the aforementioned methods and procedures applied to previous classifier development and those receiving logistic regression modeling in this current Example, a data partition approach was implemented based on certain spectral features observed in the current dataset. First, discs with perceived lipid signal in the acquired DDD-MRS spectra were partitioned into Group A (n=10). This was given its own logistic regression modeling as test #1. Next, because many negative non-painful discs were observed to have uniquely strong n-acetyl peak (PG) and weak lactate (LA) and/or alanine (AL) peaks, the PG/LAAL ratios for the remaining non-lipid disc population (n=68) were evaluated between the positive and negative control groups. A cut-off in a go/no-go voting method approach of test #2 for 'clearly negative' discs was identified at PG/LAAL peak ratios above 1.81 to create Group B successes for negative results as non-painful (n=52 of 68 discs evaluated in the non-lipid population). The third data analysis and test portion, Group C (n=16, a subset of non-lipid Group B that did not meet the test #2 criteria as having PG/MAXLAAL <1.85) were analyzed also using the logistic regression modeling per the three-step process defined above. Four statistically-significant terms and their parameter estimates were identified by the Logistic Regression Platform: ROI (e.g. voxel volume or VV) and BMI adjusted LA absorption peak; VV and BMI adjusted AL absorption peak; VV and BMI adjusted AL AUC (area under the curve) or "ALAUC"; and square root of the VV and BMI adjusted N-acetyl AUC or "NAAAUC").

Finally with respect to the DDD-MRS diagnostic processor aspects of the present Example, the spectra with suspected lipid contamination (Group A) were also analyzed using the three-step analysis procedure. This resulted in two terms that separated positive from negative discs: the square root of the VV and BMI adjusted LA peak, and the VV and BMI adjusted ratio of n-acetyl to LAAL. When taken together, the partition plus logistic regression approach success fully separated all negative from all positive discs.

Results/Data for Absorption Spectra SNR

Figure 34D:
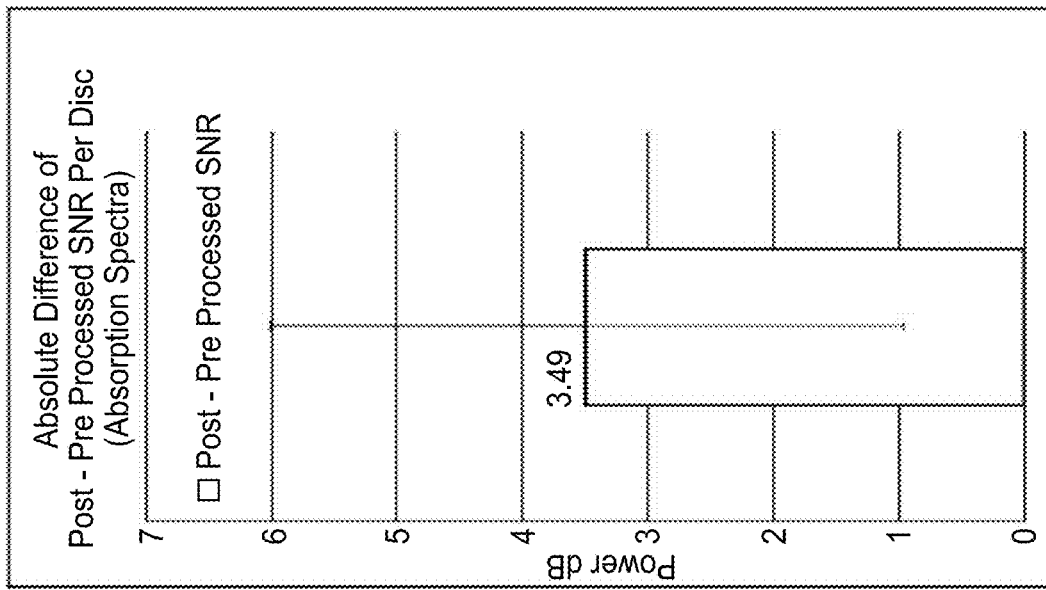
FIG. 34D shows a bar graph of mean value and standard deviation error bar of the absolute difference between post- and pre-processed SNR values for each of the discs shown in different views in FIGS. 34A-C.
Figure 34C:
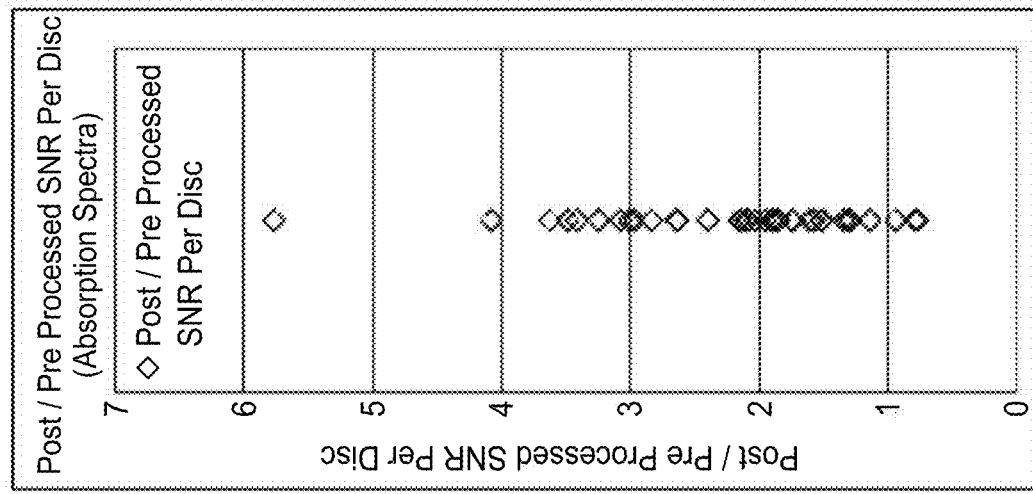
FIG. 34C shows a scatter plot histogram of the ratio of SNR values calculated post- versus pre-processing for each discs per the SNR data shown in FIGS. 34A-B.
Figure 34F:
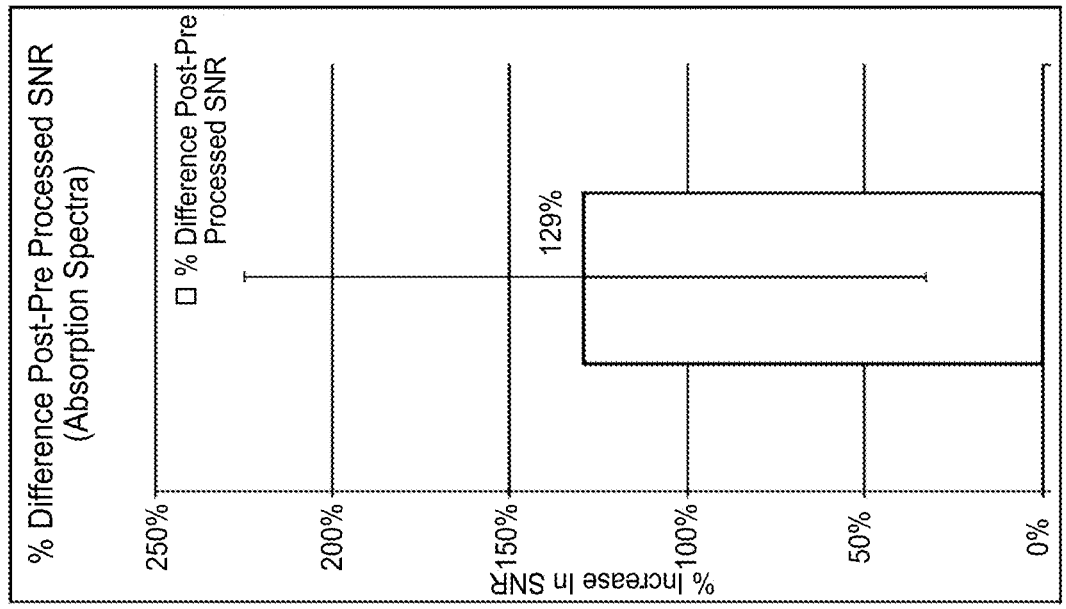
FIG. 34F shows a bar graph of the mean value and standard deviation error bar for the percent increase in SNR from pre- to post-processed MRS spectra for each of the discs further featured in FIGS. 34A-E.
Figure 34E:
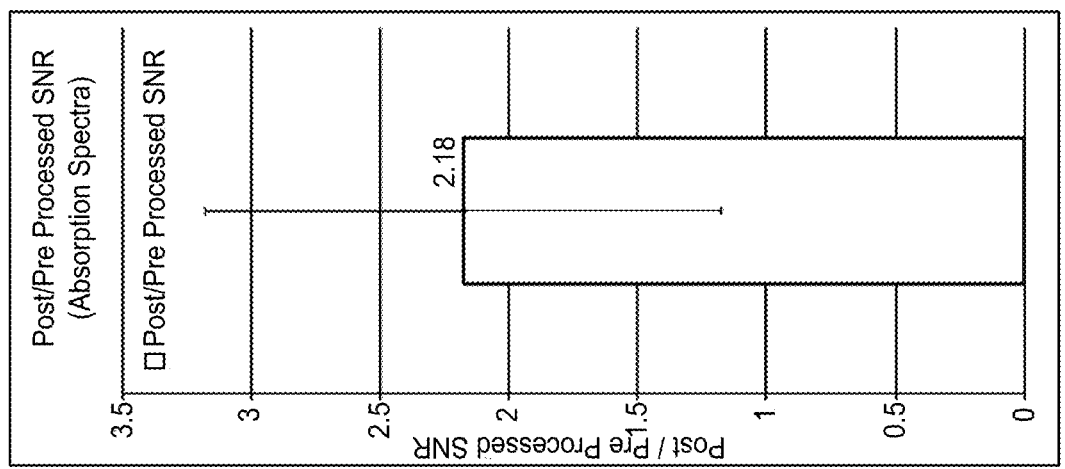
FIG. 34E shows a bar graph of mean value and standard deviation error bar of the ratio of post- to pre-processed SNR values for each of the discs shown in different views in FIGS. 34A-D.

The SNR evaluation of the post-processed versus pre-processed absorption spectra plots per this Example are shown in FIGS. 34A-F, and demonstrate significant SNR increase via the DDD-MRS signal processor aspects deployed for this data set in the Example 3, and also shows vast majority of the resulting signals to have sufficiently robust SNR for target regional chemical signal feature measurements. More specifically, FIG. 34A shows vast majority of the post-processed SNR above 3 (except only 2 cases), and in fact over 5, though much of the pre-processed spectra were below these levels. FIG. 34B shows the average pre-processed SNR of only slightly above 4, while the average post-processed SNR was about 8 and nearly ⅔ of the post-processed SNR of the real-part squared approach taken in the prior Example despite that approach squaring the signal:noise values. FIG. 34C shows the vast majority of the individual points were improved (e.g. ratio of SNR of post- vs. pre-processed signals), but for only a few (n=3) which were further observed to be quite high SNR to begin with, and with FIG. 34D showing about a 3.5 dB average SNR increase or about 2.2× (FIG. 34E) versus the pre-processed SNR.

As for the DDD-MRS diagnostic processor developed and evaluated per this Example, the best fit linear regression equations extracted from the absorption spectra are shown as follows:

Group A, test #1:

$$Score = -(-335.51971 + 0.00010632*(LAVVBMI)^2 + 873.744714*(PG/(LAALVVBMI)));$$

where LAVVBMI equals the voxel volume and BMI adjusted LA peak value.

Group B, test #2:

$$Score = -(-1.4959544 + 1.72223147*(PG(MAXLAAL)));$$

where PG/MAXLAAL equals the PG peak value divided by the maximum peak value of the LAAL region.

Group C, test #3:

$$Score = -1*(-134.40909800961 + 3.96992556918043*LAVVBMI -$$
$$2.6198628365642*ALVVBMI + 113.683315467568*$$
$$ALAUCVVBMI - 149.65896624348*SQRT(PGAUCVVBMI));$$

where LAVVBMI is the voxel volume and BMI adjusted LA peak value, ALVVBMI is the voxel volume and BMI adjusted AL peak value, ALAUCVVBMI is the AL region area under the curve as voxel volume and BMI adjusted, and PGAUCVVBMI is the PG region area under the curve as voxel volume and BMI adjusted.

Results/Data and Discussion—Diagnostic Processor

The default model used by JMP is to distribute data around 0. Results will typically provide negative results above 0, and positive results below 0. However, as this is inverse to logical presentation to match the classifications, and as in prior Examples, the negative of the classifier outputs are taken so that positive scores are associated with positive clinical tests for pain and negative scores are associated with non-painful discs.

The partitioning of spectral acquisitions based on the presence of lipid signal and on "clearly non-painful" spectral attributes (PG/MAXLAAL>1.81), as taken from absorption spectra, distinguish this classifier approach from previous efforts. The logistic regression modeling of the resulting sub-groups also provide different algorithms and varied specific factors as a result. Group A contains spectra with sufficient lipid (lipid peak at 1.3 PPM) that prevents the discrete characterization other chemical components such as PG, LA and AL. It is noted that upon evaluation of the absorption spectra results for this example, one acquisition or n=1 of n=79 total overall discs initially to be evaluated, was not considered to have sufficient signal quality (e.g. SNR too low) for robust diagnostic processing and thus excluded from that stage of processing, with resulting population of n=78 evaluated diagnostically of n=79 attempted (e.g. 99% procedural success, and <1% procedural failure rate due to low SNR processed acquisition).

Figure 35:
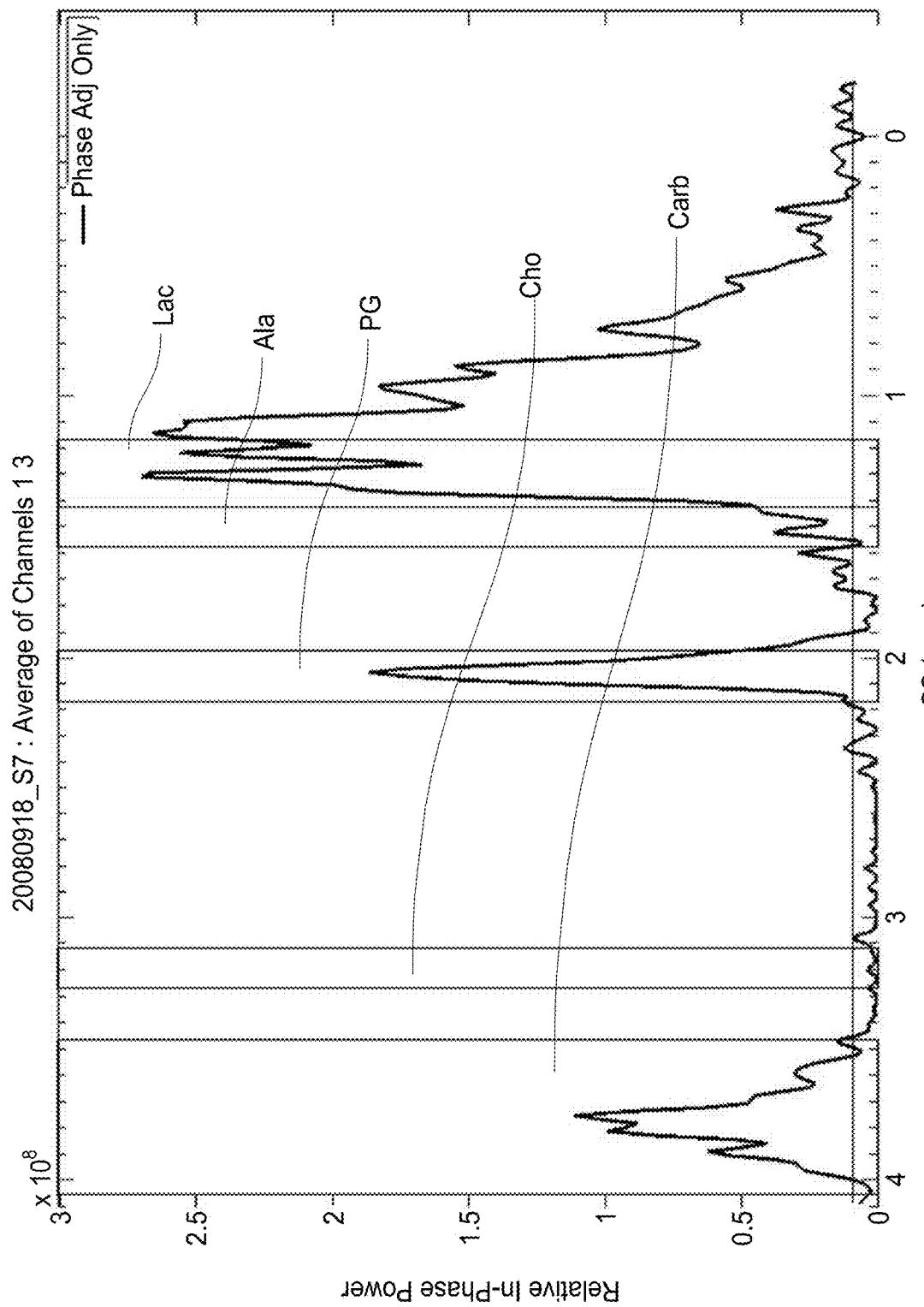
FIG. 35 shows a DDD-MRS spectrum illustrative of a perceived potential lipid signal contribution as overlaps with the regions otherwise also associated with lactic acid or lactate (LA) and alanine (AL), according to further aspects of the present disclosure and as relates to Example 3.
Figure 36:
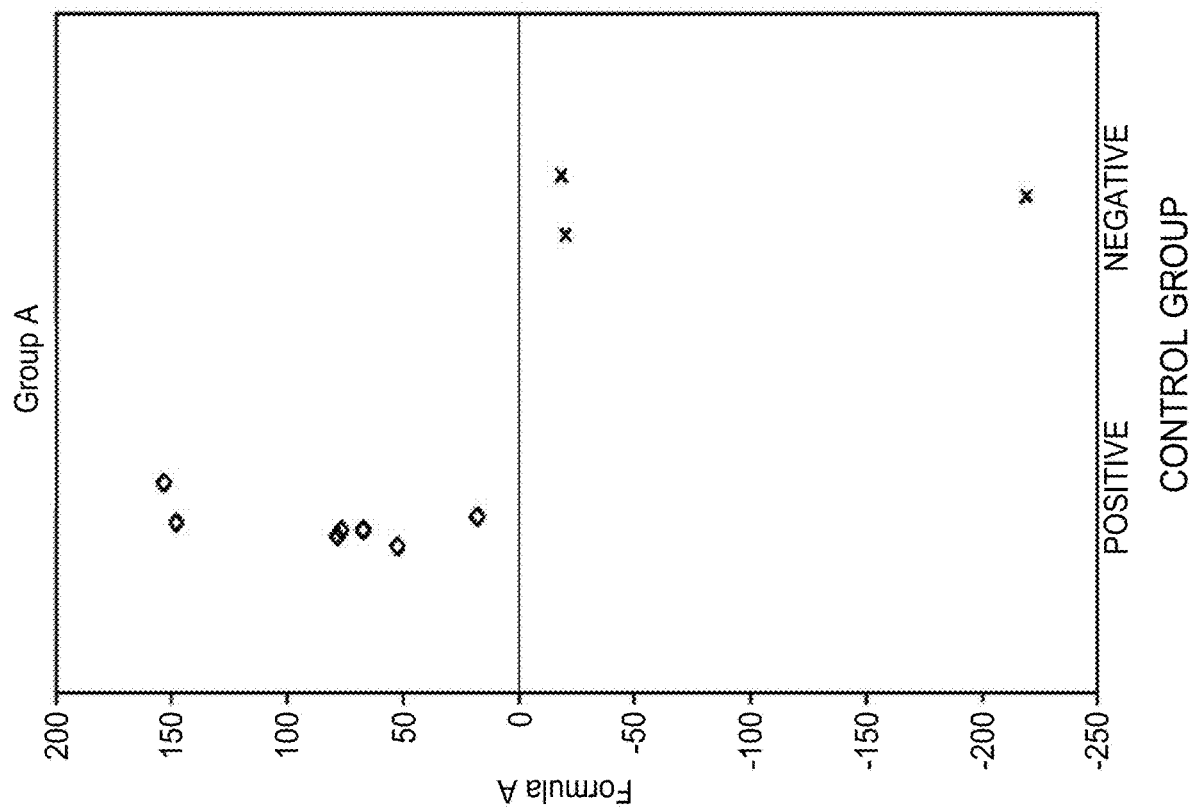
FIG. 36 shows a scatter plot histogram of DDD-MRS diagnostic algorithm results for the test population of in vivo discs, as calculated for a defined Group A evaluated for diagnostic purposes via Formula A, under the Example 3.

An example of a Group A spectra including suspected lipid signal from an asymptomatic control L5-S1 disc is shown in FIG. 35. Source of lipid in a given signal is not known, and may come from several different sources. Lipid signal is often observed however to result from capturing lipid-enriched vertebral body endplates by the voxel prescribed, and often (though not always) in an oblique, severely compromised (crushed) L51 disc. Another source of lipid contamination may be due to patient movement during the MRS acquisition, also involving end-plate artifact. It may also come as out of voxel signal in some cases, and may in fact come appropriately from within discs. Nevertheless, the prior grouping of signals with and without lipid was successful in accurately diagnosing most all discs, including all spectra with lipid across all the Examples. In this Example 3, spectra of Group A (n=10) was separated (100%) into painful and non-painful groups per test #1 and an associated probability of being painful is shown in FIG. 36. It is also observed among these spectra in this Group A that the presence of a sufficiently strong PG component in combination with lipid signal is likely related to sufficiently correlating with non-painful discs to provide the resulting reliable differentiation between positive and negative control groups.

Figure 37A:
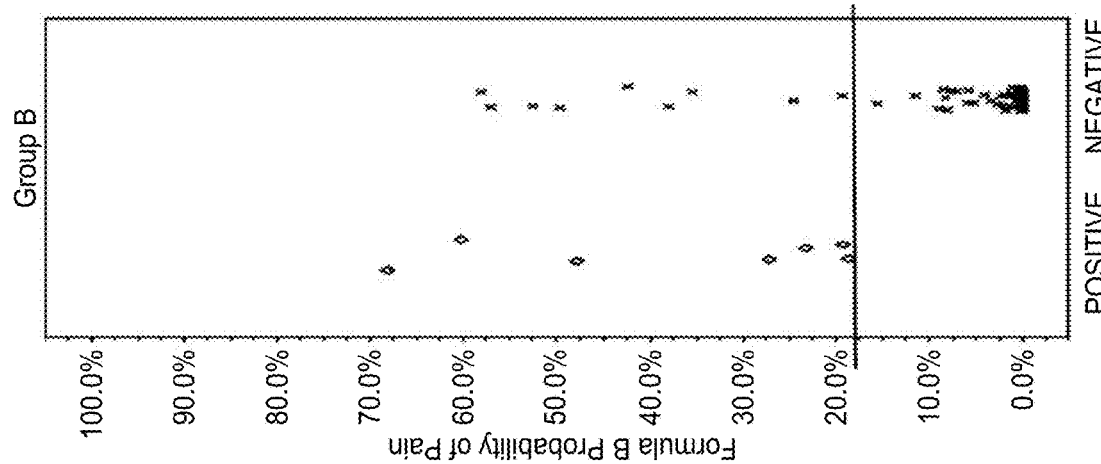
FIGS. 37A-C show scatter plot histogram of certain embodiments for the DDD-MRS diagnostic processor for discs designated as Group B under Example 3, including as shown with respect to PG/LAAL ratio results for the discs (FIG. 17A), logistic regression generated Formula B results for the discs (FIG. 17B), and the transformed % probability pain distribution for the same Group B discs as a result of the results in FIG. 17B (FIG. 17C).
Figure 37B:
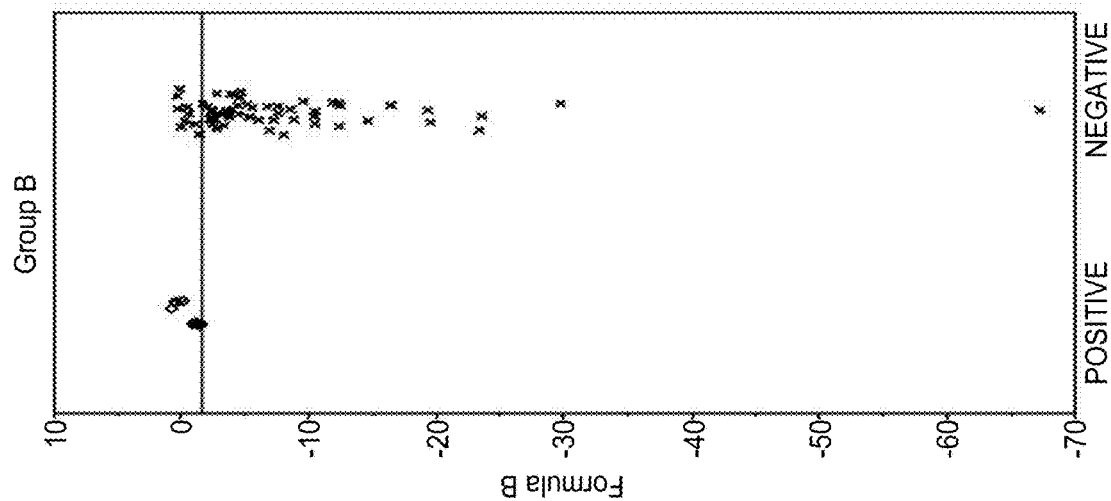
Figure 37C:
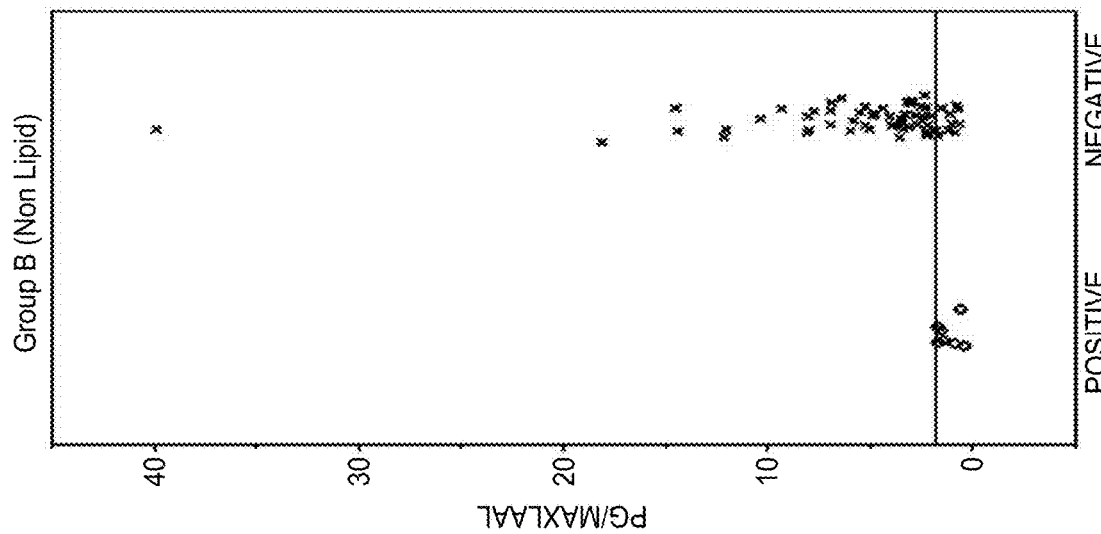

The second partition was applied to the disc population without lipid contamination (n=68). By visual observation of spectra across this population it was noted that all discs with PG/MAXLAAL value exceeding about 2. In further analysis, a threshold value of 1.85 was identified to partition only non-painful negative control discs above the threshold, and completely isolating the painful positive control disc population below the threshold, but while also including other non-painful negative control discs below this threshold. This PG/MAXLAAL partition analysis is shown in FIG. 37A. The more statistically robust linear regression model of test #2 derived and applied to Group B (n=68) is shown in FIG. 37B. The painful vs. non-painful segregations remain similar to the immediately previous analysis. The % probability painful converted format of this data distribution is shown in FIG. 37C, with threshold nearly approaching 20% differentiating all the same negative control discs, and none of the positive control discs in the group, below. (Note: Probability of being non-painful=1−pain probability).

Figure 38:
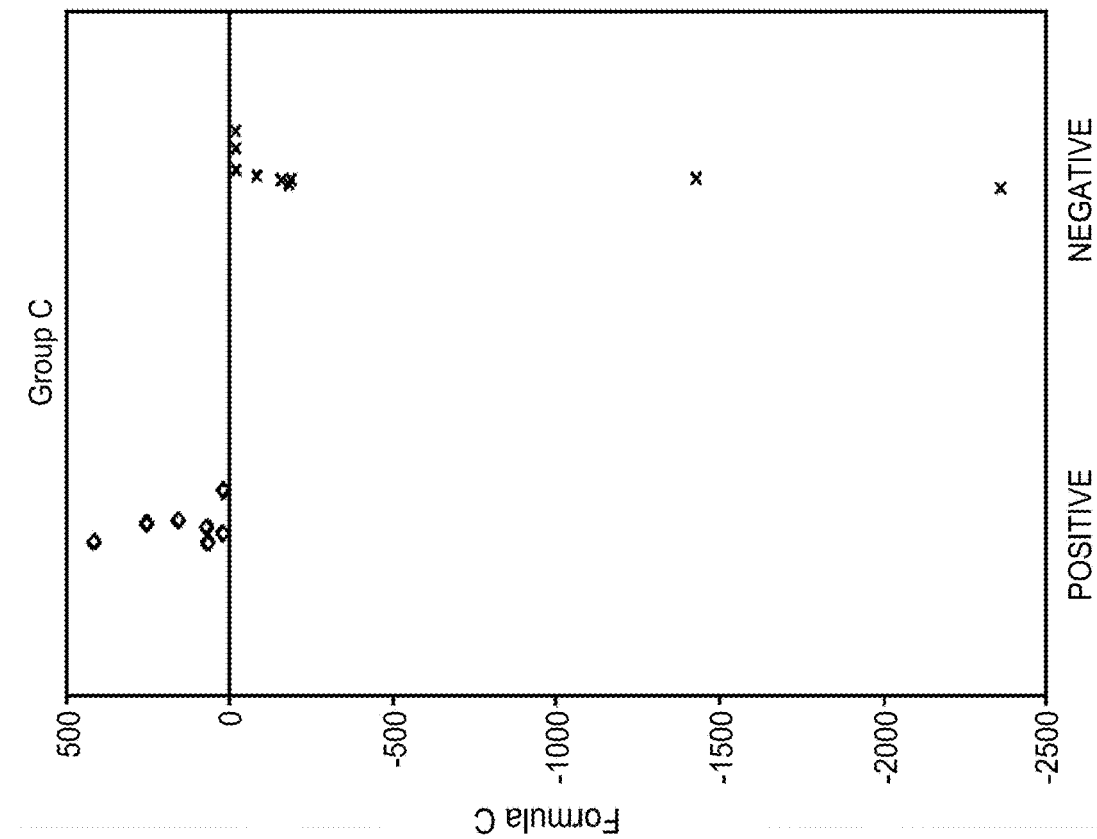
FIG. 38 shows a scatter plot histogram of certain embodiments for DDD-MRS diagnostic processor for discs designated as Group C discs under Example 3, after applying logistic regression generated Formula C to the DDD-MRS spectral data acquired for the group of discs.

The sub-population of discs from Group B with a PG/MAXLAAL<1.85 are partitioned into the third Group C (n=16), with the linear regression test #3 derived from Group C resulting in the data distribution shown in FIG. 38. There is 100% separation between these remaining positive and negative control discs in this final Group C.

The ultimate result of this applied step-wise partitioning and logistic regression diagnostic algorithm approach was 100% separation between known painful vs. non-painful results, across all of the 78 discs evaluated diagnostically.

Figure 39:
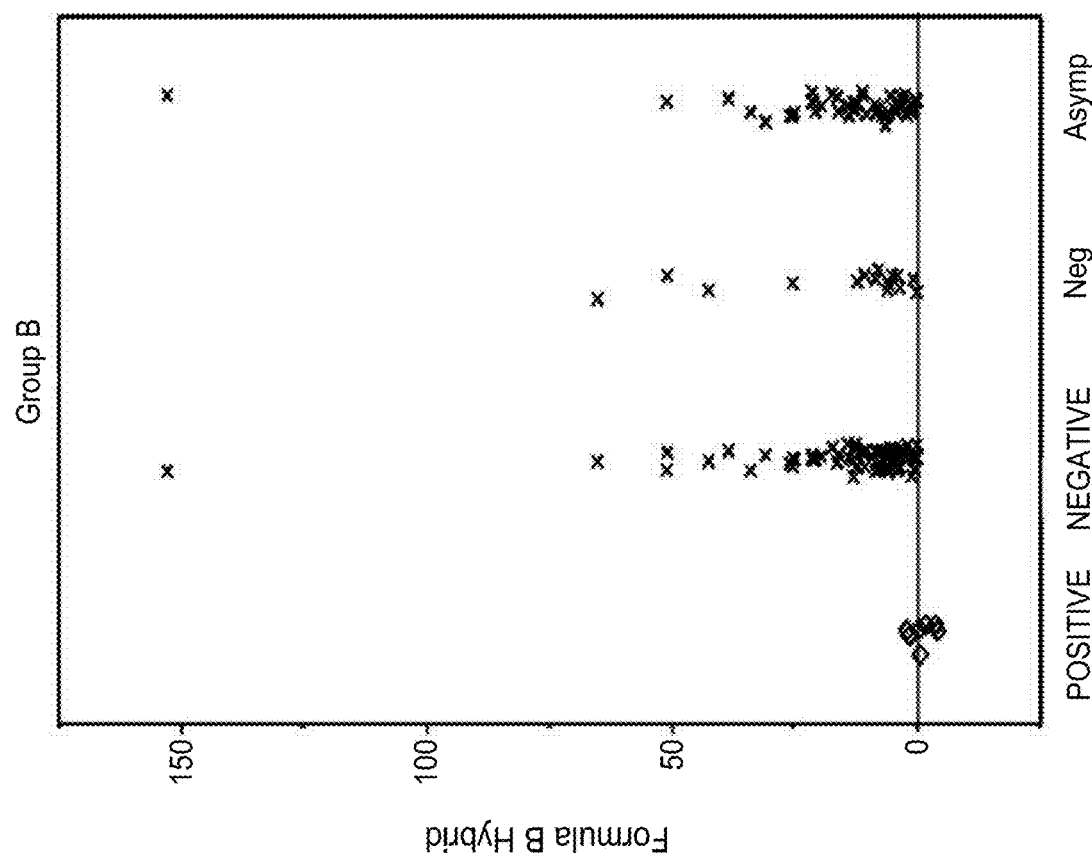
FIG. 39 shows a scatter plot histogram of another embodiment for DDD-MRS diagnostic algorithm, as applied to Group C discs under Example 3 according to a Formula B "hybrid" illustrative of yet a further embodiment of the present disclosure.

Nonetheless, it is to be appreciated that other specific diagnostic algorithmic approaches may be applied and also achieve significantly robust results. As one example, a hybrid linear regression equation consisting of terms from test #2 and test #3 (derived from Groups B and C respectfully) is provided by algorithm test #4 for Group B, shown partitioned in FIG. 39. This approach as evaluated here also still retains all 78 test discs in the overall population while resulting in 76/78 overall match to controls per only 2 presumed false negative values (two PD+ discs indicated instead as negative DDD-MRS tests as being pain free), and no false positive results. The hybrid linear regression equation coefficients range within two orders of magnitude of each other and are fully normalized or proportional, characteristics that make for a robust classifier. The hybrid equation mitigates the need to perform the PG/MAXLAAL partition.

Group B, test #4:

$$Score = -6.94869 + 0.05035*LAVVBMI -$$
$$0.028534*ALVVBMI - 0.51761*SQRT(PGAUCVVBMI) +$$
$$0.36976*ALAUCVVBMI + 4.04875*PG/MAXLAAL;$$

where LAVVBMI=LA peak adjusted by voxel volume and BMI, ALVVBMI=LA peak adjusted by voxel volume and BMI, PGAUCVVBMI is the PG area under the curve (AUC) adjusted by voxel volume and BMI, ALAUCVVBMI is the AL area under the curve (AUC) adjusted by voxel volume and BMI, and PG/MAXLAAL is the ratio PG peak to the maximum peak of either LA or AL.

According to the Examples 1-3 evaluating DDD-MRS diagnostic processor aspects of the present disclosure across clinical experience and data, features from in phase power and absorption spectra may be used to develop diagnostic classifiers with a high correlation to standard control measures for differentiating painful from non-painful discs, including highly invasive, painful, costly, and controversial needle-based provocative discography. The Example 3 in particular, pursued according to the present DDD-MRS embodiments of this disclosure, demonstrate that data from absorption mode spectral acquisitions may be used to partition spectra based on seperating lipid from non-lipid signals and via a relationship of PG/MAXLAAL prior to classification to achieve 100% procedural success and 100% accurate diagnosis. While the initial partition for lipid was done manually by visual signal quality observation believed to indicate presence or absence of lipid signal contribution, the recognition of this may be done automatically using several techniques. For example, this may be done by determining linewidth in the LAAL region (where lipid co-exists, if present), LAAL peak amplitude exceeding a threshold, LAAL peak/power (e.g. AUC), by the ability to detect a PG peak, or by the combination of any of the aforementioned techniques, as may be applied against thresholds determined empirically or otherwise to represent a valid test for the signal differentiation.

It has also been shown herein that another statistically robust hybrid linear regression equation may be used without the PG/MAXLAAL partition, at the expense of only slightly increased false negative scores (n=2).

Example 4

A DDD-MRS exam according to the DDD-MRS pulse sequence, signal processing, and certain diagnostic algorithm aspects of the present disclosure was conducted in a synthetic "phantom" spine intended to simulate certain aspects of a lumbar spine with controlled, known chemical environments with respect to aqueous preparations of varying concentrations and relative ratios between n-acetyl acetate (NAA) and lactic acid (LA) in simulated discs providing regions of interest for voxel prescription and DDD-MRS examinations for test validation purposes.

Materials and Methods

Sagittal plane MRI images from a GE Signa 3.0T of the two lumbar spine phantoms shown in FIGS. 40A-B included a longitudinal series of simulated disc chambers along a column and floating in mineral oil. The simulated disc chambers were filled with buffered solutions of lithium lactate (LA) and n-acetyl aspartate (NAA) as indicated in Table 6. Phantom "B" shown in FIG. 40A also had alternating chambers that were also filled with mineral oil to simulate vertebral bodies (VBs), whereas the Phantom "C" shown in FIG. 40B had the discs in immediately adjacent succession without intervening simulated VBs.

Voxels were prescribed within various discs among the phantoms for varied range of target chemicals. DDD-MRS pulse sequence acquisitions according to various of the present embodiments were obtained from the Signa 3T. Settings for these exams included: TR/TE settings of 1000/28 ms, NSA=150, 3rd flip angle=85, voxel dimension=5× 20×20 mm, VSS bands were default width, and sweep rate=2 Kh.

Metabolite signal (Smet) for NAA was measured by integrating signal power over a range or "bin" centered on spectral peak with width of +/−0.1 PPM. Lactate signal was measured by integrating over bin ranging from 0.1 PPM on either side of observed doublet peak. Unsuppressed water signal (Suw) measured over water peak+/−0.5 PPM. Metabolite concentrations (CM) were then calculated using the following formulaic relationship:

$$CM=(Smet/Suw) \times (Nw/Nmet) \times C_{water} \times K;$$

where Nw=2 H, Nmet=3 H (both NAA and LA), C water=55.5M, and K=correction factor for each phantom based on relaxation, signal measurement and acquisition factors. Factors underlying "K" were not characterized, thus K was solved for each acquisition based on known actual concentrations of each metabolite to derive an average K value for each phantom which was then applied uniformly across the phantom acquisitions to solve for each CM.

Results/Discussion

Results of measured/calculated concentration values per the DDD-MRS exam were compared against known values for NAA and LA, with comparison results shown in FIGS. 40C-D, respectively, and in Table 6. DDD-MRS measured vs. known concentration comparisons resulted in very high correlations of R2=0.95 for the LA comparison and R2=0.93 for the NAA comparison (after removing one clearly erroneous outlier—which resided at an exceptionally high test NAA level which is well above the typical levels considered physiologically relevant, at least for DDD pain diagnostic purposes in the lumbar spinal discs). Ratios of NAA:LA were also substantially accurate and significantly correlative, as shown in Table 6.

According to this study featured in Example 4, operation of the DDD-MRS system operation through respective modes of pulse sequence spectral acquisition, signal processing, and data extraction was verified to provide robust results with respect to NAA and LA chemical concentrations, and ratios therebetween, in this controlled simulated test environment. This provides some degree of verification with respect to the accuracy and robust operation of the DDD-MRS system in other applications for performing similar operations in vivo.

Further Discussion and Additional Aspects of the Disclosure

It is to be appreciated that the present disclosure, including by reference to the Examples, provides various aspects that can be highly beneficial, and represent new advancements that enhance the ability to perform clinically relevant MRS-based examinations of the lumbar spine, and/or of intervertebral discs, and in particular indications for diagnosing DDD pain. Each of these aspects, taken alone, is considered of independent value not requiring combination with other aspects herein disclosed. However, the combination of these aspects, and various sub-combinations apparent to one of ordinary skill, represent still further aspects of additional benefit and utility. The following are a few examples of these aspects, in addition to others noted elsewhere herein or otherwise apparent to one of ordinary skill, which aspects nonetheless not intended to be limiting to other aspects disclosed herein and are intended to be read in conjunction with the remaining disclosures provided elsewhere herein:

Channel Selection for Data Processing and Diagnosis:

Conventional MRI systems use multi-channel acquisition coils for spine detectors, which are pads that patients lye upon during a scan. The GE Signa for example uses an 8 channel acquisition coil array, of which 6 channels are typically activated for use for lumbar spine imaging and diagnosis (including for MRS). However, the system generally combines all data from these channels in producing a single "averaged" curve. For single voxel MRS, this has been determined to be highly inefficient and significant source of error in the data, in particular reducing signal-tonoise ratio. The channels vary in their geographical placement relative to lumbar discs, and are believed to be at least one source of variability between them regarding acquired signal quality for a given disc. Of the six channels, most frequently at least one of the channels is clearly "poor" data (e.g. poor signal-to-noise), and often this can mean 2 to 5 of those channels being clearly degraded vs. one or more "strong" channels. Accordingly, the present disclosure contemplates that comparing the channels, and using only the "strongest" channel(s), significantly improves signal quality and thus data acquired and processed in performing a diagnosis. This "channel isolation/selection" is considered uniquely beneficial to the DDD pain application contemplated herein, and can be done manually as contemplated herein, though the present disclosure also includes automating this operation to compare and choose amongst the channels for a given voxel scan via an automated DDD-MRS signal processor disclosed.

"Coherent" Averaging within and Between Channels:

During a single voxel scan, many repetitions are performed that are later used for averaging in order to reduce noise and increase signal-to-noise ratio in an acquired MRS spectrum. This can range from about 100 repetitions to about 600 or more, though more typically may be between about 200 to about 500, and still more frequently between about 300 to about 400, and according to one specific (though example) embodiment frequently included in the physical embodiments evaluated in the clinical study of Example 1 may be about 384 repetitions. With a TR of 1 to 2 seconds for example, this can range from less than 5 to 10 minutes time.

However, a "shift" in phase and frequency has been observed among the acquired data over these repetitions. The current standard MRI system configurations, via certain sequence routines, do not completely correct for such shifts. Thus when these repetitions are averaged the result becomes "blurred" with reduced signal amplitude relative to noise, as well as possibility for signal "broadening" or separation into multiple peaks from what should be otherwise a single, more narrow band peak.

In addition or alternative to "strongest" channel selection for processing, significant benefit and utility is contemplated herein for correcting for one or both of these phase and/or frequency "shifts" among the repetitions of an acquisition series acquired at a channel during a single voxel scan. The observed results of such processing have been higher signal quality, with higher signal-to-noise ratio, and/or more narrow defined signals at bands of interest to spectral regions associated with chemicals believed (and correlated) to be relevant for diagnosing disc pain (e.g., PG and/or LA and/or AL). It is noted, and relevant to various of the detailed embodiments disclosed herein, that the spectral peak region associated with water is typically the most prominent and highest amplitude signal across the spectrum. This peak and its location relative to a baseline is used according to certain of the present embodiments to define a given shift in a signal, and thus that shift at the water region is used to correct the entire spectral signal back to a defined baseline. As water peak shifts, or conversely is corrected, so does the rest of the spectrum including the target chemical markers relevant to conducting diagnoses.

This degree and location of the water peak may also be used to determine and edit acquisition frames which are sufficiently abnormally biased relative to the other acquisition frames to adversely impact spectral data (or unable to "grab and shift"), e.g. frame editing according to further embodiments.

Where water is not as prominent, e.g. highly desiccated discs with over suppressed water in the sequence, other reliably prominent and recognizable peaks maybe identified used for similar purpose (e.g. peaks within the PG and/or LA and/or AL regions themselves). However, due to its typical prominence and many benefits of using the water peak for these various signal processing purposes, novel approaches and settings for water suppression are contemplated and disclosed herein. This provides for a water signal, either manually or automatically, within an amplitude range that is sufficient to locate and "grab" for processing, but not so extensive to "washout" lower chemical signatures in an inappropriate dynamic range built around the higher water signal. The result of corrections contemplated herein aligns the repetitions to phase and/or frequency coherence, and thus the resulting averaging achieved is desirably more "coherent" averaging. It is further contemplated that these shifts may be observed and corrected in either time or frequency domain (especially regarding frequency shift), and while certain embodiments are described herein in detail corrections yielding similarly improved results may be made in either domain (again esp. re: frequency coherent correction).

DDD-MRS Factors, Criteria and Thresholds for Diagnostic Results

The present disclosure provides an empirically derived relationship between four weighted factors that involve data derived from three regions of MRS spectra acquired from discs that are generally associated with three different chemicals, namely PG, LA, and AL. Other support exists to suspect these identified chemicals may be active culprits in disc pain, e.g. reducing PG, and increasing LA and AL, as factored in the diagnostic relationship developed and applied herein. More directly, at least a sub-set of these factors used in this diagnostic developed relationship have been directly correlated to disc pain (e.g. PG/LA ratio per prior 11T studies performed ex vivo). These factors are further addressed in view of further supporting literature and disclosures, which are believed to support their correlation to pain, as follows.

The normal intervertebral disc is avascular and disc cells function under anaerobic conditions. (Ishihara and Urban 1999; Grunhagen, Wilde et al. 2006) Anaerobic metabolism, such as in the setting of oxygen deprivation and hypoxia, causes lactate production. (Bartels, Fairbank et al. 1998; Urban, Smith et al. 2004) Disc pH is proportional to lactate concentration. (Diamant, Karlsson et al. 1968) Lactic acid produces pain via acid sensing ion channels on nociceptors. (Immke and McCleskey 2001; Sutherland, Benson et al. 2001; Molliver, Immke et al. 2005; Naves and McCleskey 2005; Rukwied, Chizh et al. 2007) Disc acidity has been correlated with pre-operative back pain. (Diamant, Karlsson et al. 1968; Nachemson 1969; Keshari, Lotz et al. 2008)

Proteoglycan content within the nucleus pulposus, which is the primary matrix which holds water in the disc nucleus, decreases with disc degeneration, which is also associate with dehydration e.g. via "darkened" disc nuclei seen on T2 Mill. (Roughley, Alini et al. 2002; Keshari, Lotz et al. 2005; Keshari, Zektzer et al. 2005; Roberts, Evans et al. 2006) ChondVOltin sulfate proteoglycans inhibit nerve ingrowth. (Zuo, Hernandez et al. 1998; Zuo, Neubauer et al. 1998; Jones, Sajed et al. 2003; Properzi, Asher et al. 2003; Jain, Brady-Kalnay et al. 2004; Klapka and Muller 2006) Nerve in-growth is increased in degenerative painful discs. (Brown, Hukkanen et al. 1997; Coppes, Marani et al. 1997; Freemont, Peacock et al. 1997; Freemont, Watkins et al. 2002)

Discography is the current gold-standard of diagnostic care for differentiating painful discs, but is controversial due to being: invasive, painful, subjective, technique/operator dependent, frequently challenged due to high false positive rates (principally as indicated in studies with asymptomatic volunteers), and risky to the patient. (Carragee and Alamin 2001; Guyer and Ohnmeiss 2003; O'Neill and Kurgansky 2004; Cohen, Larkin et al. 2005; Carragee, Alamin et al. 2006; Carragee, Lincoln et al. 2006; Buenaventura, Shah et al. 2007; Wichman 2007; Derby, Baker et al. 2008; Scuderi, Brusovanik et al. 2008; Wolfer et al., Pain Physician 2008; 11:513-538 ISSN 1533-3159, Derby et al., 2008) The prevailing modern guidelines for performing discography generally require concordant pain intensity scores equal to or above 6 (on increasing scale of 0-10), provocation pressures of no more than 50 psi above opening pressure, and another negative control disc in order to determine a "positive discogram" result for a disc. This modern technique has been most recently suggested to provide a higher specificity (e.g. lower false positive) rates than previously alleged in other studies. (Wolfer et al., Pain Physician 2008; 11:513-538•ISSN 1533-3159) However, notwithstanding this potential improvement with modern techniques in the test's accuracy, a more recent published study has shown the invasive needle puncture of discography significantly increases disc degeneration and herniations rates. Further to this disclosure, these adverse effects of the discography needle puncture in the "negative control discs" have been alleged as possible culprit in adjacent level disc disease that often affects adverse outcomes following surgical treatments removing the "positive discogram" discs (e.g. fusion and/or disc arthroplasty).

Proteoglycan and lactate within discs have unique MR signatures that can be identified and objectively measured using MR Spectroscopy, and a calculated ratio based on these measures has significantly differentiated painful from non-painful discs in ex vivo studies of surgically removed discs. (Keshari, Lotz et al. 2008) In subsequent clinical evaluation and development, the further inclusion of alanine—related to lactate to extent of both providing biomarkers for hypoxia having reasonable suspected basis in pain cascade—has resulted in similarly accurate predictive values for the platform in vivo. In one Example, with only 6% procedural failures to make a confident diagnosis, 99% accuracy resulted and including 5/5 successes in prospective application. DDD-MRS approaches, as disclosed herein, can thus non-invasively, painlessly, and objectively measure and quantify proteoglycan and lactate-related signatures (and for alanine spectral region) of intervertebral discs in vivo using a novel software upgrade to commercially available MRI systems, and a novel diagnostic algorithm based at least in part upon these in vivo measures reliably distinguishes painful vs. non-painful discs with a lower false positive rate predicted versus discography.

The following publications are herein incorporated by reference in their entirety, and provide at least in part a bibliography of certain disclosures referenced above and otherwise elsewhere herein:

Bartels, E. M., J. C. Fairbank, et al. (1998). "Oxygen and lactate concentrations measured in vivo in the intervertebral discs of patients with scoliosis and back pain." *Spine* 23(1): 1-7; discussion 8.

Brown, M. F., M. V. Hukkanen, et al. (1997). "Sensory and sympathetic innervation of the vertebral endplate in patients with degenerative disc disease." *J Bone Joint Surg Br* 79(1): 147-53.

Buenaventura, R. M., R. V. Shah, et al. (2007). "Systematic review of discography as a diagnostic test for spinal pain: an update." *Pain Physician* 10(1): 147-64.

Carragee, E. J. and T. F. Alamin (2001). "Discography. a review." *Spine J* 1(5): 364-72.

Carragee, E. J., T. F. Alamin, et al. (2006). "Low-pressure positive Discography in subjects asymptomatic of significant low back pain illness." *Spine* 31(5): 505-9.

Carragee, E. J., T. Lincoln, et al. (2006). "A gold standard evaluation of the "discogenic pain" diagnosis as determined by provocative discography." *Spine* 31(18): 2115-23.

Cohen, S. P., T. M. Larkin, et al. (2005). "Lumbar discography: a comprehensive review of outcome studies, diagnostic accuracy, and principles." *Reg Anesth Pain Med* 30(2): 163-83.

Coppes, M. H., E. Marani, et al. (1997). "Innervation of "painful" lumbar discs." *Spine* 22(20): 2342-9; discussion 2349-50.

Derby, R., R. M. Baker, et al. (2008). "Analgesic Discography: Can Analgesic Testing Identify a Painful Disc?" *SpineLine* (November-December): 17-24.

Diamant, B., J. Karlsson, et al. (1968). "Correlation between lactate levels and pH in discs of patients with lumbar rhizopathies." *Experientia* 24(12): 1195-6.

Freemont, A. J., T. E. Peacock, et al. (1997). "Nerve ingrowth into diseased intervertebral disc in chronic back pain." *Lancet* 350(9072): 178-81.

Freemont, A. J., A. Watkins, et al. (2002). "Nerve growth factor expression and innervation of the painful intervertebral disc." *J Pathol* 197(3): 286-92.

Grunhagen, T., G. Wilde, et al. (2006). "Nutrient supply and intervertebral disc metabolism." *J Bone Joint Surg Am* 88 Suppl 2: 30-5.

Guyer, R. D. and D. D. Ohnmeiss (2003). "Lumbar discography." *Spine J* 3(3 Suppl): 11S-27S.

Immke, D. C. and E. W. McCleskey (2001). "Lactate enhances the acid-sensing Na+ channel on ischemia-sensing neurons." *Nat Neurosci* 4(9): 869-70.

Ishihara, H. and J. P. Urban (1999). "Effects of low oxygen concentrations and metabolic inhibitors on proteoglycan and protein synthesis rates in the intervertebral disc." *J Orthop Res* 17(6): 829-35.

Jain, A., S. M. Brady-Kalnay, et al. (2004). "Modulation of Rho GTPase activity alleviates chondroitin sulfate proteoglycan-dependent inhibition of neurite extension." *J Neurosci Res* 77(2): 299-307.

Jones, L. L., D. Sajed, et al. (2003). "Axonal regeneration through regions of chondroitin sulfate proteoglycan deposition after spinal cord injury: a balance of permissiveness and inhibition." *J Neurosci* 23(28): 9276-88.

Keshari, K. R., J. C. Lotz, et al. (2005). "Correlation of HR-MAS spectroscopy derived metabolite concentrations with collagen and proteoglycan levels and Thompson grade in the degenerative disc." *Spine* 30(23): 2683-8.

Keshari, K. R., J. C. Lotz, et al. (2008). "Lactic acid and proteoglycans as metabolic markers for discogenic back pain." *Spine* 33(3): 312-317.

Keshari, K. R., A. S. Zektzer, et al. (2005). "Characterization of intervertebral disc degeneration by high-resolution magic angle spinning (HR-MAS) spectroscopy." *Magn Reson Med* 53(3): 519-27.

Klapka, N. and H. W. Muller (2006). "Collagen matrix in spinal cord injury." *J Neurotrauma* 23(3-4): 422-35.

Molliver, D. C., D. C. Immke, et al. (2005). "ASIC3, an acid-sensing ion channel, is expressed in metaboreceptive sensory neurons." *Mol Pain* 1: 35.

Nachemson, A. (1969). "Intradiscal measurements of pH in patients with lumbar rhizopathies." *Acta Orthop Scand* 40(1): 23-42.

Naves, L. A. and E. W. McCleskey (2005). "An acid-sensing ion channel that detects ischemic pain." *Braz J Med Biol Res* 38(11): 1561-9.

O'Neill, C. and M. Kurgansky (2004). "Subgroups of positive discs on discography." *Spine* 29(19): 2134-9.

Properzi, F., R. A. Asher, et al. (2003). "Chondroitin sulphate proteoglycans in the central nervous system: changes and synthesis after injury." *Biochem Soc Trans* 31(2): 335-6.

Roberts, S., H. Evans, et al. (2006). "Histology and pathology of the human intervertebral disc." *J Bone Joint Surg Am* 88 Suppl 2: 10-4.

Roughley, P. J., M. Alini, et al. (2002). "The role of proteoglycans in aging, degeneration and repair of the intervertebral disc." *Biochem Soc Trans* 30(Pt 6): 869-74.

Rukwied, R., B. A. Chizh, et al. (2007). "Potentiation of nociceptive responses to low pH injections in humans by prostaglandin E2." *J Pain* 8(5): 443-51.

Scuderi, G. J., G. V. Brusovanik, et al. (2008). "A critical evaluation of discography in patients with lumbar intervertebral disc disease." *Spine J* 8(4): 624-9.

Sutherland, S. P., C. J. Benson, et al. (2001). "Acid-sensing ion channel 3 matches the acid-gated current in cardiac ischemia-sensing neurons." *Proc Natl Acad Sci USA* 98(2): 711-6.

Urban, J. P., S. Smith, et al. (2004). "Nutrition of the intervertebral disc." *Spine* 29(23): 2700-9.

Wichman, H. J. (2007). "Discography: over 50 years of controversy." *Wmj* 106(1): 27-9.

Wolfer, L. R., R. Derby, et al. (2008). "Systematic review of lumbar provocation discography in asymptomatic subjects with a meta-analysis of false-positive rates." *Pain Physician* 11(4): 513-38.

Zuo, J., Y. J. Hernandez, et al. (1998). "Chondroitin sulfate proteoglycan with neurite-inhibiting activity is up-regulated following peripheral nerve injury." *J Neurobiol* 34(1): 41-54.

Zuo, J., D. Neubauer, et al. (1998). "Degradation of chondroitin sulfate proteoglycan enhances the neurite-promoting potential of spinal cord tissue." *Exp Neurol* 154(2): 654-62.

Notwithstanding the foregoing, it is to be appreciated that despite the support for suspecting these chemicals as causes of pain, and despite a belief that these chemicals are measured and represented at least in part by the data derived from the MRS data acquired, this correlation need not be accurate in order for the data and diagnostic algorithm and approach presented herein to remain valid and highly useful.

In particular regard to MRS data derived from regions associated with LA and AL, these are quite narrowly defined ranges closely adjacent to each other, and also overlap with a much broader band associated with lipid. Accordingly, the data acquired from these two "bins" may blur between the actual two chemical sources. However, as they both relate to and are a product of abnormal cellular metabolism and hypoxia, their combination may be fairly considered a signature region more broadly for "abnormal cellular metabolism/hypoxia." Furthermore, lipid contribution may bias measurements in this region, and as lipid is a high molecular weight molecule if present the signal is typically strong and often may wash out resolution of either or both of LA or AL-based signal in the region. However, in the current experience with DDD-MRS, even where lipid signal is believed present, and even in significant degree, the acquired data intended to represent LA and AL as processed through the diagnostic algorithm and processor has not produced a false result against controls (e.g. remains an accurate result). When this happens, the diagnostic result is consistently MRS+ indicating a positive result for pain in the suspect disc. However, such lipid-related positive results occur most frequently in L5-S1 discs that are associated with a particular degenerative profile and morphology that is more reliably diagnosed as painful on MRI alone (and consistently confirmed as such via PD).

To the extent the measurements derived from the MRS "regions" believed to be associated with these chemicals, and as used in the weighted factor diagnostic algorithm developed, are applied uniformly across the different control disc populations, the diagnostic accuracy of the result prevails in the ultimate comparison data—regardless of the source of the MRS data acquired. Accordingly, the benefit and utility of the diagnostic approach is realized in its diagnostic results, and not intended to be necessarily limited and defined only by the theory as to what the underlying sources of the measured signatures are.

Conversely, it is also further contemplated and to be understood that the present disclosure provides a specific diagnostic relationship algorithm that produces a particular range of diagnostic results that compare with high correlation with control measures for pain/non-pain in discs evaluated. However, this is the result of statistically generated correlation and retrospective approach to data fitting. While appropriate for diagnostic algorithm development and the specific result disclosed herein is considered highly beneficial, this may migrate to other specific algorithms that may be more preferred though without departing from the broad scope intended for the various aspects of this disclosure. Such modifications may be the result of further data processing across more samples, for example, and may affect the "weighting" multipliers associated with each factor used in the algorithm, or which factors are featured in the algorithm, or which regions or features of the MRS spectra are even used as the signatures from which data is derived and used in the algorithm. This has been demonstrated by way of the Examples 1-3 provided herein, and wherein three different specific diagnostically relevant and viable approaches are presented and described for similar data sets (e.g. in particular comparison between Examples 2 and 3 of the same clinical data set). Still other Examples described below further illustrate this.

It is contemplated that while the DDD-MRS diagnostic processor herein disclosed and diagnostic results provided therefrom, as disclosed in context of clinical data presented under Example 1 (and late by Examples 2 and 3), provide binary MRS+ and MRS− results for severe pain and absence of severe pain in discs, respectively. However, the results are also quantified along a scaled range which may be appropriately interpreted by a diagnostician as "levels" of relevance along the pain/non-pain range. Such interpretation may impact the direction of pain management decisions, such as which discs to treat, how to treat, or not to treat at all. One example of such other way of presenting DDD-MRS diagnostic information for utility to appropriate clinicians is demonstrated by reference to the "% prediction painful" presentation of data shown and discussed herein (which may be instead or in combination also determined and presented as "% prediction non-painful"). Moreover, while the current diagnostic embodiments have been described by reference to site-specific locations of pain sources at reference discs, diagnostic value may be more generalized to confirmed presence or absence of any painful disc at all. Such may impact more general management decision, such as administration or avoidance of pain medication. Still further, the current aspects may be used to assess aspects of the chemical environments of discs, either in addition to or alternative to specific diagnostic indications such as for pain or non-pain determinations for given discs. This may be effectively utilitarian for example by providing measures of chemical biomarkers, such as PG, LA, AL, LAAL, etc., such as amounts or concentrations thereof in the tissues (and/or ratios). This may be relevant for example in other indications or applications, such as research purposes (e.g. biologics or cell therapy approaches to treating or providing prophylaxis to discs). This may be useful either prior to treatment, and/or following treatment to assess certain aspects of outcomes and progression of the treatment or underlying disease or condition intended to be treated (as may relate to chemicals being monitored).

Furthermore, in still further embodiments, the diagnostic results may be provided in different forms than as described by the specific embodiments disclosed by reference to a particular example, such as Example 1 for example. For example, binary definitive diagnoses of MRS+ and MRS− may be supplemented with "indeterminate" as a third category. This may, for example, represent a result of applying certain threshold criteria that must be met in order to make a definitive +/− determination. Such criteria may include, for example, SNR threshold of the underlying post-processed DDD-MRS spectrum from which the diagnostic data is extracted for performing the diagnoses. In another example, a defined proximity of calculated diagnostic results from the DDD-MRS diagnostic processor to the zero (0) median threshold between MRS+ and MRS− diagnoses may represent a threshold under which definitive MRS+/− determination is not decidedly made by the processor.

It is also to be further appreciated that the pulse sequence platform approach, and/or specific parameter settings, and/or signal processing approaches (and/or parameter or threshold criteria settings), may be modified. Such modifications may affect resulting spectra (and data extracted therefrom) sufficiently to redistribute the regional data used for diagnostic purposes, and may thus motivate or necessitate a re-evaluation and re-formation of the diagnostic algorithm that is appropriate for data acquired and/or processed under those modified approaches. Accordingly, while the present interactions between these component parts of an overall DDD-MRS system, and results, are considered of particular benefit for forward application in clinical use, such further modifications are also considered to fall within the broad scope of the aspects disclosed herein, and may represent for example a consequence of further development and experience as would be apparent to one of ordinary skill (though such further modifications may also provide still further benefit).

L5-S1 and Novel Detection Coils:

The L5-S1 disc is typically oriented at an oblique angle relative to other lumbar discs, and has unique shape that in many circumstances challenges the ability to prescribe voxel for adequate DDD-MRS data acquisition. The current voxelation plan for MRS generally requires a three-dimensional "cube" of space to be defined as the voxel (a pixel with volume), typically done by an operator technician on overlay to MRI images of the region. However, for this angled L5-S1 disc, the voxel volume may be maximized by angling the voxel to match the angulated disc. However, such angled voxels at this location have been observed to relate to degraded data acquisition by existing spine detector coils. Accordingly, a custom spine coil is further contemplated that angles at least one coil channel to either a pre-determined angle more representative of typical L5-S1 discs, or a range of angles may be provided by multiple such coils in a kit, or the coil channel may be given an "adjustable" angle to meet a given anatomy. Furthermore, software may be adapted to identify an angled voxel and modify the coordinate system assigned for sequence and/or multi-channel acquisition in order better acquire data from an angled voxel (e.g. where planar slices are taken through the voxel as data acquired, the planar coordinates are revised into an adjusted coordinate system that accounts for the angulation relative to the data acquisition at the channel(s)). This uniquely angled disc level is also associated with and located within a radiused curvature at the small of the back, which may be more extreme in some patients than others. While simply adjusting the angle of lower detection channel coils may improve acquisition here, further more dramatic variations are also contemplated. In one such further aspect, a detector coil array is created with smaller coils, and/or on a flexible platform that is adjusted to more accurately fit against the lower back (vs. a planar array currently used, but for curved lower spine with increasingly angulated discs toward the lower lumbar and sacral regions). Further to this approach, the relative locations and orientations of the detector coils may be sensed, with proper coordinate system assigned thereto for sequencing and acquisition during single voxel MRS of the spine (especially intervertebral discs), and which also may be adapted relative to coordinates of voxel orientation, dimensions, and shape.

T1-Rho:

An additional MRI-based pulse sequence technology has been previously disclosed called "T1-Rho". This is a sequence that has been alleged for detecting, measuring, and indicating the amount (e.g. concentration) of proteoglycan, via n-acetyl or n-acetyl acetate, in tissue, and furthermore for using this information for diagnostic benefit for some conditions. In one particular regard, this has been alleged to be potentially useful for monitoring degree of degeneration, in that reduced proteoglycan in discs may correlate to advancing degree of degeneration. While pain correlation with proteoglycan variability has not been determined, the ration of PG to other metabolites, such as for example Lactate (and/or alanine), is believed to be a consistent and potent indicator for localized discogenic pain. Accordingly, the present disclosure combines T1-Rho with other measurements, e.g. MRS measurements, in evaluating tissue chemistry for purpose of performing a diagnosis. In one particular mode contemplated herein, the T1-Rho measurement of proteoglycan/n-acetyl content is used to "normalize" or otherwise calibrate or compare an MRS measurement of that related region. In doing so, other metabolites in the MRS spectrum may be also calibrated for more accurately calculated "concentration" measurement. This calibration may be done in evaluating MRS signal quality, such as for example between channels or within a channel itself, and MRS data is used for the diagnosis. In a further mode, T1-Rho information related to PG may be used as the data for that chemical constituent in tissue, and data for another diagnostically relevant chemical, e.g. Lactate as measured for example via MRS (or other modality), may be used in combination with the PG measurement in an overall diagnostic algorithm or evaluation. Such algorithms applied for diagnostic use may be empirically driven based upon experimental data which may be conducted and acquired by one of ordinary skill for such purpose based upon this disclosure. For example, a database of sufficient patient data based on T1-rho measurements (for proteoglycan) and MRS measurements (such as for PG and/or Lactate, for example) may be correlated in a multi-variate logistic regression analysis against other pain indicators such as provocative discography or treatment outcomes, resulting in a highly correlative algorithm based upon the data fit. This may then be used prospectively in predicting or assessing localized pain in newly evaluated patient tissues. In one particular benefit, MRS techniques include particular sequence parameters that emphasize lactate for improved lactate-related data extraction, and decreasing lipid artifact (which often overlays over lactate to confound lactate data collection), but not considered as robust for other chemicals, such as potentially PG/n-acetyl. One such technique extends the time delay from magnetic activation to data collection, thus increasing overall time for repetitive scans. However, T1-Rho is relatively fast to perform relative to MRS. Accordingly, one particular further embodiment uses T1-rho for PG measurement, and MRS as enhanced for lactate measurement, and combines this data into an empirically data-driven algorithm for performing a diagnosis. Moreover, a further aspect contemplated herein uses T1-rho for PG measurement, in combination with pH or pO2 measurement (e.g. via a sensor on a needle, such as a discography needle) to monitor local acidity in the disc (also believed to relate to lactate concentration).

Diagnostic Display "Enhancing" MRI Images

The various aspects, modes, and embodiments of the present disclosure provide, among other beneficial advancements, a significant enhancement and improvement to standard MRI for locally diagnosing painful and/or non-painful discs. The utility of each of these diagnoses—painful, and non-painful—is of independent value on its own. While indicating a disc is definitively painful may often augment other clinical or diagnostic indications for directing treatment to the level, indicating a disc is definitively not painful also provides valuable information to exclude a disc as possible pain culprit and avoid unnecessary intervention to the level (especially where other clinical or diagnostic indications may indicate another level as painful, but not provide definitive answer to the other level/s). This is for example often the case with respect to L3-L4 and L4-L5 discs, where L5-S1 discs (most prevalently painful among the levels) may often be already suspect per MRI and other indications, but the higher adjacent disc levels are indeterminate.

The present aspects have been presented in terms of physical embodiments evaluated in clinical study with highly accurate results against controls. By providing a non-invasive alternative to discography as presented by these present embodiments, even if diagnostically equivalent, significant benefits are advanced by avoiding morbidity, pain, and other inefficiencies and downsides associated with that invasive test.

As an enhancement to MRI, further aspects of the present disclosure provide useful diagnostic display to indicate the results in overlay context onto the MRI image itself and providing context to the structures revealed therein, such as for example as shown in FIGS. 32A-B for two different patients receiving a DDD-MRS diagnostic exam according to Example 1.

It is to be appreciated by one of ordinary skill that the various aspects, modes, embodiments, features, and variations of the present disclosure include, without limitation, the following.

One aspect of the present disclosure is a MRS pulse sequence configured to generate and acquire a diagnostically useful MRS spectrum from a voxel located principally within an intervertebral disc of a patient. According to one mode of this aspect, the pulse sequence is configured to generate and acquire the MRS spectrum from a single voxel principally located within the disc. According to another mode of this aspect, the pulse sequence is configured to generate and acquire the MRS spectrum from the voxel located principally within a nucleus of the disc. According to another mode of this aspect, the pulse sequence is configured to generate and acquire the MRS spectrum with sufficient signal-to-noise ratio (SNR) upon appropriate post-signal processing to perform at least one of: detect and measure at least one chemical constituent within the disc; and diagnose a medical condition based upon one or more identifiable signal features along the spectrum. According to another mode, the pulse sequence is configured to generate and acquire the MRS spectrum from a single voxel principally located within a nucleus of the disc. According to another mode, the pulse sequence is configured to generate and acquire the MRS spectrum from a voxel principally located within an intervertebral disc of the lumbar spine. According to another mode, the pulse sequence is configured to generate and acquire at least one MRS spectrum from at least one voxel principally located within at least one of L3-L4, L4-L5, and L5-S1 intervertebral discs. These discs are the most predominant discs implicated by chronic, severe low back pain, and are also characterized by typically larger disc spaces than other higher disc levels and thus more conducive to single voxel spectroscopy (though not necessarily so limited to only these discs in all cases). According thus to another mode, however, the pulse sequence is configured to generate and acquire multiple MRS spectra from multiple voxels, respectively, principally located within each of L3-L4, L4-L5, and L5-S1 intervertebral discs.

According to another mode, the pulse sequence is configured to generate and acquire multiple MRS spectra from multiple voxels, respectively, principally located within each of L3-L4, and L4-L5 intervertebral discs. These discs are typically less oblique than L5-S1 disc, and thus represent different geometric, and perhaps in certain circumstances different biomechanical and/or biochemical, environments vs. typically more oblique L5-S1 disc, and thus may represent unique optimal approaches for diagnostic application of the present embodiments versus for the L5-S1 disc. According to one embodiment of this mode, the discs are substantially non-oblique, such as for example as may be relative to a relatively more oblique L5-S1 adjacent thereto. According thus to yet another mode, the pulse sequence is configured to generate and acquire the MRS spectrum from the voxel located principally within the L5-S1 intervertebral disc. As stated above, this disc level may at times present unique considerations relative to other lumbar discs that are addressed with unique relative approaches versus other lumbar discs. According to one embodiment of this mode, the disc is substantially oblique, such as for example relative to adjacent lumbar disc segments above this level. According to another mode, the pulse sequence is configured to operate in a first mode for a substantially non-oblique disc, and a second mode for a substantially oblique disc.

The present disclosure is considered readily adaptable to operate on and with multiple different specific MR systems, including of different relative field strengths and as may be made available and operate in relative custom formats from various different manufacturers, though as may be custom developed by one of ordinary skill for compatibility and optimal functionality for intended use on and with any particular MR system or category (e.g. field strength).

According to another mode therefore, the pulse sequence of the various aspects of the present disclosure is configured to generate and acquire the MRS spectrum via an NMR system of at least about 1.2 tesla (T) field strength. According to another mode, the pulse sequence is configured to generate and acquire the MRS spectrum via an NMR system of about 1.2 tesla (T) field strength. According to another mode, the pulse sequence is configured to generate and acquire the MRS spectrum via an NMR system of at least about 1.5 tesla (T) field strength. According to another mode, the pulse sequence is configured to generate and acquire the MRS spectrum via an NMR system of about 1.5 tesla (T) field strength. According to another mode, the pulse sequence is configured to generate and acquire the MRS spectrum via an NMR system of at least about 3.0 tesla (T) field strength. According to another mode, the pulse sequence is configured to generate and acquire the MRS spectrum via an NMR system of about 3.0 tesla (T) field strength. According to another mode, the pulse sequence is configured to generate and acquire the MRS spectrum via an NMR system of about 7.0 tesla (T) field strength. According to another mode, it is to be appreciated that the pulse sequence is configured to generate and acquire the MRS spectrum via an NMR system in the range of about 1.2 to about 7.0 tesla (T) field strength. According to another mode, the pulse sequence is configured to generate and acquire the MRS spectrum via an NMR system in the range of about 1.2 to about 3.0 tesla (T) field strength. According to another mode, the pulse sequence is configured to generate and acquire the MRS spectrum via an NMR system in the range of about 1.5 to about 3.0 tesla (T) field strength. While these ranges and specific field strengths noted represent existing systems available on the market today, or at least under investigation (e.g. 7.0 T), it is further contemplated that other systems outside this range may also be suitable. However, it is also to be appreciated that systems below about 1.5 or 1.2 Tesla may be challenged with respect to signal:noise ratio in many circumstances (though may nonetheless be operable suitably as intended in others). Furthermore, current experience has revealed that acquisitions following the DDD-MRS aspects of the present disclosure may be similarly robust when conducted with field strength as low as 1.5 T versus as acquired via higher 3.0 T systems (such as used in the Examples). Moreover, systems above about 3.0 T or 7.0 T may present significant safety concerns for many applications (though again may nonetheless suitable for others).

Certain pulse sequence modes of the present aspects of the disclosure are also to be appreciated as providing particular benefit for certain intended uses, including those featured specifically herein such as via the Examples. According to one such mode of the present aspects, the pulse sequence comprises a chemical shift selective (CHESS) sequence. According to another mode, the pulse sequence comprises a point resolved spectroscopy (PRESS) sequence. According to another mode, the pulse sequence comprises a combination CHESS-PRESS sequence. According to another mode, the pulse sequence comprises a combination CHESS-VSS-PRESS sequence. According to another mode, the pulse sequence comprises at least one control variable (CV) parameter setting as disclosed in Table 1. According to another mode, the pulse sequence comprises all the control variable (CV) parameter settings disclosed in Table 1. According to another mode, the pulse sequence comprises an echo time (TE) in the range of about 25 to about 40 milliseconds. According to another mode, the pulse sequence comprises an echo time of about 28 milliseconds. This specific setting, while not intended to be necessarily limiting to broad intended scope of the present aspects and modes, has been observed to provide sufficiently robust results as intended for various uses, such as according to the Examples. According to another mode, the pulse sequence comprises a repetition time (TR) in the range of about 750 to about 2000 milliseconds (2 seconds). According to another mode, the pulse sequence comprises a repetition time (TR) of about 1000 milliseconds. According to another mode, the pulse sequence comprises a repetition time of about 750 milliseconds and is configured to operate with an MR system with a field strength of between about 1.2 T and about 1.5 T. This has been observed, for example in one particular embodiment, to be particularly beneficial for 1.5T MR applications. According to another mode, the pulse sequence comprises a repetition time of between about 1000 and about 1500 milliseconds and is configured to operate with an MR system with a field strength of between about 3 T and about 7 T. According to another mode, the pulse sequence is configured to adjust the repetition time (TR) with respect to the field strength of the MR system, which may be automatic in one beneficial variation, or manually set to adjust accordingly. It is to be appreciated that these settings for TR present a certain trade off with respect to time required to complete a pulse sequence acquisition series, and thus sufficiently short times to provide adequate signal quality may be optimized for time efficiency, though longer times may be done if time is available or not of essence. Time, however, may be a significant consideration in many circumstances, such as for example for efficiency in conducting the exam in MR imaging center setting, and also patient comfort, in addition to longer times for exams increase opportunities for patient motion artifact etc. that could compromise results (to extent not countered by the various signal processing aspects of the present disclosure).

According to another mode, the pulse sequence comprises an acquisition matrix size setting of about 1 in each dimension, with a number of spatial slices setting of 1.

Relative degree of water signal in DDD-MRS pulse sequence acquisitions may be relevant to the ability to fully signal process such signals as intended by various aspects of the present disclosure, and thus certain aspects related to water suppression and water signal control are disclosed herein and to be appreciated with respect to the pulse sequence. According to another mode, the pulse sequence is configured to generate and acquire a repetitive frame MRS acquisition series from the voxel with signal-to-noise ratio (SNR) in the water region along the spectrum of multiple said frames that is sufficiently high to be identified, yet sufficiently low to provide adequate dynamic range with sufficient signal-to-noise ratio (SNR) along other chemical regions of diagnostic interest along the spectral frames to allow the other regions to be identified and evaluated, post-signal processing and post-averaging of the frames, for diagnostic use. Suppressed water signal, and control of it via the pulse sequence settings, varied over time of development across the clinical data set featured among the Examples 1-3 disclosed herein. However, as demonstrated via the highly robust ultimate results these ranges of water suppression control experienced were observed to provide sufficiently adequate results in most cases. This experience ranged between 45 and 125 degrees for $3^{rd}$ CHESS flip angle, with an average of about 120 degrees (plus/minus about 30 degrees standard deviation). However, these settings for each acquisition are discrete, and upon achieving sufficient results a chosen setting was cast for a given acquisition. The majority of acquisitions are believed sufficient at about 85 to about 100 degrees for this third CHESS flip angle, though again may be custom set in iterative experience or via automated feedback control based upon trial and error in measured signal quality.

According nonetheless to another mode of the present aspects, the pulse sequence comprises a third CHESS flip angle of at least about 45 degrees. According to another mode, the pulse sequence comprises a third CHESS flip angle of at least about 65 degrees. According to another mode, the pulse sequence comprises a third CHESS flip angle of up to about 145 degrees. According to another mode, the pulse sequence comprises a third CHESS flip angle of up to about 125 degrees. According to another mode, the pulse sequence comprises a third CHESS flip angle of between about 45 and about 145 degrees. According to another mode, the pulse sequence comprises a third CHESS flip angle between about 65 and about 125 degrees. According to another mode, the pulse sequence comprises a third CHESS flip angle that is adjustable based upon a degree of water observed in the region of interest. According to one embodiment of this mode, the degree of water is observed according to a prior test pulse sequence. According to one embodiment of this mode, the pulse sequence is configured to operate in series following the prior test pulse sequence in a common MR exam session, and the third CHESS flip angle is automatically adjustable based upon the observed degree of water in the prior test pulse sequence. According to another embodiment, the third CHESS flip angle is automatically adjustable based upon a T2-weighted acquisition value for the region of interest. According to another embodiment, the third CHESS flip angle is automatically adjustable to a value determined based upon an empirical correlation between third CHESS flip angle and T2-weighted acquisition value for the region of interest according to a prior acquisition data set. According to another mode, the pulse sequence comprises at least one of the following CHESS flip angles: about 105 degrees (angle 1); about 80 degrees (angle 2); about 125 degrees (angle 3). In some embodiments, the first CHESS flip angle can be between about 60 degrees and about 180 degrees, or between about 85 degrees and about 125 degrees. In some embodiments, the second CHESS flip angle can be between about 60 degrees and about 180 degrees, or between about 65 degrees and about 105 degrees. In some embodiments, the third CHESS flip angle can be between about 45 degrees and about 145 degrees, or between about 85 degrees and about 125 degrees, or between about 105 degrees and about 145 degrees.

Certain aspects are also disclosed related to a PRESS mode of operation. According to one such example mode, the pulse sequence comprises PRESS correction settings of about 1.2 for each of X, Y, and Z axes. Other PRESS correction settings can be used, such as values greater than 1.0 and less than about 1.5. According to another mode, the pulse sequence comprises at least one of the following PRESS flip angles: about 90 (angle 1); about 180 (angle 2); about 180 (angle 3). According to another mode, either or both of the second and third PRESS flip angles may be between about 150 and about 180 degrees, and in one particular embodiment may be for example about 167 degrees. As flip angle generally correlates with time required to conduct the exam, signal quality results may be optimally determined empirically against different flip angles, and it may also be the case that a setting (e.g. 180) may not be the exact flip angle actually deployed (e.g. may actually be different, e.g. about 167 for example).

According to another mode of the present MRS pulse sequence aspects, the pulse sequence is provided in combination with an MRS signal processor according to one or more of the various aspects, modes, embodiments, variations, and or features thereof as otherwise elsewhere herein provided.

Another aspect of the present disclosure is thus an MRS signal processor configured to process spectral data from an MRS pulse sequence.

According to one mode of this aspect, the MRS signal processor comprises a channel selector that is configured to select a sub-set of multiple channel acquisitions received contemporaneously from multiple parallel acquisition channels, respectively, of a multi-channel detector assembly during a repetitive-frame MRS pulse sequence series conducted on a region of interest within a body of a subject. According to one embodiment of this mode, the channel selector of the MRS signal processor is configured to select a sub-set of multiple channel acquisitions received contemporaneously—from multiple parallel acquisition channels, respectively, of a multi-channel detector assembly during the repetitive-frame MRS pulse sequence series conducted on a voxel principally located within an intervertebral disc within the body of the subject. According to another embodiment, the channel selector of the MRS signal processor is configured to automatically differentiate relatively stronger from weaker channel acquisitions received. According to another embodiment, the channel selector of the MRS signal processor is configured to determine and select a strongest single channel acquisition signal among the multiple channel acquisitions. According to another embodiment, the channel selector of the MRS signal processor is configured to determine and select the strongest single channel acquisition based upon a highest measured parameter of the single channel acquisition spectral series comprising at least one of amplitude, power, or signal-to-noise ratio (SNR) of water signal in the spectrum in the selected channel relative to the other channel. According to one highly beneficial variation of this embodiment, the channel selector of the MRS signal processor is configured to determine and select the strongest single acquisition channel with CHESS sequence disabled. According to another beneficial variation of this embodiment, the channel selector is configured to perform a channel selection that is based upon a frame averaged spectrum of the series acquired from the channel. According to one beneficial alternative feature of this variation, the frame averaged spectrum of the series is acquired with the CHESS disabled on unsuppressed water frames. According to another variation of this embodiment, the channel selector of the MRS signal processor is configured to determine and select a sub-set of strongest channels based upon a range threshold based from the highest measured parameter of the strongest single channel. According to another embodiment, the channel selector of the MRS signal processor is configured to determine and select one or more "strongest" channels among the series based upon a threshold criteria for a feature of the channel acquisition data. According to one beneficial variation of this embodiment, the one or more strongest channels is determined and selected by averaging the first unsuppressed water frames for each channel (with CHESS disabled) and measuring the signal to noise ratio (SNR) of the unsuppressed water signal, determine which channel has the strongest SNR and then selecting those additional channels that fall within a threshold range, e.g. about 3 dB (or may be for example a range of 1 to 6 dB) of the channel with the strongest SNR. According to still further channel selector embodiments, the channel selector is provided in combination with one or more of the various other aspects, modes, embodiments, variations, and features related to other MRS pulse sequence and/or MRS signal processor disclosures provided herein.

Another mode of the MRS signal processor aspects of the present disclosure comprises a phase shift corrector configured to recognize and correct phase shifting within a repetitive multi-frame acquisition series acquired by a multi-channel detector assembly during an MRS pulse sequence series conducted on a region of interest within a body of a subject. According to one embodiment of this mode, the phase shift corrector is configured to recognize and correct the phase shifting within a repetitive multi-frame acquisition series acquired by a multi-channel detector assembly during an MRS pulse sequence series conducted on a voxel within an intervertebral disc in the body of the patient. According to another embodiment, the phase shift corrector is configured to recognize and correct the phase shifting in the time domain. According to another embodiment, the phase shift corrector is provided in combination with one or more of the various other aspects, modes, embodiments, variations, and features related to other MRS pulse sequence and/or MRS signal processor disclosures provided herein.

Another mode of the MRS signal processor aspects of the present disclosure comprises a frequency shift corrector configured to recognize and correct relative frequency shifts between multiple acquisition frames of a repetitive multi-frame acquisition series acquired within an acquisition detector channel of a multi-channel detector assembly during a MRS pulse sequence series conducted on a region of interest within a body of a subject. According to one embodiment of this mode, the frequency shift corrector is configured to recognize and correct frequency shift error between multiple acquisition frames of a repetitive multi-frame acquisition series acquired within an acquisition detector channel of a multi-channel detector assembly during a MRS pulse sequence series conducted on a voxel within an intervertebral disc in the body of the subject. According to another embodiment, the frequency shift corrector is configured to recognize and correct the frequency shift error in the time domain. According to one beneficial example of this embodiment, the frequency shift is recognized and corrected in the time domain by the application of the inverse of a $1^{st}$ order linear curve fit of the incremental phase estimate of time domain information in the 16 frame average of unsuppressed water frames (such as for example about 16 unsuppressed water frames of the detailed illustrative embodiments and Examples disclosed herein). According to another embodiment, the frequency shift corrector is configured to recognize and correct the frequency shift error in the frequency domain. According to one beneficial example of this embodiment, the frequency shift is recognized and corrected in the frequency domain by transforming the time domain information in the unsuppressed water frames (e.g. n=16) into the frequency domain to locate the water signal peak, determine the frequency error of the water peak, and then shift the transformed suppressed water frames by the negative of the frequency error. According to another example, the frequency shift corrector is configured to identify and locate a water signal in each of multiple acquisition frames of the series, compare the location of the located water signals against a reference baseline location to determine a separation shift therebetween for each frame, and to correct the shift to align the location to the baseline location by applying an appropriate offset to all the spectral data of each frame. According to one variation of this example, the location of the water signal is estimated based upon a location range where the water signal exceeds a threshold amplitude value. According to another variation, the water signal identified and located comprises a peak value of the water signal. According to one highly beneficial feature that may be further embodied in this variation, the threshold amplitude value is greater than about 0.6 and/or less than about 0.9, and the threshold amplitude value can be 0.8 in some cases. According to another embodiment of this mode, the frequency shift corrector is provided in combination with one or more of the various other aspects, modes, embodiments, variations, and features related to other MRS pulse sequence and/or MRS signal processor disclosures provided herein.

Another yet another mode of the MRS signal processor aspects disclosed herein comprises a frame editor. According to one embodiment of this mode, the frame editor is configured to recognize at least one poor quality acquisition frame, as determined against at least one threshold criterion, within an acquisition channel of a repetitive multi-frame acquisition series received from a multi-channel detector assembly during a MRS pulse sequence series conducted on a region of interest within a body of a subject. According to one example of this embodiment, the frame editor is configured to edit out the poor quality frame from the remainder of the MRS pulse sequence series otherwise retained for further signal and/or diagnostic algorithm processing. According to another embodiment, the frame editor is configured to recognize the poor quality acquisition frame based upon a threshold value applied to error in location of recognized water signal from an assigned baseline location. According to another embodiment, the frame editor is configured to recognize the poor quality acquisition frame based upon a threshold confidence interval applied to the ability to recognize the signal location of water signal in the frame spectrum. According to one example of this embodiment, the water signal location comprises a location of a peak of the water signal. According to another example, a confidence level for the location of the water signal peak of a frame is estimated and compared to a confidence level threshold to qualify a frame for subsequent frequency correction. According to another more detailed example, a confidence level may be determined by the following steps: (1) analyze the discrete amplitude spectrum in the range of the center-tuned frequency plus and minus 40 Hz (in the case of a 3T system, half that for a 1.5T system); (2) locate the highest peak and determine its width at the half-amplitude point; (3) determine the total spectral width of all parts of the spectrum which exceed the half-amplitude point of the highest peak; (4) form the confidence estimate by taking the ratio of the spectral width of the greatest peak divided by the total spectral width which exceeds the threshold. By way of further illustration of this example, if there is only a single peak above the threshold, the confidence estimate will be 1.0, if there are many other peaks or spectral components which could be confused with the greatest one, then the estimate will reduce and ultimately approach zero (0). It is believed that this provides a simple and robust estimate of the randomness or dispersal of energy in the vicinity of the water peak. Like an entropy measure, described elsewhere herein, it has the desirable characteristic that its performance is generally believed to be invariant with amplitude. According to still another embodiment of the present mode, the frame editor is provided in combination with one or more of the various other aspects, modes, embodiments, variations, and features related to other MRS pulse sequence and/or MRS signal processor disclosures provided herein.

Another mode of the MRS signal processor aspects of the present disclosure comprises an apodizer to reduce the truncation effect on the sampled data. The apodizer according to certain embodiments is configured to apodize an MRS acquisition frame in the time domain otherwise generated and acquired via an MRS pulse sequence aspect otherwise herein disclosed, and/or as also otherwise signal processed by one or more of the various MRS signal processor aspects also otherwise herein disclosed. The apodizer according to various embodiments of this mode is provided in combination with one or more of the various other aspects, modes, embodiments, variations, and features related to other MRS pulse sequence and/or MRS signal processor disclosures provided herein.

It is to be further appreciated that the various MRS signal processor, aspects, modes, features, variations, and examples herein described may be configured according to further modes to operate and/or provide diagnostic information related to a tissue in a patient based upon an MRS spectrum in real-part squared representation of the acquired spectral data or processed spectrum. According to still further modes, such may be operated upon or presented as complex absorption spectrum of the acquired or processed data. Yet another mode contemplated operates and/or presents processed results as complex absorption spectrum and also as real part squared representation of the acquired and/or signal processed data.

Another aspect of the present disclosure is an MRS diagnostic processor configured to process information extracted from an MRS spectrum for a region of interest in a body of a subject, and to provide the processed information in a manner that is useful for diagnosing a medical condition or chemical environment associated with the region of interest.

According to one mode of this aspect, the MRS diagnostic processor is configured to process the extracted information from the MRS spectrum for a voxel principally located in an intervertebral disc of the subject, and to provide the processed information in a manner that is useful for diagnosing a medical condition or chemical environment associated with the intervertebral disc.

According to one embodiment of this mode, the MRS diagnostic processor is configured to process the extracted information from the MRS spectrum for a voxel principally located in a nucleus of the intervertebral disc, and to provide the processed information in a manner that is useful for diagnosing a medical condition or chemical environment associated with the intervertebral disc. According to another embodiment, the MRS diagnostic processor is configured to provide the processed information in a manner that is useful for diagnosing the intervertebral disc as painful. According to another embodiment, the MRS diagnostic processor is configured to provide the processed information in a manner that is useful for diagnosing the intervertebral disc as severely painful. According to another embodiment, the MRS diagnostic processor is configured to provide the processed information in a manner that is useful for diagnosing the intervertebral disc as not severely painful. According to another embodiment, the MRS diagnostic processor is configured to provide the processed information in a manner that is useful for diagnosing the intervertebral disc as substantially non-painful. According to another embodiment, the MRS diagnostic processor is configured to diagnose the disc as painful. According to another embodiment, the MRS diagnostic processor is configured to diagnose the disc as severely painful. According to another embodiment, the MRS diagnostic processor is configured to diagnose the disc as not severely painful. According to another embodiment, the MRS diagnostic processor is configured to diagnose the disc as substantially non-painful.

According to another embodiment, the MRS diagnostic processor is configured to diagnose the disc with respect to % probability the disc is painful. According to another embodiment, the MRS diagnostic processor is configured to diagnose the disc with respect to % probability the disc is not painful.

According to one variation of the preceding embodiments, the MRS diagnostic processor is configured to diagnose the disc with respect to % probability the disc is painful or not painful based upon a calculated value for the disc using acquired MRS spectral information for the disc against an empirical prior test data set of similarly calculated values for other sample discs correlated with % predictive values against known or assumed classifications for such other sample discs as painful vs. non-painful.

According to another embodiment, the MRS diagnostic processor is configured to assign a value for the disc that is referenced against a range for use in determining presence, absence, or level of pain.

According to another embodiment, the MRS diagnostic processor is configured to provide the diagnostically useful information in a display provided contextually with an MRI image of the respective lumbar spine comprising the disc. According to another embodiment, the MRS diagnostic processor is configured to provide the diagnostically useful information in a display overlay onto an MRI image of the respective lumbar spine comprising the disc. According to one variation of this embodiment, the display overlay associates the diagnostically useful information with one or more intervertebral discs evaluated. According to another variation, the display overlay comprises a scaled legend of values along a range, and an indicator of a result referenced against the range in the legend and associated with an intervertebral disc evaluated. According to another variation, the display overlay comprises both color coding and numerical coding of results in a legend and for at least one indicator of processed information associated with at least one intervertebral disc evaluated by the diagnostic processor.

According to another embodiment, the MRS diagnostic processor comprises a diagnostic algorithm empirically created by comparing acquired and processed MRS spectra for multiple intervertebral discs against control measures for pain, and that is configured to determine whether discs evaluated with the MRS spectra are painful or non-painful.

According to one variation of this embodiment, the diagnostic algorithm comprises at least one factor related to spectral information extracted from MRS spectral regions associated with at least one of proteoglycan, lactate, and alanine chemicals.

According to one applicable feature of this variation, the spectral information is extracted from an MRS spectral region associated with n-acetyl resonance associated with proteoglycan.

According to another feature of this variation, the extracted information related to at least one said region is adjusted according to an adjustment factor related to voxel volume. According to one example, the extracted information related to at least one said region is divided by voxel volume.

According to another feature of this variation, the extracted information related to at least one said region is adjusted according to an adjustment factor related to body mass index (BMI). According to one example, the extracted information related to at least one said region is multiplied by body mass index (BMI) of the patient. According to another example, the extracted information is multiplied by BMI of the patient divided by a reference BMI. According to a further example, the reference BMI is average BMI calculated across an empirical test data set from which the diagnostic algorithm is statistically developed for correlation to the classifications.

According to another feature of this variation, the extracted information related to at least one said region comprises a peak value in the region.

According to another feature of this variation, the extracted information related to at least one said region comprises a power value in the region.

According to another applicable feature, the diagnostic algorithm comprises at least two factors related to spectral information extracted from the MRS spectral regions associated with at least two of said chemicals.

According to another applicable feature, the diagnostic algorithm comprises three factors related to spectral information extracted from the MRS spectral regions associated with all three of said chemicals. According to one particularly beneficial example of this feature, each of the three factors is related to one of the proteoglycan, lactate, and alanine chemicals, respectively.

According to another applicable feature, the diagnostic algorithm comprises at least two factors related to spectral information extracted from MRS spectral regions associated with at least three said chemicals. According to one particularly beneficial example of this feature, a first factor is related to spectral information extracted from the MRS spectral region associated with proteoglycan (e.g. n-acetyl peak region), and a second factor is related to spectral information extracted from MRS spectral regions associated with lactate and alanine in combination.

According to another particularly beneficial feature, the diagnostic algorithm comprises a factor related to spectral information extracted from MRS spectral regions associated with each of lactate and alanine chemicals in combination. According to one highly beneficial example of this feature, the factor comprises maximum peak value across the combination of the lactate and alanine spectral regions. According to another highly beneficial example, the factor comprises a power value across the combination of the lactate and alanine spectral regions.

According to another applicable feature, the diagnostic algorithm comprises at least two said factors related to spectral information extracted from the MRS spectral regions associated with all three of said chemicals.

According to still another applicable feature, at least one said factor is weighted by a constant.

According to another applicable feature, at least one said factor comprises a ratio of at least two values associated with information extracted from the MRS spectra at regions associated with at least two of proteoglycan, lactate, and alanine chemicals.

According to still a further variation, the algorithm comprises four factors associated with MRS spectral data associated with proteoglycan region, lactate region, proteoglycan:lactate region ratio, and proteoglycan:alanine region ratio. According to one applicable feature of this variation, the algorithm comprises four factors associated with MRS spectral data associated with proteoglycan region divided by voxel volume, lactate region divided by voxel volume, proteoglycan:lactate region ratio, and proteoglycan:alanine region ratio. According to still another applicable feature, the four factors are weighted by constants.

According to still a further variation, the algorithm is configured to calculate a diagnostically useful value based upon PG/LA, PG/AL, PG/vol, and LA/vol factors, wherein PG=peak measurement in proteoglycan spectral region, AL=peak measurement in alanine region, LA=peak measurement in LA region, and vol=volume of prescribed voxel in the disc used for MRS data acquisition. According to still a further variation, the algorithm is configured to calculate a diagnostically useful value as follows:

Value=−[log(*PG/LA*\*(0.6390061)+*PG/AL*\*(1.45108778)+*PG*/vol\*(1.34213514)+*LA/VOL*\*(−0.5945179)−2.8750366)];

wherein PG=peak measurement in proteoglycan spectral region, AL=peak measurement in alanine region, LA=peak measurement in LA region, and vol=volume of prescribed voxel in disc used for MRS data acquisition. Further to this algorithm, however, it is to be appreciated that, though considered highly beneficial, the specific constants may be slightly varied, and aspects such as the negative and log multipliers of the overall remaining functions may not be absolutely necessary and the removal of these aspects may still provide sufficiently robust results (e.g. the negative multiplier inverts negative values, otherwise corresponding with painful results to positive numbers as more colloquially corresponding with "positive" test results indicating pain condition is present, and visa versa for negative test results; and the log function provides collapse of data distribution spread not necessary for all applications and not necessarily altering ultimate results). According to still a further applicable feature, the calculated diagnostically useful value is compared against a threshold value of zero (0) to determine pain diagnosis. According to still a further applicable feature, positive calculated values are considered painful and negative calculated values are considered non-painful diagnoses.

According to another variation, the diagnostic algorithm is based at least in part upon a feature associated with a combined spectral region associated with lactate and alanine chemicals.

According to another variation, the diagnostic algorithm is based at least in part upon a power measurement taken along an MRS spectral region that combines regions associated with lactate and alanine chemicals.

According to another mode of the MRS diagnostic processor aspects of the disclosure, the diagnostic processor is provided in combination with one or more of the various other aspects, modes, embodiments, variations, and features related to other MRS pulse sequence and/or MRS signal processor disclosures also provided herein.

According to another mode of the present aspect, the MRS diagnostic processor may be configured to implement the following equation:

$$\text{Score} = -4.6010405 + 1.58785166\,(BLA) -$$
$$0.081991\,(VBLAAL - 29.3125) * (VBLAAL - 29.3125) +$$
$$0.01483355\,(PG/MAXLAAL - 7.14499) *$$
$$(PG/MAXLAAL - 7.14499) * (PG/MAXLAAL - 7.14499) +$$
$$0.1442603\,(MAXLAAL/vol - 16.1202) * (VBLAAL - 29.3125) -$$
$$0.0008879\,(VBLAAL - 29.3125)^2 * (MAXLAAL/VOL - 16.1202)$$

where BLA is the BMI corrected LA spectral peak, VBLAAL is the ROI volume and BMI normalized sum of the LA and AL spectral peaks, MAXLAAL is the maximum of either the LA or AL peaks, and PG is the n-acetyl spectral peak.

According to another mode of the present aspect, the MRS diagnostic processor may be configured to implement one or more of the following equations:

High Lipid Classifier Score =

$-(-335.51971 + 0.00010632 * (LAVVBMI)^2 +$ $873.744714 * (PG/(LAALVVBMI)));$ where LAVVBMI equals the voxel volume and BMI adjusted LA peak value.

$PG/MAXLAAL > 1.85$, Non-lipid,

Classifier Score = $-(-1.4959544 + 1.72223147 * (PG(MAXLAAL)));$ where PG/MAXLAAL equals the PG peak value divided by the maximum peak value of the LAAL region.

$PG/MAXLAAL < 1.85$, Non-lipid, Classifier Score =

$-1 * (-134.40909800961 + 3.96992556918043 * LAVVBMI -$ $2.6198628365642 * ALVVBMI + 113.683315467568 *$ $ALAUCVVBMI - 149.65896624348 * SQRT(PGAUCVVBMI));$ where LAVVBMI is the voxel volume and BMI adjusted LA peak value, ALVVBMI is the voxel volume and BMI adjusted AL peak value, ALAUCVVBMI is the AL region area under the curve as voxel volume and BMI adjusted, and PGAUCVVBMI is the PG region area under the curve as voxel volume and BMI adjusted.

It is to be appreciated that these formulaic relationships shown above, and elsewhere herein, are examples of highly accurate results that have been enjoyed with the present embodiments when put into practice. However, the examples are also provided in fine detail for full disclosure and understanding. These finer details are not intended to be necessarily limiting in all cases. For example, many of the constants disclosed herein are shown to many decimal points, which is the format generated by the engineering platforms employed to generate them. It would be readily apparent to one of ordinary skill that these likely could be significantly truncated or rounded without significant degradation or departing from the scope of the present disclosure. In addition, in order to provide abundance of understanding and disclosure, certain theories and explanations may be put forth and postulated herein, which may not be fully accurate, and are not necessary in order to fully embrace and enjoy the present embodiments and invention. The novelty and beneficial utility of the present embodiments may be fully appreciated and enjoyed without being bound by theory, as should be appreciated by one of ordinary skill.

Another aspect of the present disclosure comprises a diagnostic system configured to generate information useful for diagnosing a medical condition or chemical environment in a tissue of a subject based at least in part upon a combination of lactate-related and alanine-related factors measured or estimated in the tissue. According to one mode of this aspect, the diagnostic system is configured to generate the useful information based at least in part upon one combination lactate-alanine (LAAL)-related diagnostic factor related to a combination of lactate-related and alanine-related factors measured or estimated in the tissue. According to one embodiment of this mode, the combination LAAL factor provides useful information as a LAAL biomarker for hypoxia in the tissue. According to another embodiment of this mode, the diagnostic system is further configured to provide the useful information based on the LAAL factor in combination with a second factor related to a third chemical-related factor measured or estimated in the tissue. According to one variation of this embodiment, the third chemical-related factor comprises a biomarker associated with enervation of the tissue. According to another variation of this embodiment, the third chemical-related factor is associated with proteoglycan content in the tissue. According to another mode of this aspect, the diagnostic system comprises an MRS diagnostic processor, and the lactate-related and alanine-related factors comprise features associated with lactate-related and alanine-related regions of an MRS spectrum of a region of interest in the tissue. According to one embodiment of this mode, the MRS diagnostic processor is further configured to generate the useful information based at least in part upon one combination lactate-alanine (LAAL)-related diagnostic factor related to a combination of the lactate-related and alanine-related factors measured or estimated in the tissue. According to one variation of this embodiment, the combination LAAL factor comprises a maximum peak spectral value in the combined LAAL region of the MRS spectrum. According to another variation of this embodiment, the combination LAAL factor comprises a measured or estimated overall power value in the combined LAAL region of the MRS spectrum.

Another aspect of the present disclosure is an MRS system comprising an MRS pulse sequence, MRS signal processor, and MRS diagnostic processor, and which is configured to generate, acquire, and process an MRS spectrum for providing diagnostically useful information associated with a region of interest in a body of a patient.

According to one mode of this aspect, the MRS system comprising the MRS pulse sequence, MRS signal processor, and MRS diagnostic processor, is configured to generate, acquire, and process the MRS spectrum for a voxel principally located in an intervertebral disc in the body of the patient and to provide diagnostically useful information associated with the disc. According to one embodiment of this mode, the voxel is principally located in a nucleus of the disc. According to another embodiment of this mode, the diagnostically useful information is useful for diagnosing pain or absence of pain associated with the disc.

Various further modes of this aspect are contemplated that comprise one or more of the various aspects, modes, embodiments, variations, and features of the MRS pulse sequence, MRS signal processor, and MRS diagnostic processor as elsewhere described herein.

According to one such further mode, for example, the MRS pulse sequence comprises a combination CHESS-PRESS sequence. According to another example of such a mode, the MRS pulse sequence comprises a combination CHESS-VSS-PRESS sequence.

According to another such further mode, the MRS pulse sequence comprises a TE of about 28 ms and a TR of about 1000 ms, whereas TE according to further embodiments can range from between about 25 to about 40 ms and TR can typically range from between about 750 to about 2000 ms.

According to another such further mode, the MRS signal processor comprises at least one of a channel selector, a phase shift corrector, an apodizer, a frame editor, a frequency shift corrector, and a frame averaging combiner.

According to another mode, the MRS diagnostic processor is configured to calculate and provide diagnostically useful information for diagnosing pain associated with at least one intervertebral disc based upon at least one MRS spectral region associated with at least one of proteoglycan, lactate, and alanine chemicals. According to one embodiment of this mode, information associated with each of the MRS spectral regions associated with each of these chemicals is used by the MRS diagnostic processor in providing the diagnostically useful information. According to another embodiment, a combination LAAL factor associated with a combination of the lactate-related and alanine-related MRS spectral regions is used. According to one variation of this embodiment, the combination LAAL factor is used in further combination with a second factor associated with a proteoglycan-related (such as for example n-acetyl) MRS spectral region for an overall diagnostic algorithm.

According to another mode of the various aspects above, each or all of the respective MRS system components described is provided as user or controller operable software in a non-transitory computer readable storage medium configured to be installed and operated by one or more processors. According to one embodiment of this mode, a non-transitory computer operable storage medium is provided and stores the operable software.

The following issued US patents are also herein incorporated by reference in their entirety: U.S. Pat. Nos. 5,617,861; 5,903,149; 6,617,169; 6,835,572; 6,836,114; 6,943,033; 7,042,214; 7,319,784; 8,344,728; 8,761,860; 8,825,131; 8,965,094; 9,161,735; and 9,280,718.

The following US Patent Application Publication is herein incorporated by reference in its entirety: US2007/0253910.

The following PCT Patent Application Publications are also herein incorporated by reference in their entirety: WO 2009/058915; and WO 2011/047197.

Some aspects of the systems and methods described herein can advantageously be implemented using, for example, computer software, hardware, firmware, or any combination of computer software, hardware, and firmware. Computer software can comprise computer executable code stored in a computer readable medium that, when executed, performs the functions described herein. In some embodiments, computer-executable code is executed by one or more general purpose computer processors. A skilled artisan will appreciate, in light of this disclosure, that any feature or function that can be implemented using software to be executed on a general purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

A skilled artisan will also appreciate, in light of this disclosure, that multiple distributed computing devices can be substituted for any one computing device illustrated herein. In such distributed embodiments, the functions of the one computing device are distributed (e.g., over a network) such that some functions are performed on each of the distributed computing devices.

Some embodiments of the present invention may be described with reference to equations, algorithms, and/or flowchart illustrations of methods according to embodiments of the invention. These methods may be implemented using computer program instructions executable on one or more computers. These methods may also be implemented as computer program products either separately, or as a component of an apparatus or system. In this regard, each equation, algorithm, or block or step of a flowchart, and combinations thereof, may be implemented by hardware, firmware, and/or software including one or more computer program instructions embodied in computer-readable program code logic. As will be appreciated, any such computer program instructions may be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, may be implemented by special purpose hardware-based computer systems which perform the specified functions or steps, or combinations of special purpose hardware and computer-readable program code logic means.

Furthermore, computer program instructions, such as embodied in computer-readable program code logic, may also be stored in a computer readable memory (e.g., a non-transitory computer readable medium) that can direct one or more computers or other programmable processing devices to function in a particular manner, such that the instructions stored in the computer-readable memory implement the function(s) specified in the block(s) of the flowchart(s). The computer program instructions may also be loaded onto one or more computers or other programmable computing devices to cause a series of operational steps to be performed on the one or more computers or other programmable computing devices to produce a computer-implemented process such that the instructions which execute on the computer or other programmable processing apparatus provide steps for implementing the functions specified in the equation(s), algorithm(s), and/or block(s) of the flowchart(s).

Figure 41A:
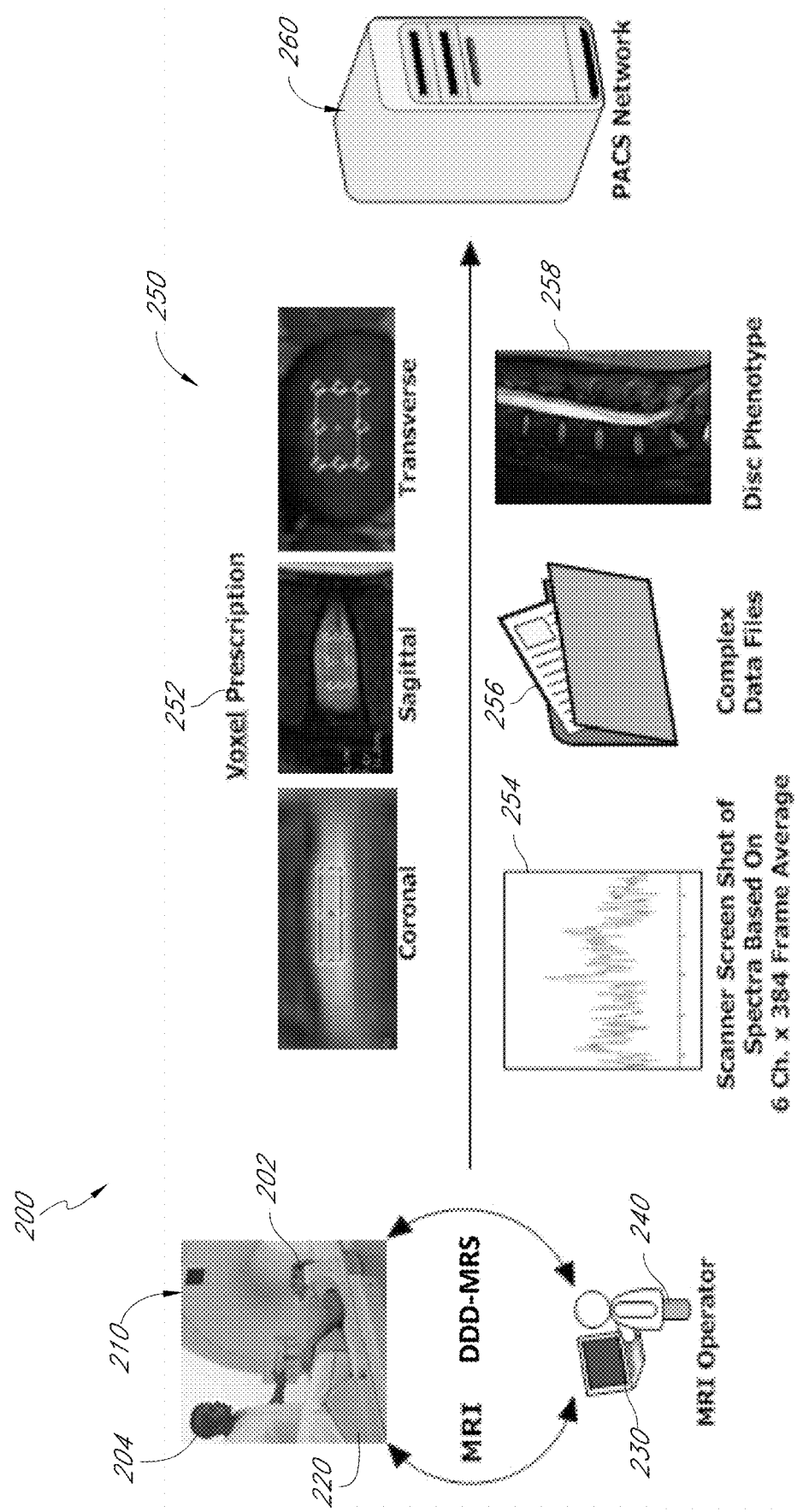
FIGS. 41A-B show schematic flow diagrams of a DDD-MRS exam, including DDD-MRS pulse sequence, DDD-MRS signal processing, and DDD-MRS algorithm processing, and various data communication aspects, according to certain further aspects of the present disclosure.
Figure 41B:
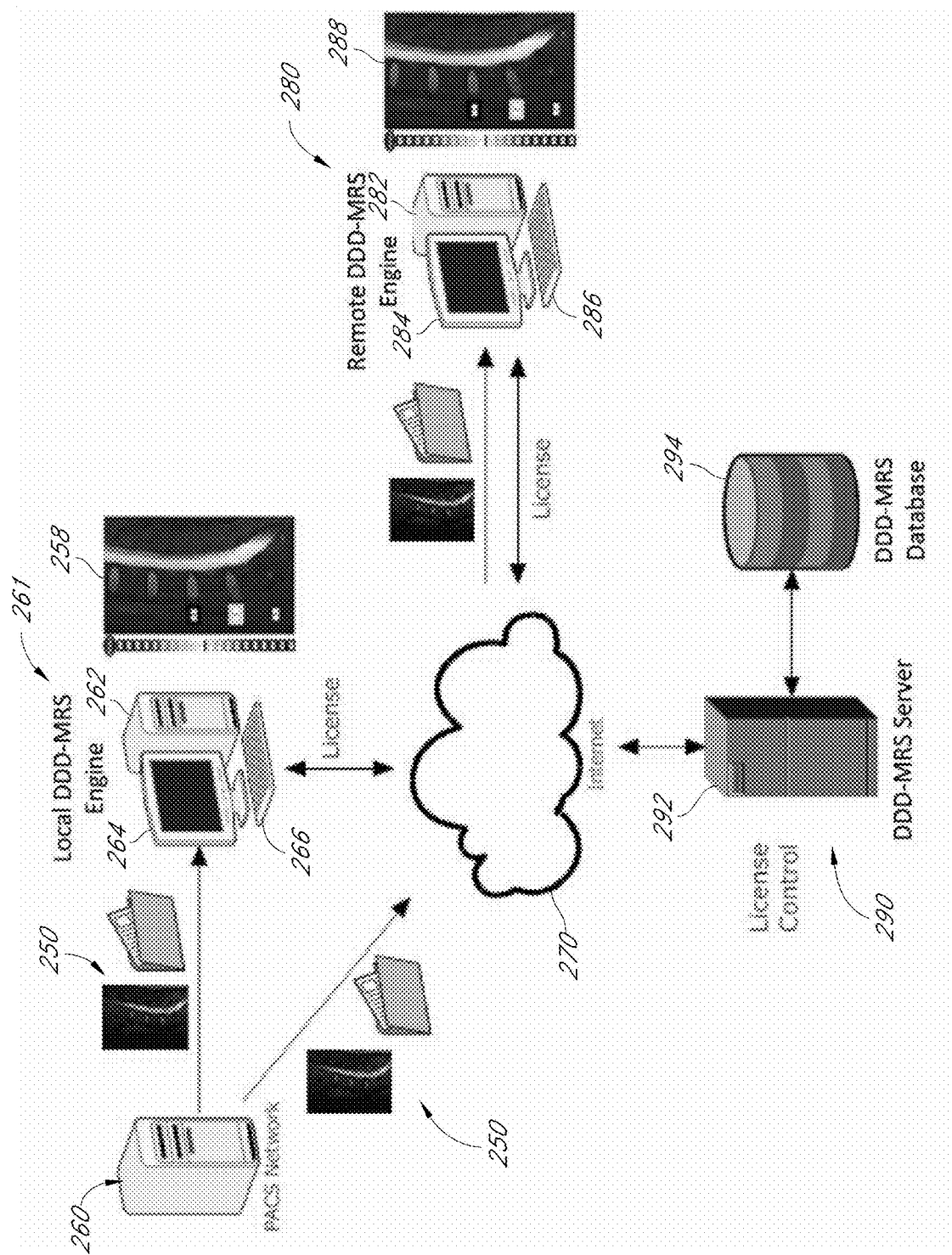

While various alternative modalities may be employed as stated, one particular example of an overall diagnostic system 200 and various related functional interfacing components are shown in FIGS. 41A-B and referenced with respect to schematic flow of an exam and related steps post-DDD-MRS pulse sequence acquisition as follows. FIG. 41A shows a DDD-MRS pulse sequence acquisition and output communication flow diagram. An MRI exam is first conducted on the patient 202 who typically is slid supine into MR system 210 while lying on a spine detector coil 220 that acquires the MR and MRS signals. This is followed by the DDD-MRS pulse sequence, as also conducted via the same MR system 210 and by a trained operator/technician 204. Data representative of the anatomy of the patient 202 is generated 258 (e.g., data representative of the chemical makeup of an area of interest inside the intervertebral disc of the patient's spine 252). The results are then packaged in a data archive folder 250 that includes information related to the MRI image 258 (if taken and retained for this purpose), voxel prescription in various relevant planes 252, pre-packaged output spectra 254 (if desired for any further use, or not), complex data files for the acquired series 256. This is sent via PACS 260 for storage and/or further communication either as push or pull for further processing. In some embodiments, the MR system 210 may be operated by a computer system or terminal 230 that can be located remotely or can be integrated into the MR system 210, to allow one or more operators 240 (or the technician 204) to provide instructions or other information to the MR system 210.

As shown in FIG. 41B, this data package 250 may then be accessed or pushed from the PACS 260 to another local DDD-MRS engine 261, which may be a local computer 262 (and related peripheral devices such as display 264 and keyboard 266), work station, or other modality, or terminal (e.g., terminal 230), which may conduct the DDD-MRS signal processing and/or diagnostic processing and for packaged display of results as appropriate. This may be monitored via other remote device 290, such as via the internet 270 as shown schematically in FIG. 41B—and this may include for example license monitoring such as on a "per click" or "volume"-related use license fee basis or other such use monitoring purposes (e.g. data collection and analysis purposes, e.g. for trials, studies, registries, etc.). The more remote processors may be a central server 292 providing certain SAAS support to the system, or again for more monitoring. These files, at any stage, can be configured to push or be pulled electronically, such as to a remote DDD-MRS station 280 with engine components including a computer 282, monitor 284, keyboard 286, where diagnostic results such as overlaid images 288 may be seen and analyzed for example and the various processors may be stored and employed for functional use in a variety of single or multiple coordinated locations and controllers or computers, with ultimate flexibility re: specific modality for operation and storage 294 and/or communication of results.

While certain embodiments of the disclosure have been described, these embodiments have been presented by way of example only, and are not intended to limit the scope of the broader aspects of the disclosure. Indeed, the novel methods, systems, and devices described herein may be embodied in a variety of other forms. For example, embodiments of one illustrated or described DDD-MRS system component may be combined with embodiments of another illustrated or described DDD-MRS system component. Moreover, the DDD-MRS system components described above, e.g. pulse sequence, signal processor, or diagnostic processor, may be utilized for other purposes. For example, an MRS system (or component sequence, signal processor, or diagnostic processor useful therewith or therein), may be configured and used in manners consistent with one or more broad aspects of this disclosure for diagnosing other tissue environments or conditions than pain within an intervertebral disc. Or, such may be usefully employed for diagnosing pain or other tissue environments or conditions in other regions of interest within the body. Such further applications are considered within the broad scope of disclosure contemplated herein, with or without further modifications, omissions, or additions that may be made by one of ordinary skill for a particular purpose. Furthermore, various omissions, substitutions and changes in the form of the methods, systems, and devices described herein may be made without departing from the spirit of the disclosure. Components and elements may be altered, added, removed, or rearranged. Additionally, processing steps may be altered, added, removed, or reordered. While certain embodiments have been explicitly described, other embodiments will also be apparent to those of ordinary skill in the art based on this disclosure.

In one embodiment, a computing system, comprising one or more microprocessors receiving at least one signal responsive to data collected in an MR scanner, is configured to implement a magnetic resonance spectroscopy (MRS) processing system configured to process a repetitive frame MRS spectral acquisition series generated and acquired for a voxel principally located within an intervertebral disc via an MRS pulse sequence, and acquired at multiple parallel acquisition channels of a multi-coil spine detector assembly, in order to provide diagnostic information associated with the disc, comprising: an MRS signal processor comprising a channel selector, a phase shift corrector, a frequency shift corrector, a frame editor, and a channel combiner, and configured to receive and process the MRS spectral acquisition series for the disc and to generate a processed MRS spectrum for the series with sufficient signal-to-noise ratio (SNR) to acquire information associated with identifiable features along MRS spectral regions associated with unique chemical constituents in the disc; and an MRS diagnostic processor configured to extract data from identifiable chemical regions in the processed MRS spectrum in a manner that provides diagnostic information for diagnosing a medical condition or chemical environment associated with the disc.

In one embodiment, a physical computer readable medium stores computer executable code that causes a computing system to implement a magnetic resonance spectroscopy (MRS) processing system configured to process a repetitive frame MRS spectral acquisition series generated and acquired for a voxel principally located within an intervertebral disc via an MRS pulse sequence, and acquired at multiple parallel acquisition channels of a multi-coil spine detector assembly, in order to provide diagnostic information associated with the disc, comprising: an MRS signal processor comprising a channel selector, a phase shift corrector, a frequency shift corrector, a frame editor, and a channel combiner, and configured to receive and process the MRS spectral acquisition series for the disc and to generate a processed MRS spectrum for the series with sufficient signal-to-noise ratio (SNR) to acquire information associated with identifiable features along MRS spectral regions associated with unique chemical constituents in the disc; and an MRS diagnostic processor configured to extract data from identifiable chemical regions in the processed MRS spectrum in a manner that provides diagnostic information for diagnosing a medical condition or chemical environment associated with the disc.

In one embodiment, a magnetic resonance spectroscopy (MRS) processing method is used for processing a repetitive frame MRS spectral acquisition series generated and acquired for a voxel principally located within an intervertebral disc via an MRS pulse sequence, and acquired at multiple parallel acquisition channels of a multi-coil spine detector assembly, and for providing diagnostic information associated with the disc, the method comprising: receiving the MRS spectral acquisition series from the multiple acquisition channels; signal processing the MRS acquisition series, comprising selecting one or more channels among the parallel channels based upon a predetermined criteria, recognizing and correcting phase shift error among multiple frames within the series of a channel acquisition, recognizing and correcting a frequency shift error between multiple frames within the series of the channel acquisition, recognizing and editing out frames from the series based upon a predetermined criteria, combining selected and corrected channels for a combined average processed MRS spectrum; and diagnostically processing the processed MRS spectrum by extracting data from identifiable chemical regions in the processed MRS spectrum and processing the extracted data in a manner that provides MRS-based diagnostic information for diagnosing a medical condition or chemical environment associated with the disc.

In one embodiment, a computing system, comprising one or more microprocessors receiving at least one signal responsive to data collected in an MR scanner, is configured to implement a medical diagnostic system, comprising: a signal processor configured to signal process a repetitive multi-frame MRS pulse sequence acquisition series of MRS spectra frames received from multiple acquisition channels of a detector assembly during a MRS pulse sequence series conducted on a region of interest (ROI) within a tissue in a body of a subject; and wherein the signal processor comprises a channel selector configured to measure a parameter related to MRS spectral signal quality for the acquired MRS spectral series from each acquisition channel, compare the measured parameters for the respective channels against at least one threshold criteria for channel selection, identify a number of selected channels which meet or exceed the threshold criteria and a number of other failed channels which fail to meet the threshold criteria, and retain the selected channels and discard the failed channels from the acquisition series.

In one embodiment, a physical computer readable medium stores computer executable code that causes a computing system to implement a medical diagnostic system, comprising: a signal processor configured to signal process a repetitive multi-frame MRS pulse sequence acquisition series of MRS spectra frames received from multiple acquisition channels of a detector assembly during a MRS pulse sequence series conducted on a region of interest (ROI) within a tissue in a body of a subject; and wherein the signal processor comprises a channel selector configured to measure a parameter related to MRS spectral signal quality for the acquired MRS spectral series from each acquisition channel, compare the measured parameters for the respective channels against at least one threshold criteria for channel selection, identify a number of selected channels which meet or exceed the threshold criteria and a number of other failed channels which fail to meet the threshold criteria, and retain the selected channels and discard the failed channels from the acquisition series.

In one embodiment, a computing system, comprising one or more microprocessors receiving at least one signal responsive to data collected in an MR scanner, is configured to implement a medical diagnostic system, comprising: a signal processor configured to process a repetitive multi-frame MRS pulse sequence acquisition series of MRS spectra frames received from an acquisition channel of a detector assembly during a MRS pulse sequence series conducted on a region of interest (ROI) within a tissue in a body of a subject; wherein the signal processor comprises a frame editor configured to measure a parameter related to signal quality for the MRS spectrum for each acquired frame of the acquisition series, compare the measured values for the parameter for the respective frames against a threshold criteria, and designate a number of successful frames that meet the threshold criteria and a number of failed frames that fail to meet the threshold criteria; and wherein the frame editor is further configured to retain successful frames in the acquisition series, and edit out the failed frames from the acquisition series if number of successful frames meets or exceeds a minimum frame number threshold, but to retain at least some of the failed frames in the acquisition series if the number of successful frames is below the minimum frame number threshold.

In one embodiment, a physical computer readable medium stores computer executable code that causes a computing system to implement a medical diagnostic system, comprising: a signal processor configured to process a repetitive multi-frame MRS pulse sequence acquisition series of MRS spectra frames received from an acquisition channel of a detector assembly during a MRS pulse sequence series conducted on a region of interest (ROI) within a tissue in a body of a subject; wherein the signal processor comprises a frame editor configured to measure a parameter related to signal quality for the MRS spectrum for each acquired frame of the acquisition series, compare the measured values for the parameter for the respective frames against a threshold criteria, and designate a number of successful frames that meet the threshold criteria and a number of failed frames that fail to meet the threshold criteria; and wherein the frame editor is further configured to retain successful frames in the acquisition series, and edit out the failed frames from the acquisition series if number of successful frames meets or exceeds a minimum frame number threshold, but to retain at least some of the failed frames in the acquisition series if the number of successful frames is below the minimum frame number threshold.

In one embodiment, a computing system, comprising one or more microprocessors receiving at least one signal responsive to data collected in an MR scanner, is configured to implement a medical diagnostic system, comprising: a signal processor configured to process a repetitive multi-frame MRS pulse sequence acquisition series of MRS spectra frames received from an acquisition channel of a detector assembly during a MRS pulse sequence series conducted on a region of interest (ROI) within a tissue in a body of a subject; wherein the signal processor comprises a frequency error corrector configured to calculate a confidence level in an ability to estimate frequency shift error for the MRS spectra of each frame of the series, compare each calculated confidence level for each frame against at least one threshold criteria, and determine a number of successful frames that meet or exceed the threshold criteria and a number of other failed frames that fail to meet the threshold criteria; and wherein the signal processor is further configured to automatically determine whether to (a) edit out the failed frames from the acquisition series and perform frequency shift error correction via the frequency error corrector in a manner to at least in part reverse the frequency shift error estimate on each of the successful frames, if the number of successful frames meets or exceeds a minimum threshold number, or (b) retain at least some of the failed frames and not perform frequency error correction to the series via the frequency error corrector if the number of successful frames is below the minimum threshold.

In one embodiment, a physical computer readable medium stores computer executable code that causes a computing system to implement a medical diagnostic system, comprising: a signal processor configured to process a repetitive multi-frame MRS pulse sequence acquisition series of MRS spectra frames received from an acquisition channel of a detector assembly during a MRS pulse sequence series conducted on a region of interest (ROI) within a tissue in a body of a subject; wherein the signal processor comprises a frequency error corrector configured to calculate a confidence level in an ability to estimate frequency shift error for the MRS spectra of each frame of the series, compare each calculated confidence level for each frame against at least one threshold criteria, and determine a number of successful frames that meet or exceed the threshold criteria and a number of other failed frames that fail to meet the threshold criteria; and wherein the signal processor is further configured to automatically determine whether to (a) edit out the failed frames from the acquisition series and perform frequency shift error correction via the frequency error corrector in a manner to at least in part reverse the frequency shift error estimate on each of the successful frames, if the number of successful frames meets or exceeds a minimum threshold number, or (b) retain at least some of the failed frames and not perform frequency error correction to the series via the frequency error corrector if the number of successful frames is below the minimum threshold.

In one embodiment, a computing system, comprising one or more microprocessors receiving at least one signal responsive to data collected in an MR scanner, is configured to implement a medical diagnostic system, comprising: a signal quality evaluator configured to automatically determine whether or not an MRS spectrum acquired from a region of interest (ROI) in a tissue in a body of a subject via an MRS pulse sequence series exam of the ROI comprises a regional signature signal along the MRS spectrum that is characteristic of lipid.

In one embodiment, a physical computer readable medium stores computer executable code that causes a computing system to implement a medical diagnostic system, comprising: a signal quality evaluator configured to automatically determine whether or not an MRS spectrum acquired from a region of interest (ROI) in a tissue in a body of a subject via an MRS pulse sequence series exam of the ROI comprises a regional signature signal along the MRS spectrum that is characteristic of lipid.

In one embodiment, a computing system, comprising one or more microprocessors receiving at least one signal responsive to data collected in an MR scanner, is configured to implement a medical diagnostic system, comprising: a diagnostic processor configured to provide diagnostic information for diagnosing a medical condition or chemical environment associated with a region of interest (ROI) in a tissue in a body of a subject based at least in part upon at least one chemical factor related to information extracted from the ROI and associated with lactate (LA) and alanine (AL) chemicals.

In one embodiment, a physical computer readable medium stores computer executable code that causes a computing system to implement a medical diagnostic system, comprising: a diagnostic processor configured to provide diagnostic information for diagnosing a medical condition or chemical environment associated with a region of interest (ROI) in a tissue in a body of a subject based at least in part upon at least one chemical factor related to information extracted from the ROI and associated with lactate (LA) and alanine (AL) chemicals.

In one embodiment, a computing system, comprising one or more microprocessors receiving at least one signal responsive to data collected in an MR scanner, is configured to implement a medical diagnostic system, comprising: a diagnostic processor configured to provide diagnostic information for diagnosing a medical condition or chemical environment associated with a region of interest (ROI) in a tissue in a body of a subject based at least in part upon a chemical factor related to information extracted from the ROI and associated with a chemical and as adjusted by an adjustment factor that comprises at least one of a voxel-related adjustment factor associated with a voxel prescribed to correspond with the ROI and related to the information extracted, and a subject-dependent variable-related adjustment factor associated with the subject.

In one embodiment, a physical computer readable medium stores computer executable code that causes a computing system to implement a medical diagnostic system, comprising: a diagnostic processor configured to provide diagnostic information for diagnosing a medical condition or chemical environment associated with a region of interest (ROI) in a tissue in a body of a subject based at least in part upon a chemical factor related to information extracted from the ROI and associated with a chemical and as adjusted by an adjustment factor that comprises at least one of a voxel-related adjustment factor associated with a voxel prescribed to correspond with the ROI and related to the information extracted, and a subject-dependent variable-related adjustment factor associated with the subject.

In one embodiment, a computing system, comprising one or more microprocessors receiving at least one signal responsive to data collected in an MR scanner, is configured to implement a medical diagnostic system, comprising: a diagnostic processor configured to provide diagnostic processed information for diagnosing a medical condition or chemical environment associated with a region of interest (ROI) in a tissue in a body of a subject based at least in part upon taking a first MRS measurement for a chemical factor taken at a region of an MRS spectrum acquired from the ROI and associated with a chemical and comparing the first MRS measurement against a value derived from a different second measurement and that is associated with an amount of the chemical in the ROI.

In one embodiment, a physical computer readable medium stores computer executable code that causes a computing system to implement a medical diagnostic system, comprising: a diagnostic processor configured to provide diagnostic processed information for diagnosing a medical condition or chemical environment associated with a region of interest (ROI) in a tissue in a body of a subject based at least in part upon taking a first MRS measurement for a chemical factor taken at a region of an MRS spectrum acquired from the ROI and associated with a chemical and comparing the first MRS measurement against a value derived from a different second measurement and that is associated with an amount of the chemical in the ROI.

In one embodiment, a computing system, comprising one or more microprocessors receiving at least one signal responsive to data collected in an MR scanner, is configured to implement a medical diagnostic system, comprising: a diagnostic processor configured to provide diagnostic information for diagnosing a medical condition or chemical environment associated with a region of interest (ROI) of a tissue in a body of a subject based at least in part upon a chemical factor related to information extracted from the ROI and associated with a chemical; and wherein said diagnostic information comprises a probability value assigned to a likelihood that the medical condition or chemical environment meets certain criteria in the ROI.

In one embodiment, a physical computer readable medium stores computer executable code that causes a computing system to implement a medical diagnostic system, comprising: a diagnostic processor configured to provide diagnostic information for diagnosing a medical condition or chemical environment associated with a region of interest (ROI) of a tissue in a body of a subject based at least in part upon a chemical factor related to information extracted from the ROI and associated with a chemical; and wherein said diagnostic information comprises a probability value assigned to a likelihood that the medical condition or chemical environment meets certain criteria in the ROI.

In one embodiment, a medical diagnostic method comprises: using a computing system to implement a signal processor for signal processing a repetitive multi-frame MRS pulse sequence acquisition series of MRS spectra frames received from multiple acquisition channels of a detector assembly during a MRS pulse sequence series conducted on a region of interest (ROI) within a tissue in a body of a subject; and wherein the signal processing further comprises using one or more microprocessors to operate a channel selector for measuring a parameter related to MRS spectral signal quality for the acquired MRS spectral series from each acquisition channel, comparing the measured parameters for the respective channels against at least one threshold criteria for channel selection, identifying a number of selected channels which meet or exceed the threshold criteria and a number of other failed channels which fail to meet the threshold criteria, and retaining the selected channels and discarding the failed channels from the acquisition series.

In one embodiment, a medical diagnostic method comprises: using a computing system for signal processing a repetitive multi-frame MRS pulse sequence acquisition series of MRS spectra frames received from an acquisition channel of a detector assembly during a MRS pulse sequence series conducted on a region of interest (ROI) within a tissue in a body of a subject; wherein the signal processing further comprises using a computing system for implementing a frame editor for measuring, using one or more microprocessors, a parameter related to signal quality for the MRS spectrum for each acquired frame of the acquisition series, comparing, using the one or more microprocessors, the measured values for the parameter for the respective frames against a threshold criteria, and designating, using the one or more microprocessors, a number of successful frames that meet the threshold criteria and a number of failed frames that fail to meet the threshold criteria; and wherein the frame editing further comprises retaining, using the one or more microprocessors, successful frames in the acquisition series, and editing out the failed frames from the acquisition series if the number of successful frames meets or exceeds a minimum frame number threshold, but retaining at least some of the failed frames in the acquisition series if the number of successful frames is below the minimum frame number threshold.

In one embodiment, a medical diagnostic method, comprising: using a computing system to execute executable code for implementing a signal processor for processing a repetitive multi-frame MRS pulse sequence acquisition series of MRS spectra frames received from an acquisition channel of a detector assembly during a MRS pulse sequence series conducted on a region of interest (ROI) within a tissue in a body of a subject; wherein the signal processing further comprises using a computing system to execute executable code for operating a frequency error corrector for calculating, using one or more microprocessors, a confidence level in an ability to estimate frequency shift error for the MRS spectra of each frame of the series, comparing, using the one or more microprocessors, each calculated confidence level for each frame against at least one threshold criteria, and determining, using the one or more microprocessors, a number of successful frames that meet or exceed the threshold criteria and a number of other failed frames that fail to meet the threshold criteria; and wherein the signal processing further comprises using a computing system to execute executable code for automatically determining whether to (a) edit out the failed frames from the acquisition series and perform frequency shift error correction via the frequency error corrector in a manner to at least in part reverse the frequency shift error estimate on each of the successful frames, if the number of successful frames meets or exceeds a minimum threshold number, or (b) retaining at least some of the failed frames and not performing frequency error correction to the series via the frequency error corrector if the number of successful frames is below the minimum threshold.

In one embodiment, a medical diagnostic method comprises: using a computing system to execute executable code to implement a signal quality evaluator for automatically determining, using one or more microprocessors, whether or not an MRS spectrum acquired from a region of interest (ROI) in a tissue in a body of a subject via an MRS pulse sequence series exam of the ROI comprises a regional signature signal along the MRS spectrum that is characteristic of lipid.

In one embodiment, a medical diagnostic method comprises: using a computing system to execute executable code to implement a diagnostic processor for providing, using one or more microprocessors, diagnostic information for diagnosing a medical condition or chemical environment associated with a region of interest (ROI) in a tissue in a body of a subject based at least in part upon at least one chemical factor related to information extracted from the ROI and associated with lactate (LA) and alanine (AL) chemicals.

In one embodiment, a medical diagnostic method, comprising: using a computing system to execute executable code to implement a diagnostic processor for providing diagnostic information for diagnosing a medical condition or chemical environment associated with a region of interest (ROI) in a tissue in a body of a subject based at least in part upon a chemical factor related to information extracted from the ROI and associated with a chemical and comprising adjusting, using one or more microprocessors, the chemical factor by an adjustment factor that comprises at least one of a voxel-related adjustment factor associated with a voxel prescribed to correspond with the ROI and related to the information extracted, and a subject-dependent variable-related adjustment factor associated with the subject.

In one embodiment, a medical diagnostic method, comprising: using a computing system to execute executable code to implement a diagnostic processor for providing processed diagnostic information for diagnosing a medical condition or chemical environment associated with a region of interest (ROI) in a tissue in a body of a subject based at least in part upon taking a first MRS measurement for a chemical factor taken at a region of an MRS spectrum acquired from the ROI and associated with a chemical, and comparing, using one or more microprocessors, the first MRS measurement against a value derived from a different second measurement and that is associated with an amount of the chemical in the ROI.

In one embodiment, a medical diagnostic method comprises: using a computing system to execute executable code to implement a diagnostic processor for providing diagnostic information for diagnosing a medical condition or chemical environment associated with a region of interest (ROI) of a tissue in a body of a subject based at least in part upon a chemical factor related to information extracted from the ROI and associated with a chemical; and using a computing system to execute executable code for providing, using one or more microprocessors, the diagnostic information that comprises a probability value assigned to a likelihood that the medical condition or chemical environment meets certain criteria in the ROI.

Propionic Acid and Other Pain Biomarkers

In certain further examples, other spectral regions are also contemplated for diagnostic and/or monitoring purposes that may be similar as elsewhere herein described, and/or which may present certain different aspects or related benefits.

According to one specific further example, one or more spectral factors along a spectral region located below (e.g. parts per million or 'ppm' on the chemical shift or 'c.s.' scale) the range typically associated with lactic acid—e.g. below 1.2 ppm—is analyzed, such as for diagnostic or monitoring purposes, including but not limited to those described herein for intervertebral disc, other form of musculoskeletal joint, and/or other applications of spectroscopy-based diagnosis or monitoring associated with tissue chemistry. In one such particular mode, this range may be chosen to include a peak region that corresponds with propionic acid (PA), such as may be typically located at or relatively closely around about 1.04 ppm. According to the typical resolution of clinical scanners, this specifically defined target location provides a helpful reference, but the actual PA peak could potentially vary or shift along a range that may be above and/or below this reference value, such as for example in a range of about 0.2 ppm from between about 0.9 ppm to about 1.1 ppm. While LA may be reasonably considered to correspond with a range from about 1.2 to about 1.4 ppm, these upper and lower reference numbers are not necessarily strictly limiting to the potential location where an LA peak may be located. Shifting via in vivo acquisitions using commercial clinical scanners could also blur an LA peak slightly outside that range, such as for example between about 1.0, 1.5, or 1.1 ppm on one end to about 1.45 or even about 1.5 ppm on the other end of the range (e.g. see ranges elsewhere herein disclosed by way of such examples, e.g. by reference to FIGS. 9A-C; e.g. range examples of from about 1.2 to about 1.45 ppm for LA, and from about 1.45 to about 1.6 or higher, e.g. up to about 1.65 or even about 1.7 or 1.75 ppm, for AL).

It is thus contemplated, as elsewhere herein described by reference to "LAAL" range encompassing both LA and AL peak ranges, that the ppm range associated with PA may abut or overlap with, and thus may be combined with as a broader multi-marker range, other adjacent ranges representing other chemical markers. In one such regard, in particular regard to the spectral resolution derived from clinical in vivo scans, the upper end of the potential PA range may also be considered to abut or even overlap with the bottom end of the range for LA (or LAAL, as the case may be). Various permutations of such combined ranges are thus also contemplated in further embodiments. One such example, which may be represented by the letters "LAPA" for illustration, represents such a combined range corresponding with each of LA and PA. Such an embodiment may correspond, for example, with a range from the bottom of a PA-associated range (e.g. as low as or below about 0.9 ppm, and which may even be for example as low as about 0.75 ppm or even about 0.5 ppm), to the high end of an LA associated range (e.g. up to about 1.4 ppm or even about 1.45 ppm or 1.5 ppm). Another embodiment quantitatively analyzes a combined range corresponding with each of AL, LA, and PA (e.g. "ALPA"). For further illustration, this may be for example from the lower end of (or below) the PA range (e.g. such as ppm examples described above), to the upper end of the AL peak range (e.g. up to about 1.6, 1.65, or even about 1.7 ppm).

It is appreciated, according to the various aspects and embodiments of this disclosure, that a range that is broader than but still including the regional spectral expression or peak location corresponding with a particular chemical entity would be considered to 'correspond' with that chemical, such as for example considering that the presence or absence of the chemical's spectral expression may influence quantitative measurements that are taken over the broader range (e.g., discrete or combined multi-peak values, e.g., maximum peak value over the range, and/or max or combined area under the curve (AUC), power, full width at half maximum (FWHM), or signal-to-noise ratio (SNR) aspects of such a respective spectral range).

It is also appreciated that peak expression within even very specific and/or narrow ranges known to correspond with or be associated with one such specific chemical (or chemical type, class, or group sharing similar structures or bond) may also correspond with other potential chemicals sharing at least some aspects of that spectral expression.

In certain examples of the foregoing, and relating to still further embodiments of this disclosure, certain types of lipids and/or breakdown components of chondroitin sulfate or proteoglycans may have chemical spectral expressions in a range that may overlap with, abut, or at least exist nearly adjacent to, a spectral range assigned to correspond with PA and/or LA (including for example a broad combined range for the two) or their spectral expressions. In particular examples for such a range that may be considered to be adjacent to and/or below LA, each of the chemical constituents valine, leucine, and isoleucine have been observed to correspond with an MRS peak signature of about 0.9 ppm. According to the less than exactly perfect spectral resolution of clinical scanners (e.g. 15 T, 3 T, or more recently 7 T), such expressions could be slightly above or below this discrete value, and which may thus by near to, abut, or even overlap with a range corresponding with PA expression, e.g. about 1.04 ppm.

According thus to still further embodiments of this disclosure, spectral measurements are taken from a spectral interrogation over a range that may correspond with PA in addition to one or more of these other chemicals. In one such example for illustration, a range for biomarker measurement is assigned from as low as about 0.75 or even 0.5 ppm up to about 1.0 or even about 1.05 or 1.1 ppm, and may thus correspond with any one or a combination of PA, valine, leucine, isoleucine, or certain lipids associated with that range. It is also contemplated that certain such additional chemicals, such as leucine for example, may also have certain bioactivity related to pain. Accordingly, measured expression over a combined range as described may correspond with PA expression, or expression of another chemical such as leucine, or a combination thereof—yet while the measurement may provide a useful biomarker for pain based on the expression in the range that is not necessarily tied to a specific one of the potential chemical sources of that expression. In the case of ALPA range measurements, for example, the maximum or combined peak value, power, or AUC over the range may relate to or be influenced by AL, LA, or PA (or other such chemicals as described), or a combination of them, and in any case may provide a useful 'combination biomarker' that relates to pain—whether that measured expression derives from hypoxic acidity in the tissue, e.g. associated with LAAL, or bacterial infection in the tissue, e.g. associated with PA (as further described elsewhere herein).

It is appreciated according to the various embodiments described herein that a combined spectral measurement range corresponding with such multiple chemicals may provide a useful single biomarker for pain-related expression. In addition to such embodiments where a combination range is employed, in some instances however, it is also appreciated that a combination of multiple measurements taken from multiple discrete ranges for each such chemical may be instead performed and generate similar, or in any event beneficially useful, results.

The MRS-based spectral measurements featured among the present embodiments and along a range corresponding with PA expression provides many benefits. In certain particular regards, PA is produced by certain bacteria. Accordingly, certain further embodiments of this disclosure relate such MRS spectral measurements corresponding with PA to bacterial infection. Such embodiments include or relate to, without limitation, the following.

Although low back pain (LBP) may relate to a number of different spinal pathologies, vertebral bone marrow lesions visualized as Modic changes (MC) on magnetic resonance imaging (MRI) have a high specificity for discogenic LBP. MC are typically described as MRI signal intensity changes which are not related to marrow malignancy or pyogenesis. LBP patients with MC report a greater frequency and duration of LBP episodes, seek care more often, and have a higher risk for a poor outcome versus LBP patients without MC. However, the etiopathogenesis of MC has not been previously well understood. Three interconvertible types of MC exist with MC type 1 (MC1) being the most symptomatic and typically considered to represent fibrovascular granulation tissue. It has been suggested that in some cases occult discitis, in particular with the bacteria *Propionibacteria acnes* (*P. acnes*), is the reason for MC1. *P. acnes* is an anaerobic aerotolerant Gram-positive opportunistic pathogen that has been implicated in prosthetic joint infections, acne vulgaris, endocarditis, and osteomyelitis. The full name, *Propionibacterium acnes*, derives from its ability to generate propionic acid (PA), which is a waste product of acne bacteria metabolism. *P. acnes* also forms part of the normal resident microbiota of the skin, oral cavity and the gastrointestinal and genitourinary tracts.

*P. acnes* infection has also been specifically identified in intervertebral discs of LBP patients. In one example, *P. acnes* infection was isolated and confirmed in between 38-53% of herniated disc surgical samples. The confirmed presence of *P. acnes* in existed disc tissue has also been observed to correspond with a high percentage of newly formed MC1. In addition, a high degree of positive therapeutic effect has also been observed following antibiotic treatment of MC1 patients enrolled in a double-blinded clinical trial.

How *P. acnes* seeds into the disc and could cause MC1 is not fully understood. However, one suspicion is that *P. acnes* enters the blood stream during innocuous events such as tooth brushing, or through haematogenous spread from a distant septic location. When disc immunoisolation is violated by disc herniation or endplate damage (both of which associate with MC1), it is suspected that blood borne *P. acnes* may invade the disc and proliferate.

At least one recent animal study demonstrated that *P. acnes* can proliferate within the disc environment and induce changes in adjacent vertebra similar to Modic lesions observed in back pain patients. This study demonstrated that *P. acnes* induces endplate and trabecular bone resorption that are likely caused by catabolic factors secreted from the infected disc. Degenerating discs produce osteoclastic factors, and discs adjacent to MC produce even more so. This is supported by observations of more eroded bone surfaces in biopsies from MC1-related tissues. These osteoclastic factors are not only secreted by disc cells, but direct bone lysis can be potentiated by PA as a key metabolite of *P. acnes*. Consequently, osteolysis is a reported clinical finding that can be caused by *P. acnes*. For example, in acne fulminans, a severe form of acne vulgaris, and in SAPHO (synovitis, acne, pustulosis, hyperostosis and osteitis) syndrome, *P. acnes* have been recovered from osteolytic bones and bone resorption is a common finding in pyogenic vertebral osteomyelitis that can be caused by *P. acnes*. Furthermore, *P. acnes* also produce lipases that catalyze the breakdown of fats into glycerol and free fatty acids. Bone marrow is rich of fat and hence, lipase draining from the disc into the marrow leads to an accumulation of free fatty acids in the bone marrow. Free fatty acids bind to toll-like receptors (TLRs), which are expressed on many bone marrow cells (i.e. myeloid cells, dendritic cells, fibroblasts) and further increase the inflammatory burden. Fatty acids also inhibit osteoblast differentiation and promote osteoclast differentiation by binding to Peroxisome proliferator-activated receptor gamma (PPARγ). Furthermore, TLRs are receptors for damage-associated molecular patterns (DAMPs), which include many matrix breakdown products (e.g. fibronectin, short hyaluronic acid fragments, collagen-2) that are generated in degenerating discs and endplates. Furthermore, *P. acnes* secrete peptidoglycan-polysaccharide, which further increase the total amount of TLR ligands. Consequently, cytokines, bacterial metabolites, and matrix fragments draining from a *P. acnes* infected disc into the bone marrow can directly or indirectly cause reactive bone marrow changes. The following publication is hereby incorporated by reference in its entirety: Dudli, S. et al. "*Propionibacterium acnes* infected intervertebral discs cause vertebral bone marrow lesions consistent with Modic changes." J. Orthop. Res. 2016 August 34(8):1447-55.

The following disclosures are also incorporated by reference in their entirety:

1. Vos T, Flaxman A D, Naghavi M, et al. 2012. Years lived with disability (YLDs) for 1160 sequelae of 289 diseases and injuries 1990-2010: a systematic analysis for the Global Burden of Disease Study 2010. Lancet 380(9859): 2163-96.
2. Thompson K J, Dagher A P, Eckel T S, et al. 2009. Modic changes on M R images as studied with provocative diskography: clinical relevance—a retrospective study of 2457 disks. Radiology 250(3):849-55.
3. Modic M T, Steinberg P M, Ross J S, et al. 1988. Degenerative disk disease: assessment of changes in vertebral body marrow with M R imaging. Radiology 166(1 Pt 1): 193-9.
4. Jensen T S, Karppinen J, Sorensen J S, et al. 2008. Vertebral endplate signal changes (Modic change): a systematic literature review of prevalence and association with non-specific low back pain. Eur. Spine J. 17(11): 1407-22.
5. Jensen O K, Nielsen C V, Sorensen J S, Stengaard-Pedersen K. 2014. Type 1 Modic changes was a significant risk factor for 1-year outcome in sick-listed low back pain patients: a nested cohort study using magnetic resonance imaging of the lumbar spine. Spine J. 14(11):2568-81.
6. Schistad El, Espeland A, Rygh L J, et al. 2014. The association between Modic changes and pain during 1-year follow-up in patients with lumbar radicular pain. Skeletal Radiol. 43(9):1271-9.
7. Järvinen J, Karppinen J, Niinimäki J, et al. 2015. Association between changes in lumbar Modic changes and low back symptoms over a two-year period. BMC Musculoskelet. Disord. 16(1):98.
8. Albert H B, Lambert P, Rollason J, et al. 2013. Does nuclear tissue infected with bacteria following disc herniations lead to Modic changes in the adjacent vertebrae? Eur. Spine J. 22(4):690-6.

9. Vowels B R, Yang S, Leyden J J. 1995. Induction of proinflammatory cytokines by a soluble factor of *Propionibacterium acnes*: implications for chronic inflammatory acne. Infect. Immun. 63(8):3158-65.
10. McDowell A, Barnard E, Nagy I, et al. 2012. An expanded multilocus sequence typing scheme for *Propionibacterium acnes*: investigation of "pathogenic", "commensal" and antibiotic resistant strains. PLoS One 7(7): e41480.
11. Valanne S, McDowell A, Ramage G, et al. 2005. CAMP factor homologues in *Propionibacterium acnes*: A new protein family differentially expressed by types I and II. Microbiology 151(5):1369-1379.
12. Stirling A, Worthington T, Rafiq M, et al. 2001. Association between sciatica and *Propionibacterium acnes*. Lancet 357(9273):2024-5.
13. Rollason J, McDowell A, Albert H B, et al. 2013. Genotypic and antimicrobial characterisation of *Propionibacterium acnes* isolates from surgically excised lumbar disc herniations. Biomed Res. Int. 2013:530382.
14. Albert H B, Sorensen J S, Christensen B S, Manniche C. 2013. Antibiotic treatment in patients with chronic low back pain and vertebral bone edema (Modic type 1 changes): a double-blind randomized clinical controlled trial of efficacy. Eur. Spine J. 22(4):697-707.
15. Fritzell P, Bergstrom T, Welinder-Olsson C. 2004. Detection of bacterial DNA in painful degenerated spinal discs in patients without signs of clinical infection. Eur. Spine J. 13(8):702-6.
16. Wedderkopp N, Thomsen K, Manniche C, et al. 2009. No evidence for presence of bacteria in modic type I changes. Acta Radiol. 50(1):65-70.
17. Arndt J, Charles Y P, Koebel C, et al. 2012. Bacteriology of degenerated lumbar intervertebral disks. J. Spinal Disord. Tech. 25(7):E211-6.
18. Bhanji S, Williams B, Sheller B, et al. 2002. Transient bacteremia induced by toothbrushing a companson of the Sonicare toothbrush with a conventional toothbrush. Pediatr. Dent. 24(4):295-9.
19. Urquhart D M, Zheng Y, Cheng A C, et al. 2015. Could low grade bacterial infection contribute to low back pain? A systematic review. BMC Med. 13(1):13.
20. Weiner B K, Vilendecic M, Ledic D, et al. 2015. Endplate changes following discectomy: natural history and associations between imaging and clinical data. Eur. Spine J. 24(11):2449-57.
21. Kerttula L, Luoma K, Vehmas T, et al. 2012. Modic type I change may predict rapid progressive, deforming disc degeneration: a prospective 1-year follow-up study. Eur. Spine J. 21(6):1135-42.
22. Holm S, Baranto A, Kaigle Holm A, et al. 2007. Reactive changes in the adolescent porcine spine with disc degeneration due to endplate injury. Vet. Comp. Orthop. Traumatol. 20(1):12-7.
23. McDowell A, Valanne S, Ramage G, et al. 2005. *Propionibacterium acnes* types I and II represent phylogenetically distinct groups. J. Clin. Microbial. 43(1):326-34.
24. Nadkami M A, Martin F E, Jacques N A, Hunter N. 2002. Determination of bacterial load by real-time PCR using a broad-range (universal) probe and primers set. Microbiology 148(1):257-266.
25. Muhl H, Kochem A-J, Disqué C, Sakka S G. 2010. Activity and DNA contamination of commercial polymerase chain reaction reagents for the universal 16S rDNA real-time polymerase chain reaction detection of bacterial pathogens in blood. Diagn. Microbial. Infect. Dis. 66(1):41-9.
26. Burke J, Watson R, McCormack D, et al. 2003. Endplate changes are associated with increased disc inflammatory mediator production. J Bone Jt. Surg Br 85-B(Supp II): 164.
27. Klawitter M, Hakozaki M, Kobayashi H, et al. 2014. Expression and regulation of toll-like receptors (TLRs) in human intervertebral disc cells. Eur. Spine J. 23(9):1878-91.
28. Quero L, Klawitter M, Schmaus A, et al. 2013. Hyaluronic acid fragments enhance the inflammatory and catabolic response in human intervertebral disc cells through modulation of toll-like receptor 2 signaling pathways. Arthritis Res. Ther. 15(4):R94.
29. Ellman M B, Kim J-S, An H S, et al. 2012. Toll-like receptor adaptor signaling molecule MyD88 on intervertebral disk homeostasis: In vitro, ex vivo studies. Gene 505(2):283-90.
30. Wang J, Tian Y, Phillips K L E, et al. 2013. Tumor necrosis factor $\alpha$- and interleukin-1$\beta$-dependent induction of CCL3 expression by nucleus pulposus cells promotes macrophage migration through CCR1. Arthritis Rheum. 65(3): 832-42.
31. Le Maitre C L, Hoyland J A, Freemont A J. 2007. Catabolic cytokine expression in degenerate and herniated human intervertebral discs: 1L-1$\beta$ and TNF$\alpha$ expression profile. Arthritis Res. Ther. 9(4):R77.
32. Burke J G, G Watson R W, Conhyea D, et al. 2003. Human nucleus pulposis can respond to a pro-inflammatory stimulus. Spine (Phila. Pa. 1976). 28(24):2685-93.
33. Li B, Dong Z, Wu Y, et al. 2015. Association between Lumbar Disc degeneration and *Propionibacterium Acnes* Infection: Clinical Research and Preliminary Exploration of Animal Experiment. Spine (Phila. Pa. 1976). [Epub ahead of print].
34. Ferguson S J, Ito K, Nolte L P. 2004. Fluid flow and convective transport of solutes within the intervertebral disc. J. Biomech. 37(2):213-21.
35. Mirantes C, Passegué E, Pietras E M. 2014. Pro-inflammatory cytokines: Emerging players regulating HSC function in normal and diseased hematopoiesis. Exp. Cell Res.:1-7.
36. Dudli S, Sing D, Burch S, et al. 2016. Molecular and Cellular Changes in Vertebral Bone Marrow Lesions. In: Annual Meeting American Academy of Orthopaedic Surgeons. Orlando; Paper 454.
37. Dudli S, Haschtmann D, Ferguson S J. 2012. Fracture of the vertebral endplates, but not equienergetic impact load, promotes disc degeneration in vitro. J. Orthop. Res. 30(5):809-16.
38. Torkki M, Majuri M-L, Wolff H, et al. 2015. Osteoclast activators are elevated in intervertebral disks with Modic changes among patients operated for herniated nucleus pulposus. Eur. Spine J. [Epub ahead of print].
39. Perilli E, Parkinson I H, Truong L-H, et al. 2014. Modic (endplate) changes in the lumbar spine: bone microarchitecture and remodelling. Eur. Spine J. 24(9):1926-34.
40. Mackiewicz Z, Salo J, Konttinen Y T, et al. 2009. Receptor activator of nuclear factor kappa B ligand in an experimental intervertebral disc degeneration. Clin. Exp. Rheumatol. 27(2):299-306.
41. Laasonen L S, Karvonen S L, Reunala T L. 1994. Bone disease in adolescents with acne fulminans and severe cystic acne: radiologic and scintigraphic findings. AJR. Am. J. Roentgenol. 162(5):1161-1165.
42. Ziegler P, Boettcher S, Takizawa H, et al. 2016. LPS-stimulated human bone marrow stroma cells support myeloid cell development and progenitor cell maintenance. Ann. Hematol. 95(2): 173-8.
43. Wan Y, Chong L-W, Evans R M. 2007. PPAR-gamma regulates osteoclastogenesis in mice. Nat. Med. 13(12): 1496-503.
44. Piccinini A M, Midwood K S. 2010. DAMPening inflammation by modulating TLR signalling. Mediators Inflamm. 2010.
45. Oegema T R, Johnson S L, Aguiar D J, Ogilvie J W. 2000. Fibronectin and its fragments increase with degeneration in the human intervertebral disc. Spine (Phila. Pa. 1976). 25(21):2742-7.
46. Patel K B, Poplawski M M, Pawha P S, et al. 2014. Diffusion-weighted MRI "claw sign" improves differentiation of infectious from degenerative modic type 1 signal changes of the spine. AJNR. Am. J. Neuroradiol. 35(8):1647-52.
47. Di Martino A, Merlini L, Faldini C. 2013. Autoimmunity in intervertebral disc herniation: from bench to bedside. Expert Opin. Ther. Targets 17(12):1461-70.
48. Ulrich J A, Liebenberg E C, Thuillier D U, et al. 2007. ISSLS prize winner: repeated disc injury causes persistent inflammation. Spine (Phila. Pa. 1976). 32, 2812-9.
49. Bendix T, Sorensen J S, Henriksson G A C, et al. 2012. Lumbar modic changes—a comparison between findings at low- and high-field magnetic resonance imaging. Spine (Phila. Pa. 1976). 37, 1756-62.
50. McDowell A, Perry A L, Lambert P A, er al. 2008. A new phylogenetic group of *Propionibacterium acnes*. J. Med. Microbial. 57, 218-24.
51. Sharif, H. S. Role of M R imaging in the management of spinal infections. 1992. AJR Am J Roentgenol 158, 1333-1345.
52. Bertok L. 2005. Natural immunity, First Edit. Elsevier Science; 291 p. 53. Inagawa H, Kohchi C, Soma G-1. 2011. Oral administration of lipopolysaccharides for the prevention of various diseases: benefit and usefulness. Anticancer Res. 31(7):2431-6.
54. Chen Z, Zheng Y, Yuan Y, et al. (2016) Modic Changes and Disc Degeneration Caused by Inoculation of *Propionibacterium acnes* inside Intervertebral Discs of Rabbits: A Pilot Study. Biomed Res Int 2016:9612437.
55. Keshari et al., Spine (2005), Vol 30, Number 23, pp 2683-2688.
56. Keshari et al., Spine (2008), 33(3): pp. 312-317.
57. Magnetic Resonance in Medicine, 62: 1140-1146 (2009).
58. Freemont, A J., (2009) Rheumatology; 48:5-10.
59. Dudli, S. et al. "*Propionibacterium acnes* infected intervertebral discs cause vertebral bone marrow lesions consistent with Modic changes." J. Orthop. Res. 2016 August 34(8): 1447-55.
60. Patel, K. B., et al. "Diffusion-Weighted MRI "Claw Sign" Improves Differentiation of Infectious from Degenerative Modic Type 1 Signal Changes of the Spine," AJNR Am J Neuroradiol 35:1647-52 August 2014.

As would be appreciated by one of ordinary skill, various aspects of the disclosures that are herein incorporated by reference are further contemplated in combination with the various embodiments of the present disclosure, and which combinations comprise yet further embodiments of this disclosure.

Example 5

This example represents still further embodiments of this disclosure. Materials and methods are briefly described regarding the approach taken for clinical MRS data acquisitions and post-processing, and constitute further embodiments of this disclosure in combination with the approaches described of this Example for performing MRS spectral measurements and processing to derive resulting chemical monitoring and/or diagnostic information. In addition, it is also contemplated that such further measurements and processing of the post-processed spectral information are also considered embodiments of this disclosure without being necessarily tied to and regardless of the particular data acquisition or spectral processing performed to produce such post-processed spectra.

In-vivo MRS acquisitions were performed in lumbar discs of chronic, severe low back pain patients using a Siemens 3T Verio model MR scanner. Raw MRS data was processed generally according to similar techniques as herein described. Along various ranges along the post-processed spectra for each disc, various spectral features were measured, including without limitation peak value, signal-to-noise ratio (SNR), and area under the curve (AUC). The ranges corresponded with CA (carbohydrate or collagen), PG (proteoglycan), AL, LA, and PA. Measurements were also taken for combination ranges for LAAL (combined AL+LA ranges) and ALPA (combined LAAL+PA ranges). CA and PG were considered structural markers which are expected and have been observed to decrease with increased degeneration of disc tissue, while the LAAL and ALPA constituents were considered pain markers that are expected to increase with pain. Various ratios of the spectral measurements were calculated with pain markers in the numerator and degeneration markers in the denominator. According to this approach, the numerator is expected to increase and the denominator is expected to decrease, thus both sides of the ratio expected to contribute to the same direction of increasing the ratio in degenerative painful discs versus other non-painful discs. Six such ratios were calculated as follows: LAAL/PG, LAAL/CA, maxALPA/PG, maxALPA/CA, sumALPA/PG, and sumALPA/CA. In this particular example, AUC measurements were used. "maxALPA" represented the AUC for the largest peak identified along the ALPA range. "sumALPA" represented the combined AUC for all peaks identified along the ALPA range. The ratio values were then normalized against a maximum threshold value assigned to each such ratio, and such that the respective ratio could not exceed that threshold (i.e. 'saturation'), and such that the maximum value for each of the six ratios for each disc is 1. The normalized ratios for each disc were then added for a "Total Score" for the disc, with a maximum possible Total Score of 6. These Total Scores for each disc were then normalized between the discs within each patient by dividing each disc's Total Score by the maximum Total Score between the discs examined in the patient, thus deriving a Normalized Score for each disc within the patient and with the highest Normalized Score among the patient's discs equal to 1.

According to the foregoing summary description, FIG. 42 shows an example of a 'heat map' of combined biomarker measurements related to six spectral chemical measurement ratios for each of five lumbar discs from a DDD-MRS exam conducted in a lumbar spine of a Patient 1 of this Example 5.

FIGS. 43A-C and 44A-C show various aspects of the results of a DDD-MRS clinical patient study for Patent Examples 1 and 2, respectively, of this Example 5 and that each had a successful outcome after fusion surgery following provocative discogram ("PD+"=painful, "PD−"=non-painful) diagnostic guidance. Total Scores and Normalized Scores are shown for each lumbar disc L51 (L5-S1), L45 (L4-L5), L34 (L3-L4), L23 (L2-L3), and L12 (L1-L2) examined in the study. More specifically, FIGS. 43A and 44A each show Oswestry Disability Index (ODI) results (0-100 scale from low to high disability index, respectively), while FIGS. 43B and 44B show Visual Analog Scale (VAS) scores for back pain (0-10 scale from low to high level of pain, respectively), at the follow-up periods shown after surgery in each respective patient's case. FIGS. 43C and 44C show Total and Normalized Scores for these respective discs in each of these respective patients, and as they are clearly aligned with the PD+/− results in each case.

Conversely, FIGS. 45A-C and 46A-C show various aspects of the results of a DDD-MRS clinical patient study for Patient Examples 3 and 4, respectively, of this Example 5. Each of these patients did not have a successful outcome and was without significant pain relief after fusion surgery following provocative discogram ("PD+"=painful, "PD−"=non-painful) diagnostic guidance. More specifically, FIGS. 45A and 46A each show oswestry disability index (ODI) results, while FIGS. 45B and 46B show visual analog scale (VAS) scores for back pain, in each case without significant drop in these pain-related standard measures at the follow-up periods shown after surgery in each respective patient's case. FIGS. 45C and 46C show Total and Normalized Scores for these respective discs in each of these respective patients. There is clear alignment and agreement between the relatively high DDD-MRS based scores and the PD+ results and DDD-MRS scores in each of these respective Patient examples. The scores were also significantly lower in the respective PD− discs for each of these Patients, relative to the scores for the PD+ disc in those patients. However, those PD− disc scores were nonetheless significant and higher than other remote discs not located in the suspect painful region of the respective patients' spines. In these patients, adjacent disc disease in these PD− discs was believed to develop post-fusion surgery in the adjacent PD+ levels. Adjacent segment disease is a leading cause of fusion failure. Accordingly, it is apparent that the DDD-MRS scores for the PD− discs in the failed fusion patients 3 and 4 with adjacent segment disc disease were clearly more expressive of the total and normalized scores than in the other two patients 1 and 2 that did not develop such adjacent segment disease and had successful surgical outcomes with pain relief.

These patient examples of this Example 5 and as shown in FIGS. 42-46C thus suggest that the approach according to these embodiments is useful for both indicating painful discs pre-surgically and for appropriate diagnostic direction for the targeted surgery to such discs, and also for predicting discs adjacent to such primary painful levels that may not be severely painful at the time of surgery, but may develop into a painful issue post adjacent segment fusion. It is further appreciated that the various embodiments herein disclosed provide various benefits, including without limitation to: (a) diagnose painful or infected discs; (b) serve as a benchmark to follow and prognosticate future painful discs (e.g. adjacent level disease), (c) serve as a measurement tool for therapies targeting disk pathology or infection (e.g. regeneration, cells/biologics, antibiotics) via longitudinal or otherwise post-treatment disc chemistry monitoring; and/or (d) guide treatment algorithms.

It is also further appreciated that the specific approach described above for Example 5 and shown by way of examples in FIGS. 42-46C represents one specific approach with respect to factoring of such ratios and their use in deriving scores for diagnostic purposes. As apparent to one of ordinary skill from this disclosure, however, this specific approach—while highly beneficial as illustrated in these exemplary patients—is not intended to be limiting and other modifications or variants can be made within the intended broad scope of this disclosure. For example, weighted factoring can be applied to such ratios to emphasize some more than others in their ultimate combination for scoring. In one such example for illustration, factors are shown in parenthesis for each ratio, totally 10 total possible points in the overall Total Score: LAAL/PG (4), LAAL/CA (1), maxALPA/PG (2), maxALPA/CA (1), sumALPA/PG (1), sumALPA/CA (1). In another example for illustration, the first four factors can be given weights of 2, with the last two factors listed given weights of 1. Moreover, the first factor can be given a weight of 3, leaving a free weight to apply to another factor's emphasis. Of course, the total number of 10 is not necessarily limiting, although is considered beneficial for ease of understanding—and whatever factoring is chosen for whatever resulting maximum scores, then can always be normalized to another number (e.g. 10).

In some cases, back pain can be caused by a disc infection by *P. acnes*. This anaerobic bacterium can be normally present on the skin and/or gastrointestinal tract, and can enter the bloodstream and enter the normally avascular intervertebral disc, such as through a breach in the outer annulus fibrosus or vertebral endplate. The avascular disc can be an ideal environment for *P. acnes* growth, and the resulting inflammation can trigger back pain, such as painful bone marrow edema (Modic changes) in adjacent vertebra. A primary metabolic product from *P. acnes* bacteria is propionic acid. The accumulation of this acid in infected discs may be a source of pain in affected patients. Propionic acid can also serve as a biomarker for disc infection, which can help medical practitioners to identify patients and spinal levels that can be treated (e.g., with antibiotics). As discussed herein, magnetic resonance spectroscopy (e.g., single voxel MRS) can be used for non-invasive measurements relating to propionic acid in a subject (e.g., in a patient's spine). In some cases, treatment of the *P. acnes* bacteria (e.g., using antibiotics) can reduce the patient's back pain without invasive surgery. Because the MRS procedure can be non-invasive patient discomfort and injury can be reduced as compared to, for example, a disc tissue biopsy and tissue culture. Also, the occurrence of false positives due to sample contamination can be reduced using the non-invasive MRS procedures disclosed herein. Also, by identifying which areas of the subject (e.g., of the spine) have *P. acnes* bacteria infection, a targeted antibiotic treatment can be used, which can reduce treatment side effects.

Example Method

Figure 47:
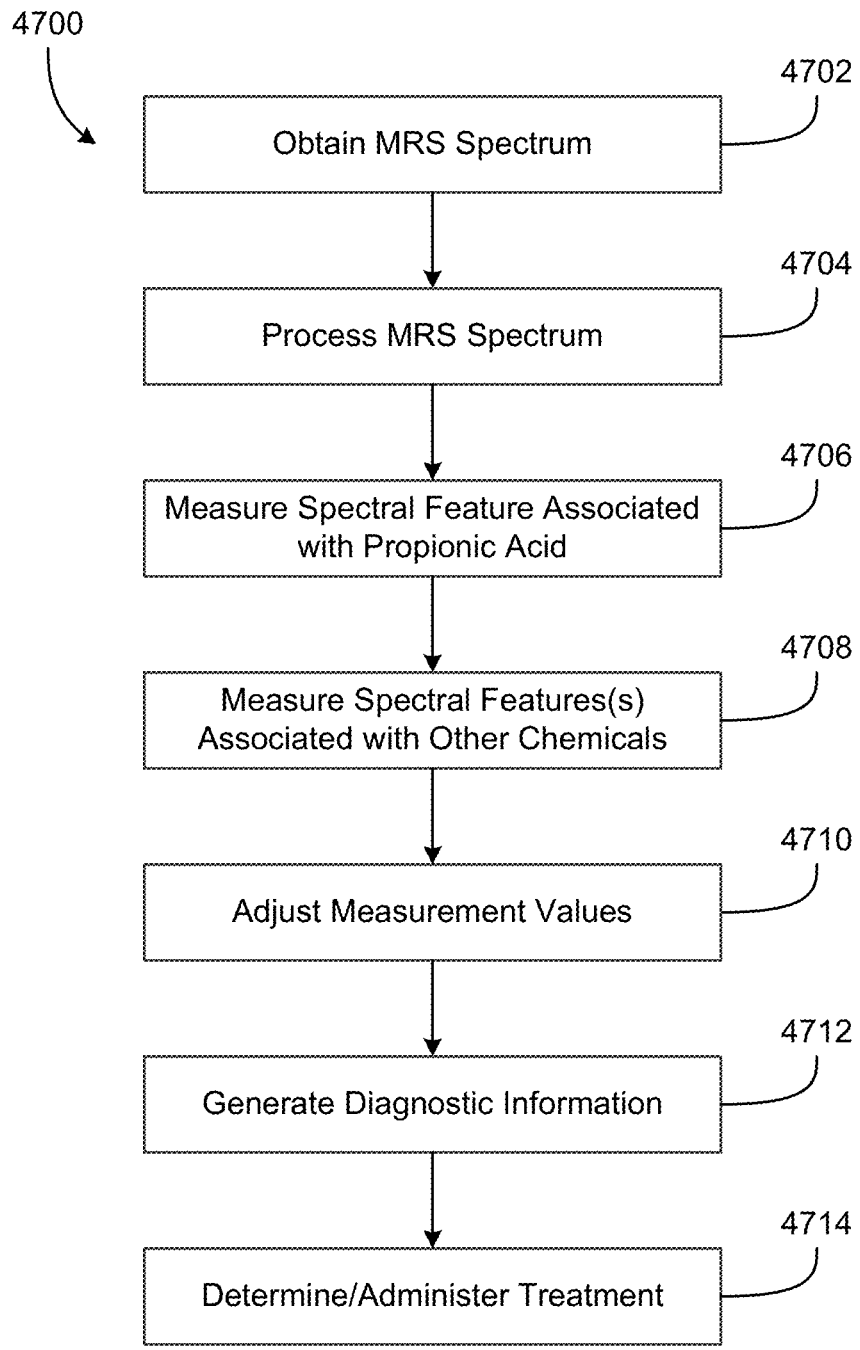
FIG. 47 is a flowchart that shows an example embodiment of a method 4700 for diagnosing and/or treating a subject.

FIG. 47 is a flowchart that shows an example embodiment of a method 4700 for diagnosing and/or treating a subject. The method of FIG. 47 can be performed by systems (e.g., MR systems) similar to those discussed in connection with other embodiments disclosed herein. Although various features will be described in connection with diagnosing a patient experiencing back pain, the method 4700 can also apply to diagnostic and/or therapeutic methods applied to other regions of the body, such as other joints or other bodily tissue. At block 4702, a MRS spectrum can be obtained. For example an MR system can generate a MRS pulse sequence and can acquire an MRS spectrum that results from the MRS pulse sequence, as discussed herein. A series of frames can be obtained from one or more channels, in some implementations. At block 4704, the MRS spectrum can be processed. An MRS signal processor can perform signal processing operations to produce a processed MRS spectrum, as discussed herein. For example, processing operations including channel selection, frame editing, frequency shift correction, etc. can be performed, such as using a hardware computer processor. In some instances, the signal processing can improve the signal to noise ratio (SNR) of the MRS spectrum. By way of example, an MR system can be used to produce MRS spectra such as those shown in FIGS. 43C, 44C, 45C, and 46C, which can correspond to intervertebral discs in a patient's spine.

At block 4706, a measurement is taken for a spectral feature associated with propionic acid (PA). The measured spectral feature can be a peak maximum value, a power value, a value of the area under the curve (AUC), a full width at half maximum (FWHM) value, etc. In some embodiments, a PA spectral peak can be identified, such as within a spectral range associated with PA (e.g., between about 0.9 ppm to about 1.1 ppm, although other values can be used, as discussed herein), and a measurement can be taken using the identified PA spectral peak and/or the identified spectral range associated with PA. In some embodiments, the measurement associated with PA can be influenced by other chemical constituents (e.g., lactate (LA), alanine (AL), valine, leucine, and isoleucine). The measurement associated with PA can be a combined measurement that also includes one or more additional biomarkers (e.g., lactate (LA), alanine (AL), leucine, etc.). As discussed herein, a LAPA-related measurement can be taken from the spectral range that includes both LA and PA, an ALPA-related measurement can be taken from the spectral range that includes AL, LA, and PA peak regions. In some case a maximum (e.g., highest or tallest) peak in the region (e.g., in the AL, LA, and PA combined regions for maxALPA) can be used for the measurement, or a sum of multiple peaks in the region (e.g., in the AL, LA, and PA combined regions for sumALPA) can be used for the measurement.

At block 4708, one or more spectral features associated with one or more other chemicals can be measured. For example, one or more measurements for proteoglycan (PG), carbohydrate or collagen, lactic acid or lactate (LA), alanine (LA), and/or LAAL can be taken that is separate from the measurement associated with PA. These one or more measurements can use, for example, a peak maximum value, a power value, a value of the area under the curve (AUC), a full width at half maximum (FWHM) value, etc. A maximum peak can be used for the measurement (e.g., MAXLAAL) and/or a sum of multiple peaks in a region (e.g., SUMLAAL) can be used.

At block 4710, one or more of the measurements can optionally be adjusted to provide one or more adjusted values. For example, one or more of the measured values can be adjusted for BMI and/or voxel volume, as discussed herein.

At block 4712, diagnostic information can be generated, such as based at least in part on the PA-related measurement. For example, in some embodiments, the system can determine a score for the region of interest (ROI). That score can be used to diagnose the bodily tissue associated with the ROI. For example, in the embodiments associated with FIGS. 42-46C scores were determined for the various intervertebral discs. In some embodiments, the system can take measurements for two or more locations and can compare those locations to generate the diagnostic information. By way of example, in the embodiment of FIG. 44C, scores of 1.29, 0.00, 1.23, 0.00, and 2.93 were determined for the respective L12, L23, L34, L45, and L51 discs. In some embodiments, the scores can be normalized, as discussed herein. For example, the scores of FIG. 44C can be normalized to 0.44, 0.00, 0.42, 0.00, and 1.00, respectively. In some embodiments, the score can be compared to one or more threshold values to determine whether a region of interest (e.g., a disc) will be diagnosed as painful or non-painful and/or whether the ROI will be diagnosed as being infected with bacteria. In some cases, multiple threshold values can be used to indicate a degree of pain and/or infection or to indicate a degree of confidence for the diagnosis.

The scores for multiple regions of interest (ROIs) can be compared to facilitate diagnosis. For example, comparing L45 and L51 in the embodiment of FIG. 44C, a score of 2.93 can indicate a disc that is more likely to be infected with bacteria (e.g., *P. acnes*) or otherwise be painful, as compared to a disc with a score of 0.00, or 1.23. The scores can be calculated in various different manners. In some cases a high score can indicate a disc that is likely painful and/or infected with bacteria, while in other cases a low score could indicate a disc that is likely painful and/or infected with bacteria. In some embodiments, the diagnostic information can be generated without calculating a score. For example, various comparisons and relationship determinations can be used to determine diagnostic information. For example, with reference to FIG. 44C, the system can determine that the L51 disc is more likely to be painful and/or infected with bacteria than the L45 disc merely based on comparisons of values (e.g., PA-related measurements), without calculating scores for the discs. A formula, look-up-table, and/or algorithm can be used to determine a score, or to otherwise generate the diagnostic information.

Various different measured or determined values and ratios thereof can be used to determine the diagnostic information, and various constants can also be used, such as any combination of the following: a spectral feature measurement along the PA-related region of the MRS spectrum (PA); a spectral feature measurement along the LA-related region of the MRS spectrum (LA); a spectral feature measurement along the AL-related region of the MRS spectrum (AL); a spectral feature measurement along the ALPA region that comprises a combination of the PA-, LA-, and AL-related regions of the MRS spectrum (ALPA); a spectral feature measurement along the LAPA region that comprises a combiatino of the PA- and LA-related regions of the MRS spectrum (LAPA); a spectral feature measurement along the LAAL region that comprises a combiatino of the AL- and LA-related regions of the MRS spectrum (LAAL); a spectral feature measurement along the PG-related region of the MRS spectrum (PG); a spectral feature measurement along the CA-related region of the MRS spectrum (CA); and a spectral feature measurement along the collagen-related region of the MRS spectrum (COL). Any of these spectral feature measurements can be of various different types, such as an area under the curve (AUC), a FWHM value, a highest peak value, a power value, a signal to noise ratio value, etc. Where multiple regions are combined, the multiple regions can be combined by using the maximum value from the combined regions (MAX), or the multiple regions can be combined by summing the values from each of the combined regions (SUM). Any of the spectral feature measurements can be adjusted, such as for body mass index (BMI or B) and/or for voxel volume (VV or V). Any permutation of these features can be used as factors for determining the diagnostic information.

The diagnostic information can be based at least in part on relationships between two or more of the factors, such as ratios between one or more pairs of factors. For example, the diagnostic information can be based at least in part on one or more of MAXALPA/PG, MAXALPA/CA, SUMALPA/PG, and SUMALPA/CA. "MAXALPA" can be a spectral feature measurement for a maximum peak region along a combined AL, LA, and PA (ALPA) region of the MRS spectrum. "SUMALPA" can be a combined sum of spectral peak feature measurements for multiple peaks identified along the ALPA region. A comparison or relationship (e.g., a ratio) between any combination of the permutations of the features described herein can be used to determine the diagnostic information.

The diagnostic information can be based at least in part on a spectral feature measurement relating to PA. As discussed herein, in some instances the presence of PA can be an indication of bacterial infection (e.g., *P. acnes*). Accordingly, a higher PA-related measurement can indicate a higher likelihood that the region of interest (e.g., the disc) has a bacterial infection, which in some cases can cause pain.

At block 4714, a treatment can be determined and/or administered. For example, if a determination is made that the region of interest (e.g., an intervertebral disc) has a bacterial infection (e.g., based at least in part on the PA-related measurement), an antibiotic treatment can be determined and/or administered. In some instances, an antibiotic treatment can resolve a painful bacterial infection without the need for surgery. In some instances, the diagnostic information can determine that a region of interest is painful, but not due to a bacterial infection, and a treatment different than antibiotics can be determined and/or administered (e.g., a disc fusion surgery). Accordingly, the use of PA-related measurements in generating the diagnostic information can improve the diagnosis and enable a medical practitioner to better treat the patient.

Many modifications to the method of FIG. 47 are possible. Operations can be omitted, combined, or reordered, and additional operations can be added. For example, in some embodiments, block 4714 can be omitted, and no treatment can be determined or administered. The method can be a diagnostic method. Blocks 4702 and/or 4704 can be omitted, and a MRS spectrum can be received from a difference source to be used for diagnostic analysis. In some embodiments, block 4708 can be omitted and/or block 4710 can be omitted. Various operations that are shown in separate blocks or that are discussed separately can be combined or performed simultaneously.

Example 6

It is appreciated that the aspects of this disclosure illustrated in Example 5 may be varied in terms of the specific implementations of particular embodiments deployed in that Example. For example, other saturization normalization thresholds and/or differential weighting factors may be applied to the respective ratios used. This is further developed by way of this Example 6.

Methods

More specifically according to this Example 6, 607 lumbar discs in 129 chronic, severe discogenic low back pain patients were evaluated in a non-significant risk clinical investigational study, conducted under Investigational Review Board (IRB) approval. Similar ratios as used in the prior Example were used for LAAL/PG, LAAL/CA, maxALPA/PG, maxALPA/CA, sumALPA/PG, sumALPA/CA to calculate scores for each disc. However, their calculations and processing into scores were conducted as follows.

Spectral peaks of a post-processed absorption spectrum for each disc were first identified based upon certain spectroscopic calculated measurements and threshold criteria: i.e. identified spectral peaks or 'maxima' with SNR above a threshold, e.g. at least about 4.0 or about 4.5, and located between spectral 'troughs' or 'minima' with a difference in peak-to-trough amplitude of at least a certain minimum criteria (e.g. as some factor of estimated noise floor, to separate actual chemical resonance peaks from merely superimposed noise artifacts). Each such identified peak was then 'curve fit' using a Lorentzian estimation based on calculations of the respective peak amplitude value and full width half max (FWHM) value between side walls of the spectrum on either side of the peak along the chemical shift (cs) x-axis of the spectrum. For such identified peaks that did not have unique FWHM side walls of the spectrum associated with only that peak, i.e. shared a side wall with another intervening peak identified by the above criteria, the two peaks closest to the left and right side walls, respectively, were uniquely assigned those respective side walls and for which a ½ FWHM was calculated and inflected for the Lorentzian curve fitting. For any intervening additional peak(s) between such right and left peaks of such a region, and which thus are not associated with any unique side wall to be associated only with that respective peak, theoretical extrapolations were made from the spectral slopes downward from the adjacent minima troughs on either side of the respective peak and for conducting FWHM calculations for that peak's respective Lorentzian curve fitting. The respective Lorentzian curve fits for each peak were used for purpose of AUC calculations for the respectively identified peak. Overlaps between adjacent Lorentzian curve fits were treated by terminating the boundary for the area used for AUC calculation at the point of overlap.

Such identified peaks, according to the above method, were then located within respective spectral ranges along the chemical shift (cs) axis to identify and assign them to particular respective chemicals with peak signatures associated with such cs ranges. In cases where multiple peaks were identified in a particular chemical range, the SNR and peak amplitude for the respective chemical was assigned to the maximum SNR and peak amplitude calculated among the multiple peaks in the respective chemical range; whereas the AUC for the respective chemical was assigned to a summation of the AUCs calculated under each respectively identified peak in the respective chemical range.

The identified ratios according to this method were also calculated using peak amplitude value, and area under the curve (AUC), for each respective peak region associated with the chemical ranges identified by the ratio labels above. These two separate peak and AUC feature bases for the ratios, after applying the maximum saturation threshold normalization, were then averaged to provide peak-AUC average ratios. The maximum saturation threshold values used were 1.0, 2.5, 1.0, 2.5, 1.5, and 3.5 for the LAAL/PG, LAAL/CA, maxALPA/PG, maxALPA/CA, sumALPA/PG, sumALPA/CA ratios, respectively, resulting in a maximum total saturation threshold normalized value for each ratio of 1.0. The differential weighting factors were then applied to these averaged & saturation normalized ratios, which were then summed to generate "total scores" for each disc. More specifically, the weighting factors used were 4, 1, 2, 1, 1, and 1 for the respective LAAL/PG, LAAL/CA, max- ALPA/PG, maxALPA/CA, sumALPA/PG, sumALPA/CA ratios. This resulted in a possible total score range of 0-10 for each disc. These total scores for each disc in a patient study were then normalized to the highest total score in that patient study to generate 'normalized scores' for each disc in the patient (ie. maximum 1.0 for the highest disc score).

The disc MRS data and scores generated according to the above methods were analyzed for discs in the study population: with voxel volumes <1.0 cc and z-axis dimensions <=4 mm (discs outside these thresholds were observed to be less reliable for generating robustly measurable, high SNR, artifact free spectra); and after excluding n=27 discs due to specifically observed spectral artifacts comprising at least one of poor shim (high FWHM for water signal in the spectrum above a threshold value, e.g. 45), low SNR (e.g. below 4.5 for the measured metabolite range from 0.5 to 4.1, or more specifically between ALPA and PG ranges e.g. about 0.5 to about 2.3), or patient motion (as identified by significant change in energy in lipid peak range during the multi-FID acquisition exam) and/or otherwise excessive lipid. This represented n=409 total discs evaluated, including n=194 discs that either (1) received provocative discogram (n=182) with either (a) PD-results as negative or non-painful (n=98 discs), or (b) PD+ results as positive or painful (n=84 discs), or (2) did not receive discogram but were diagnosed as painful and to receive surgical treatment for other reasons in patients receiving discogram at other disc levels (n=12 discs).

Figure 48A:
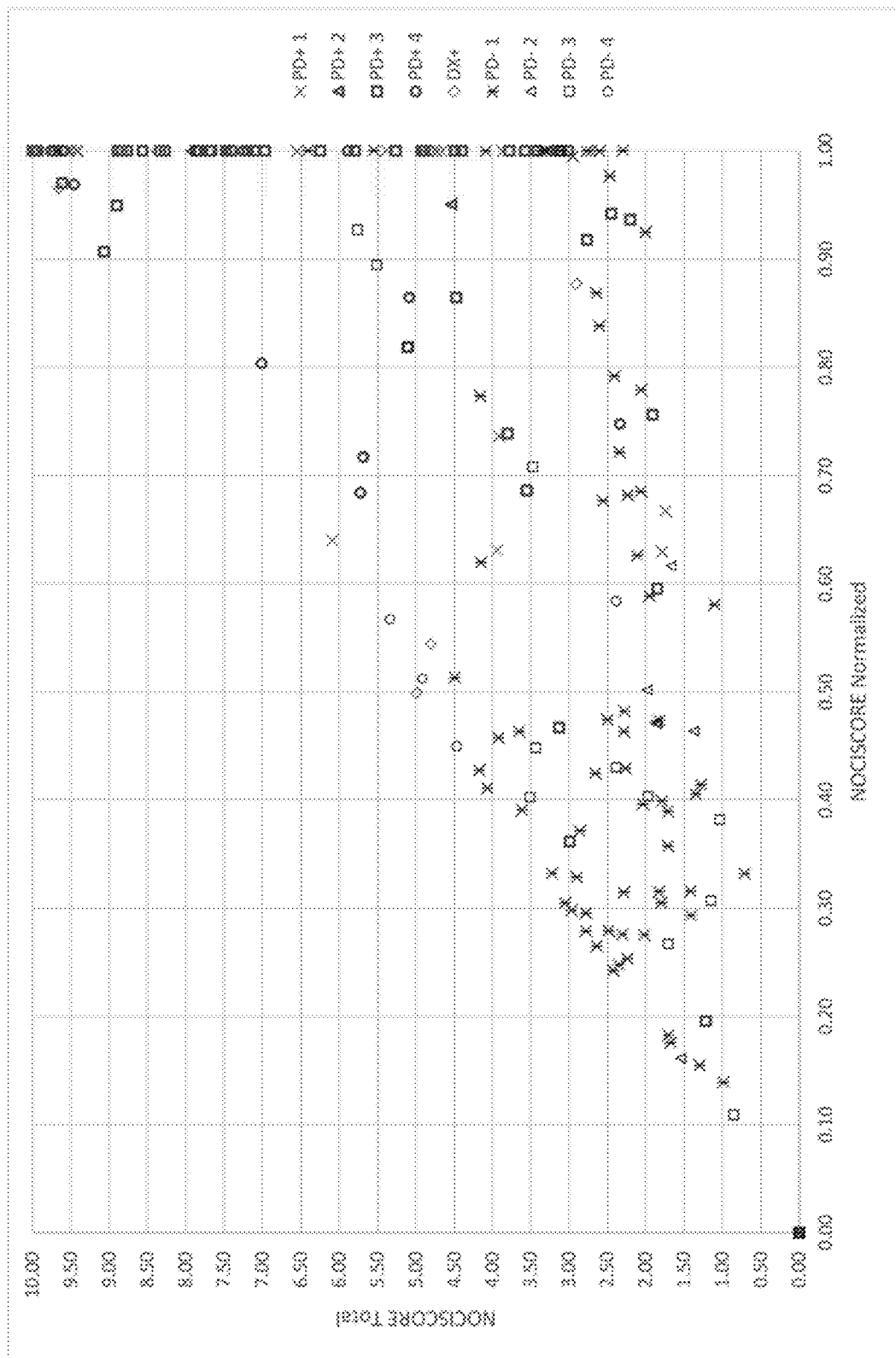
FIG. 48A shows a histrogram plot of certain clinical data according to further aspects related to Example 6 of this disclosure.

FIG. 48A shows a plot of total score ("NOCISCORE™ Total") versus normalized score ("NOCISCORE™ Normalized") for the above referenced n=194 discs as follows: "PD+1"=non-herniated PD+ discs; "PD+2"=non-herniated PD+ discs with known abnormal co-morbidity other than internal disc chemistry that could affect PD+/- results; "PD+3"=herniated PD+ discs; "PD+4"=herniated PD+ discs also with known abnormal co-morbidity; "DX+"=discs diagnosed as painful for other reasons than discogram, and not receiving discogram, in patients receiving discogram at other disc levels; "PD- 1"=non-herniated PD- discs; "PD-2"=non-herniated PD- discs with known abnormal co-morbidity other than internal disc chemistry that could affect PD+/- results; "PD- 3"=herniated PD- discs; "P- 4"=herniated PD- discs also with known abnormal co-morbidity.

Figure 48B:
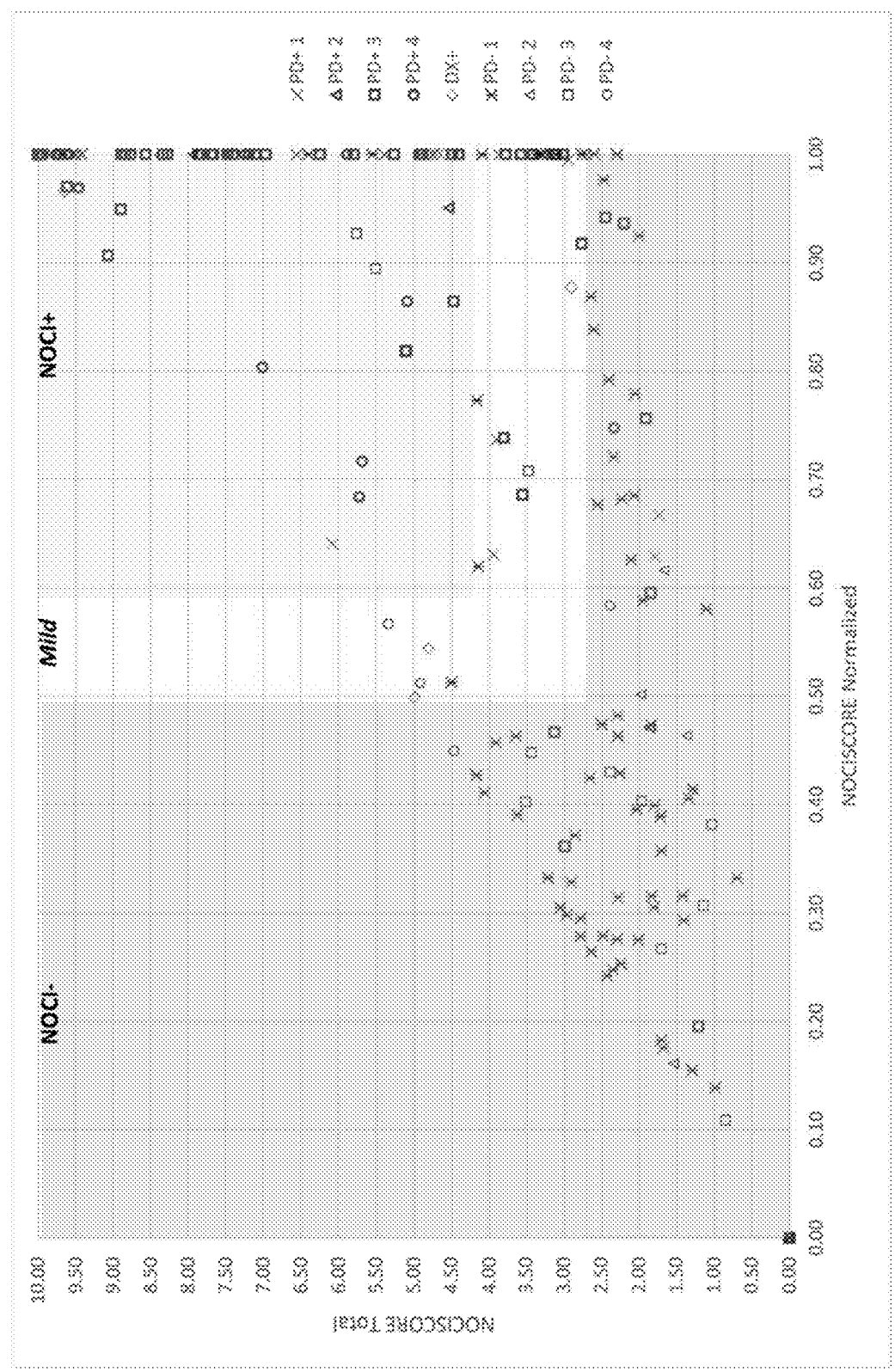
FIG. 48B shows the same histogram plot for the same information shown in FIG. 48A, except with certain classifier ranges overlayed onto the plotted data.

FIG. 48B shows the same plot as FIG. 48A, except with certain ranges identified for assigning classifications of the NOCISCORE-based calculations for correlations to the PD+/- control results as follows. A first range is assigned "NOCI-" for correlation to PD- discs and corresponds with a NOCISCORE Total <2.7 or a NOCISCORE Normalized <0.49. A second range is assigned "NOCI+" for correlation to PD+ discs and corresponds with a NOCISCORE Total >4.25 and a NOCISCORE Normalized >0.59. A third range is assigned "NOCImild" or "Mild" and captures discs with NOCISCORES that do not fall within the first or second ranges for NOCI- or NOCI+ assigned classifiers, respectively.

After removing n=32 NOCI 'mild' results (n=17 of the PD+ discs, or 9% of data; n=15 of the PD- discs or 8% of the data) according to these assigned ranges per the data distribution illustrated in FIG. 48B, n=162 discs remain that were either NOCI+ or NOCI- and that either (1) received provocative discogram with either (a) PD- results as negative or non-painful (n=83 discs), or (b) PD+ results as positive or painful (n=70 discs), or (2) did not receive discogram but were diagnosed as painful and to receive surgical treatment for other reasons in patients receiving discogram at other disc levels (n=9 discs).

According to these assigned thresholds for NOCI+/- (& indeterminate "mild") classifications, correlations to PD+/- results as a control test measure, and resulting diagnostic performance measures compared to the PD controls (Sensitivity, Specificity, Positive Predictive Value (PPV), Negative Predictive Value (NPV), and Overall accuracy), are shown in FIG. 49.

Figure 50A:
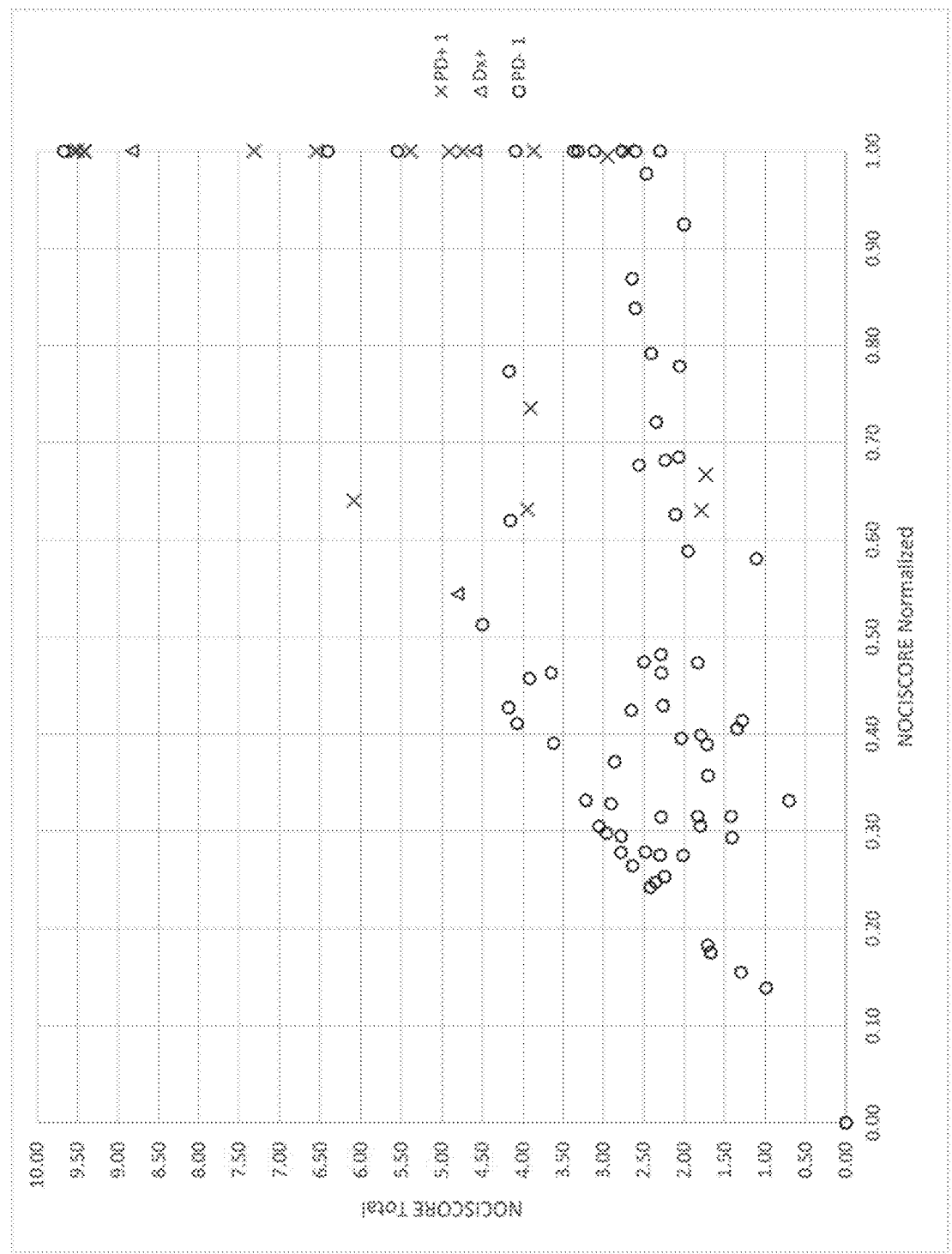
FIGS. 50A-B show similar plots of the same data as shown in FIGS. 48A-B, except after filtering out certain data.
Figure 50B:
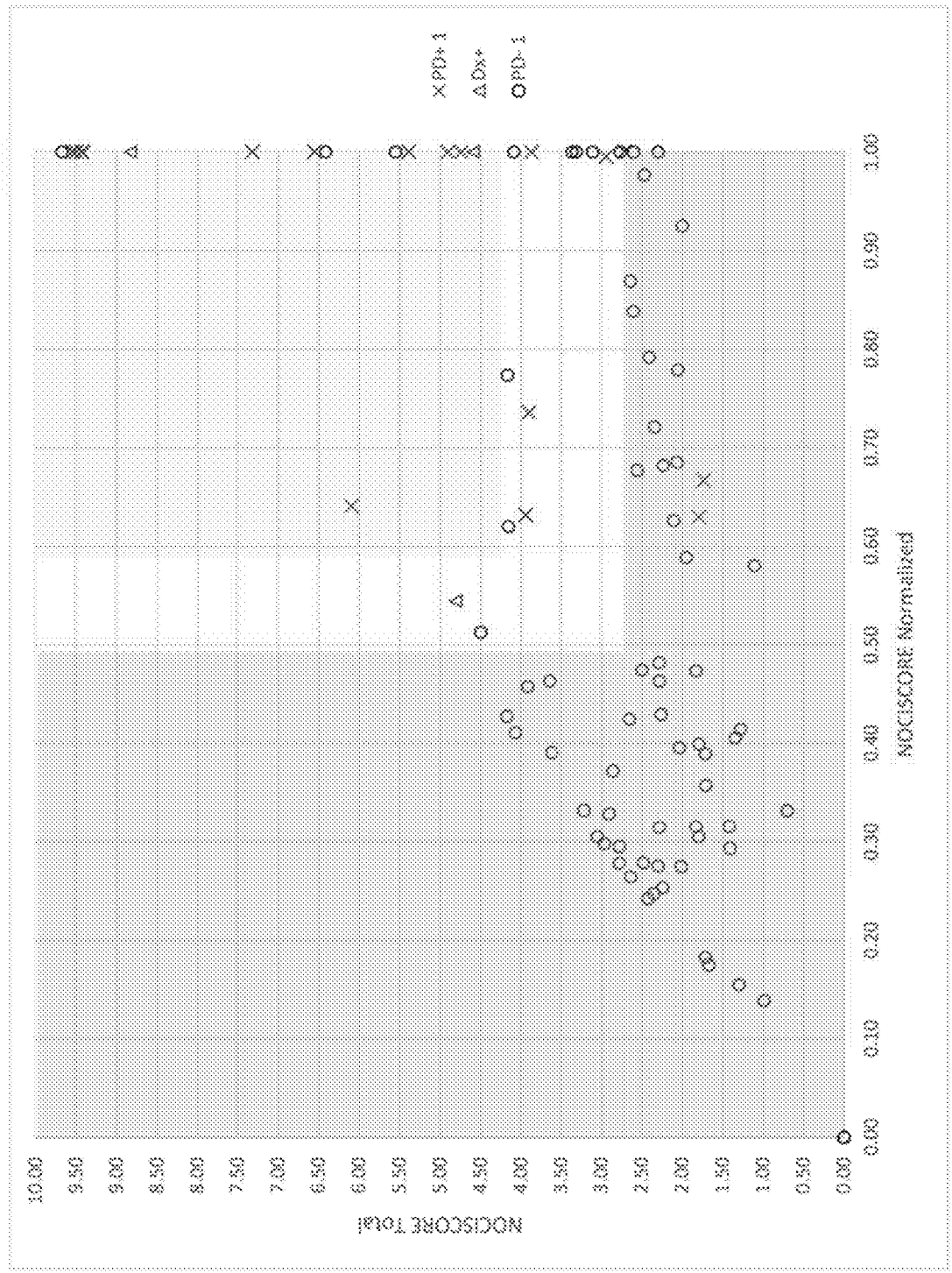

FIGS. 50A-B show similar plots of the same data as FIGS. 48A-B, and with similarly applied NOCI+/mild/- thresholds, except after filtering out data for discs that are classified as herniated and/or with potentially relevant co-morbidities apart from disc chemistry, thus to reflect a more isolated population of only non-herniated discs without other known co-morbidities. In other words, this data reflects correlations to PD+/- control results that are more isolated to disc chemistry changes as the potential cause of pain—and which is the actual condition as potential cause of pain that is tested with the spectroscopic approach.

FIG. 51 shows similar diagnostic correlation and performance data versus discogram controls as shown in FIG. 49, except for the 'non-herniated only' filtered data shown and described by reference to FIGS. 50A-B.

According to the data as thus illustrated by FIGS. 48A-51, the correlation of the spectroscopic approach according to this Example 6 is quite high versus discogram. While it is a high 84+% for all discs in the population (including herniations & co-morbidities), it is even higher at about 94% for non-herniated discs without such recognized co-morbidities.

Further to this Example 6, n=51 of the patients that were also treated surgically at the PD+ disc levels were also evaluated for surgical outcomes and in relation to the relative MRS-based NOCISCORE and NOCI+/mild/- classifications for the discs in the respective patients.

Figure 52:
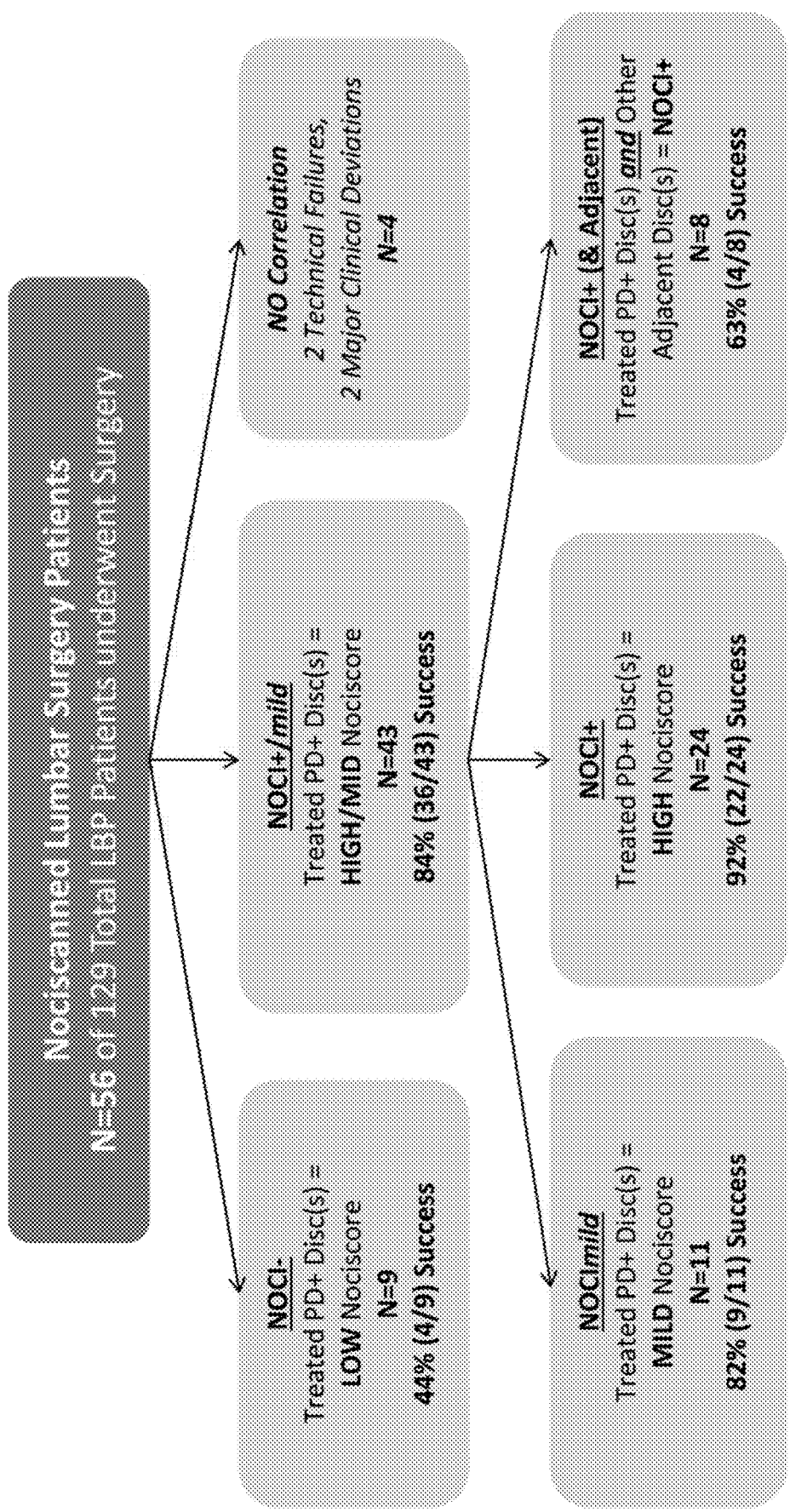
FIG. 52 shows a flow chart of certain surgical treatment patients of Example 6, and their treatment success outcomes rates, in relation to the diagnostic classification performed according to further aspects of Example 6.
Figure 53:
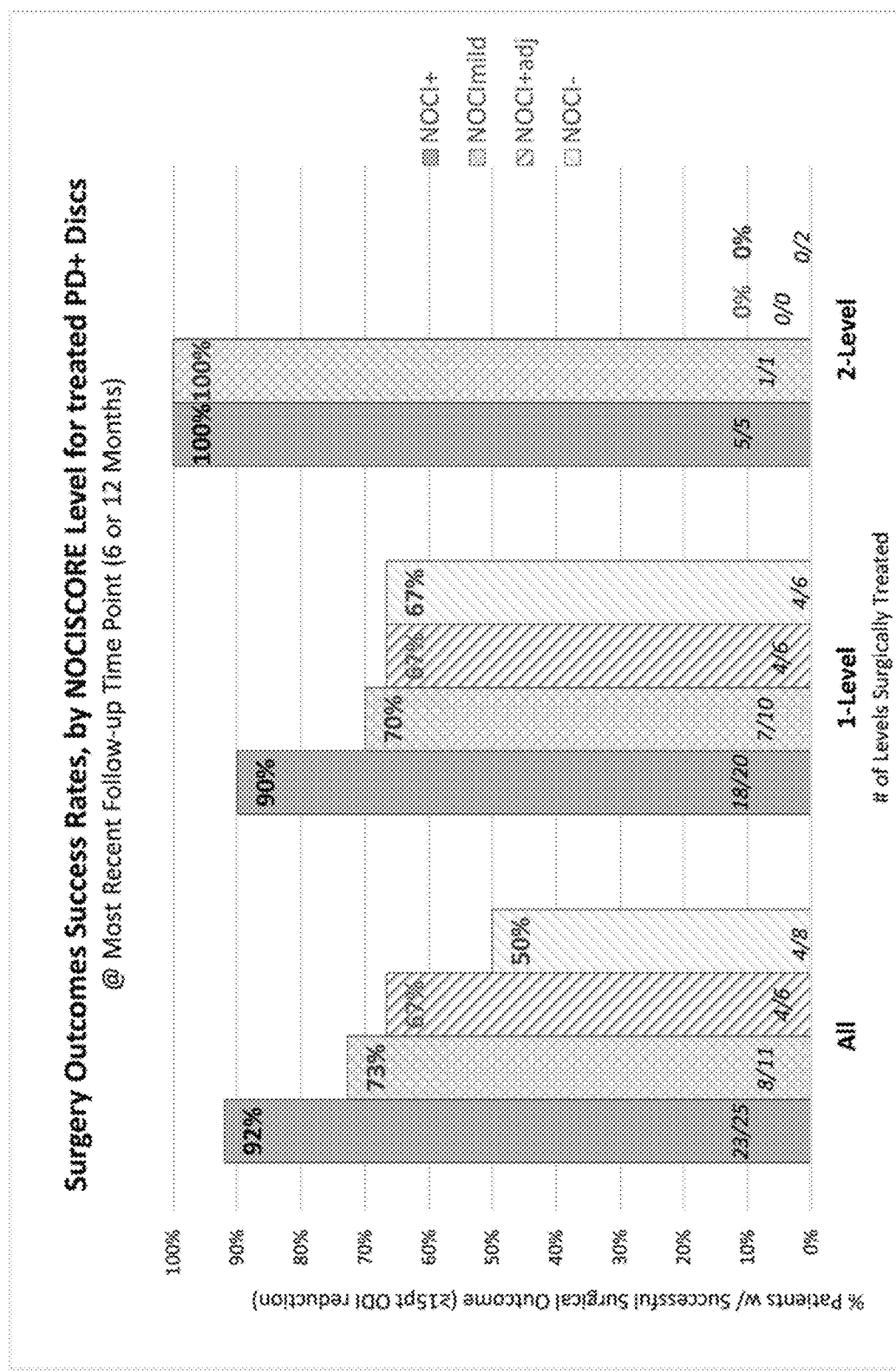
FIG. 53 shows a bar graph of % surgical outcomes success rates, versus # of disc levels treated, for different surgical patient sub-groups based on classified diagnosis according to still further aspects of Example 6.

FIGS. 52-53 illustrate such NOCISCORE and NOCI+/mild/- classification correlations to surgical outcomes, per the following description. The surgical outcomes measures were based on success or failure for a patient to achieve 'significant improvement' as represented by at least a 15 point reduction in Oswestry Disablity Index (ODI), per 0-100 scale (100 being highest disability). This change in ODI was measured from pre-surgery baseline to post-surgical follow-up time points of 6 months and 12 months (the data featured herein reflects the most recent of such time points for the respective patients at the time of this disclosure). The surgical patients were categorized for purpose of analysis as follows: NOCI+ (treated PD+ disc/s had a high NOCISCORE as 'NOCI+'), NOCImild (treated PD+ disc/s had a moderate NOCISCORE as 'NOCImild'), NOCI+Adj (treated PD+ disc/s plus at least one other non-treated non-PD+ disc had relatively high NOCISCORES as NOCI+), NOCI- (treated PD+ disc/s had relatively low NOCISCORE as NOCI-).

As is demonstrated in this data, patients receiving treatment at PD+_levels that were also NOCI+ enjoyed an extremely high 92% successful outcome rate (23/25 patients)—and whereas one of the only two patients who did not meet the success criteria missed doing so by only 1 point on ODI reduction (a 14 point reduction), and in fact demonstrated significant improvement by another standard measure—Visual Analog Scale (VAS). In contrast, patients receiving surgery at PD+ levels that were NOCI- had only a 50% successful outcome rate (4/8 patients)—the majority of which were herniated discs. The scale between these two extremes—NOCImild and NOCI+adj—demonstrated a tiered reduction of 73% success (8/11) for NOCImild and 67% success (4/6) for NOCI+adj discs. This data thus suggests that NOCISCORE and NOCI+/mild/- classifications according to this example provides a valuable tool for painful disc diagnosis and treatment algorithm consideration. This approach proposes beneficial value, either for use in conjunction with discogram, or in the alternative to discogram (which is known to be highly invasive, painful, risky, and potential source itself of future degeneration and/or herniations in untreated discs).

The specific application featured in this Example 6 is thus considered to provide distinct benefits. However, it is also considered an example but not necessarily limiting to broader aspects illustrated by the example. It is appreciated, for example, that variations may be made from various details of this specific embodiment and to suit a particular purpose, and without departing from the broad intended scope of these various aspects. Such variations could include, for example, weighting or normalization threshold values, the specific combination of ratios used, and/or customization of such calculation bases to particular disc or patient phenotypes (e.g. herniated vs. non-herniated, high BMI vs. low BMI patients, lower lumbar vs. higher situated discs, consideration of other co-morbidities, etc.).

Still further examples include applying the data shown and described for further processing, such as for example to convert NOCICORES to % probability PD+ or PD−, e.g. as may be performed via statistical modeling by this or another patient population of empirical data. In further regards, additional evaluation of spectroscopic data across other patient populations may yield different specific calculated bases for such scoring and/or classification, yet while still preserving the broad aspects illustrated by this example.

Example 7

This example provides certain information related to bacterial infection of discs and thus providing certain relations to various embodiments herein described by reference to such disc infections and related spectroscopic analysis, e.g. in relation to propionic acid (PA). In addition, this example also provides further disclosure of still further embodiments in which such spectroscopic evidence, e.g. of PA, may be combined with other imaging evidence of infection for a combined diagnostic system and method with enhanced diagnostic reliability based on such combined evidence and related measures. In such regards, to the extent imaging evidence of infection is described, such may be interpreted visually by a trained imaging diagnostician, or may be determined via imaging processing such as via a computer processor operating according to a set of instructions that determines the absence or presence (and possibly to what extent) of the respective bacterial infection signature in the image. For example, T1 or T2-weighted images (or other suitable imaging pulse sequence results) can be processed to identify sufficient changes in contrast or other quantifiable measure in the image to identify the presence (and potentially extent or volume of) a modic lesion, e.g. MC1 type lesion. According to certain embodiments, such imaging-based determination of infection based on such an identifiable signature in an image, is combined with PA spectroscopic calculated measure, in order to diagnose a tissue region as infected or not infected. These combined approaches may be performed in the same tissue region, or adjacent regions to the extent their determinations may be combined for a combined diagnosis for a broader region that encompasses both sub-regions. For example, spectroscopy may be performed in a disc, whereas the imaging based determination may be made in the adjacent end-plate or vertebral body, such that determination of a possible infection at both points increases a likelihood injection is present in the disc 'level' (which may be considered to also include the end-plate and/or adjacent vertebral body). According to such approaches, while one or both such determinations may not be 100% perfectly reliable in determining presence of infection, the presence of both determinations may significantly increase the diagnostic acuity in making the determination.

Modic type I change (MC1) are vertebral bone marrow lesions adjacent to degenerated discs that can be specific for discogenic low back pain. Occult discitis, in particular with *Propionibacteria acnes* (*P. acnes*), has been suggested as a possible etiology. Antibiotic therapy can be considered for patients with MC1. While some studies report up to 40% infection rate in herniated discs, others fail to detect infected discs and attribute reports of positive cultures to contamination during sampling procedure. Whether it is biologically plausible for *P. acnes* to cause MC1 was investigated. A study was performed to test if *P. acnes* can proliferate within discs and cause reactive changes in the adjacent bone marrow. *P. acnes* was aseptically isolated from a symptomatic human L4/5 disc with MC1 and injected into rat tail discs. Proliferation of *P. acnes* and up-regulation of IL-1 and IL-6 within three days of inoculation was demonstrated. At day-7, disc degeneration was apparent along with fibrotic endplate erosion. TNF-α immunoreactivity was enhanced within the effected endplates along with cellular infiltrates. The bone marrow appeared normal. At day-14, endplates and trabecular bone close to the disc were almost completely resorbed and fibrotic tissue extended into the bone marrow. T-cells and TNF-α immunoreactivity were identified at the disc/marrow junction. On MRI, bone marrow showed MC1-like changes. It was concluded that *P. acnes* proliferate within the disc, induce degeneration, and cause MC1-like changes in the adjacent bone marrow.

Low back pain (LBP) is a disabling condition with detrimental consequences due to increased use of health care services and work disability. Although LBP relates to different spinal pathologies, vertebral bone marrow lesions visualized as Modic changes (MC) on magnetic resonance imaging (MRI) have a high specificity for discogenic LBP. MC are MRI signal intensity changes which are not related to marrow malignancy or pyogenesis. LBP patients with MC report a greater frequency and duration of LBP episodes, seek care more often, and have a higher risk for a poor outcome. However, the etiopathogenesis of MC was not fully understood. Generally, three interconvertible types of MC exist with MC type 1 (MC1) generally being the most symptomatic and representing fibrovascular granulation tissue.

In some cases occult discitis, in particular with the bacteria *Propionibacteria acnes* (*P. acnes*), may be the reason for MC1. *P. acnes* is an anaerobic aerotolerant Gram-positive opportunistic pathogen implicated in prosthetic joint infections, acne vulgaris, endocarditis, and osteomyelitis. *P. acnes* also forms part of the normal resident microbiota of the skin, oral cavity, and the gastrointestinal and genitourinary tracts. In some cases, *P. acnes* can be isolated from 38% to 53% of herniated disc surgical samples. High percentages of newly formed MC1 can be found if *P. acnes* was found in excised disc tissue. In some cases, Antibiotic treatment can have positive effects on MC1 patients. In contrast, in some instance no *P. acnes* is found in excised disc tissue, and some attribute the few positive samples to contamination during isolation.

How *P. acnes* seeds into the disc and could cause MC1 was not previously well understood. *P. acnes* may enter the blood stream during innocuous events such as tooth brushing, or through haematogenous spread from a distant septic location. When disc immunoisolation is violated by disc herniation or endplate damage (both of which can associate with MC1), blood borne *P. acnes* may invade the disc and proliferate. The potential for *P. acnes* to survive and proliferate within the disc, and trigger reactive bone marrow changes in adjacent vertebra had not been previously demonstrated. This example involves use of the rat-tail model to investigate the disc and vertebral response to intradiscal *P. acnes* injection.

A rat tail model was chosen because rat tail discs can be big enough to be manipulated, because rat tail marrow can be responsive to disc manipulation, and because rat tails can be easy to MR image with high resolution. Ten 8-week-old female Sprague-Dawley rats were used. The rats were housed in pairs and given 3 days to acclimate to the housing facility. Environmental enrichment included bedding, one red tinted tube, and one wooden chew block. Animals were monitored at least every second day. No adverse events were observed. Rats were randomly assigned to gene transcription analysis (n=4), histology and immunohistochemistry (n=4), and MRI (n=2).

*P. acnes* was aseptically isolated from tissue surgically removed from a human L4/5 disc that had MC1 present for more than a year. The patient (33 years, female, BMI 25.3) underwent discectomy and decompression because of chronic LBP with pain and numbness in both legs. Prior to surgery, serial epidural steroid injections relieved pain for 1-2 months each. Disc tissue was minced using a sterile scalpel and cultured aerobically and anaerobically. *P. acnes* bacteria were cultured on *Brucella* agar and cryopreserved at −80° C. in 25% glycerol. Subculture colonies of this *P. acnes* strain were suspended in phosphate buffered saline (PBS) for rat injection. The strain type was determined by sequencing the recA gene. *P. acnes* were boiled for 10 min in H2O, centrifuged for 10 min at 15,000 g, and supernatant was collected. recA was amplified according to manufacturer protocol (Bioneer E-2011, Alameda, Calif.) using the primers PAR-1 (−96 to −75) (5'-AGCTCGGTGGGGTTCTCT-CATC-3') and PAR-2 (+1,105 to +1,083) (5'-GCTTCCT-CATACCACTGGTCATC-3') and purified with Qiaquick (Qiagen, Valencia, Calif.). The 1,201-bp amplicon was verified by agarose electrophoresis. Sequencing was done by MCLAB (San Francisco, Calif.). Sequence alignment against *P. acnes* strain types IA, IB, II, and III (Gene bank accession no: AY642061, DQ672252, AY642055, NC_006085) revealed 100% identity with strain type II.

Caudal vertebrae (Ca)2/3 to Ca1/8 (n=6 per animal) were dissected as spinal segments (disc/endplates with half vertebrae on each side) and assigned to a sampling time (24 h, 72 h) and a treatment (*P. acnes*, PBS). After 6 days of in vitro culture in DMEM/F12 supplemented with 10% fetal calf serum, 50 µg/ml penicillin, 100 U/ml streptomycin, and 25 µg/ml L-ascorbate, antibiotics were removed and specimens were cultured for another 24 h. 1.5 µl *P. acnes* (OD600=3.0) or PBS was injected into the nucleus pulposus (NP) using a 33G 10 µl Hamilton syringe (n=6 per day and condition). Prior to injection, a part of the NP was aspirated from the contra-lateral side with a 23G needle in order to depressurize the disc and facilitating the injection. After 24 h and 72 h specimens were transferred to RNA-later® (Sigma-Aldrich, St. Louis, Mo.), agitated for 1 day at room temperature and frozen at −20° C. until further processed. The NP was dissected, pulverized using a freezer-mill (Retsch MM301, Newtown, Pa.) and dissolved in Trizol. RNA was isolated with two steps of chloroform extraction and purified with Qiagen RNeasy mini columns. cDNA was synthesized (Bio-Rad, Hercules, Calif., iScript cDNA Synthesis Kit) and the gene expression of GAPDH (LifeTechnologies, Grand Island, N.Y., Rn01775763_g1), IL1A (LifeTechnologies Rn00566700_ml), IL6 (LifeTechnologies Rn01410330_m1), TNFA (LifeTechnologies Rn01525859_g1), and the bacterial ribosomal protein 16S were quantified with TaqMan probes. For 16S, universal bacterial primer/probes were used. The 16S expression in control samples was considered to be background signal due to reagent contamination with bacterial DNA. Data were normalized to GAPDH and control sample and evaluated with the comparative Cq method using the software R (version 2.15.1). Significant differences were detected by comparing ΔCq values of *P. acnes* and PBS treated discs with t-tests. Standard devia-tions were calculated from ΔCq and converted to fold-change.

1.5 µl *P. acnes* was injected into caudal vertebrae Ca2/3, Ca4/5, Ca5/6, and Ca7/8 by the surgical technique used for in vitro specimens as described above (n=4 per day). 1.5 µl PBS (sham) was injected into Ca3/4 and Ca6/7 (n=2 per day). Animals were euthanized after 1, 3, 7, and 14 days (n=1 per day) and treated spinal segments were dissected within 30 min. Specimens from day-3, -7, and -14 were fixed for 4-5 days in 10% neutral buffered formalin and decalcified with EDTA. Seven microliters sagittal sections were either stained with Heidenhain trichrome to visualize connective tissue or immunohistochemically analyzed for TNF-α and T-cells (CD3). TNF-α immunoreactivity was analyzed with goat polyclonal anti-human TNF-α (Santa-Cruz SC-1348 M18, Paso Robles, Calif.) and the Vector Elite ABC Kit (Vector Laboratories, Burlingame, Calif.). CD3 immunoreactivity was analyzed with rabbit polyclonal anti-human CD3 IgG (Biocare CP 215 A, Concord, Calif.) and the Innovex Animal IHC Kit (Innovex, Richmond, Calif.). Whereas TNF-α is an early phase cytokine and indicates an active inflammation, T-cell infiltration is delayed and indicates an adaptive immune response. Gram staining was done on specimens from day-1 to validate that *P. acnes* do not leak out of the disc. Since formalin and EDTA inhibit Gram staining, day-1 specimens were dissected as bone-free disc/endplate specimens, cryo-sectioned, and stained with McDonald's Gram™ stain kit (American MasterTech, Lodi, Calif.). Histological data were qualitatively interpreted.

1.5 µl of *P. acnes* (n=4) was injected into caudal vertebrae Ca4/5 and Ca5/6 of two animal by the surgical technique used for in vitro specimens as described above. Using similar techniques, 1.5 µl of PBS (sham) was injected into Ca3/4 and Ca6/7 (n=4). At day 20, animals were anesthetized with isoflurane and tails were placed in a 27 mm ID linear polarized birdcage coil and scanned with an Agilent/Varian 7T 300 MHz Horizontal Bore MRI. Mid-sagittal T1-weighted (T1w) and T2-weighted (T2w) images were acquired. For T1w images, a spin echo sequence was used (TR=500, TE=15, field of view=25.6×12.8 mm with in-plane resolution 100 µm and slice thickness=1 mm and two repetitions). For T2w images, a gradient echo sequence was used (TR=100, TE=10, flip angle=15°, field of view=25.6× 12.8 mm, in-plane resolution 100 µm, thickness=1 mm, 32 repetitions). MRI data were qualitatively interpreted.

Figure 54:
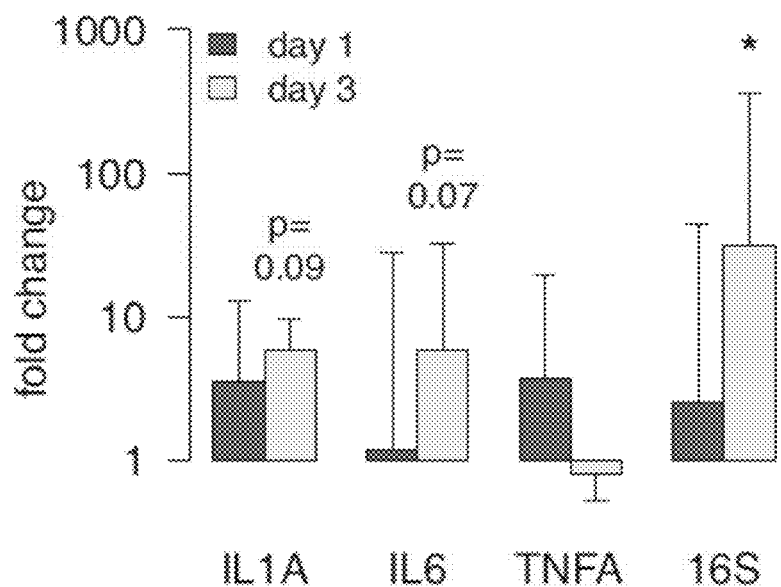
FIG. 54 shows gene transcription (fold change relative to unaffected control disc) in the nucleus pulposus cells from a P. acnes infected rat-tail disc.

All animals showed no signs of pain or discomfort indicative of sepsis. Pre-procedural weight for histology was 184±4 g, for gene transcription analysis and MRI 234±8 g. Twenty-four hours after *P. acnes* injection no significant expression level changes were observed for the genes studied. Seventy-two hours after injection, the amount of 16S RNA was significantly increased (31.1±12.5-fold, p<0.05). FIG. 48 shows gene transcription in the nucleus pulposus of *P. acnes* injected rat-tail disc explants (n=6). Values were normalized to glyceraldehyde 3-phosphate dehydrogenase and relative to control (PBS injection). The chart of FIG. 54 shows mean value+standard deviation. In FIG. 54, * indicates p<0.05. An up-regulation trend for IL-1A (5.9±2.6-fold, p=0.09) and IL-6 (5.8±6.3-fold, p=0.07) was also noted at 72 h.

Figure 55:
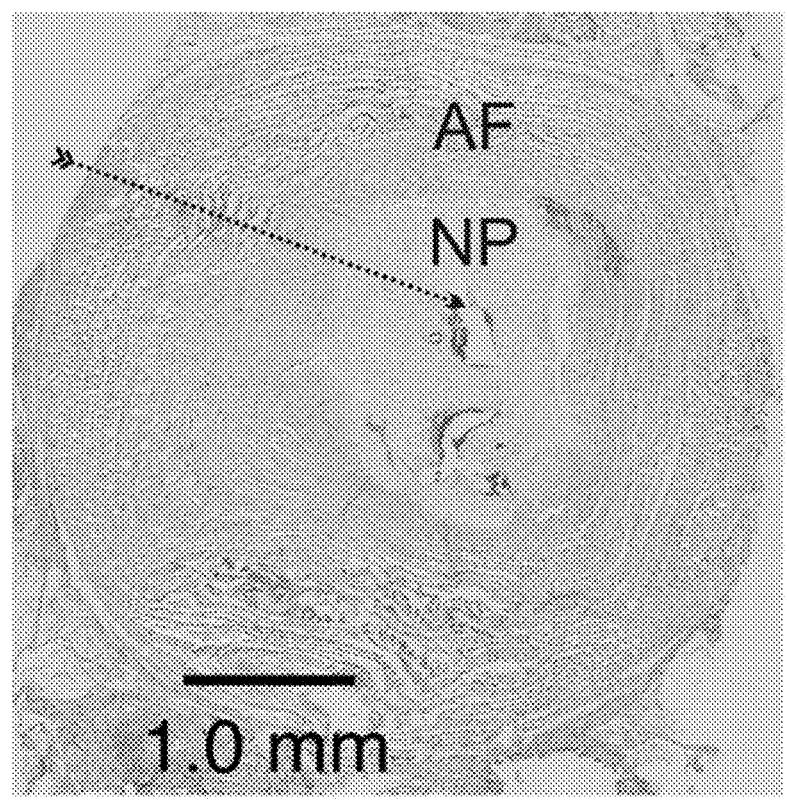
FIG. 55 is a photomicrograph of a Gram stained transverse section of a rat-tail disc injected with P. acnes, demonstrating the presence of P. acne in the nucleus.

Gram staining revealed that most injected bacteria stayed within the NP or at the interface between the NP and the inner anulus fibrosus. FIG. 49 is a photomicrograph of a Gram stained transverse section of a rat-tail disc injected with *P. acnes* (Original magnification (2×)). In FIG. 55, the arrow indicates the injection trajectory, NP indicates nucleus pulposus, and AF indicates annulus fibrosus. Only few bacteria were found along the injection tract.

Figure 56:
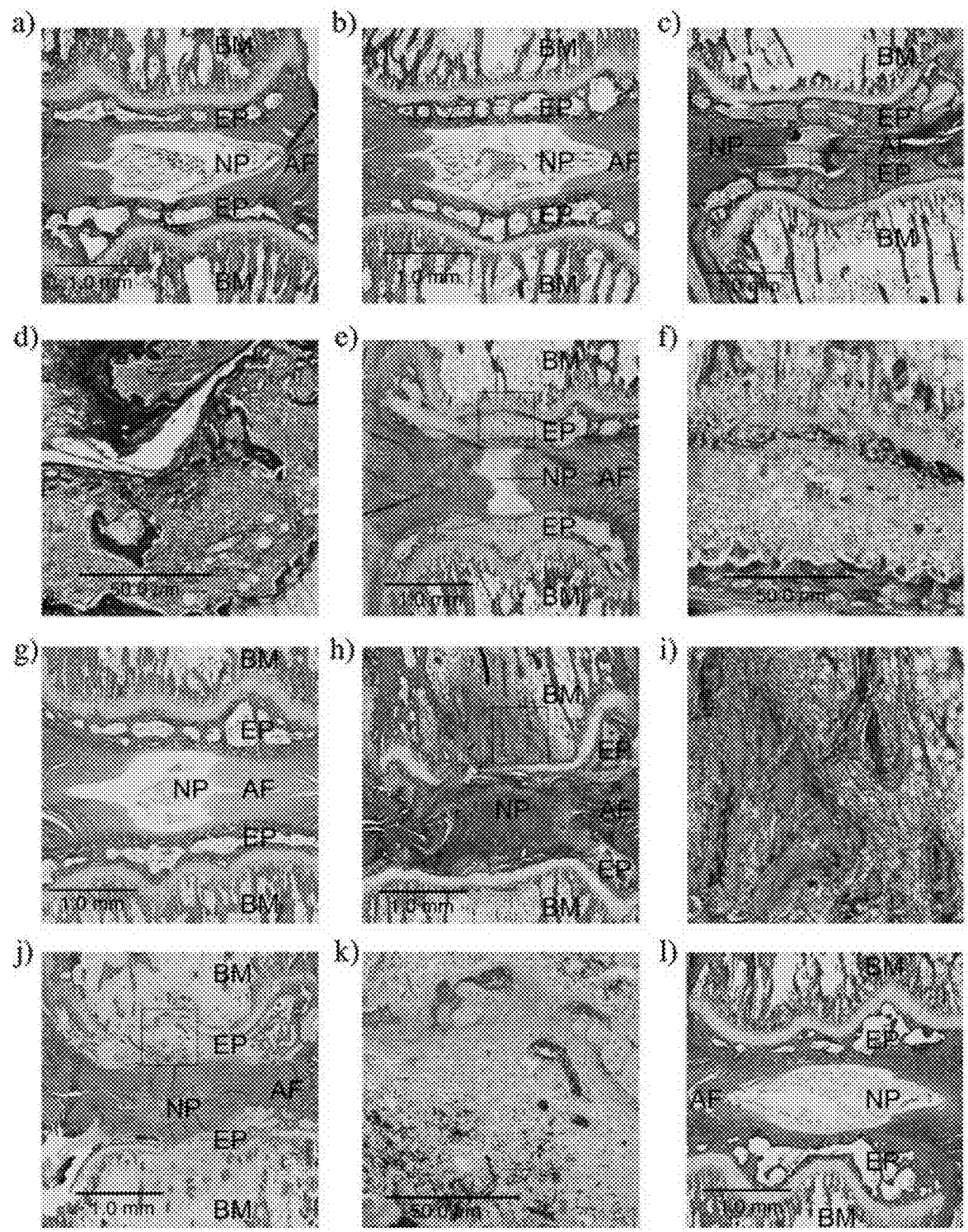
FIG. 56 shows photomicrographs of representative sagittal sections of rat-tail intervertebral discs stained with Heidenhain trichrome that demonstrate degenerative changes associated with P. acne infection. Panel (a) depicts 3 days after infection, (c-f) after 7-days, and (h-k) show after 14-days. Panels (b, g, and l) are for control, uninfected discs.

FIG. 56 shows photomicrographs of representative sagittal sections of rat-tail intervertebral discs stained with Heidenhain trichrome to distinguish connective tissue (e.g., collagen), and bone or dense connective tissue, and Erythrocytes or cell nuclei. In FIG. 50 slides (a) and (b) correspond to day-3, slides (c) to (g) correspond to day-7, and slides (h) to (l) correspond to day-14. All slides in FIG. 50 are from *P. acnes* injected discs except that slides (b, g, and l) are sham control. Slides (d, f, i, and k) are 20× magnification of the indicated area of slides (c, e, h, and j), respectively, and the other slides are 4× magnifications. In FIG. 56, the injection trajectory is perpendicular to the view. In FIG. 56, NP indicates nucleus pulposus, AF indicates annulus fibrosus, EP indicates endplate, and BM indicates bone marrow.

Heidenhain staining revealed no endplate or bone marrow changes at day-3. (See FIG. 56, slide (a)). At day-7, endplates were filled or partially replaced with fibrovascular tissue in three of four *P. acnes* treated segments (see slides (c)-(f) of FIG. 56) and in none of PBS treated segments (see slide (g) of FIG. 56). At day-14, all of the *P. acnes* treated segments showed fibrovascular tissue within the endplates and bone marrow in some cases (see slides (h)-(k) of FIG. 56). Notably, endplates were almost completely resorbed with a dramatic decrease in the trabecular bone mass, e.g., evidenced by the loss of red staining (see slide (i) of FIG. 56). New fibrovascular tissue was always accompanied by cellular infiltrates (see slides (d), (f), (i), and (k) of FIG. 56). No bone marrow changes were seen in the control group at any time point (see slides (b), (g), and (l) of FIG. 56). Degenerative changes of the intervertebral disc were always more severe if fibrotic endplate/marrow changes were present.

Figure 57:
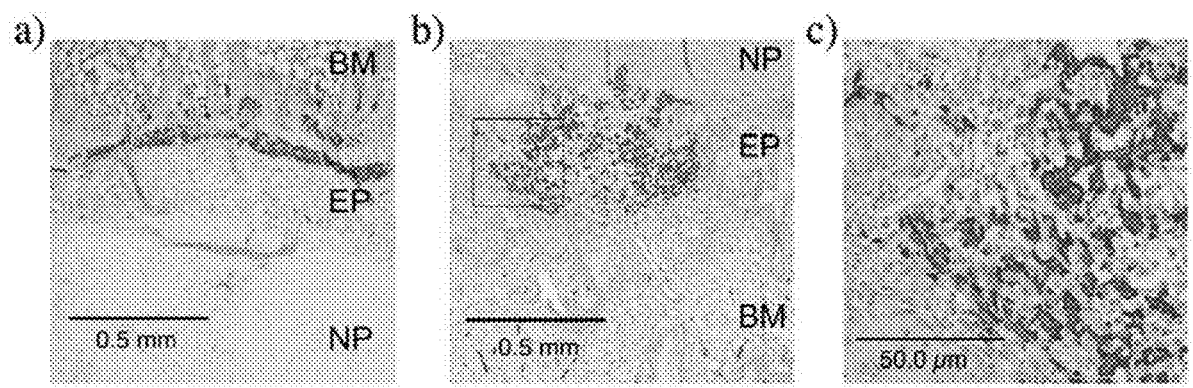
FIG. 57 shows representative photomicrographs at different magnifications that were taken from the disc/bone marrow junction demonstrating marrow changes induced by P. acne disc infection.

TNF-α and CD3 immunoreactivity was only seen in conjunction with fibrotic changes in the endplates or the bone marrow. At day-3, TNF-α immunoreactivity was not higher in the endplates and the bone marrow of *P. acnes* treated specimens as compared to controls (not shown). However, at day-7 in three of four, and at day-14 in four of four *P. acnes* treated specimens demonstrated increased TNF-α immunoreactivity. FIG. 57 shows TNF-α immunoreactivity in *P. acnes* injected discs after 7 days at slide (a) and 14 days at slides (b and c). FIG. 57 shows representative photomicrographs that were taken from the disc/bone marrow junction. Slide (c) is a 40× magnifications of the indicated area of slide (b). Slides (a and b) are 10× magnifications. Dark areas can indicate specific TNF-α immunoreactivity. Cell nuclei can be shown. In FIG. 51, NP indicates nucleus pulposus, EP indicates endplate, and BM indicates bone marrow. Injection trajectory is perpendicular to the view in FIG. 51. Slide (a) of FIG. 57 is the same spinal segment as in slide (e) of FIG. 56 and slide (b) of FIG. 57 is the same spinal segment as in slide (j) of FIG. 56. Reactivity was associated with neovascularity, and was highest within the resorbed endplates and at focal points of the growth plate on the side away of the disc. Most TNF-α immunoreactivity appeared to be extracellular (see slide (c) of FIG. 57). At day-3, no T-cells were observed in any of the spinal segments (not shown in FIG. 57). At day-7, few T-cells were noted in the endplates in two of four *P. acnes* treated segments.

Figure 58:
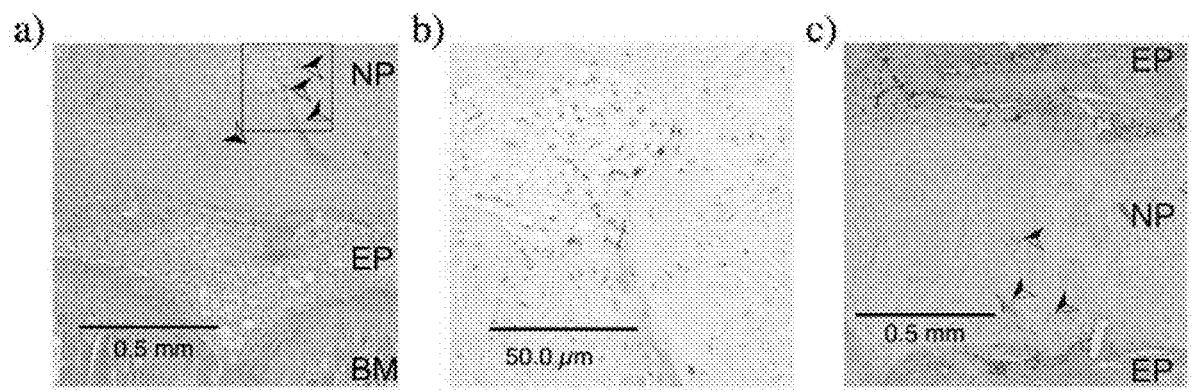
FIG. 58 shows CD3 immunoreactivity (identifies T-cells) in P. acnes injected discs after 7-days (a-b) and 14-days (c).

FIG. 58 shows CD3 immunoreactivity in *P. acnes* injected discs after 7 days for slides (a and b) and 14 days for slide (c). The representative photomicrographs of FIG. 52 were taken from the disc and endplates. Slide (b) of FIG. 58 is a 40× magnifications of the indicated area of slide (a). Slides (a and c) of FIG. 58 are 10× magnifications. Dark areas can indicate specific CD3 immunoreactivity. Cell nuclei can be shown. In FIG. 52, NP indicates nucleus pulposus, EP indicates endplate, and BM indicates bone marrow. In FIG. 52, the injection trajectory is perpendicular to the view. The arrow heads in FIG. 52 point at groups of CD3-positive cells within the disc. Slide (a) of FIG. 58 is the same spinal segment as in slide (e) of FIG. 56, and slide (b) of FIG. 58 is the same spinal segment as in slide (h) of FIG. 56. In one spinal segment T-cells were observed in the disc but not in the endplate or bone marrow (see slides (a) and (b) of FIG. 58). At day-14, T-cells were found in the endplates in three of four *P. acnes* treated segments (see slide (c) of FIG. 58). Two of them also showed T-cells infiltration into the disc. Generally, T-cell infiltration was low to moderate in these cases. Areas of TNF-α reactivity occasionally showed higher CD3 reactivity.

All changes, that is, fibrotic tissue, TNF-α reactivity, and T-cell infiltration occurred coincidently in both the caudal and cranial endplates/bone marrow and were close to the mid-coronal line (adjacent to the NP or the inner anulus fibrosus).

Figure 59:
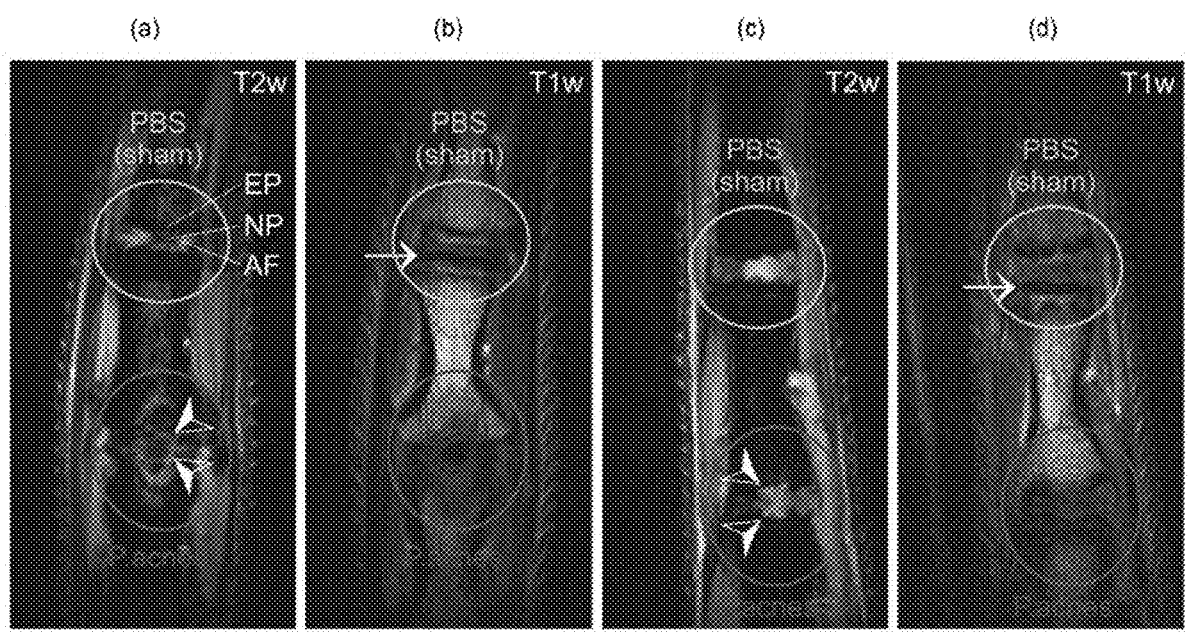
FIG. 59 shows MR images of P. acnes injected discs (bottom discs) and PBS injected discs (top discs), demonstrating bone marrow changes (Modic changes) that associate with P. acne infection.

In Example 7, all MR images of the discs injected with *P. acnes* showed anatomical changes. FIG. 59 shows MR images of *P. acnes* injected discs (bottom discs) and PBS injected discs (top discs). Sides (a and b) of FIG. 59 correspond to rat 1, and slides (c and d) of FIG. 59 correspond to rat 2. Slides (a and c) are T2w images, and Slides (b and d) are T1w images. In FIG. 59, EP indicates endplate, NP indicates nucleus pulposus, and AF indicates anulus fibrosus. Injection trajectory is perpendicular to the view in FIG. 59. In FIG. 59, arrow heads point at increased signal intensities in the endplates on T2w images of *P. acnes* injected discs, and arrows point at clearly demarcated endplates on T1w images of PBS injected discs. On T2w, *P. acnes* injected discs appeared hypointense, and the endplate regions adjacent to the NP appeared hyperintense (see slides (a) and (c) of FIG. 59) compared to PBS injected discs. The hyperintense zone extended into the bone marrow in two of four *P. acnes* injected discs. On T1w, *P. acnes* injected discs were hypo- or iso-intense (see slides (b) and (d) of FIG. 59). Hypointensity was more pronounced in the NP. The bone marrow close to the disc appeared hypointense in three of four *P. acnes* injected discs. Stronger signal intensity changes in the disc generally associated with marrow changes that penetrated deeper into the vertebra, with deepest penetration in the mid-coronal line. PBS injected discs showed clearly demarcated endplates (see slides (b) and (d) of FIG. 59) whereas the endplates of *P. acnes* injected discs were diffuse and not well demarcated from the disc nor the bone marrow.

One goal of the study of Example 7 was to test whether *P. acnes* can trigger reactive bone marrow changes adjacent to an infected spinal disc. The data demonstrated that intradiscal injection of a clinically relevant *P. acnes* strain causes MC1-like changes on MRI and can trigger the histologic hallmarks of MC1, which are fibrotic changes of the endplates and bone marrow with immune cell infiltration, endplate damage, bone resorption, and disc degeneration. Therefore, disc infection with *P. acnes* should be considered as a plausible MC1 etiology.

This study utilized a rat-tail model where *P. acnes* was injected into discs with intact vertebral endplates. Yet, disc infection had detrimental consequences for the adjacent vertebral bone marrow. The temporal "inside-out" progression, and the simultaneous cranial/caudal occurrence of the marrow changes together suggest that factors secreted within the disc drain into adjacent vertebrae and trigger the pathological marrow changes. Intradiscal up-regulation of IL-1 and IL-6 3 days after *P. acnes* injection indicates a key role for pro-inflammatory cytokines in MC pathoetiology. This is in agreement with reports of increased IL-6, IL-8, and PGE-2 expression in human discs adjacent to MC. While *P. acnes* is not the only etiology of MC, *P. acnes* infection is a plausible cause for disc inflammation. Disc cells express toll-like receptors (TLRs) which recognize polysaccharides of bacterial cell wall proteins. TLR2 ligation in disc cells triggers IL-1/-6/-8, COX-2, MMP-3, and MM-13 production, which aggravate disc degeneration and induce the release of chemokines. The degenerative effects of *P. acnes* on discs was demonstrated in a rabbit disc herniation model, where *P. acnes* were injected into discs.

MC associate with endplate damage that can increase the efflux of cytokines into the bone marrow. This is because endplate damage disrupts the tightly controlled metabolite transport between the disc and the bone marrow and leads to a hydraulic coupling. In the bone marrow, pro-inflammatory cytokines promote fibrotic changes and skew the hematopoietic elements toward the myeloid lineage, which results in an over-production of granulocytes, monocytes/macrophages, erythrocytes, and megakaryocytes. These closely agree with myelopoietic dysregulation in human MC bone marrow. Despite the association of MC with endplate damage and disc inflammation, and the association of endplate damage with disc inflammation, a causal link between bone marrow changes and endplate damage has never been demonstrated. The study of Example 7 reveals that endplate damage and bone marrow changes are closely linked and that endplate damage precedes bone mar row changes in discs infected with *P. acnes*.

*P. acnes*-induced endplate and trabecular bone resorption was observed that are likely caused by catabolic activities. Degenerating discs produce more osteoclastic factors and discs adjacent to MC produce even more. This is supported by observations of more eroded bone surfaces in biopsies from MC1. Additionally, experimental endplate damage has been linked to upregulation of the osteoclastic Receptor Activator of NF-kB Ligand (RANKL) in vivo. While this RANKL upregulation was proposed to be triggered by altered mechanical loads in endplate damage regions, it underscores the importance of endplate damage in reactive marrow changes.

Observation of large amounts of bone resorption within only 2 weeks is unlikely to be due to only cytokines and osteoclastic factors released by disc cells. Direct bone lysis potentiated by propionic acid, a key metabolite of *P. acnes*, is possible as well. Osteolysis is a reported clinical finding that can be caused by *P. acnes*. For example, in acne fulminans, a severe form of acne vulgaris, and in SAPHO (synovitis, acne, pustulosis, hyperostosis, and osteitis) syndrome, *P. acnes* have been recovered from osteolytic bones and bone resorption is a common finding in pyogenic vertebral osteomyelitis that can be caused by *P. acnes*. Furthermore, *P. acnes* also produce lipases which catalyze the breakdown of fats into glycerol and free fatty acids. Bone marrow is rich of fat and hence, lipase draining from the disc into the marrow leads to an accumulation of free fatty acids in the bone marrow. Free fatty acids bind to TLR's, which are expressed on many bone marrow cells (e.g., myeloid cells, dendritic cells, fibroblasts) and further increase the inflammatory burden. Fatty acids also inhibit osteoblast differentiation and promote osteoclast differentiation by binding to Peroxisome proliferator-activated receptor gamma (PPARγ). Furthermore, TLR's are receptors for damage-associated molecular patterns (DAMPs), which include many matrix breakdown products (fibronectin, short hyaluronic acid fragments, collagen-2) that are generated in degenerating discs and endplates. Lastly, *P. acnes* secrete peptidoglycan-polysaccharide, which further increase the total amount of TLR ligands. Consequently, cytokines, bacterial metabolites, and matrix fragments draining from a *P. acnes* infected disc into the bone marrow can directly or indirectly cause reactive bone marrow changes.

MC may have several etiologies, with *P. acnes* infection of the disc being one of them. The shape of MC on sagittal Mill distinguishes infectious from noninfectious etiology, where the absence of a claw-shape (bigger anterior lesion size) is specific for disc infection. This is in agreement with the mid-coronal reaction pattern in MRI and histology, that is, fibrosis, TNF-α and CD3 reactivity, seen in this current study. This observation suggests that the efflux of inflammatory mediators from the disc was highest mid-coronally or that an additional pro-inflammatory reaction specific for the mid-coronal region occurred, such as an autoimmune response against NP material. However, TNF-α and T-cell infiltration overlapped only occasionally. Therefore, T-cells do not appear to be the main source of TNF-α, but rather, inflammation is brought about by an innate immune response. Since T-cells were also found in the anulus fibrosus and NP, they are most likely part of an adaptive immune response against *P. acnes*, which reside within the NP.

Although rat tail bone marrow can be reactive to disc manipulation, the notochordal cell phenotype in rat tail NPs may affect the pathobiology of the bone marrow changes. It should also be noted that the injected dose of *P. acnes* in this current study is likely higher than in the clinical situation of occult *P. acnes* discitis and therefore causes an accelerated pathogenesis. Since the activation thresholds for the innate immune system are largely different in human and rats, the amounts cannot be directly compared. For example LD50 of lipopolysaccharides are 1-4 ng/kg in human and about 10 mg/kg in rats. Nevertheless, the model of Example 7 should be considered as a discitis or spondylodiscitis model rather than a disc degeneration model of low virulent occult discitis. On the other hand, hypointense discs on T2 MRI in this model indicate disc degeneration and is in contrast to findings in patients with spondylodiscitis which have hyperintense disc signals. Furthermore, discitis and spondylodiscitis typically occur in immunocompromised patients and have a clinical presentation. In rabbits, infection of the disc with *Staphylococcus aureus*, the most common reason for spondylodiscitis, can even be lethal. However, the rats showed no signs of discomfort indicative of sepsis. Therefore, subsequent work can investigate the dose-response relationship of intradiscal *P. acnes* injection and reisolate *P.*

*acnes* from injected discs to fulfill Koch's 4th postulate. Yet, the use of a *P. acnes* strain isolated from a human MC1 disc reinforces the clinical relevance of the findings. The different strain types express various amounts of virulence factors and even within one strain type, differences exist. The strain type 2 isolated and used in this study is the most commonly found in disc isolates and has a lower skin occurrence than other strains, which lowers the risk of using a strain introduced by sampling contamination. In contrast, strain type IA is abundant on the skin and expresses considerably lower levels of some virulence factors, which likely lowers the potential to trigger MC1. Nevertheless, it is the most commonly used in *P. acnes* studies. While intravenous injected strain type IA did not home to herniated discs in a rabbit model, it remains to be determined whether this is also true for *P. acnes* type 2. The presented model allows now to investigate the clinical relevance of the different strains.

The appearance of Modic lesions may be sensitive to MR field strength and specific sequence protocols. To maximize resolution and minimize signal-to-noise for this small animal study this study utilized a very high field strength scanner (7 T). Therefore, while this study does demonstrate bone marrow changes consistent with traditional MC, other MR systems could be used. The study of Example 7 indicates that *P. acnes* injected into rat-tail discs can cause changes in the adjacent bone marrow consistent with MC1. Therefore, it is biologically plausible that *P. acnes* can cause MC1 in the clinical setting.

In some embodiments, MRI images can be used to diagnose infection (e.g., a *P. acnes* infection). For example, identification of Modic changes (MC) (e.g., MC1) in MRI images (e.g., for a spine) can be an indication of bacterial infection (e.g., *P. acnes* infection). Analysis of MRI images can be used in conjunction with MRS (e.g., using a propionic acid-related signature) to diagnose a *P. acnes* infection. In some instances, the MRS signature for propionic acid can also be associated with other chemicals (e.g., valine, leucine, and/or isoleucine), which can result in false positive diagnoses of a *P. acnes* infection. Using analysis of MRI images together with the MRS determinations can improve the diagnosis (e.g., by reducing false positives). For example, if an MRS analysis indicates that PA is present (e.g., at a threshold value or score), then a MRI analysis identifying Modic changes can support, confirm, or bolster the diagnosis of *P. acnes* infection. Conversely, if an MRS analysis indicates that PA is present (e.g., at a threshold value or score), then a MRI analysis identifying a lack of Modic could question or change a diagnosis of *P. acnes* infection. A lack of MC can lead to a conclusion that the perceived PA-related measurement was in fact due to one or more other chemicals that have similar MRS signatures.

In some embodiments, a diagnostic processor can be configured to consider both MRS information (e.g., including one or more PA-related measurements) and MRI analysis (e.g., a presence, or absence, or degree of Modic changes) to determine a diagnosis (e.g., of *P. acnes* infection). The diagnostic processor can use a formula, a look-up-table, etc. to determine diagnostic information (e.g., relating to a *P. acnes* infection) based on both MRS and MRI information.

As discussed herein, the spectroscopic identification of a PA spectral signature can provide potential evidence of *P. acnes* infection. As demonstrated in the example, MRI indication of MC1 end plate changes also provides evidence of *P. acnes* infection. Each of these diagnostic applications of MR having been shown to provide such potential evidence, a combination of each indication (e.g., MRS signature of PA and MRI signature of MC1) thus further enhances the diagnostic evidence of the *P. acnes* infection. Accordingly, a combination system and method that uses MRI for a determination of MC1 signature, and uses MRS for determining a PA signature, comprises yet a further aspect of this disclosure.

Further modes of this aspect thus include, without limitation, using such a combination system and method for: diagnosing a disc level as infected; using the combination evidence for screening for potential administration of antibiotic treatment administration; and preparing for administration, and/or actually administering, such an antibiotic treatment (which may be pharmaceutical or other form of molecular entity, energy delivery, etc. as appropriate according to one of ordinary skill for antibiotic treatment).

As would be apparent to one of ordinary skill, such further modes of this aspect are similarly applicable to other aspects, modes, embodiments, and features of this disclosure. Moreover, it is appreciated that the system and method above for using MRI evidence of MC1 in the setting of spinal discs has other correlaries and similarly applicable to other tissues, e.g., MRI evidence of potential infection in a tissue combined with MRS-based signature of potential infection in the same tissue. Such other applications are thus contemplated as yet further aspects of this disclosure.

With reference to FIG. 47, in some embodiments further operations can be performed for using MRI evidence to generate the diagnostic information. For example the method 4700 can include obtaining one or more MRI images (e.g., using the same MR system that is used to produce the MRS spectrum, or from a different source) and analyzing the one or more MRI images to identify a presence, or absence, or degree of an MRI feature (e.g., Modic change (MC)) associated with the region of interest (ROI) (e.g., intervertebral disc). For example, image processing operations can be performed on the one or more MRI images. In some implementations, one or more processed MRI images can be produced, which can be configured to emphasize the MRI feature (e.g., MC). Image processing operations can be performed to automatically identify the presence, or absence, or degree of the MRI feature, and in some cases a value or score can be produced that is associated with the MRI feature. The diagnostic information generated at block 4712 can be based at least in part on the MRI information (e.g., the value or score associated with the targeted MRI feature).

The following publication is hereby incorporated by reference in its entirety: Patel, K. B., et al. "Diffusion-Weighted MRI "Claw Sign" Improves Differentiation of Infectious from Degenerative Modic Type 1 Signal Changes of the Spine," AJNR Am J Neuroradiol 35:1647-52 August 2014. The disclosure of this reference suggests evidence of yet another MRI-based signature related to Modic changes for potential infection identification at disc-vertebral body endplate junction. Further aspects, modes, and embodiments of this disclosure thus combines this use of MRI for identification of such signatures with the other embodiments disclosed herein—and with further value and benefit contemplated by the enhanced diagnostic acuity of such a combinatorial approach.

Example 8

A study was performed relating to identification of a nuclear magnetic resonance (NMR) biomarker for *Propionibacterium acnes* infected intervertebral discs. Discogenic low back pain (LBP) often coincides with vertebral bone marrow lesions (Modic changes). Patients with Modic changes (MC) report a greater frequency and duration of LBP episodes, seek care more often, and have a higher risk for a poor outcome. Bacterial infection of the intervertebral disc can be a causal reason in some MC phenotypes. *P. acnes* produce propionic acid, which has a NMR profile. The goal of the study of Example 8 was to test the feasibility of in vivo magnetic resonance spectroscopy (MRS) to detected *P. acnes* infected of intervertebral discs.

A colony of *P. acnes* was aseptically isolated from a human intervertebral disc with MC type 1. Two experiments were conducted: (1) *P. acnes* were anaerobically cultured and bacterial metabolites were extracted with 6% perchloric acid from dilution series of *P. acnes*. High-resolution NMR at 14 T were recorded. (2) Intervertebral discs were isolated from fresh bovine tails and injected either with 50 µl *P. acnes* ($\sim 10^8$ bacteria) (n=3) or with 50 µl of 650 mM propionic acid at pH7 (n=3). NMR spectra before and after injection were acquired with a 2 cm surface coil at 7 T. Extracts from the discs tissues were prepared and analyzed by high-resolution NMR at 14 T.

Figure 60:
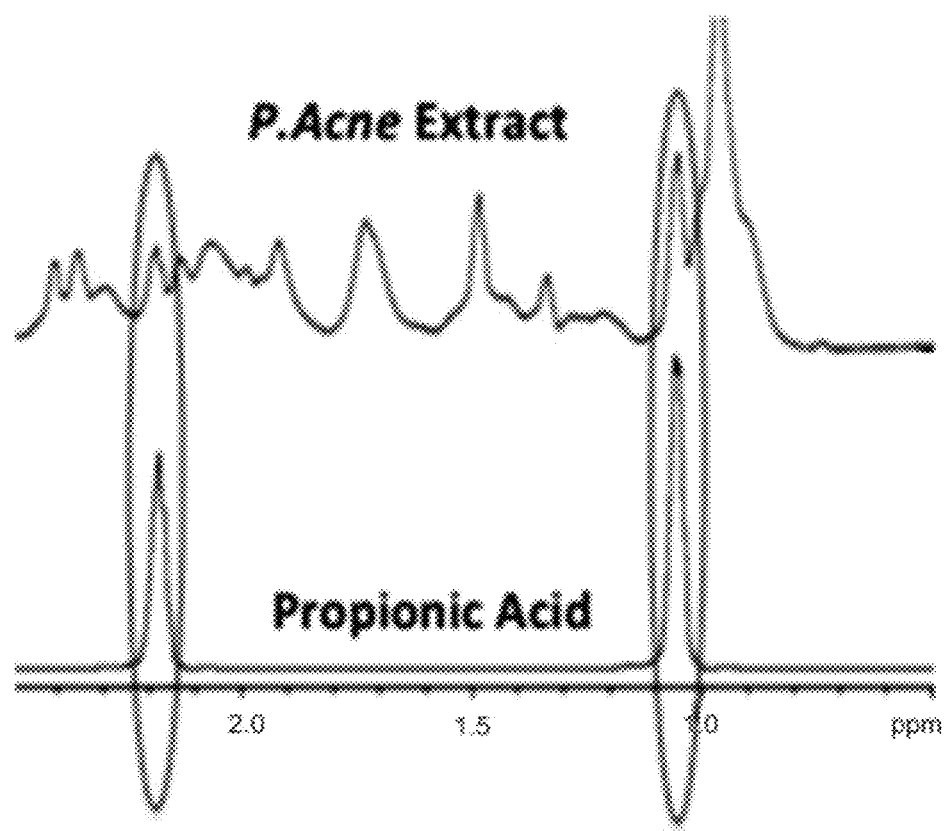
FIG. 60 shows a chart that includes NMR spectra of propionic acid and P. acnes extract.
Figure 61:
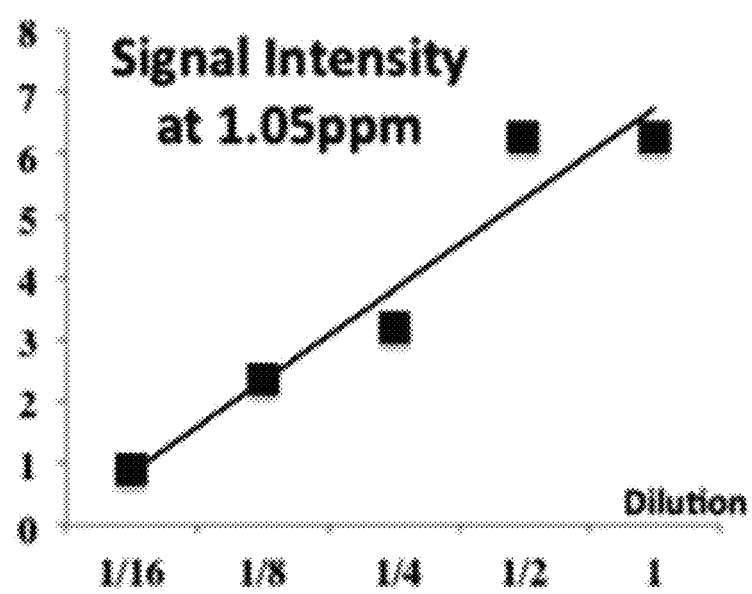
FIG. 61 shows a plot of intensity of the signal at ~1.0 ppm as a function of P. acnes concentration.

For experiment 1, extracts from *P. acnes* show NMR peaks at ~1.0 and ~2.1 ppm. Propionic acid also has peaks at ~1.0 and ~2.1 ppm. FIG. 60 shows a chart that includes NMR spectra of propionic acid and *P. acnes* extract. The *P. acnes* spectrum is offset in vertically from the propionic acid spectrum. The peaks at ~1.0 and ~2.1 ppm are circled in FIG. 60. The intensity of the peak at ~1.0 ppm correlated linearly with the *P. acnes* concentration. FIG. 61 shows a plot of intensity of the signal at ~1.0 ppm as a function of *P. acnes* concentration.

Figure 62:
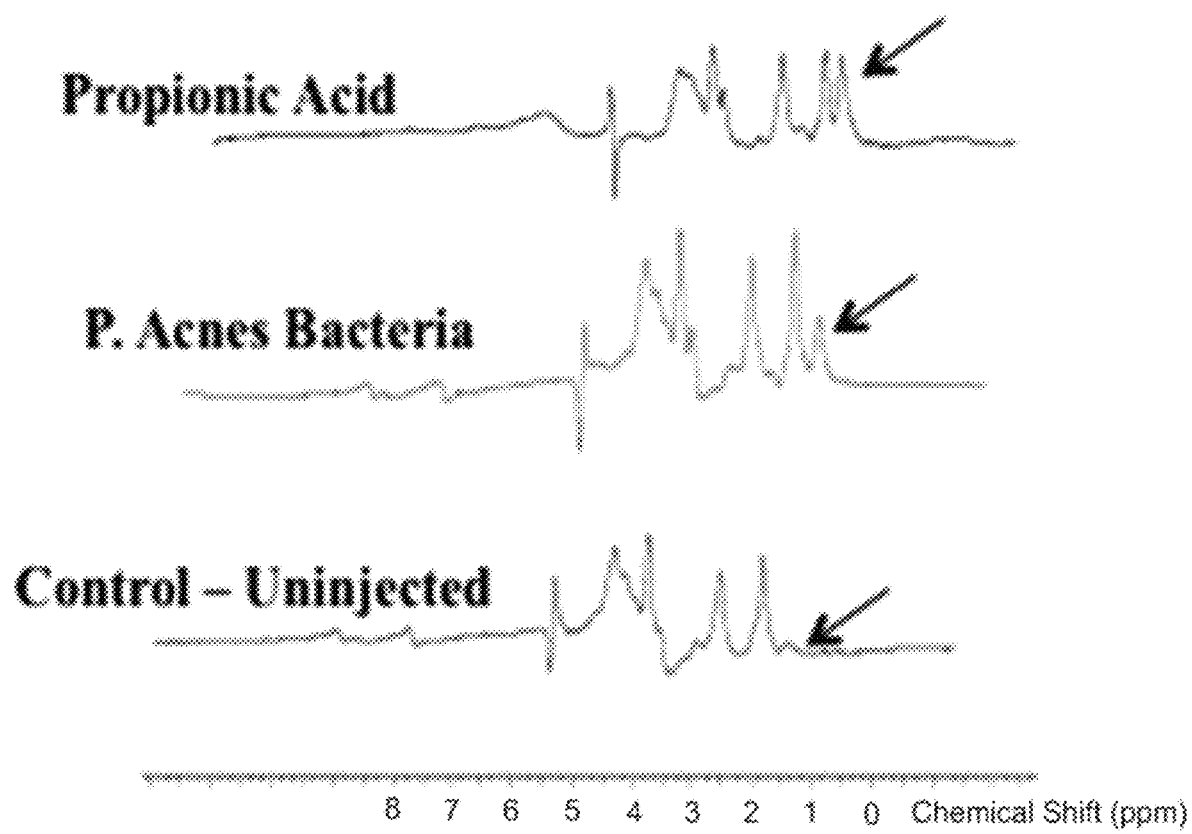
FIG. 62 shows NMR spectra collected from intact bovine tail discs: uninjected bovine disk (bottom line); injected with P. acnes (middle line); and with propionic acid (top line).

For experiment 2, FIG. 62 shows NMR spectra of uninjected bovine disk (bottom line), injected with *P. acnes* (middle line) and with propionic acid (top line). After injection of *P. acnes* (middle line) and propionic acid (top line) into bovine tail discs, MRS revealed an additional peak at ~1.0 ppm.

In this study, the feasibility of utilizing in vivo MRS to detect *P. acnes* infection of intervertebral discs was tested. It was found that extracts from *P. acnes* have NMR signals at ~1.0 ppm and ~2.1 ppm, which are characteristic for propionic acid. Since the ~1.0 ppm peak correlated linearly which the *P. acnes* concentration, this peak is specific for *P. acnes* and can serve as a biomarker, such as for diagnostic methods and systems. In-vivo MRS of *P. acnes* or propionic acid injected bovine tail revealed that the ~1.0 ppm peak of propionic acid is detectable with in vivo MRS. The 2.1 ppm overlaps with proteoglycans and in some cases is not used as biomarker for *P. acnes* infection. This study suggests that *P. acnes* infection of intervertebral discs can be detected with in vivo MRS. NMR signal at near 1.0 ppm can serve as biomarker for *P. acnes* infection.

The methods and processes described herein may have fewer or additional steps or states and the steps or states may be performed in a different order. Not all steps or states need to be reached. The methods and processes described herein may be embodied in, and fully or partially automated via, software code modules executed by one or more general purpose computers. The code modules may be stored in any type of computer-readable medium or other computer storage device (e.g., a non-transitory computer-readable medium). Some or all of the methods may alternatively be embodied in whole or in part in specialized computer hardware. The systems described herein may optionally include displays, user input devices (e.g., touchscreen, keyboard, mouse, voice recognition, etc.), network interfaces, etc. The results of the disclosed methods may be stored in any type of computer data repository, such as relational databases and flat file systems that use volatile and/or non-volatile memory (e.g., magnetic disk storage, optical storage, EEPROM and/or solid state RAM).

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks, steps, and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integer to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "may," "might," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, and at least one of Z to each be present.

Various user inputs may be used, such as voice commands, text entry, gestures, mouse clicks, etc. User inputs may, by way of example, be provided via an interface or in response to a prompt (e.g., a voice or text prompt). By way of example an interface may include text fields, wherein a user provides input by entering text into the field. By way of further example, a user input may be received via a menu selection (e.g., a drop down menu, a list or other arrangement via which the user can check via a check box or otherwise make a selection or selections, a group of individually selectable icons, a menu selection made via an interactive voice response system, etc.). When the user provides an input or activates a control, a corresponding computing system may perform a corresponding operation (e.g., store the user input, process the user input, provide a response to the user input, etc.). Some or all of the data, inputs and instructions provided by a user may optionally be stored in a system data store (e.g., a database), from which the system may access and retrieve such data, inputs, and instructions. The notifications and user interfaces described herein may be provided via a Web page, a dedicated or non-dedicated phone application, computer application, a short messaging service message (e.g., SMS, MMS, etc.), instant messaging, email, push notification, audibly, and/or otherwise.

The user terminals described herein may be in the form of a desktop computer, mobile communication device (e.g., a cell phone, a Von' equipped mobile device, etc.), laptop, tablet computer, interactive television, game console, media streaming device, head-wearable display, virtual reality display/headset, augmented reality display/headset, networked watch, etc. The user terminals may optionally include displays, user input devices (e.g., touchscreen, keyboard, mouse, voice recognition, etc.), network interfaces, etc.

The present disclosure describes various aspects, modes, embodiments, variations, and features, each is not necessarily tied nor solely responsible for each of the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various steps or phases. It will be understood that in many cases, certain steps and/or phases may be combined together such that multiple steps and/or phases can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed. While various further embodiments are described below as "claims," and are not intended to be necessarily limited by features in the disclosure above, their respective combinations with the embodiments of the above disclosure are also contemplated hereunder as yet further embodiments of this disclosure. Also, some representative features are listed below and their respective combinations with the embodiments of the above disclosure are also contemplated hereunder as yet further embodiments of this disclosure Description of Some Representative Features 1. A magnetic resonance spectroscopy (MRS) processing system configured to process a repetitive frame MRS spectral acquisition series generated and acquired for a voxel principally located within an intervertebral disc via an MRS pulse sequence, and acquired at multiple parallel acquisition channels of a multi-coil spine detector assembly, in order to provide diagnostic information associated with the disc, comprising:

an MRS signal processor comprising a channel selector, a phase shift corrector, a frequency shift corrector, a frame editor, and a channel combiner, and configured to receive and process the MRS spectral acquisition series for the disc and to generate a processed MRS spectrum for the series with sufficient signal-to-noise ratio (SNR) to acquire information associated with identifiable features along MRS spectral regions associated with unique chemical constituents in the disc; and an MRS diagnostic processor configured to extract data from at least one identifiable chemical region in the processed MRS spectrum, and comprising a region corresponding with propionic acid (PA), in a manner that provides diagnostic information for diagnosing a medical condition or chemical environment associated with the disc.

2. The MRS processing system of feature 1, wherein the MRS diagnostic processor is configured to provide diagnostic information for diagnosing the disc as painful or non-painful, or infected by bacteria.

3. The MRS processing system of feature 1, wherein the MRS diagnostic processor is configured to diagnose the disc as painful or non-painful, or infected by bacteria, and to indicate the diagnosis to a user.

4. The MRS processing system of feature 1, wherein the MRS signal processor and MRS diagnostic processor are provided in a computer readable storage medium.

5. The MRS processing system of feature 1, further comprising a diagnostic display comprising a visual indicator overlay onto an MRI image of a region of the spine that includes the disc.

6. The MRS processing system of feature 1, wherein at least one of the channel selector, phase shift corrector, frequency shift corrector, and frame editor comprises a water detector and is configured to operate at least in part based on the ability to detect water.

7. The MRS processing system of feature 1, wherein the diagnostic processor is configured to calculate a diagnostic value associated with at least one of degenerative pain or bacterial infection based at least in part on a combination of (i) at least one measured feature of the signal along at least one region of the processed MRS spectrum associated with PA, and (ii) at least one measured feature of the signal along at least one region of the processed MRS spectrum associated with another chemical comprising proteoglycan, lactate, or alanine chemicals.

8. The MRS processing system of feature 7, wherein the diagnostic value is derived from at least one calculated ratio between at least two said measured features along at least two said regions associated with at least two said chemicals, wherein at least one said chemical comprises PA.

9. The MRS processing system of feature 7, wherein the diagnostic value is further based at least in part upon a contained volume of the voxel.

10. A magnetic resonance spectroscopy (MRS) processing method for processing a repetitive frame MRS spectral acquisition series generated and acquired for a voxel principally located within an intervertebral disc via an MRS pulse sequence, and acquired at multiple parallel acquisition channels of a multi-coil spine detector assembly, and for providing diagnostic information associated with the disc, comprising:
receiving the MRS spectral acquisition series from the multiple acquisition channels;
signal processing the MRS acquisition series, comprising selecting one or more channels among the parallel channels based upon a predetermined criteria, recognizing and correcting phase shift error among multiple frames within the series of a channel acquisition, recognizing and correcting a frequency shift error between multiple frames within the series of the channel acquisition, recognizing and editing out frames from the series based upon a predetermined criteria, combining selected and corrected channels for a combined average processed MRS spectrum; and
diagnostically processing the processed MRS spectrum by extracting data from at least one identifiable chemical region in the processed MRS spectrum, and comprising a region corresponding at least in part with propionic acid (PA), and processing the extracted data in a manner that provides MRS-based diagnostic information for diagnosing a medical condition or chemical environment associated with the disc.

11. The method of feature 10, wherein the MRS-based diagnostic information provided is useful for diagnosing the disc as painful or non-painful, or as infected by bacteria.

12. The method of feature 10, further comprising diagnosing the disc as either painful or non-painful, or as infected by bacteria, based upon the MRS-based diagnostic information.

13. The method of feature 10, further comprising displaying the diagnostic MRS-based information as a visual indicator overlay onto an MRI image of a region of the spine that includes the disc.

14. The method of feature 10, further comprising performing at least one of channel selection, phase shift correction, frequency shift correction, and frame editing based upon detection of a feature of water signal among the acquisition frames.

15. The method of feature 10, further comprising providing the diagnostic information based at least in part on measuring a combination of (i) at least one feature of the signal along at least one region of the processed MRS spectrum associated with proteoglycan, lactate, and alanine chemicals, and (ii) at least one feature of the signal along at least one region of the processed MRS spectrum associated with PA.

16. The method of feature 15, further comprising calculating at least one ratio between at least two said measured features along at least two said regions associated with at least two said chemicals, wherein at least one said chemical comprises PA.

17. The method of feature 15, further comprising deriving the diagnostic information based at least in part upon a calculated contained volume of the voxel.

18. The system of feature 1, wherein the MRS signal processor further comprises an apodizer configured to apodize an MRS spectrum.

19. The method of feature 10, further comprising apodizing an MRS spectrum.

20. A medical diagnostic system, comprising:
a signal processor configured to signal process a repetitive multi-frame MRS pulse sequence acquisition series of MRS spectra frames received from multiple acquisition channels of a detector assembly during a MRS pulse sequence series conducted on a region of interest (ROI) within a tissue in a body of a subject;
wherein the signal processor comprises a channel selector configured to measure a parameter related to MRS spectral signal quality for the acquired MRS spectral series from each acquisition channel, compare the measured parameters for the respective channels against at least one threshold criteria for channel selection, identify a number of selected channels which meet or exceed the threshold criteria and a number of other failed channels which fail to meet the threshold criteria, and retain the selected channels and discard the failed channels from the acquisition series; and
a diagnostic processor configured to measure a spectral feature along a region of a post-processed spectrum produced by the signal processor, wherein the region corresponds with propionic acid (PA).

21. A medical diagnostic system, comprising:
a signal processor configured to process a repetitive multi-frame MRS pulse sequence acquisition series of MRS spectra frames received from an acquisition channel of a detector assembly during a MRS pulse sequence series conducted on a region of interest (ROI) within a tissue in a body of a subject;
wherein the signal processor comprises a frame editor configured to measure a parameter related to signal quality for the MRS spectrum for each acquired frame of the acquisition series, compare the measured values for the parameter for the respective frames against a threshold criteria, and designate a number of successful frames that meet the threshold criteria and a number of failed frames that fail to meet the threshold criteria;
wherein the frame editor is further configured to retain successful frames in the acquisition series, and edit out the failed frames from the acquisition series if number of successful frames meets or exceeds a minimum frame number threshold, but to retain at least some of the failed frames in the acquisition series if the number of successful frames is below the minimum frame number threshold; and
a diagnostic processor configured to measure a spectral feature along a region of a post-processed spectrum produced by the signal processor, wherein the region corresponds with propionic acid (PA).

22. A medical diagnostic system, comprising:

a signal processor configured to process a repetitive multi-frame MRS pulse sequence acquisition series of MRS spectra frames received from an acquisition channel of a detector assembly during a MRS pulse sequence series conducted on a region of interest (ROI) within a tissue in a body of a subject;

wherein the signal processor comprises a frequency error corrector configured to calculate a confidence level in an ability to estimate frequency shift error for the MRS spectra of each frame of the series, compare each calculated confidence level for each frame against at least one threshold criteria, and determine a number of successful frames that meet or exceed the threshold criteria and a number of other failed frames that fail to meet the threshold criteria;

wherein the signal processor is further configured to automatically determine whether to (a) edit out the failed frames from the acquisition series and perform frequency shift error correction via the frequency error corrector in a manner to at least in part reverse the frequency shift error estimate on each of the successful frames, if the number of successful frames meets or exceeds a minimum threshold number, or (b) retain at least some of the failed frames and not perform frequency error correction to the series via the frequency error corrector if the number of successful frames is below the minimum threshold; and a diagnostic processor configured to measure a spectral feature along a region of a post-processed spectrum produced by the signal processor, wherein the region corresponds with propionic acid (PA).

23. A medical diagnostic system, comprising:

a signal quality evaluator configured to automatically determine whether or not an MRS spectrum acquired from a region of interest (ROI) in a tissue in a body of a subject via an MRS pulse sequence series exam of the ROI comprises a regional signature signal along the MRS spectrum that is characteristic of lipid.

24. A medical diagnostic system, comprising:

a diagnostic processor configured to provide diagnostic information for diagnosing a medical condition or chemical environment associated with a region of interest (ROI) in a tissue in a body of a subject based at least in part upon at least one chemical factor related to information extracted from the ROI and associated with propionic acid (PA), and which may also be in combination with at least one other chemical factor and which may be associated with at least one of lactate (LA) and alanine (AL) chemicals.

25. A medical diagnostic system, comprising:

a diagnostic processor configured to provide diagnostic information for diagnosing a medical condition or chemical environment associated with a region of interest (ROI) in a tissue in a body of a subject based at least in part upon a chemical factor related to information extracted from the ROI and associated with a propionic acid (PA) chemical and as adjusted by an adjustment factor that comprises at least one of a voxel-related adjustment factor associated with a voxel prescribed to correspond with the ROI and related to the information extracted, and a subject-dependent variable-related adjustment factor associated with the subject.

26. A medical diagnostic system, comprising:

a diagnostic processor configured to provide diagnostic processed information for diagnosing a medical condition or chemical environment associated with a region of interest (ROI) in a tissue in a body of a subject based at least in part upon taking a first MRS measurement for a propionic acid (PA) chemical factor taken at a region of an MRS spectrum acquired from the ROI and associated with a chemical and comparing the first MRS measurement against a value derived from a different second measurement and that is associated with an amount of the PA in the ROI.

27. A medical diagnostic system, comprising:

a diagnostic processor configured to provide diagnostic information for diagnosing a medical condition or chemical environment associated with a region of interest (ROI) of a tissue in a body of a subject based at least in part upon a chemical factor related to information extracted from the ROI and associated with a propionic acid (PA) chemical; and wherein said diagnostic information comprises a probability value assigned to a likelihood that the medical condition or chemical environment meets certain criteria in the ROI.

28. The system of feature 20, wherein:

the channel selector is configured to automatically differentiate relatively stronger from weaker channel acquisitions received.

29. The system of feature 20, wherein:

the channel selector is configured to determine and select a strongest single channel acquisition signal among the multiple channel acquisitions.

30. The system of feature 29, wherein:

the channel selector is configured to determine and select the strongest single channel acquisition based upon a highest measured value for a parameter of the single channel's acquired MRS spectral series relative to the measured values for similar parameters for the acquired MRS spectral series from the other channels, and wherein the parameter comprises at least one of amplitude, power, or signal-to-noise ratio (SNR) of a recognized reference signal in the respective MRS spectra.

31. The system of feature 29, wherein the channel selector is configured to determine and select a set of multiple channels considered strongest channels based upon the respective measured values for the parameters for the MRS spectral series from each of said channels satisfying a range threshold based from the highest measured value of the strongest single channel.

32. The system of feature 20, wherein the channel selector is configured to evaluate at least two first and second reference signals in the MRS spectrum and to determine which among them to use as the reference signal in the channel selection, based upon relative signal quality of the respective first and second reference signals for such use.

33. The system of feature 32, wherein the reference signal comprises a water signal in the spectrum.

34. The system of feature 20, wherein the selection is based upon a frame averaged spectrum of the MRS pulse sequence series acquired from the channel.

35. The system of feature 20, wherein the measured parameter comprises a measured feature of a water signal region of the acquired MRS spectra in unsuppressed water frames of the acquired series for the channels.

36. The system of feature 35, wherein the MRS pulse sequence comprises a CHESS-PRESS sequence, and the measured feature of the water signal region is acquired for one or more frames with the CHESS sequence disabled.

37. The system of feature 20, wherein:

the measured parameter comprises a signal: noise ratio (SNR) measurement.

38. The system of feature 37, wherein the SNR is calculated at least in part by obtaining an average power value for signal along a first earlier portion of unsuppressed water FID frames, and an average power value for noise in a second later portion of the unsuppressed water FID frames.

39. The system of feature 38, wherein the first earlier portion comprises about the first 100 data points, and the second later portion comprises about the last 100 points, each respectively of the unsuppressed water FID frames.

40. The system of feature 37, wherein a first channel with the largest SNR, and other channels within a pre-determined SNR range of that first channel's largest SNR, are selected.

41. The system of feature 40, wherein the pre-determined range comprises about 3 dB.

42. The system of feature 21, wherein the frame editor is configured to recognize poor quality acquisition frames of a channel acquisition series, as determined by the comparison of the measured parameter value for said frames against the threshold criteria.

43. The system of feature 42, wherein the frame editor is configured to recognize poor quality acquisition frames of a channel acquisition series, as determined based upon a threshold value applied to error in peak location of a recognized reference signal of the MR spectrum from an assigned baseline location.

44. The system of feature 43, wherein the frame editor is configured to determine a confidence level in an ability to recognize a peak location of a reference signal for each frame spectrum of the channel series, compare the confidence level against a threshold confidence interval applied to the reference peak location ability, and recognize poor quality frames of the series as falling outside of the confidence interval.

45. The system of feature 43, wherein the frame editor is configured to recognize poor quality frames based upon a confidence in the frequency error estimate for a peak reference signal in the frame MRS spectrum.

46. The system of feature 43, wherein the frame editor is configured to recognize poor quality frames based upon a frequency error estimate for a location of a peak reference signal in the frame MRS spectrum.

47. The system of feature 43, wherein the frame editor is configured to recognize poor quality frames based upon both an estimated confidence in a frequency error estimate and the frequency error estimate for the frames based on analyzing the characteristics of the peak and the noise in a band across a proscribed range around the center-tuned frequency for the peak location for the channel series.

48. The system of any one of features 43-47, wherein the reference signal comprises residual water in water suppressed frames of the acquisition series.

49. The system of feature 47, wherein the band comprises a proscribed range of between about 40 Hz and about 80 Hz, the largest peak in the band is assumed to be the water peak and which is qualified by the confidence estimate.

50. The system of feature 49, wherein the MRS pulse sequence series is conducted via a 3.0 Tesla MR system and the range is about 80 Hz 51. The system of feature 49, wherein the MRS pulse sequence series is conducted via a 1.5T MR system and the range is about 40 Hz.

52. The system of feature 47, wherein the frame editor is configured to recognize a frame as poor quality and designate the frame as a failed frame if the confidence estimate does not meet or exceed a pre-determined threshold criteria value.

53. The system of feature 52, wherein the pre-determined threshold criteria value is about 0.7.

54. The system of feature 52, wherein the pre-determined threshold criteria value is about 0.8.

55. The system of feature 21, wherein the minimum frame number threshold is about 96 frames.

56. The system of feature 21, wherein the frame editor is configured to operate on the MRS spectra of the channel acquisition series in the frequency domain.

57. The system of feature 21, wherein the frame editor is configured to operate on the MRS spectra of the channel acquisition series after phase error correction of the channel series in the time domain, and then transformation from the time domain into the frequency domain prior to frame editing.

58. The system of feature 21, wherein frame editor is configured to identify frames from a channel series which present a signal quality that varies sufficiently from an expected or observed acquisition result across other frames such that they should be excluded.

59. The system of feature 21, wherein the signal processor further comprises at least one additional signal processing operator comprising at least one of a channel selector, phase shift corrector, an apodizer, a frequency shift corrector, and a channel combiner, and which is configured to further signal process the MRS pulse sequence acquisition series according to at least one other signal processing operation in addition to the frame editing conducted by the frame editor.

60. The system of feature 59, wherein the frame editor is configured to perform the frame editing after the at least one other signal processing operation is conducted on the acquired MRS pulse sequence series.

61. The system of feature 59, wherein the frame editor is configured to perform the frame editing prior to the at least one other signal processing operation which is configured to be performed on only the acquired MRS pulse sequence series frames retained by the frame editor.

62. The system of feature 59, wherein the frame editor is configured to perform the frame editing after channel selection of multiple said acquisition channels acquiring the acquired series frames in parallel, and prior to frequency correction of the channel selected and frame edited acquisition series.

63. The system of feature 62, wherein the frame editor is configured to edit frames determined to comprise lipid signal from frames determined to be substantially without lipid signal.

64. The system of feature 22, wherein the frequency error corrector is further configured to perform the frequency shift error correction for a frame at least in part by determining a relative shift error of a respective identified reference peak location in the frame relative to a reference baseline location assigned for the reference peak, and correcting for the relative shift error by applying a correction shift to the MRS spectrum of the respective frame that equals the inverse of the identified relative shift error for the frame.

65. The system of feature 23, wherein the signal quality evaluator is configured to determine the regional signature signal that is characteristic of lipid based upon at least one of peak value, power value, or SNR value exceeding a predetermined ratio, or a relationship between peak and line width of the signal.

66. The system of feature 23, wherein the signal quality evaluator is configured to evaluate individual or sub-sets of frames of the MRS acquisition series, and further comprising a frame editor which is configured to edit acquisition series frames which contain lipid signal signatures from frames which do not as determined by the signal quality evaluator.

67. The system of feature 23, wherein the signal quality evaluator is configured to monitor signal quality and determine the presence or absence of lipid signal signature in an MRS acquisition series while the MRS pulse sequence series is being conducted on the ROI.

68. The system of feature 67, further comprising a feedback control system configured to enable modification of at least one parameter of the MRS pulse sequence during an exam based upon the monitored signal quality and lipid signal signature determination.

69. The system of feature 68, wherein the feedback control system is configured to allow re-prescription of a voxel with respect to a ROI associated with the MRS pulse sequence exam as directed in response to the determination of lipid signal signature in the MRS spectral acquisition.

70. The system of feature 23, wherein the signal quality evaluator is configured to determine the presence or absence of lipid signal signature for a portion of an MRS acquisition series via post-signal processing after the MRS pulse sequence series exam is conducted.

71. The system of feature 23, wherein the signal quality evaluator is configured to determine the presence or absence of the lipid signal for a final processed averaged MRS spectrum resulting from an MRS pulse sequence series exam.

72. The system of feature 23, further comprising a signal processor with a lipid editor that is configured to perform a signal processing routine that is configured to edit out a lipid signal signature from the MRS spectrum.

73. The system of feature 71, further comprising:
a diagnostic processor configured to provide diagnostic information for diagnosing a medical condition or chemical environment associated with the ROI based at least in part upon at least one chemical factor related to information extracted from the MRS spectra acquired from the ROI, and that is configured to process such extracted information from MRS spectra that comprise lipid signal signature separately from MRS spectral information related to MRS spectra that do not.

74. The system of feature 24, wherein said at least one chemical factor comprises a single chemical factor related to a combination of (i) a propionic acid (PA)-related measurement, and (ii) another chemical-related measurement comprising at least one of LA-related and AL-related measurements associated with the ROI.

75. The system of feature 74, wherein the one chemical factor comprises a combined estimated or measured concentration for both the PA and the other chemical in the ROI.

76. The system of feature 74, wherein the one chemical factor comprises a combined estimated or measured amount for both the PA and the other chemical in the ROI.

77. The system of feature 74, wherein the one chemical factor comprises a maximum estimated or measured concentration for either of the PA and the other chemical in the ROI.

78. The system of feature 74, wherein the one chemical factor comprises a maximum estimated or measured amount for either of the PA and the other chemical in the ROI.

79. The system of feature 24, wherein the one chemical factor provides a biomarker for at least one of hypoxia and bacterial infection in the ROI.

80. The system of feature 24, wherein the diagnostic processor is configured to provide the diagnostic information based upon another chemical factor related to information extracted from the ROI and associated with a third chemical.

81. The system of feature 80, wherein the other chemical factor comprises at least one of an AL-related, LA-related, proteoglycan-related, GAG-related, and collagen-related factor.

82. The system of feature 81, wherein the third chemical comprises at least one of AL, LA, proteoglycan, GAG, and collagen.

83. The system of feature 24, wherein the diagnostic processor comprises an MRS diagnostic processor configured to provide the diagnostic information based at least in part upon information extracted from at least two regions of an MRS spectrum acquired from a voxel prescribed to correspond with the ROI according to an MRS pulse sequence series exam, and which two regions are associated with PA and LA.

84. The system of feature 83, wherein the MRS diagnostic processor is configured to provide the diagnostic information based at least in part upon a maximum peak value measured between at least each of the PA-related and LA-related regions of the MRS spectrum.

85. The system of feature 83, wherein the MRS diagnostic processor is configured to provide the diagnostic information based at least in part upon a combination of peak values at least at each of the PA-related and LA-related regions of the MRS spectrum.

86. The system of feature 83, wherein the MRS diagnostic processor is configured to provide the diagnostic information based at least in part upon a combined measured power between each of at least the PA-related and LA-related regions of the MRS spectrum.

87. The system of feature 83, wherein the MRS diagnostic processor is configured to provide the diagnostic information based at least in part upon information extracted from a combination ALPA region that comprises a combination of the PA, LA, and AL-related regions of the MRS spectrum combined.

88. The system of feature 87, wherein the MRS diagnostic processor is configured to provide the diagnostic information based at least in part upon a maximum peak value measured in the ALPA region of the MRS spectrum.

89. The system of feature 87, wherein the MRS diagnostic processor is configured to provide the diagnostic information based at least in part upon a total power value measured in the ALPA region of the MRS spectrum.

90. The system of feature 89, wherein the total power value measured in the ALPA region of the MRS spectrum comprises an integrated area under the curve (AUC) for the ALPA region.

91. The system of feature 83, wherein the MRS diagnostic processor is configured to provide the diagnostic information to diagnose a medical condition or chemical environment associated with an intervertebral disc in a spine of a subject based upon the extracted information from the MRS spectrum taken from a voxel prescribed to correspond with the ROI in the disc nucleus.

92. The system of any one of features 20-25, further comprising a MRS diagnostic processor configured to provide the diagnostic information to diagnose a medical condition or chemical environment associated with an intervertebral disc in a spine of a subject based upon the extracted information from an MRS spectrum taken from a voxel prescribed to correspond with the ROI in the disc nucleus.

93. The system of Feature 25, wherein the adjustment factor comprises a combination of the voxel-related adjustent factor and other subject-dependent variable-related adjustment factor.

94. The system of feature 25, wherein the voxel-related adjustment factor comprises a volume of the voxel as a divisor to the chemical factor.

95. The system of feature 25, wherein the other subject-dependent variable-related adjustment factor comprises a factor related to a subject-dependent variable such as at least one of height, weight, % body fat, body mass index (BMI), gender.

96. The system of feature 25, wherein the subject-dependent variable-related adjustment factor comprises a BMI-adjustment factor which is a BMI value calculated for the subject and divided by a mean BMI derived empirically either by a test population used to derive the diagnostically correlative relationship or as may be otherwise established.

97. The system of feature 91 or 92, wherein the diagnostic information is based at least in part upon a relationship between measurements taken at regions of the MRS spectrum associated with PG, LA, AL, and PA chemicals.

98. The system of feature 97, wherein the relationship comprises at least one of factors: LAAL/PG, LAAL/CA, maxALPA/PG, maxALPA/CA, sumALPA/PG, and sumALPA/CA; and wherein "PG" is a spectral feature measurement along the PG region of the MRS spectrum, "LAAL" is a spectral feature measurement in a combined LA and AL (LAAL) region of the MRS spectrum corresponding with a combination of LA and AL regions of the spectrum, "CA" is a spectral feature measurement along the carbohydrate (CA) region of the MRS spectrum, "maxALPA" is a spectral feature measurement for a maximum peak region along a combined AL, LA, and PA (ALPA) region of the MRS spectrum, "sumALPA" is a combined sum of spectral peak feature measurements for multiple peaks identified along the ALPA region, and the spectral feature comprises at least one of peak value, signal:noise ratio (SNR), and area under the curve (AUC) for a respective peak along the MRS spectrum.

99. The system of feature 98, wherein the diagnostic information is based upon a combination of said ratios in a weighted factor relationship providing a score based upon a differential weighting between the ratios and that is useful for determining whether a disc may be at least one of (i) painful or non-painful and (ii) infected by bacteria.

100. The system of feature 97, wherein the relationship is based upon factors: BALPA, VBALPA, MAXALPA, and PG;

wherein "BALPA" is a spectral feature measurement for the ALPA region adjusted by a body mass index (BMI) adjustment factor, "VBALPA" is a sum of spectral feature measurements taken in AL, LA, and PA regions (ALPA) and as adjusted by a first adjustment factor associated with a volume of the voxel corresponding with the ROI volume (V) and a second adjustment factor associated with BMI, "MAXALPA" is a maximum of spectral feature measurements taken at either the AL, LA, or PA regions, and "PG" is a spectral feature measurement value at the PG region of the MRS spectrum and associated with n-acetyl acetate.

101. The system of feature 100, wherein the relationship is furthermore based upon factors: BALPA, VBALPA, MAXALPA/PG, MAXALPA/CA, and MAXALPA/VOL, where "VOL" is also V (voxel volume).

102. The system of feature 101, wherein the diagnostic information is based upon the following weighted factor relationship providing a threshold for determining whether a disc may be painful or non-painful, or infected by bacteria: Threshold=C1+C2*(BLA)-C3*(VBALPA-C4)* (VBALPA-C5)+C6*(PG/MAXALPA-C7)*(PG/MAX-ALPA-C8)*(PG/MAXALPA-C9)+C10*(MAXALPA/VOL-C11)*(VBALPA-C12)-C13*(VBALPA-C14)$^2$* (MAXALPA/VOL-C15), wherein C1-C15 are constants and ALPA in at least one of the associated variables comprises either a sum or a maximum of spectral feature measurements for one or more peaks along the ALPA region.

103. The system of feature 24, wherein the diagnostic processor is configured to provide the diagnostic information based upon a relationship between (i) at least one of PG-related and CA-related, and (ii) at least one of LA-related, AL-related, and PA-related, factors associated with the ROI.

104. The system of feature 91, wherein said relationship comprises a ratio between a PG-related measurement and at least one of a LA-related measurement, AL-related measurement, and PA-related measurement.

105. The system of feature 92, wherein the relationship comprises at least two of LAAL/PG, LAAL/CA, maxALPA/PG, maxALPA/CA, sumALPA/PG, and sumALPA/CA.

106. The system of feature 92, wherein the relationship further comprises PG and ALPA, as both divided by a voxel volume of a voxel, and/or a BMI-adjustment factor.

107. The system of feature 97, wherein the relationship further comprises a differentiating between first and second disc groups having relatively unique lipid-related signatures, applying a first relationship to discs having lipid and a second relationship for discs not having lipid.

108. The system of feature 107, wherein the diagnostic processor is further configured to apply the second relationship to the second group, though while passing those of the second group not meeting certain criteria of the second relationship are passed onward to yet a third group and third relationship applied.

109. The system of feature 108, wherein the first relationship comprises factors: LAVV, PG, and LAALVVBMI, where "LAVVBMI" equals a voxel volume and BMI adjusted LA peak value, and LAALVVBMI is similarly adjusted factor but for combination LA and AL (LAAL) peak values, and wherein a PA-related value is further included in at least one of said factors.

110. The system of feature 109, wherein the diagnostic information is based upon the following weighted factor relationship providing a threshold for determining whether a disc may be painful or non-painful, or infected by bacteria: Threshold=-(C1+C2*(LAVVBMI)$^2$+C3*(PG/(LAALVVBMI))), where LAVVBMI equals the voxel volume and BMI adjusted LA peak value, wherein C1-C3 are constants, and wherein a PA-related value is further included in such weighted factor relationship.

111. The system of feature 108, wherein the second relationship comprises factors PG and MAXLAAL or MAXALPA, wherein "PG" is proteoglycan-related regional measurements of the MRS spectrum, and MAXLAAL is the maximum value between the combined LAAL region of the spectrum, and MAXALPA is the maximum value between the combined ALPA region of the spectrum.

112. The system of feature 111, wherein the second relationship comprises a factor PG/MAXLAAL or its inverse, or MAXALPA/PG, or its inverse.

113. The system of feature 112, wherein the diagnostic information is based upon the following weighted factor second relationship providing a threshold for determining whether a disc may be painful or non-painful, or infected by bacteria: Threshold=-(C1+C2*(PG(MAXLAAL))); where PG/MAXLAAL equals the PG peak value divided by the maximum peak value of the LAAL region, wherein C1-C2 are constants, and further wherein a PA-related factor is further included in such weighted factor relationship.

114. The system of feature 108, a third relationship based upon discs not meeting threshold criteria of first and second relationships comprises the following factors: LAVVBMI, ALVVBMI, ALAUCVVBMI, and PGAUCVVBMI; where LAVVBMI is the voxel volume and BMI adjusted LA peak value, ALVVBMI is the voxel volume and BMI adjusted AL peak value, ALAUCVVBMI is the AL region area under the curve as voxel volume and BMI adjusted, and PGAUCVVBMI is the PG region area under the curve as voxel volume and BMI adjusted, and wherein a PA-related factor is further included in such weighted factor relationship.

115. The system of feature 114, wherein the third relationship further comprises: Score=C1*(C2+C3*LAVVBMI−C4*ALVVBMI+C5*ALAUCVVBMI−C6*SQRT(PGAUCVVBMI)), wherein C1-C6 comprise constants, and further wherein a PA-related factor is further included in such weighted factor relationship.

116. The system of feature 108, a third relationship based upon discs not meeting threshold criteria of first and second relationships comprises the following factors: LAVVBMI, ALVVBMI, ALAUCVVBMI, and PGAUCVVBMI; where LAVVBMI is the voxel volume and BMI adjusted LA peak value, ALVVBMI is the voxel volume and BMI adjusted AL peak value, ALAUCVVBMI is the AL region area under the curve as voxel volume and BMI adjusted, and PGAUCVVBMI is the PG region area under the curve as voxel volume and BMI adjusted, and wherein a PA-related factor is further included in such weighted factor relationship.

117. The system of feature 116, wherein the third relationship further comprises: Score=C1*(C2+C3*LAVVBMI−C4*ALVVBMI+C5*ALAUCVVBMI−C6*SQRT(PGAUCVVBMI)), wherein C1-C6 comprise constants, and a PA-related factor is further included in such weighted factor relationship.

118. The system of feature 26, wherein the different second measurement comprises at least one of a T1-rho pulse sequence measurement, a sodium (NA+) imaging pulse sequence measurement, a chemical assay measurement, a quantified molecular imaging measurement.

119. The system of feature 26, wherein the first MRS measurement comprises a measurement taken at an MRS spectral region associated with PG and compared against the derived value from the second measurement.

120. The system of feature 26, wherein the comparison with the second measurement comprises a calibration of the first MRS measurement with respect to the chemical in the ROI.

121. The system of feature 120, based upon said calibration the first MRS measurement is configured to estimate concentration for the chemical in the ROI.

122. The system of feature 26, wherein the second measurement comprises a measurement for water via T2 MRI used to calibrate a water peak signal according to an MRS acquisition, which may thereafter be used to calibrate other regions of the MRS spectra.

123. The system of any one of features 1, 20-27, or 73, further comprising a MRS diagnostic processor configured to calculate and provide diagnostic information for diagnosing pain or bacterial infection associated with, or a chemical environment within, at least one intervertebral disc based upon at least one signal processed MRS spectral region associated with propionic acid and at least one of proteoglycan, lactate, and alanine chemicals.

124. The system of any one of features 1, 20-27, or 73, wherein the diagnostic processor is configured to provide diagnostic information related to a medical condition or chemical environment in each disc of a lower lumbar spine.

125. The system of feature 124, wherein the information comprises a single calculated score via the developed set of criteria based upon weighted factors derived from regions of the acquired MRS signals and associated with at least four chemicals comprising proteoglycan (PG), lactic acid (LA), alanine (AL), and propionic acid (PA).

126. The system of any one of features 30, 32, 33, 43, 44, 45, 46, or 126, wherein the reference signal comprises a non-water chemical signal in the spectrum.

127. The system of feature 126, wherein the reference signal comprises a target chemical biomarker related to the diagnosis of the medical condition or chemical environment of the region of interest.

128. The system of feature 127, wherein the reference signal comprises a proteoglycan (PG)-related region of the MRS spectrum.

129. The system of feature 128, wherein the reference signal comprises an n-acetyl acetate (NAA)-related region of the MRS spectrum.

130. The system of feature 127, wherein the reference signal comprises a lactic acid (LA)-related, alanine (AL)-related, or propionic acid (PA)-related region of the MRS spectrum.

131. The system of any one of features 20, 22, or 23 wherein the signal processor further comprises:
a frame editor configured to measure a parameter related to signal quality for the MRS spectrum for each acquired frame of an acquisition series for a channel, compare the measured values for the parameter for the respective frames against a threshold criteria, and designate a number of successful frames that meet the threshold criteria and a number of failed frames that fail to meet the threshold criteria; and
wherein the frame editor is further configured to retain successful frames in the acquisition series, and edit out the failed frames from the acquisition series if number of successful frames meets or exceeds a minimum threshold number, but to retain at least some of the failed frames in the acquisition series if the number of successful frames is below the minimum threshold.

132. The system of any one of features 1, 20, or 21, wherein the signal processor further comprises:
a frequency error corrector configured to calculate a confidence level in an ability to estimate frequency shift error for the MRS spectra of each frame of a channel acquisition series, compare each calculated confidence level for each frame against at least one threshold criteria, and determine a number of successful frames that meet or exceed the threshold criteria and a number of other failed frames that fail to meet the threshold criteria; and
wherein the signal processor is further configured to automatically determine whether to (a) edit out the failed frames from the acquisition series and perform frequency shift error correction via the frequency error corrector in a manner to at least in part reverse the frequency shift error estimate on each of the successful frames, if the number of successful frames meets or exceeds a minimum threshold number, or (b) retain at least some of the failed frames and not perform frequency error correction to the series via the frequency error corrector if the number of successful frames is below the minimum threshold.

133. The system of any one of features 1, 20-22, or 24-27, further comprising:
a signal quality evaluator configured to automatically determine whether or not an acquired MRS spectrum for an acquisition channel of a detector assembly acquired during an MRS pulse sequence series exam comprises a recognizable signature signal that is characteristic of lipid.

134. The system of feature 133, wherein the signature lipid signal determination is based upon at least one of signal power or peak values, SNR, and peak value taken in combination with line width of the lipid signal region.

135. The system of any one of features 20, 22, or 73, further comprising:
a diagnostic processor configured to provide diagnostic information for diagnosing a medical condition or chemical environment associated with the ROI based upon the acquired MRS pulse sequence series post-signal processing with the signal processor.

136. The system of any one of features 10, 24, 25, 26, or 27, further comprising a signal processor configured to signal process acquired MRS spectral frames of an MRS pulse sequence series exam of a region of interest in a body of a subject.

137. The system according to any one of features 1 and 20-24, further comprising:
a diagnostic processor configured to provide diagnostic information for diagnosing a medical condition or chemical environment associated with the region of interest (ROI) based at least in part upon a chemical factor related to information extracted from the ROI and associated with a propionic acid (PA) chemical and as adjusted by a voxel-related adjustment factor associated with a voxel prescribed to correspond with the ROI and related to the information extracted, or by another other subject-dependent variable-related adjustment factor associated with the subject.

138. The system according to any one of features 1 and 20-24, further comprising:
a diagnostic processor configured to provide processed diagnostic information for diagnosing a medical condition or chemical environment associated with a region of interest (ROI) in a tissue in a body of a subject based at least in part upon taking a first MRS measurement for a chemical factor taken at a region of an MRS spectrum acquired from the ROI and associated with a propionic acid (PA) chemical and comparing the first MRS measurement against a value derived from a different second measurement and that is associated with an amount of the chemical in the ROI.

139. The system of any one of features 1 and 20-24, further comprising:
a diagnostic processor configured to provide diagnostic information for diagnosing a medical condition or chemical environment associated with a region of interest (ROI) of a tissue in a body of a subject based at least in part upon a chemical factor related to information extracted from the ROI and associated with a propionic acid (PA) chemical; and
wherein said diagnostic information comprises a probability value assigned to a likelihood that the medical condition or chemical environment meets certain criteria in the ROI.

140. The system of any one of features 1 or 20-24, further comprising a non-invasive diagnostic sensor configured to non-invasively acquire the extracted information from the ROI.

141. The system of feature 140, wherein the non-invasive diagnostic sensor comprises an MR system.

142. The system of feature 141, wherein the MR system comprises an MR scanner and a detector coil assembly.

143. The system according to any one of features 1-9 or 20-142, further comprising a computing system comprising one or more computing devices, said computing system configured to implement each said processor.

144. A computing system comprising one or more computing devices, said computing system configured to implement the respective processors according to the medical diagnostic system of any one of features 1-9 or 20-142.

145. A physical computer storage medium storing computer executable code that causes a computing system to implement the medical diagnostic system of any one of features 1-9 or 20-142.

146. A system according to any one of features 1-9 or 20-142, further comprising a physical computer storage medium storing computer executable code that causes a computing system to implement the processors.

147. A physical computer storage storing computer executable code that causes a computing system to implement the processors of the medical diagnostic systems of any one of features 1-9 or 20-142.

148. The method of Feature 10, further comprising using at least one computing system comprising one or more microprocessors to execute executable code in order to conduct the receiving, signal processing, and diagnostically processing of the MRS spectral acquisition series acquired from the multiple acquisition channels and representative of a chemical environment within the intervertebral disc.

149. A medical diagnostic method, comprising:
using a computing system to operate a signal processor for signal processing a repetitive multi-frame MRS pulse sequence acquisition series of MRS spectra frames received from multiple acquisition channels of a detector assembly during a MRS pulse sequence series conducted on a region of interest (ROI) within a tissue in a body of a subject;
wherein the signal processing further comprises using a computing system to operate a channel selector for measuring a parameter related to MRS spectral signal quality for the acquired MRS spectral series from each acquisition channel, comparing the measured parameters for the respective channels against at least one threshold criteria for channel selection, identifying a number of selected channels which meet or exceed the threshold criteria and a number of other failed channels which fail to meet the threshold criteria, and retaining the selected channels and discarding the failed channels from the acquisition series;
measuring a spectral feature of a post-processed MRS spectrum produced by the signal processing and along a region of the MRS spectrum corresponding with propionic acid (PA); and
determining a chemical condition of the ROI or medical condition of the subject based at least in part on the PA-related measurement.

150. A medical diagnostic method, comprising:
using a computing system for signal processing a repetitive multi-frame MRS pulse sequence acquisition series of MRS spectra frames received from an acquisition channel of a detector assembly during a MRS pulse sequence series conducted on a region of interest (ROI) within a tissue in a body of a subject;
wherein the signal processing further comprises using a computing system for operating a frame editor for measuring a parameter related to signal quality for the MRS spectrum for each acquired frame of the acquisition series, comparing the measured values for the parameter for the respective frames against a threshold criteria, and designating a number of successful frames that meet the threshold criteria and a number of failed frames that fail to meet the threshold criteria;
wherein the frame editing further comprises retaining successful frames in the acquisition series, and editing out the failed frames from the acquisition series if the number of successful frames meets or exceeds a minimum frame number threshold, but retaining at least some of the failed frames in the acquisition series if the number of successful frames is below the minimum frame number threshold;

measuring a spectral feature of a post-processed MRS spectrum produced by the signal processing and along a region of the MRS spectrum corresponding with propionic acid (PA); and determining a chemical condition of the ROI or medical condition of the subject based at least in part on the PA-related measurement.

151. A medical diagnostic method, comprising:

using a computing system to execute executable code for operating a signal processor for processing a repetitive multi-frame MRS pulse sequence acquisition series of MRS spectra frames received from an acquisition channel of a detector assembly during a MRS pulse sequence series conducted on a region of interest (ROI) within a tissue in a body of a subject;

wherein the signal processing further comprises using a computing system to execute executable code for operating a frequency error corrector for calculating a confidence level in an ability to estimate frequency shift error for the MRS spectra of each frame of the series, comparing each calculated confidence level for each frame against at least one threshold criteria, and determining a number of successful frames that meet or exceed the threshold criteria and a number of other failed frames that fail to meet the threshold criteria;

wherein the signal processing further comprises using a computing system to execute executable code for automatically determining whether to (a) edit out the failed frames from the acquisition series and perform frequency shift error correction via the frequency error corrector in a manner to at least in part reverse the frequency shift error estimate on each of the successful frames, if the number of successful frames meets or exceeds a minimum threshold number, or (b) retaining at least some of the failed frames and not performing frequency error correction to the series via the frequency error corrector if the number of successful frames is below the minimum threshold;

measuring a spectral feature of a post-processed MRS spectrum produced by the signal processing and along a region of the MRS spectrum corresponding with propionic acid (PA); and determining a chemical condition of the ROI or medical condition of the subject based at least in part on the PA-related measurement.

152. A medical diagnostic method, comprising:

using a computing system to execute executable code to operate a signal quality evaluator for automatically determining whether or not an MRS spectrum acquired from a region of interest (ROI) in a tissue in a body of a subject via an MRS pulse sequence series exam of the ROI comprises a regional signature signal along the MRS spectrum that is characteristic of lipid;

measuring a spectral feature of a post-processed MRS spectrum produced by the signal processing and along a region of the MRS spectrum corresponding with propionic acid (PA); and determining a chemical condition of the ROI or medical condition of the subject based at least in part on the PA-related measurement.

153. A medical diagnostic method, comprising:

using a computing system to execute executable code to operate a diagnostic processor for providing diagnostic information for diagnosing a medical condition or chemical environment associated with a region of interest (ROI) in a tissue in a body of a subject based at least in part upon at least one chemical factor related to information extracted from the ROI and associated with a combination of (i) propionic acid (PA), and (ii) at least one of lactate (LA) and alanine (AL), chemicals.

154. A medical diagnostic method, comprising:

using a computing system to execute executable code to operate a diagnostic processor for providing diagnostic information for diagnosing a medical condition or chemical environment associated with a region of interest (ROI) in a tissue in a body of a subject based at least in part upon a chemical factor related to information extracted from the ROI and associated with a propionic acid (PA) chemical and comprising adjusting the chemical factor by an adjustment factor that comprises at least one of a voxel-related adjustment factor associated with a voxel prescribed to correspond with the ROI and related to the information extracted, and a subject-dependent variable-related adjustment factor associated with the subject.

155. A medical diagnostic method, comprising:

using a computing system to execute executable code for operating a diagnostic processor for providing processed diagnostic information for diagnosing a medical condition or chemical environment associated with a region of interest (ROI) in a tissue in a body of a subject based at least in part upon taking a first MRS measurement for a chemical factor taken at a region of an MRS spectrum acquired from the ROI and associated with a propionic acid (PA) chemical, and comparing the first MRS measurement against a value derived from a different second measurement and that is associated with an amount of the chemical in the ROI.

156. A medical diagnostic method, comprising:

using a computing system to execute executable code for operating a diagnostic processor for providing diagnostic information for diagnosing a medical condition or chemical environment associated with a region of interest (ROI) of a tissue in a body of a subject based at least in part upon a chemical factor related to information extracted from the ROI and associated with a propionic acid (PA) chemical; and using a computing system to execute executable code for providing the diagnostic information that comprises a probability value assigned to a likelihood that the medical condition or chemical environment meets certain criteria in the ROI.

157. The system of feature 92, wherein the diagnostic system is configured to provide diagnostic information related to pain or bacterial infection associated with the disc, or otherwise related to a chemical environment within the disc.

158. The system of feature 23, further comprising a diagnostic processor configured to provide diagnostic information based at least in part upon a spectral feature measurement along a region of the MRS spectrum corresponding with propionic acid (PA) and at least one other chemical.

159. The system of any one of features 24-27 or 158, wherein the diagnostic processor comprises an MRS diagnostic processor configured to provide the diagnostic information to diagnose a medical condition or chemical environment associated with an intervertebral disc in a spine of a subject based upon the extracted information from an MRS spectrum taken from a voxel prescribed to correspond with the ROI in the disc nucleus.

160. The system of feature 159, wherein the MRS diagnostic processor is further configured to provide diagnostic information based upon the extracted information to diagnose pain associated with, or a chemical environment within, the intervertebral disc.

161. The system according to any one of features 1-9, 20-142, or 157-160 further comprising a computing system comprising one or more microprocessors receiving at least one signal responsive to data collected in an MR scanner, said computing system configured to implement each said processor.

162. A computing system comprising one or more microprocessors receiving at least one signal responsive to data collected in an MR scanner, said computing system configured to implement the respective processors according to the medical diagnostic system of any one of features 1-9, 20-142, or 157-160.

163. A non-transitory computer readable medium storing computer executable code configured to cause one or more microprocessors to implement the medical diagnostic system of any one of features 1-9, 20-142, or 157-160.

164. A system according to any one of features 1-9, 20-142, or 157-160 further comprising a non-transitory computer readable medium storing computer executable code that is configured to cause one or more microprocessors to implement the processors.

165. A physical computer readable medium storing computer executable code that causes one or more microprocessors to implement the processors of the medical diagnostic systems of any one of features 1-9, 20-142, or 157-160.

166. A method, comprising:
  measuring a level of propionic acid (PA) in a region of tissue of a subject; and
  diagnosing or determining a medical condition of the subject or chemical environment of the tissue based upon the measurement.

167. The method of feature 166, wherein the measuring is performed using an imaging or spectroscopy tool and based upon a measurable parameter corresponding with PA.

168. The method of feature 166 or 167, wherein the medical condition comprises at least one of pain and bacterial infection.

169. The method of any one of features 166, 167, or 168, wherein the tissue comprises an intervertebral disc.

TABLE 1

Examples of CV Variables for DDD-MRS CHESS-VSS-PRESS pulse sequence for generating MRS spectra useful for post-processing and diagnosing DDD pain of lumbar intervertebral discs (e.g. in a 3.0 Tesla MRI system)

| CV Variable | Value |
|---|---|
| TE (usec) | 28000 |
| TR (usec) | 1000000 |
| Acquisition Matrix Size | 1 |
| Acquisition Matrix Size | 1 |
| Number of spatial slices | 1 |
| Water Suppression Method | 1 |

TABLE 1-continued

Examples of CV Variables for DDD-MRS CHESS-VSS-PRESS pulse sequence for generating MRS spectra useful for post-processing and diagnosing DDD pain of lumbar intervertebral discs (e.g. in a 3.0 Tesla MRI system)

| CV Variable | Value |
|---|---|
| CHESS Flip Angle 1 | 1050 |
| CHESS Flip Angle 2 | 800 |
| CHESS Flip Angle 3 | 125 |
| VSS Band Configuration | 7 |
| PRESS Correction -X axis | 1.2 |
| PRESS Correction -Yaxis | 1.2 |
| PRESS Correction -Z axis | 1.2 |
| Number of Frames | 300 |
| PRESS Flip Angle 1 | 90 |
| PRESS Flip Angle 2 | 167 |
| PRESS Flip Angle 3 | 167 |
| PRESS Correction Function | 0 |

TABLE 2

Example 1, DDD-MRS Clinical Study Group Demographics and Comparison

DDD-MRS Clinical Study - Group Demographics

| | Pain Patients | Asymptomatics | | p value |
|---|---|---|---|---|
| By SUBJECT (n = 31) | | | | |
| n= | 12 | 19 | | |
| Male | 7 (58%) | 9 (47%) | | |
| Female | 5 (42%) | 10 (53%) | | |
| Age | 46.6 ± 9.4 | 32.4 ± 11.3 | ** | 0.0006 |
| Height | 68.3 ± 4.1 | 66.8 ± 4.5 | | 0.1805 |
| Weight | 172.5 ± 38.5 | 151 ± 36.3 | | 0.0639 |
| BMI | 25.9 ± 4.4 | 23.7 ± 3.99 | | 0.0824 |
| By DISCS (n = 52) | | | | |
| n= | 25 | 27 | | |
| Male | 16 (64%) | 16 (59%) | | |
| Female | 9 (36%) | 11 (41%) | | |
| Age | 46.2 ± 9.04 | 35.2 ± 14.6 | ** | 0.0010 |
| Height | 68.7 ± 4.03 | 67.9 ± 4.5 | | 0.2584 |
| Weight | 177.4 ± 39.3 | 157.6 ± 39.5 | * | 0.0381 |
| BMI | 26.2 ± 4.4 | 23.8 ± 4.3 | * | 0.0280 |
| By DISCS (n = 52) | Pos. Controls | Neg. Controls | | p value |
| n= | 13 | 39 | | |
| Male | 8 (62%) | 24 (62%) | | |
| Female | 5 (38%) | 15 (38%) | | |
| Age | 46 ± 9.7 | 38.7 ± 13.9 | * | 0.0445 |
| Height | 68.9 ± 3.7 | 68.1 ± 4.4 | | 0.2661 |
| Weight | 182.4 ± 35.9 | 162 ± 40.8 | | 0.0570 |
| BMI | 26.9 ± 4.2 | 24.4 ± 4.5 | * | 0.0402 |

TABLE 3

Example 1, Comparison of Clinical DDD-MRS Results (MRS+/−) vs. Positive and Negative Controls, per Disc

| | DDD-MRS Results Presumed TRUE | DDD-MRS Results Presumed FALSE | % Match |
|---|---|---|---|
| 3T Pain (All Disco) | 23 | 2 | 92.0% |
| 3T Pos Control (Pain, PD+) | 12 | 1 | 92.3% |
| 3T Neg Control (Pain, PD−) | 11 | 1 | 91.7% |
| 3T Neg Control (Asymptomatic) | 27 | 0 | 100.0% |
| 3T Neg Control (All, PD− + Asymptomatics) | 38 | 1 | 97.4% |
| 3T All | 50 | 2 | 96.2% |

TABLE 4

Example 1, Comparison of Clinical DDD-MRS Results (MRS+/−) vs. Positive and Negative Controls, per Conventional Diagnostic Performance Measures: Sensitivity, Specificity, Positive Predictive Value (PPV), Negative Predictive Value (NPV), Global Performance Accuracy (GPA).

|  | DDD-MRS Diagnostic Performance |
| --- | --- |
| Sensitivity | 92.3% |
| Specificity | 97.4% |
| PPV | 92.3% |
| NPV | 97.4% |
| GPA | 96.2% |

TABLE 5

Example 2, Clinical Data Set (retrospective and prospective combined)

| | (pain) mean ± St. Dev. | (volunteer) mean ± St. Dev. | p value |
| --- | --- | --- | --- |
| By Subject | | | |
| Age (yrs) | 45.7 ± 8.9 | 36 ± 12.9 | p = 0.0005 |
| Height (in) | 67.8 ± 4 | 67.2 ± 4.4 | p = 0.251 |
| Weight (lbs) | 166.4 ± 39.1 | 154.3 ± 32.7 | p = 0.126 |
| BMI | 25.2 ± 4.4 | 23.9 ± 3.5 | p = 0.147 |
| n= | 14 | 28 | |
| Male | 7 | 14 | |
| Female | 7 | 14 | |
| By Disc (per Subject Group) | | | |
| Age (yrs) | 45.9 ± 8.8 | 35.2 ± 14.6 | p = 0.001 |
| Height (in) | 68.1 ± 3.92 | 68 ± 4.4 | p = 0.358 |
| Weight (lbs) | 170 ± 40 | 160.7 ± 32.1 | p = 0.087 |
| BMI | 25.5 ± 4.4 | 24.3 ± 3.4 | p = 0.063 |
| n= | 30 | 49 | |
| Male | 16 | 28 | |
| Female | 14 | 21 | |
| By Disc (per +/−Control Group) | | | |
| | (+control) mean ± St. Dev. | (−control) mean ± St. Dev. | p value |
| Age (yrs) | 45.3 ± 9.2 | 41.7± 13.2 | p = 0.05 |
| Height (in) | 68.4 ± 3.7 | 68 ± 4.3 | p = 0.398 |
| Weight (lbs) | 175.4 ± 38.5 | 161.6 ± 34.4 | p = 0.138 |
| BMI | 26.2 ± 4.4 | 24.4 ± 3.7 | p = 0.093 |
| n= | 15 | 64 | |
| Male | 8 | 36 | |
| Female | 7 | 28 | |

TABLE 6

DDD-MRS Disc Phantom: Expected vs. Measured (Example 4)

| | PG Concentration (mM) | | | LA Concentration (mM) | | | PG/LA Ratio | | |
| --- | --- | --- | --- | --- | --- | --- | --- | --- | --- |
| Phantom/Disc | Expected | Measured | % Diff | Expected | Measured | % Diff | Expected | Measured | % Diff |
| C/1 | 7 | 7.7 | 9% | 7 | 7.0 | 0% | 1 | 1.09 | 9% |
| C/2 | 14 | 12.4 | −11% | 14 | 11.9 | −15% | 1 | 1.04 | 4% |
| C/3 | 21 | 21.9 | 4% | 21 | 25.4 | 21% | 1 | 0.86 | −14% |
| B/1 | 28 | 30.3 | 8% | 28 | 29.4 | 5% | 1 | 1.03 | 3% |
| B/2 | 42 | 57.9 | 38% | 14 | 16.4 | 17% | 3 | 3.54 | 18% |
| B/3 | 14 | 14.6 | 4% | 42 | 51.4 | 22% | 0.33 | 0.28 | −14% |
| B/4 | 28 | 23.9 | −14% | 28 | 25.0 | −11% | 1 | 0.96 | −4% |
| B/5 | 42 | 34.3 | −18% | 14 | 11.2 | −20% | 3 | 3.07 | 2% |

What is claimed is:

1. A diagnostic system for providing diagnostic information for diagnosing whether a region of interest (ROI) in an intervertebral disc in a spine of a patient is infected with bacteria, the diagnostic system comprising:
   a magnetic resonance (MR) system configured to:
      generate and acquire a magnetic resonance spectroscopy (MRS) spectral acquisition series of data for a voxel located within the region of interest (ROI) using an MRS pulse sequence;
      obtain one or more MRI images of a region of the spine associated with the intervertebral disc;
   an MRS signal processor configured to process the MRS spectral acquisition series of data to produce a processed MRS spectrum; and
   a diagnostic processor configured to:
      analyze a spectral peak region of the processed MRS spectrum that corresponds with propionic acid (PA) and that includes at least a portion below a range associated with lactic acid (LA) to identify a spectral feature that comprises a spectral peak;
      calculate a measurement for the spectral feature;
      process the one or more MRI images to extract an MRI signature of Modic change (MC) in the spine; and
      generate the diagnostic information for diagnosing whether the region of interest (ROI) in the intervertebral disc is infected with bacteria using the calculated measurement and the MRI signature.

2. The system of claim 1, wherein the bacteria is Propionibacteria *acnes* (*P.acnes*).

3. The system of claim 1, wherein the diagnostic processor is configured to calculate a diagnostic value that is indicative of a presence or absence of bacterial infection based at least in part on a calculated ratio between (i) the calculated measurement corresponding with PA, and (ii) at least a measured second calculated measurement for at least a second feature along at least a second spectral region of the processed MRS spectrum that corresponds with at least one of proteoglycan (PG), lactate (LA), alanine (AL), or carbohydrate (CA) chemicals.

4. The system of claim 1, wherein the diagnostic processor is configured to determine the diagnostic information based at least in part upon a second calculated measurement derived from information extracted from a second ROI in a second intervertebral disc in the spine, wherein the second calculated measurement corresponds with at least one chemical factor in the second ROI comprising propionic acid (PA).

5. A method for providing diagnostic information for diagnosing whether a region of interest (ROI) in an intervertebral disc in a spine of a patient is infected with bacteria, the method comprising:

generating and acquiring a magnetic resonance spectroscopy (MRS) spectral acquisition series of data for a voxel located within the region of interest (ROI) in the intervertebral disc using an MRS system with an MRS scanner comprising a magnet and operated according to an MRS pulse sequence to generate the series of data and a detector assembly configured for receiving the series of data;

signal processing the MRS spectral acquisition series of data to produce a processed MRS spectrum;

analyzing a spectral peak region of the processed MRS spectrum that corresponds at least in part with propionic acid (PA) and that includes at least a portion below a range associated with lactic acid (LA) to identify a spectral feature that comprises a spectral peak;

calculating a measurement for the spectral feature; and generating the diagnostic information for diagnosing whether the region of interest (ROI) in the intervertebral disc is infected with bacteria using the calculated measurement.

6. The method of claim 5, further comprising:
obtaining one or more MRI images of a region of the spine associated with the intervertebral disc; and
extract a MRI signature associated with Modic change (MC) in the spine of the patient from the one or more MRI images, wherein the diagnostic information is generated using the MRI signature.

7. The method of claim 5, wherein the bacteria is Propionibacteria acnes (P.acnes).

8. The method of claim 5, further comprising:
generating and acquiring a second MRS spectral acquisition series of data for a second voxel located within a second region of interest (ROI) in a second intervertebral disc using the MRS system;
signal processing the second MRS spectral acquisition series of data to produce a second processed MRS spectrum;
identifying a spectral feature along a spectral peak region of the second processed MRS spectrum that corresponds at least in part with propionic acid (PA);
calculating a measurement for the spectral feature to produce a second calculated measurement associated with the second ROI; and
generating the diagnostic information using the second calculated measurement.

9. The method of claim 8, further comprising:
determining a first score for the ROI based at least in part on the calculated measurement;
determine a second score for the second ROI based at least in part on the second calculated measurement; and
compare the first score to the second score, wherein the diagnostic information is based at least in part on the comparison.

10. The method of claim 5, wherein the signal processing, the identifying of the spectral feature, the calculating of the measurement, and the generating of the diagnostic information is performed by at least one computer processor.

11. The method of claim 5, further comprising preparing an antibiotic treatment for administration to the patient in response to the diagnostic information.

12. The method of claim 5, further comprising calculating at least a second measurement for at least a second spectral feature along at least a second respective spectral peak region of the processed MRS spectrum associated with at least one of proteoglycan (PG), carbohydrate (CA), lactate (LA), or alanine (AL) chemicals, and wherein the diagnostic information is further based at least in part on the second calculated measurement.

13. The method of claim 12, further comprising calculating a diagnostic value derived at least in part on a ratio between the calculated measurement and the second calculated measurement.

14. A diagnostic system for providing diagnostic information for diagnosing whether a region of interest (ROI) in an intervertebral disc in a spine of a patient is infected with bacteria, the diagnostic system comprising:

a magnetic resonance spectroscopy (MRS) signal processor configured to receive a multi-frame MRS spectral acquisition series generated for a voxel principally located within the region of interest (ROI) in the intervertebral disc via an MRS pulse sequence, the MRS signal processor configured to process the MRS spectral acquisition series to produce a processed MRS spectrum;

an MRS diagnostic processor configured to:
analyze a spectral peak region of the processed MRS spectrum that comprises a region corresponding at least in part with propionic acid (PA) and that includes at least a portion below a range associated with lactic acid (LA) to identify a spectral feature that comprises a spectral peak;
calculate a measurement for the spectral feature; and
generate the diagnostic information for diagnosing whether the region of interest (ROI) in the intervertebral disc is infected with bacteria using the calculated measurement;

wherein each of the MRS signal processor and MRS diagnostic processor comprises at least one of:
(a) at least one computer processor, and
(b) software provided in computer-readable non-transitory storage and that is configured to be run by at least one computer processor.

15. The system of claim 14, further comprising a magnetic resonance (MR) system that is configured to produce one or more MRI images of the spine, and wherein the diagnostic processor is configured to generate the diagnostic information based at least in part on an MRI signature of modic change (MC) in the spine of the patient.

16. The system of claim 14, wherein the bacteria is Propionibacteria acnes (P.acnes).

17. The system of claim 14, further comprising an MRS system with an MRS scanner comprising a magnet and operable according to the MRS pulse sequence to generate the MRS spectral acquisition series and a detector assembly configured for receiving the MRS spectral acquisition series.

18. The system of claim 14, wherein the spectral peak region comprises a combined spectral peak region corresponding with both propionic acid (PA) and lactate (LA) (LAPA).

19. The system of claim 14, wherein the spectral peak region comprises a combined spectral peak region corresponding with each of propionic acid (PA), lactate (LA), and alanine (AL) (ALPA).

20. The system of claim 14, wherein the diagnostic processor is configured to calculate a diagnostic value that is indicative of a presence or absence of bacterial infection based at least in part on a combination of (i) the calculated measurement corresponding with PA, and (ii) at least a measured second calculated measurement for at least a second feature along at least a second spectral region of the processed MRS spectrum that corresponds with at least one of proteoglycan (PG), lactate (LA), alanine (AL), or carbohydrate (CA) chemicals.

21. The system of claim 14, wherein the diagnostic processor is configured to calculate a diagnostic value derived from at least one calculated ratio between at least two calculated measurements for at least two respective features along at least two respective spectral peak regions of the processed MRS spectrum and associated with at least two chemicals in the ROI, wherein at least one said chemical comprises PA.

22. The system of claim 14, wherein the diagnostic information is further based at least in part upon a contained volume of the voxel.

23. The system of claim 14, wherein the calculated measurement is adjusted by a subject-related adjustment factor associated with a known value or condition of a subject-dependent variable comprising at least one of height, weight, percentage body fat, body mass index (BMI), and gender.

24. The system of claim 14, wherein the diagnostic processor is configured to determine the diagnostic information based at least in part upon a second calculated measurement derived from information extracted from a second ROI in a second intervertebral disc in the spine, wherein the second calculated measurement corresponds with at least one chemical factor in the second ROI comprising propionic acid (PA).

25. The system of claim 24, wherein the diagnostic processor is configured to calculate a first score for the ROI based at least in part on the calculated measurement, to calculate a second score for the second ROI based at least in part on the calculated second measurement, and to determine the diagnostic information based at least in part on the first score and the second score.

* * * * *